(12) United States Patent
Koenig et al.

(10) Patent No.: US 8,193,318 B2
(45) Date of Patent: *Jun. 5, 2012

(54) FCγRIIB SPECIFIC ANTIBODIES AND METHODS OF USE THEREOF

(75) Inventors: Scott Koenig, Rockville, MD (US); Maria Concetta Veri, Denwood, MD (US); Nadine Tuaillon, Gettysburg, PA (US); Ezio Bonvini, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 437 days.

This patent is subject to a terminal disclaimer.

(21) Appl. No.: 12/186,058

(22) Filed: Aug. 5, 2008

(65) Prior Publication Data

US 2009/0076251 A1    Mar. 19, 2009

Related U.S. Application Data

(63) Continuation-in-part of application No. 10/643,857, filed on Aug. 14, 2003, now Pat. No. 7,425,620, and a continuation-in-part of application No. 10/524,134, filed as application No. PCT/US03/25399 on Aug. 14, 2003, now Pat. No. 7,425,619, and a continuation-in-part of application No. 11/108,135, filed on Apr. 15, 2005, now abandoned, and a continuation-in-part of application No. 11/305,787, filed on Dec. 15, 2005, now abandoned.

(60) Provisional application No. 60/403,266, filed on Aug. 14, 2002, provisional application No. 60/562,804, filed on Apr. 16, 2004, provisional application No. 60/582,044, filed on Jun. 21, 2004, provisional application No. 60/582,045, filed on Jun. 21, 2004, provisional application No. 60/654,713, filed on Feb. 18, 2005, provisional application No. 60/636,663, filed on Dec. 15, 2004.

(51) Int. Cl.
*C07K 16/00* (2006.01)
*C12P 21/08* (2006.01)
*C07K 14/00* (2006.01)

(52) U.S. Cl. ............... 530/387.1; 530/387.3; 530/388.1; 530/388.22; 530/388.7; 530/389.1

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. |
| 4,752,601 A | 6/1988 | Hahn |
| 5,024,835 A | 6/1991 | Rao et al. |
| 5,225,539 A | 7/1993 | Winter |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,723,584 A | 3/1998 | Schatz |
| 5,736,135 A | 4/1998 | Goeddel et al. |
| 5,736,137 A | 4/1998 | Anderson et al. |
| 5,837,243 A | 11/1998 | Deo et al. |
| 5,874,239 A | 2/1999 | Schatz |
| 5,877,396 A | 3/1999 | Ravetch et al. |
| 5,888,533 A | 3/1999 | Dunn |
| 5,932,433 A | 8/1999 | Schatz |
| 5,945,115 A | 8/1999 | Dunn et al. |
| 5,985,599 A | 11/1999 | Mckenzie et al. |
| 6,019,968 A | 2/2000 | Platz et al. |
| 6,025,485 A | 2/2000 | Kamb et al. |
| 6,114,147 A | 9/2000 | Frenken et al. |
| 6,132,764 A | 10/2000 | Li et al. |
| 6,132,992 A | 10/2000 | Ledbetter et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |

(Continued)

FOREIGN PATENT DOCUMENTS

EP    0 327 378    8/1989

(Continued)

OTHER PUBLICATIONS

Rader et al. PNAS. 1998. 95:8910-8915.*
Rankin, et al. CD32B, the human inhibitory Fc-γ receptor IIB, as a target for monoclonal antibody therapy of B-cell lymphoma, Blood Journal, Oct. 1, 2006, vol. 108, No. 7 pp. 2384-2391.
Extended Search Report EP07799049 (PCT/US2007/072151) (2010) (7 pages).
Holliger, P. et al. (1993) "Diabodies: Small bivalent and bispecific antibody fragments", Proc. Natl. Acad. Sci. (U.S.A.) 90(14): 6444-6448.
Lu, D. et al. (2003) "Di-diabody: a novel tetravalent bispecific antibody molecule by design", J. Immunol. Meth. 279: 219-232.
Wu et al. (2001) "Multimerization of a chimeric anti-CD20 single-chain Fv-Fc fusion protein is mediated through variable domain exchange", Protein Engineering 14(2): 1025-1033.

(Continued)

*Primary Examiner* — Chun Dahle
(74) *Attorney, Agent, or Firm* — William C. Schrot; Jeffrey I. Auerbach; The Auerbach Law Firm, LLC

(57) ABSTRACT

The present invention relates to antibodies or fragments thereof that specifically bind FcγRIIB with greater affinity than said antibodies or fragments thereof bind FcγRIIA. The present invention also encompasses the use of an anti-FcγRIIB antibody or an antigen-binding fragment thereof for the treatment, prevention, management, or amelioration of a disease or disorder. The invention further provides methods of enhancing the therapeutic effect of therapeutic antibodies by administering the antibodies of the invention to enhance the effector function of the therapeutic antibodies. The invention also provides methods of enhancing efficacy of a vaccine composition by administering the antibodies of the invention with a vaccine composition. The invention also provides methods of breaking tolerance to an antigen by administering an antigen-antibody complex and an antibody of the invention.

6 Claims, 62 Drawing Sheets

U.S. PATENT DOCUMENTS

Figure 1A:
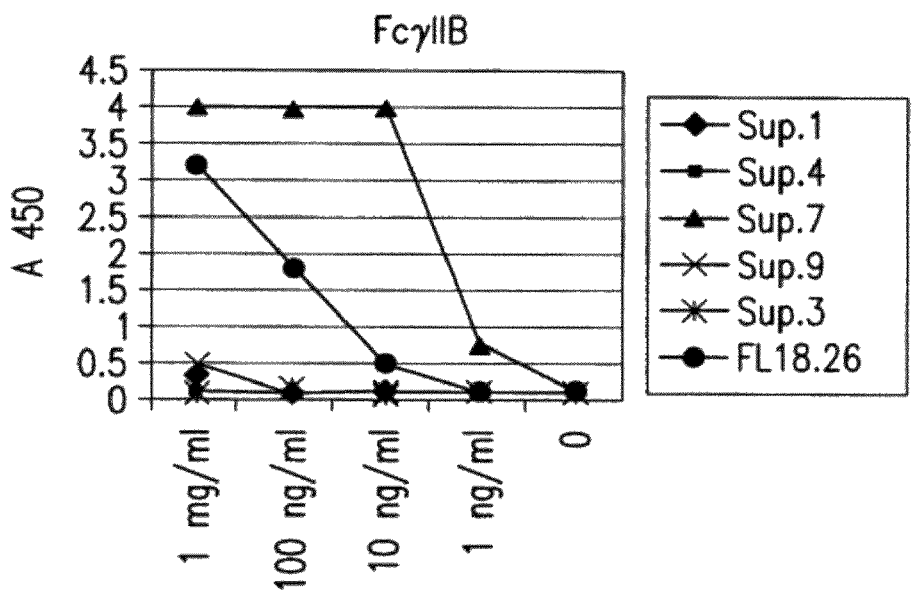

| | | | |
|---|---|---|---|
| 6,277,375 B1 | 8/2001 | Ward | |
| 6,300,065 B1 | 10/2001 | Kieke et al. | |
| 6,339,069 B1 | 1/2002 | Meers et al. | |
| 6,420,149 B1 | 7/2002 | Fukuda et al. | |
| 6,423,538 B1 | 7/2002 | Wittrup et al. | |
| 6,455,263 B2 | 9/2002 | Payan | |
| 6,472,511 B1 | 10/2002 | Leung et al. | |
| 6,528,624 B1 | 3/2003 | Idusogie et al. | |
| 6,538,124 B1 | 3/2003 | Idusogie et al. | |
| 6,548,640 B1 | 4/2003 | Winter | |
| 6,696,550 B2 | 2/2004 | Larosa et al. | |
| 6,737,056 B1 | 5/2004 | Presta | |
| 6,821,505 B2 | 11/2004 | Ward | |
| 6,982,321 B2 | 1/2006 | Winter | |
| 7,315,786 B2 | 1/2008 | Dahiyat et al. | |
| 7,317,091 B2 | 1/2008 | Lazar et al. | |
| 7,355,008 B2 | 4/2008 | Stavenhagen et al. | |
| 7,425,619 B2 | 9/2008 | Koenig et al. | |
| 7,425,620 B2 | 9/2008 | Koenig et al. | |
| 7,521,542 B2 * | 4/2009 | Johnson et al. | 424/133.1 |
| 7,632,497 B2 | 12/2009 | Stavenhagen | |
| 7,655,229 B2 | 2/2010 | Chan et al. | |
| 7,662,925 B2 | 2/2010 | Lazar et al. | |
| 7,662,926 B2 | 2/2010 | Chan et al. | |
| 7,786,270 B2 * | 8/2010 | Johnson et al. | 530/387.3 |
| 2001/0036459 A1 | 11/2001 | Ravetch | |
| 2002/0004587 A1 | 1/2002 | Miller et al. | |
| 2002/0028486 A1 | 3/2002 | Morrison et al. | |
| 2003/0077282 A1 | 4/2003 | Bigler et al. | |
| 2003/0115614 A1 | 6/2003 | Kanda et al. | |
| 2003/0158389 A1 | 8/2003 | Idusogie et al. | |
| 2003/0190319 A1 | 10/2003 | Adolf et al. | |
| 2003/0207346 A1 | 11/2003 | Arathoon et al. | |
| 2004/0002587 A1 | 1/2004 | Watkins et al. | |
| 2004/0110226 A1 | 6/2004 | Lazar et al. | |
| 2004/0132101 A1 | 7/2004 | Lazar et al. | |
| 2004/0185045 A1 | 9/2004 | Koenig et al. | |
| 2004/0191244 A1 | 9/2004 | Presta | |
| 2004/0220388 A1 | 11/2004 | Mertens et al. | |
| 2004/0235065 A1 | 11/2004 | Hansen et al. | |
| 2005/0025764 A1 | 2/2005 | Watkins et al. | |
| 2005/0037000 A1 | 2/2005 | Stavenhagen et al. | |
| 2005/0054832 A1 | 3/2005 | Lazar et al. | |
| 2005/0064514 A1 | 3/2005 | Stavenhagen et al. | |
| 2005/0090648 A1 | 4/2005 | Tsurushita et al. | |
| 2005/0215767 A1 | 9/2005 | Koenig et al. | |
| 2005/0260213 A1 | 11/2005 | Koenig et al. | |
| 2006/0013810 A1 | 1/2006 | Johnson et al. | |
| 2006/0024298 A1 | 2/2006 | Lazar et al. | |
| 2006/0073142 A1 | 4/2006 | Chan et al. | |
| 2006/0134709 A1 | 6/2006 | Stavenhagen et al. | |
| 2006/0177439 A1 | 8/2006 | Koenig et al. | |
| 2007/0004909 A1 | 1/2007 | Johnson et al. | |
| 2007/0036799 A1 | 2/2007 | Stavenhagen et al. | |
| 2007/0253948 A1 | 11/2007 | Chan et al. | |
| 2008/0044417 A1 | 2/2008 | Johnson et al. | |
| 2008/0051563 A1 | 2/2008 | Lazar et al. | |
| 2008/0131435 A1 | 6/2008 | Stavenhagen et al. | |
| 2008/0138344 A1 | 6/2008 | Stavenhagen et al. | |
| 2008/0286819 A1 | 11/2008 | Ravetch et al. | |
| 2009/0053218 A1 | 2/2009 | Koenig et al. | |

FOREIGN PATENT DOCUMENTS

| | | |
|---|---|---|
| EP | 0 332 865 | 9/1989 |
| EP | 0 629 703 | 12/1994 |
| EP | 0 359 096 | 11/1997 |
| EP | 0 953 639 | 11/1999 |
| EP | 1 006 183 | 6/2000 |
| EP | 0 343 950 | 10/2000 |
| WO | WO 88/07089 | 9/1988 |
| WO | WO 89/07142 | 8/1989 |
| WO | WO 92/16562 | 10/1992 |
| WO | WO 93/22332 | 11/1993 |
| WO | WO 94/18330 | 8/1994 |
| WO | WO 94/29351 | 12/1994 |
| WO | WO 95/05468 | 2/1995 |
| WO | WO 97/28267 | 8/1997 |
| WO | WO 97/34631 | 9/1997 |
| WO | WO 97/44362 | 11/1997 |
| WO | WO 98/05787 | 2/1998 |
| WO | WO 98/23289 | 6/1998 |
| WO | WO 98/52975 | 11/1998 |
| WO | WO 99/19362 | 4/1999 |
| WO | WO 99/41285 | 8/1999 |
| WO | WO 99/43713 | 9/1999 |
| WO | WO 99/51642 | 10/1999 |
| WO | WO 99/58572 | 11/1999 |
| WO | WO 00/09560 | 2/2000 |
| WO | WO 00/42072 | 7/2000 |
| WO | WO 01/79299 | 10/2001 |
| WO | WO 02/02781 | 1/2002 |
| WO | WO 02/060919 | 8/2002 |
| WO | WO 02/086070 | 10/2002 |
| WO | WO 03/035835 | 5/2003 |
| WO | WO 03/066095 | 8/2003 |
| WO | WO 03/074679 | 9/2003 |
| WO | WO 2004/016750 | 2/2004 |
| WO | WO 2004/029207 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2005/018669 | 3/2005 |
| WO | WO 2005/070963 | 8/2005 |
| WO | WO 2005/110474 | 11/2005 |
| WO | WO 2005/115452 | 12/2005 |
| WO | WO 2006/020114 | 2/2006 |
| WO | WO 2006/028956 | 3/2006 |
| WO | WO 2006/066078 | 6/2006 |
| WO | WO 2006/088494 | 8/2006 |
| WO | WO 2006/113665 | 10/2006 |
| WO | WO 2007/021841 | 2/2007 |
| WO | WO 2007/024249 | 3/2007 |
| WO | WO 2007/106707 | 9/2007 |
| WO | WO 2008/002933 | 1/2008 |
| WO | WO 2008/009545 | 1/2008 |
| WO | WO 2008/019199 | 2/2008 |
| WO | WO 2009/083009 | 7/2009 |
| WO | WO 2009/151717 | 9/2009 |

OTHER PUBLICATIONS

Sleister et al., "Subtractive Immunization; A tool for the generation of discriminatory antibodies to proteins of similar sequence," Journal of Immunological Methods 261: 213-220, (2002).

Eddy, S.R. (2004) "*Where Did the BLOSUM62 Alignment Score Matrix Come From?*," Nature Biotech. 22(8):1035-1036.

Henikoff, J.G. (1992) "Amino acid substitution matrices from protein blocks," Proc. Natl. Acad. Sci. (USA) 89:10915-10919.

Karlin, S. et al. (1990) "*Methods for Assessing the Statistical Significance of Molecular Sequence Features by Using General Scoring Schemes*," Proc. Natl. Acad. Sci. (USA) 87:2264-2268.

Altschul, S.F. (1991) "*Amino Acid Substitution Matrices From an Information Theoretic Perspective*," J. Mol. Biol. 219, 555-565.

Abra et al. The next generation of liposome delivery systems: recent experience with tumor-targeted, sterically-stabilized immunoliposomes and active-loading gradients. J Liposome Res. Feb.-May 2002;12(1-2):1-3.

Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.

Altman et al., "Phenotypic Analysis of Antigen-Specific T Lymphocytes", Science 274:94-96, 1996.

Amit et al. (1986) Three-dimensional structure of an antigen-antibody complex at 2.8 A resolution.; Science 233:747-753.

Angal et al., "A single amino acid substitution abolishes the heterogeneity of chimeric mouse/human (IgG4) antibody," Mol Immunol 30 :105-108, 1993.

Armour et al., "The contrasting IgG-binding interactions of human and herpes simplex virus Fc receptors," Biochemical Society Transactions 30:495-500, 2002.

Armour et al., "Recombinant human IgG molecules lacking Fcgamma receptor I binding and monocyte triggering activities," Eur J Immunol 29:2613-2624, 1999.

Armour et al., "Differential binding to human FcgammaRIIa and FcgammaRIIb receptors by human IgG wildtype and mutant antibodies," Mol Immunol 40 :585-593, 2003.

Armstrong, S. et al. "Heterogeneity of IgG1 monoclonal anti-Rh(D): an investigation using ADCC and macrophage binding assays," Brit. J. Haematol. 66:257-262 (1987).

Bachmann et al. (2005) "Recall Proliferation of Memory CD8+ T Cells and Antiviral Protection," J. Immunol. 175:4677-4685.

Baggiolini M, Dewald B. "Cellular models for the detection and evaluation of drugs that modulate human phagocyte activity," Experientia. Oct. 15;44(10):841-848, 1988.

Bendas G, Immunoliposomes: a promising approach to targeting cancer therapy. BioDrugs. 2001;15(4):215-24.

Bendig, M.M. (1995) Methods: A Companion to Methods in Enzymology 8:83-93.

Bernard et al. (1986) "A unique epitope on the CD2 molecule defined by the monoclonal antibody 9-1: epitope-specific modulation of the E-rosette receptor and effects on T-cell functions," Hum. Immunol. 17(4):388-405.

Bewarder et al., 1996, "In vivo and in vitro specificity of protein tyrosine kinases for immunoglobulin G receptor (FcgammaRII) phosphorylation," Mol. Cell. Biol. 16 (9):4735-43.

Billadeau et al., ITAMs versus ITIMs: striking a balance during cell regulation, J Clin Invest. Jan. 2002;109(2):161-8.

Boder and Wittrup, 1997, "Yeast surface display for screening combinatorial polypeptide libraries", Nature Biotechnology 15:553-557.

Boder and Wittrup, "Optimal screening of surface-displayed polypeptide libraries," Biotechnol Prog 14:55-62, 1998.

Boder and Wittrup, "Yeast surface display for directed evolution of protein expression, affinity, and stability," Methods in Enzymology 328:430-444, 2000.

Boder et al., "Directed evolution of antibody fragments with monovalent femtomolar antigen-binding affinity," Proc. Natl. Acad. Sci. USA 97:10701-10705, 2000.

Bolland et al., Genetic modifiers of systemic lupus erythematosus in Fc.gamma.RIIB(-/-) mice. J Exp Med. May 6, 2002;195(9):1167-74.

Bolland and Ravetch., Inhibitory pathways triggered by ITIM-containing receptors. Adv Immunol. 1999;72:149-177.

Boruchov et al., Activating and inhibitory IgG Fc receptors on human DCs mediate opposing functions. The Journal of Clinical Investigation 115; 10:2914-2923, 2005.

Boruchov et al., "Expression and Modulation of the Inhibitory Fcγ Receptor, FcγRIIB (CD32B), on Human Dendritic Cells (DCs)," Blood 102(11):Abstract #1908, 2003.

Boyer et al. (1999) "Relative cytotoxic activity of immunotoxins reactive with different epitopes on the extracellular domain of the c-erbB-2 (HER-2/neu) gene product p185," Int. J. Cancer. 82(4):525-531.

Brauweiler et al., Partially distinct molecular mechanisms mediate inhibitory Fc.gamma.RIIB signaling in resting and activated B cells. J Immunol. 2001;167:204-211.

Bredius et al., "Role of neutrophil Fc gamma RIIa (CD32) and Fc gamma RIIIb (CD16) polymorphic forms in phagocytosis of human IgG1- and IgG3-opsonized bacteria and erythrocytes," Immunology 83:624-630, 1994.

Brekke et al., "Human IgG isotype-specific amino acid residues affecting complement-mediated cell lysis and phagocytosis.," Eur J Immunol 24:2542-2547, 1994.

Brown (2001) "Factors Modifying the Migration of Lymphocytes Across the Blood-Brain Barrier," Int Immunopharmacol. Nov. 2001;1(12):2043-62.

Brown EJ., "In Vitro Assays of Phagocytic Function of Human Peripheral Blood Leukocytes: Receptor Modulation and Signal Transduction," vol. 45 (Microbes as Tools for Cell Biology) in *Methods in Cell Biololgy*, Russell ed. Academic Press Inc. pp. 147-164, 1994.

Budde et al., Specificity of CD32 mAB for Fc.gamma.RIIa, Fc.gamma.RIIb1, and Fc.gamma.RIIb2 expressed in transfected mouse B cells and BHK-21 cells. Leukocyte Typing V: White cell differentiation antigens. 1995;828-832 (Schlossman, Boumsell, Gilks, Harlan, Kishomoto, eds.).

Burgess et al. (1990) "Possible dissociation of the heparin-binding and mitogenic activities of the heparin-binding (acidic fibroblast) growth factor-1 from its receptor binding activities by site directed mutagenesis of a single lysine residue," J. Cell Biol. 111:2129-2138.

Burlmeister et al., "Crystal structure of the complex of rat neonatal Fc receptor with Fc," Nature 372:379-383, 1994.

Burton and Woof, "Human antibody effector function," Advances in Immunology 51:1-84, 1992.

Burton et al., "Molecular recognition of antibody (IgG) by cellular Fc receptor (FcRI)," Mol Immunol 25:1175-1181, 1988.

Burton, "Immunoglobulin G: functional sites," Mol Immunol 22:161-206, 1985.

Callanan et al., The IgG Fc Receptor, Fc.gamma.RIIB is a target for deregulation by chromosomal translocation in malignant lymphoma. PNAS. Jan. 2000;97(1):309-314.

Canfield and Morrison, "The binding affinity of human IgG for its high affinity Fc receptor is determined by multiple amino acids in the CH2 domain and is modulated by the hinge region," J Exp Med 173:1483-1491, 1991.

Campbell et al. (2003) "Monoclonal antibody therapy for lymphoma," Blood Rev. 17(3):143-152.

Cameron et al., Differentiation of the human monocyte cell line, U937, with dibutyryl cyclicAMP induces the expression of the inhibitory Fc receptor, Fc.gamma.RIIb. Immunol Lett. Oct. 1, 2002;83(3):171-9.

Camilleri-Broet et al., Fc.gamma.RIIB is differentially expressed during B cell maturation and in B-cell lymphomas. Br J Haematol. 2004;124(1):55-62.

Caron et al., "Engineered humanized dimeric forms of IgG are more effective antibodies," J Exp Med 176 :1191-5, 1992.

Carter et al., "Humanization of an anti-p185HER2 antibody for human cancer therapy," Proc. Natl. Acad. Sci. USA 89:4285-4289, 1992.

Cartron et al., "Therapeutic activity of humanized anti-CD20 monoclonal antibody and polymorphism in IgG Fc receptor FcgammaRIIIa gene," Blood 99 :754-758, 2002.

Cassard et al., Modulation of tumor growth by inhibitory Fc.gamma. receptor expressed by human melanoma cells. The J Clin Invest. Nov. 2002;110(10):1549-1557.

Casset et al. (2003) A peptide mimetic of an anti-CD4 monoclonal antibody by rational design, Biochem. Biophs. Res. Commun 307:198-205.

Cavacini et al. (1995) "Influence of heavy chain constant regions on antigen binding and HIV-1 neutralization by a human monoclonal antibody," J Immunol. 155(7):3638-3644.

Chappel et al., "Identification of the Fc gamma receptor class I binding site in human IgG through the use of recombinant IgG1/IgG2 hybrid and point-mutated antibodies," Proc. Natl. Acad. Sci USA 88:9036-9040, 1991.

Chappel et al., "Identification of a secondary Fc gamma RI binding site within a genetically engineered human IgG antibody," J Biol. Chem 268:25124-25131, 1993.

Chattergee et al. (1994) "Idiotypic Antibody Immunotherapy of Cancer," Cancer Immuno. Immunother. 38:75-82.

Chen, et al. (1999) "Selection and Analysis of an Optimized Anti-VEGF Antibody: Crystal Structure of an Affinity-Matured Fab in Complex with Antigen," J. Molec. Biol. 293:865-881.

Ciccimarra et al., "Localization of the IgG effector site for monocyte receptors," Proc. Natl. Acad. Sci. U.S.A. 72 :2081-2083, 1975.

Clynes and Ravetch, "Cytotoxic antibodies trigger inflammation through Fc receptors," Immunity 3:21-26, 1995.

Clynes et al., "Modulation of immune complex-induced inflammation in vivo by the coordinate expression of activation and inhibitory Fc receptors," J Exp Med 189:179-185, 1999.

Clynes et al., "Inhibitory Fc receptors modulate in vivo cytoxicity against tumor targets," Nature Medicine 6 :443-446, 2000.

Clynes et al., "Fc receptors are required in passive and active immunity to melanoma," Proc. Natl. Acad. Sci USA 95:652-656, 1998.

Clynes et al., "Uncoupling of immune complex formation and kidney damage in autoimmune glomerulonephritis," Science 279:1052-1054, 1998.

Colman, P.M. (1994) "Effects of amino acid sequence changes on antibody-antigen interactions," Res. Immunol. 145:33-36.

Daeron et al., The Same Tyrosine Based Inhibition Motif, in the Intracytoplasmic Domain of Fc.gamma.RIIB, regulates negatively BCR, TCR- and FcR dependent cell activation. Immunity. Nov. 1995;3: 635-646.

Damle et al., B-cell chronic lymphocytic leukemia cells express a surface membrane phenotype of activated, antigen-experienced B lymphocytes. Blood Jun. 1, 2002;99(11):4087-4093.

Davies et al., Expression of GnTIII in a recombinant anti-CD20 CHO production cell line: Expression of antibodies with altered glycoforms leads to an increase in ADCC through higher affinity for Fc.sub..gamma. RIII. Biotechnol Bioeng. Aug. 20, 2001;74(4):288-94.

Davies et al. (1995) Antibody VH domains as small recognition units, Bio/Technology 13:475-479.

de Haas, Wien Kin "IgG-Fc receptors and the clinical relevance of their polymorphisms," Wien Klin Wochenscha 113:825-831, 2001.

Deisenhofer, "Crystallographic refinement and atomic models of a human Fc fragment and its complex with fragment B of protein A from Staphylococcus aureus at 2.9- and 2.8-A resolution," Biochem. 20:2361-2370, 1981.

Deo et al., "Clinical significance of IgG Fc receptors and Fc gamma R-directed immunotherapies," Immunology Today 18:127-135, 1997.

DePascalis et al. (2002) "Grafting of Abbreviated Complementarity Determining Regions Containing Specificity Determining Residues Essential for Ligand Contact to Engineer a Less Immunogenic humanized monoclonal antibody," J. Immunol. 169:3076-3084.

De Santes et al. (1992) "Radiolabeled Antibody Targeting of the Her-2/neu Oncoprotein," Cancer Res. 52:1916-1923.

Dermer (1994) "Another Anniversary for the War on Cancer," Biotechnology 12:320 (1994).

Ding et al., Inhibition of the function of the Fc.gamma.RIIB by a monoclonal antibody to thymic shared antigen-1, a Ly-6 family antigen. Immunology. Sep. 2001;104(1):28-36.

Dumoulin et al. (2002) Single-domain antibody fragments with high conformational stability, Protein Science 11:500-512.

Duncan and Winter, "The binding site for C1q on IgG," Nature 332:738-740, 1988.

Duncan and Winter, "Localization of the binding site for the human high-affinity Fc receptor on IgG," Nature 332:563-564, 1988.

Edberg et al., "Modulation of Fcgamma and Complement Receptor Function by the Glycosyl-Phosphatidylinositol-Anchored Form of FcgammaRIII," Journal of Immunology 152: 5826-5835, 1994.

Efferson et al. (2005) "Stimulation of Human T Cells by an Influenza A Vector Expressing a CTL Epitope from the HER-2/neu Protooncogene Results in Higher Numbers of Antigen Specific TCRhi Cells than Stimulation with Peptide," Anticancer Research 25:715-724.

Ellman, J. et al. "Biosynthetic Method for Introducing Unnatural Amino Acids Site-Specifically into Proteins," Methods Enzymol. 202:301-336, 1991.

Eppstein et al., Biological activity of liposome-encapsulated murine interferon .gamma. is mediated by a cell membrane receptor. Proc Natl Acad Sci U S A. Jan. 1985;82(11):3688-9.

Fanger et al., Production and use of anti-FcR bispecific antibodies. Immunomethods. Feb. 1994;4(1):72-81.

Farag, et al., Fc.gamma.RIIIa and Fc.gamma.RIIIa polymorphisms do not predict response to Rituximab in B-cell chronic lymphocytic leukemia. Blood. Oct. 16, 2003 (15 pp.).

Flesch and Neppert, "Functions of the Fc receptors for immunoglobulin G," J Clin Lab Anal 14:141-156, 2000.

Fidler, I. J., Macrophages and metastasis—a biological approach to cancer therapy. Cancer Res. Oct. 1985;45(10):4714-26.

Fleit et al., 1995 "Cross-linking of mAb to Fc.gamma.RII results in tyrosine phosphorylation of multiple polypeptides including Fc.gamma.RII itself." Leukocyte Typing V: White cell differentiation antigens 826-827 (Schlossman, Boumsell, Gilks, Harlan, Kishomoto, eds.).

Gamberale et al., 2003, "To the Editor: Expression of Fc.gamma. receptors type II (Fc.gamma.RII) in chronic lymphocytic leukemia B cells." Blood (Correspondence) 102(7):2698-2699.

Gerber et al., Stimulatory and inhibitory signals originating from the macrophage Fc.gamma. receptors. Microbes Infect. Feb. 2001;3(2):131-9.

Gergeley et al., "Fc receptors on lymphocytes and K cells," Biochemical Society Transactions 12:739-743, 1984.

Gergely and Sarmay, "The two binding-site models of human IgG binding Fc gamma receptors," FASEB J 4:3275-3283, 1990.

Greenwood and Clark, Effector functions of matched sets of recombinant human IgG subclass antibodies. (final version edited Feb. 11, 1993).

Greenwood et al., "Structural motifs involved in human IgG antibody effector functions," Eur J Immunol 23:1098-1104, 1993.

Greenwood et al., "Engineering multiple-domain forms of the therapeutic antibody CAMPATH-1H: effects on complement lysis," Therapeutic Immunology 1:247-255, 1994.

Gura (1997) "Systems for Identifying New Drugs Are Often Faulty," Science 278:1041-1042.

Hadley et al., "The functional activity of Fc gamma RII and Fc gamma RIII on subsets of human lymphocytes," Immunology 76:446-451, 1992.

Hatta et al., "Association of Fc gamma receptor IIIB, but not of Fc gamma receptor IIA and IIIA polymorphisms with systemic lupus erythematosus in Japanese," Genes and Immunity 1:53-60, 1999.

Hayes, Fc Engineering to Enhance Monoclonal Antibody Effector Functions. (Presentation) Xecor, CA, 2003.

Henry et al. (2004) "A prostate-specific membrane antigen-targeted monoclonal antibody-chemotherapeutic conjugate designed for the treatment of prostate cancer," Cancer Res. 64(21):7995-8001.

Herzenberg et al., "The history and future of the fluorescence activated cell sorter and flow cytometry: a view from Stanford," Clinical Chem. 2002:48:1819-1827, 2002.

Heyman, "Regulation of antibody responses via antibodies, complement, and Fc receptors," Annu Rev Immunol 18:709-737, 2000.

Hogarth et al., "Characterization of FcR Ig-binding sites and epitope mapping," Immunomethods 4 :17-24, 1994.

Holler et al., "In vitro evolution of a T cell receptor with high affinity for peptide/MHC," Proc. Natl. Acad. Sci. U.S.A. 97 :5387-92, 2000.

Holm et al, (2007) "Functional Mapping and Single Chain Construction of the Anti-Cytokeratin 8 Monoclonal Antibody TS1," Molecular Immunology 44:1075-1084.

Holmes et al., Alleles of the Ly-17 alloantigen define polymorphisms of the murine IgG Fc receptor. Proc Natl Acad Sci USA. Nov. 1985;82(22):7706-10.

Holt, L.J. (2003) "Domain Antibodies: Proteins for Therapy," TRENDS in Biochemistry 21(11)484-490.

Hulett et al., "Identification of the IgG binding site of the human low affinity receptor for IgG Fc gamma RII. Enhancement and ablation of binding by site-directed mutagenesis," J. Biol. Chem. 269:15287-15293, 1994.

Hulett et al., "Multiple regions of human Fc gamma RII (CD32) contribute to the binding of IgG," J. Biol. Chem. 270:21188-21194, 1995.

Hulett et al., "Chimeric Fc receptors identify functional domains of the murine high affinity receptor for IgG," J Immunol 147 :1863-1868, 1991.

Hwang et al., Hepatic uptake and degradation of unilamellar sphingomyelin/cholesterol liposomes: a kinetic study. Proc Natl Acad Sci U S A. Jul. 1980;77(7):4030-4.

Ibragimova et al. (1999) "Stability of the beta-sheet of the WW domain: A molecular dynamics simulation study," Biophys. J. 77(4):2191-2198.

Idusogie et al., "Mapping of the C1q binding site on rituxan, a chimeric antibody with a human IgG1 Fc," J Immunol 164: 4178-4184, 2000.

Idusogie et al., "Engineered antibodies with increased activity to recruit complement," J Immunol 166 :2571-2575, 2001.

Isaacs et al., "A therapeutic human IgG4 monoclonal antibody that depletes target cells in humans," Clin Exp Immunol 106 :427-433, 1996.

Isaacs et al., "Therapy with monoclonal antibodies. An in vivo model for the assessment of therapeutic potential," J Immunol 148 :3062-3071, 1992.

Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.

Jain et al. "Barriers to Drug Delivery in Solid Tumors," Scientific American Jul. 1994:58-65.

Jassal et al., "Remodeling glycans on IgG by genetic re-engineering," Biochem Soc Trans 26 :S113, 1998.

Jefferis and Lund, "Interaction sites on human IgG-Fc for FcgammaR: current models," Immunology Letters 82 :57-65, 2002.

Jefferis et al., "Recognition sites on human IgG for Fc gamma receptors: the role of glycosylation," Immunol Lett 44 :111-7, 1995.

Jefferis et al., "IgG-Fc-mediated effector functions: molecular definition of interaction sites for effector ligands and the role of glycosylation," Immunol Rev 163:59-76, 1998.

Jefferis et al., "Molecular definition of interaction sites on human IgG for Fc receptors (huFc gamma R)," Mol Immunol 27 :1237-1240, 1990.

Jendeberg et al., "Engineering of Fc(1) and Fc(3) from human immunoglobulin G to analyse subclass specificity for staphylococcal protein A," J Immunological Methods 201 :25-34, 1997.

Jiang et al. (Epub Nov. 9, 2004) "A novel peptide isolated from a phage display peptide library with trastuzumab can mimic antigen epitope of HER-2," J Biol Chem 280(6):4656-4662.

Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.

Kadar et al., "Modulatory effect of synthetic human IgG Fc peptides on the in vitro immune response of murine spleen cells," Int J Immunpharmacol 13 :1147-55, 1991.

Kagari et al., Essential Role of Fc.gamma. Receptors in anti-type II collagen antibody induced arthritis. J. Immunol. Apr. 2003;170:4318-24.

Kang, C.Y. et al. (1988) "Inhibition of Self-Binding Antibodies (Autobodies) by a VH-Derived Peptide," Science 240(4855):1034-1036.

Kato et al., "Structural basis of the interaction between IgG and Fcγ receptors," J Mol Biol 295:213-224, 2000.

Keler et al., "Differential effect of cytokine treatment on Fc alpha receptor I- and Fc gamma receptor I-mediated tumor cytotoxicity by monocyte-derived macrophages," J. of Immunol. 164:5746-52, 2000.

Kepley et al. "Co-aggregation of FcgammaRII with FcepsilonRI on human mast cells inhibits antigeninduced secretion and involves SHIP-Grb2-Dok complexes" J. Biol. Chem. 279(34) 35139-35149, 2004.

Kieke et al., "Selection of functional T cell receptor mutants from a yeast surface-display library," Proc. Natl. Acad. Sci. U.S.A. 96 :5651-56, 1999.

Kim et al., "Analysis of FcγRIII and IgG Fc polymorphism reveals functional and evolutionary implications of protein-protein interaction," J Mol Evol 53:1-9, 2001.

Kim et al. (2002) "Both the epitope specificity and isotype are important in the antitumor effect of monoclonal antibodies against Her-2/neu antigen," Int. J. Cancer. 102(4):428-434.

Kimura et al. (1981) "A new mouse cell-surface antigen (Ly-m20) controlled by a gene linked to M1s locus and defined by monoclonal antibodies," Immunogenetics. 14(1-2):3-14.

Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.

Klein et al., "Expression of biological effector functions by immunoglobulin G molecules lacking the hinge region," Proc. Natl. Acad. Sci. U.S.A. 78 :524-528, 1981.

Koene et al., "Fc gammaRIIIa-158V/F polymorphism influences the binding of IgG by natural killer cell Fc gammaRIIIa, independently of the Fc gammaRIIIa-48L/R/H phenotype," Blood 90 :1109-1114, 1997.

Kranz et al., "Mechanisms of ligand binding by monoclonal antifluorescyl antibodies," J. Biol. Chem. 257:6987-6995, 1982.

Kumpel, B.M. Brit. "Human monoclonal anti-D antibodies," J. Haematol. 71:415-420 (1989).

Kurlander et al., 1986, "Comparison of intravenous gamma globulin and a monoclonal anti-Fc receptor antibody as inhibitors of immune clearance in vivo in mice." J. Clin. Invest. 77(6):2010-2018.

Lazar et al. (1988) Transforming growth factor a: mutation of aspartic acid 47 and leucine 48 results in different biological activities, Molec. Cell. Biol. 8:1247-1252.

Le Gall, F. et al. (Epub May 4, 2004) "Effect of Linker Sequences Between the Antibody Variable Domains on the Formation, Stability and Biological Activity of a Bispecific Tandem Diabody," Protein Eng Des Sel. 17(4):357-366.

Lehmann et al., "Phagocytosis: measurement by flow cytometry," J Immunol Methods. 243(1-2):229-42, 2000.

Lehrnbecher et al., "Variant genotypes of the low-affinity Fcgamma receptors in two control populations and a review of low-affinity Fcgamma receptor polymorphisms in control and disease populations," Blood 94:4220-4232, 1999.

Lewis et al. (1993) "Differential responses of human tumor cell lines to anti-p185HER2 monoclonal antibodies," Cancer Immunol Immunother. 37(4):255-263.

Li et al. (2007) Regeneration of nigrostriatal dopaminergic axons by degradation of chondroitin sulfate is accompanied by elimination of the fibrotic scar and glia limitans in the lesion site. J. Neurosci. Res. 85:636-547.

Li et al., "Reconstitution of human Fc gamma RIII cell type specificity in transgenic mice," J Exp Med 183 :1259-1263, 1996.

Lifely et al., Glycosylation and biological activity of CAMPATH-1H expressed in different cell lines and grown under different culture conditions. Glycobiology. Dec. 1995;5(8):813-22.

Lin et al., Colony-stimulating factor 1 promotes progression of mammary tumors to malignancy. J Exp Med. 2001;193(6):727-739.

Lin et al., The macrophage growth factor CSF-1 in mammary gland development and tumor progression. J Mammary Gland Biol Neoplasia. 2002;7(2):147-62.

Liu et al., "Production of a mouse-human chimeric monoclonal antibody to CD20 with potent Fc-dependent biologic activity," J. Immunol. 139:3521-3526, 1987.

Looney et al., 1986, "Human Monocytes and U(#& Cells Bear Two Distinct Fc Receptors for IgG." J. Immunol. 136(5):1641-1647.

Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.

Lund et al., "Oligosaccharide-protein interactions in IgG can modulate recognition by Fc gamma receptors," FASEB J 9 :115-119, 1995.

Lund et al., "Human Fc gamma RI and Fc gamma RII interact with distinct but overlapping sites on human IgG," J Immunol 147 :2657-62, 1991.

Lund et al., "Multiple interactions of IgG with its core oligosaccharide can modulate recognition by complement and human Fc gamma receptor I and influence the synthesis of its oligosaccharide chains," J Immunol 157 :4963-4969, 1996.

Lund et al., "Multiple binding sites on the CH2 domain of IgG for mouse Fc gamma R11," Molecular Immunology 29:53-59, 1992.

Lyden et al., The Fc receptor for IgG expressed in the villus endothelium of human placenta is Fc.gamma. RIIb2. J Immunol. Mar. 15, 2001;166(6):3882-9.

MacCallum et al. (1996) "Antibody-Antigen Interactions: Contact Analysis and Binding Site Topography," J. Molec. Biol. 262:732-745.

Malbec et al., Fcs receptor I-associated lyn-dependent phosphorylation of Fc.gamma. receptor IIB during negative regulation of mast cell activation. J Immunol. Feb. 15, 1998;160(4):1647-58.

Maenaka et al., "The human low affinity Fcgamma receptors IIa, IIb, and III bind IgG with fast kinetics and distinct thermodynamic properties," J Biol Chem 48 :44898-904, 2001.

Maresco et al., 1999, "The SH2-Containing 5'-Inositol Phosphatase (SHIP) Is Tyrosine Phosphorylated after Fc.gamma. Receptor Clustering in Monocytes." J. Immunol. 162:6458-6465.

Maruyama K, In vivo targeting by liposomes. Biol Pharm Bull. Jul. 2000;23(7):791-9.

Masui et al. (1986) "Mechanism of antitumor activity in mice for anti-epidermal growth factor receptor monoclonal antibodies with different isotypes.," Canc. Res. 46:5592-5598.

McDevitt et al. "An alpha-particle emitting antibody ([213Bi]J591) for radioimmunotherapy of prostate cancer.," Cancer Res. 60(21):6095-6100, 2000.

Melero et al. (1998) The frequent expansion of a subpopulation of B cells that express RF-associated cross-reactive idiotypes: evidence from analysis of a panel autoreactive monoclonal antibodies; Scand. J. Immunol. 48:152-158 1998.

Michaelsen et al., "One disulfide bond in front of the second heavy chain constant region is necessary and sufficient for effector functions of human IgG3 without a genetic hinge," Immunolgy 91 :9243-9247, 1994.

Metcalfe, Mast Cells, Physiol Rev. Oct. 1997;77(4):1033-79.

Micklem et al., Different isoforms of human FcRII distinguished by CDw32 antibodies. J Immunol. Mar. 1990;144:2295-2303.

Morgan et al., "The N-terminal end of the CH2 domain of chimeric human IgG1 anti-HLA-DR is necessary for C1q, Fc gamma RI and Fc gamma RIII binding," Immunology 86 :319-324, 1995.

Morrison et al., "Structural determinants of IgG structure," Immunologist 2 :119-124, 1994.

Munn et al., "Phagocytosis of tumor cells by human monocytes cultured in recombinant macrophage colony-stimulating factor," J Exp Med. 172(1):231-7, 1990.

Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.

Nakamura et al., Fc.gamma. receptor IIB-deficient mice develop Goodpasture's Syndrome upon immunization with Type IV collagen: a novel murine model for Autoimmune Glomerular Basement Membrane Disease. J. Exp. Med. Mar. 6, 2000;191(5):899-905.

Neuberger et al., "Recombinant antibodies possessing novel effector functions," Nature 312 :604-608, 1984.

Norderhaug et al., "Chimeric mouse human IgG3 antibodies with an IgG4-like hinge region induce complement-mediated lysis more efficiently than IgG3 with normal hinge," Eur J Immunol 21:2379-84, 1991.

Noren, C.J. et al. "A General Method for Site-Specific Incorporation of Unnatural Amino Acids into Proteins," Science 244:182-188, 1989.

Norris et al., A naturally occurring mutation in Fc.gamma.RIIA: A Q to K.sup.127 change confers unique IgG binding properties to the R.sup.131 allelic form of the receptor. Blood. Jan. 15, 1998;91(2):656-662.

Nose and Leanderson, "Substitution of asparagine324 with aspartic acid in the Fc portion of mouse antibodies reduces their capacity for C1q binding," Eur J Immunol 19 :2179-81, 1989.

Okazaki et al., "Fucose depletion from human IgG1 oligosaccharide enhances binding enthalpy and association rate between IgG1 and FcgammaRIIIa," J Mol Biol 336 :1239-1249, 2004.

Orfao and Ruiz-Arguelles, "General concepts about cell sorting techniques," Clinical Biochem. 29:5-9, 1996.

Ott, V.L. et al. "FcgammaRIIB as a potential molecular target for intravenous gamma globulin therapy," J. Allergy Clin Immunol. Oct. 2001:S95-S98.

Ott et al., Downstream of Kinase, p62.sup.dok, Is a mediator of Fc.gamma.RIIB inhibition of Fc.epsilon.RI signaling. J. of Immunol. 2002;168:4430-9.

Panka et al. (1988) Variable region framework differences result in decreased or increased affinity of variant anti-digoxin antibodies. Proc. Natl. Acad. Sci. USA 85:30803084.

Pardridge et al., Blood-brain barrier drug targeting: The future of brain drug development. Molecular Interventions. 2003, 3;2:90-105. See particularly pp. 91-96.

Park YS, Tumor-directed targeting of liposomes. Biosci Rep. Apr. 2002;22(2):267-81.

Park et al., Immunoliposomes for cancer treatment. Adv Pharmacol. 1997;40:399-435.

Partridge et al., "The use of anti-IgG monoclonal antibodies in mapping the monocyte receptor site on IgG," Mol Immunol. 23(12):1365-72, 1986.

Paul, William E, (1993) "Fundamental Microbiology, 3 Ed." pf. 242, 292-296.

Pereira et al. (1998) Cardiolipin Binding a light Chain from Lupus-prone Mice; Biochem. 37:1460-1437.

Perussia "Human Natural Killer Cell Protocols" in *Methods Molecular Biology*. vol. 121 (Campbell et al. eds.) Humana Press Inc., Totowa, NJ. 179-92, 2000.

Pettersen et al. (1999) "CD47 Signals T Cell Death," J. Immunol. 162(12):7031-7040.

Pluckthun, A. et al. (1997) "New protein engineering approaches to multivalent and bispecific antibody fragments," Immunotechnology 3(2):83-105.

Polson, A.G. et al. (Epub Mar. 20, 2007) "Antibody-Drug Conjugates Targeted to CD79 for the Treatment of Non-Hodgkin Lymphoma," Blood. 110(2):616-623.

Press et al. (1988) "Ricin A-chain containing immunotoxins directed against different epitopes on the CD2 molecule differ in their ability to kill normal and malignant T cells," J. Immunol. 141(12):4410-4417.

Presta, L.G. et al. (2005) "Selection, Design and Engineering of Therapeutic Antibodies," J. Allergy Clin. Immunol. 116(4):731-736.

Presta LG, "Engineering antibodies for therapy," Curr Pharm Biotechnol. Sep. 2002;3(3):237-56.

Pricop et al., "Differential modulation of stimulatory and inhibitory Fc.gamma. receptors on human monocytes by Th1 and Th2 cytokines," J Immunol. Jan. 1, 2001;166(1):531-7.

Pulford et al., 1995 "M6.5: The immunocytochemical distribution of CD16, CD32, and CD64 antigens." Leukocyte Typing V: White cell differentiation antigens 817-821 (Schlossman, Boumsell, Gilks, Harlan, Kishomoto, eds.) pp. 817-821.

Pulford et al., A new monoclonal antibody (KB61) recognizing a novel antigen which is selectively expressed on a subpopulation of human B lymphocytes. Immunology. Jan. 1986;57(1):71-6.

Qin et al., Fc.gamma. receptor IIB on follicular dendritic cells regulates the B cell recall response. J Immunol. 2000;164:6268-6275.

Radaev and Sun, "Recognition of immunoglobulins by Fcgamma receptors," Molecular Immunology 38 :1073-1083, 2001.

Ravetch and Bolland, "IgG Fc receptors," Annu Rev Immunol 19:275-90, 2001.

Ravetch and Clynes, "Divergent roles for Fc receptors and complement in vivo," Annu Rev Immunol 16:421-432, 1998.

Ravetch and Kinet, "Fc receptors," Annu Rev Immunol 9:457-492, 1991.

Ravetech and Lanier, "Immune inhibitory receptors," Science 290:84-89, 2000.

Ravetch et al., Fc receptors: rubor redux. Cell. Aug. 26, 1994;78(4):553-60.

Redpath et al., "The influence of the hinge region length in binding of human IgG to human Fcgamma receptors," Hum Immunol 59 :720-727, 1998.

Reali et al., IgEs targeted on tumor cells: therapeutic activity and potential in the design of tumor vaccines. Cancer Res. 2001;61(14): 5517-22.

Reff et al., "Depletion of B cells in vivo by a chimeric mouse human monoclonal antibody to CD20," Blood 83:435-445, 1994.

Reff et al., "A review of modifications to recombinant antibodies: attempt to increase efficacy in oncology applications," Critical Reviews in Oncology/Hematology 40: 25-35; 2001.

Riechmann et al., "Reshaping human antibodies for therapy," Nature. 332(6162):323-7, 1988.

Riemer et al. (Epub Jan. 8, 2005) "Matching of trastuzumab (Herceptin) epitope mimics onto the surface of Her-2/neu—a new method of epitope definition.," Mol Immunol. 42(9):1121-1124.

Routledge et al., The effect of aglycosylation on the immunogenicity of a humanized therapeutic CD3 monoclonal antibody. Transplantation. Oct. 27, 1995;60(8):847-53.

Rudikoff et al. (1982) "Single amino acid substitution altering antigen-binding specificity" Proc. Natl. Acad. Sci. USA 79:1979-1983.

Samsom et al. (2005) Fc gamma RIIB regulates nasal and oral tolerance: a role for dendritic cells Immunol. 174:5279-5287.

Samuelsson et al., Anti-inflammatory activity of IVIG mediated through the inhibitory Fc receptor. Science. Jan. 19, 2001; 291:484-486.

Sarkar et al., Negative signaling via Fc.gamma.RIIB1 in B cells blocks phospholipase C.sub..gamma.2 tyrosine phosphorylation but not Syk or Lyn activation. J Biol Chem. Aug. 16, 1996;271(33):20182-6.

Sarmay et al., "The effect of synthetic peptides corresponding to Fc sequences in human IgG1 on various steps in the B cell activation pathway," Eur J Immunol 18 :289-294, 1988.

Sarmay et al., "Ligand inhibition studies on the role of Fc receptors in antibody-dependent cell-mediated cytotoxicity," Mol Immunol 21 :43-51, 1984.

Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.

Sautes-Fridman et al., "Fc gamma receptors: a magic link with the outside world," ASHI Quarterley, 4th Quarter:148-151, 2003.

Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).

Schatz et al., "Use of peptide libraries to map the substrate specificity of a peptide-modifying enzyme: a 13 residue consensus peptide specifies biotinylation in *Escherichia coli*," Bio/Technology 11:1138-1143, 2000.

Scholl et al., Is colony-stimulating factor-1 a key mediator of breast cancer invasion and metastasis? Mol Carcinog. 7(4):207-11, 1993.

Schuna et al., 2000, "New Drugs for the treatment of rheumatoid arthritis." Am J. Health Syst. Phar, 57:225-237.

Seaver (1994) "Monoclonal Antibodies in Industry: More Difficult than Originally Thought," Genetic Engineering News 14(14):10, 21.

Sensel et al., "Amino acid differences in the N-terminus of C(H)2 influence the relative abilities of IgG2 and IgG3 to activate complement," Molecular Immunology 34:1019-1029, 1997.

Shields et al., Lack of fucose on human IgG1 N-linked oligosaccharide improves binding to human Fc.gamma. RIII and antibody-dependent cellular toxicity. J Biol Chem. Jul. 26, 2002;277(30):26733-40.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.

Shopes et al., "Recombinant human IgG1-murine IgE chimeric Ig. Construction, expression, and binding to human Fc gamma receptors," J Immunol 145 :3842-3848, 1990.

Shopes, "A genetically engineered human IgG mutant with enhanced cytolytic activity," J Immunol 148 :2918-2922, 1992.

Shopes, "A genetically engineered human IgG with limited flexibility fully initiates cytolysis via complement," Molecular Immunology 30 :603-609, 1993.

Shusta et al., "Yeast polypeptide fusion surface display levels predict thermal stability and soluble secretion efficiency," J Mol Biol 292:949-956, 1999.

Shusta et al., "Increasing the secretory capacity of *Saccharomyces cerevisiae* for production of single-chain antibody fragments," Nature Biotechnology 16:773-777, 1998.

Shusta et al., "Directed evolution of a stable scaffold for T-cell receptor engineering," Nature Biotechnology 18:754-759, 2000.

Siberil, S. et al. (2006) "Molecular Aspects of Human FcgammaR Interactions with IgG: Functional and Therapeutic Consequences," Immunol. Lett. 106:111-118 (2006).

Skolnick et al. (2000) From Genes to Protein Structure and Function: Novel Aspects of Computational Approaches in the Genomic Era, Trends in Biotechnology 18:34-39.

Smith and Morrison, "Recombinant polymeric IgG: an approach to engineering more potent antibodies," Bio/Technology 12:683-688, 1994.

Sondermann and Oosthuizen, "The structure of Fc receptor/Ig complexes: considerations on stoichiometry and potential inhibitors," Immunology Letters, 82:51-56, 2002.

Sondermann et al., "Molecular basis for immune complex recognition: a comparison of Fc-receptor structures," J. Mol. Biol. 309:737-749, 2001.

Sondermann et al., "Crystal structure of the soluble form of the human fcgamma-receptor IIb: a new member of the immunoglobulin superfamily at 1.7 A resolution," EMBO J 18:1095-1103, 1999.

Sondermann et al., "The 3.2-A crystal structure of the human IgG1 Fc fragment-Fc gammaRIII complex," Nature 406:267-273, 2000.

Stancovski et al. (1991) "Mechanistic aspects of the opposing effects of monoclonal antibodies to the ERBB2 receptor on tumor growth," Proc Natl Acad Sci U S A. 88(19):8691-8695.

Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.

Strohmeier et al., "Role of the Fc gamma R subclasses Fc gamma RII and Fc gamma RIII in the activation of human neutrophils by low and high valency immune complexes," J Leukocyte Biol 58:415-422, 1995.

Su et al., Expression profile of Fc.gamma.RIIB on leukocytes and its dysregulation in systemic lupus erythematosus. J. Immunol. 178:3272-3280, 2007.

Sylvestre and Ravetch, "A dominant role for mast cell Fc receptors in the Arthus reaction," Immunity 5:387-390, 1996.

Sylvestre and Ravetch, "Fc receptors initiate the Arthus reaction: redefining the inflammatory cascade," Science 265:1095-1098, 1994.

Takai et al., "FcR gamma chain deletion results in pleiotrophic effector cell defects," Cell 76 :519-529, 1994.

Takai et al., "Augmented humoral and anaphylactic responses in Fc gamma RII-deficient mice," Nature 379:346-349, 1996.

Takai, "Roles of Fc receptors in autoimmunity," Nature Reviews 2:580-592, 2002.

Tam et al., A bispecific antibody against human IgE and human Fc.gamma.RII that inhibits antigen-induced histamine release by human mast cells and basophils. Allergy 2004;59:772-780.

Tamm et al., "The IgG binding site of human FcγRIIIB receptor involves CC' and FG loops of the membrane-proximal domain," J Biol Chem 271:3659-3666, 1996.

Tao and Morrison, Studies of aglycosylated chimeric mouse-human IgG. Role of carbohydrate in the structure and effector functions mediated by the human IgG constant region. J Immunol. Oct. 15, 1989;143(8):2595-601.

Tao et al., "The differential ability of human IgG1 and IgG4 to activate complement is determined by the COOH-terminal sequence of the CH2 domain," J Exp Med 173:1025-1028, 1991.

Tao et al., "Structural features of human immunoglobulin G that determine isotype-specific differences in complement activation," J Exp Med 178:661-667, 1993.

Todorovska et al., Design and application of diabodies, triabodies and tetrabodies for cancer targeting. J Immunol Methods. Feb. 1, 2001;248(1-2):47-66.

Tridandapandi et al., "Regulated Expression and Inhibitory Function of FcgammaRIIB in Human Monocytic Cells," Journal of Biological Chemistry 277(7): 5082-5089, 2002.

Umana et al., Engineered glycoforms of an antineuroblastoma IgG1 with optimized antibody-dependent cellular cytotoxic activity. Nat Biotechnol. Feb. 1999;17(2):176-80.

Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.

Van Antwerp and Wittrup, "Fine affinity discrimination by yeast surface display and flow cytometry," Biotechnol Prog 16:31-37, 2000.

Van den Beuken et al. (2001) Building novel binding ligands to B7.1 and B7.2 based on human antibody single variable light chain domains; J. Molec. Biol. 310:591-601.

Van De Winkel et al., 1995, "CD32 cluster workshop report." Leukocyte Typing V: White Cell differentiation antigens 823-825 (Schlossman, Boumsell, Gilks, Harlan, Kishomoto, eds.).

Van Nguyen et al., Colony stimulating factor-1 is required to recruit macrophages into the mammary gland to facilitate mammary ductal outgrowth. Dev Biol. 2002;247(1):11-25.

Van Sorge et al., "FcgammaR polymorphisms: Implications for function, disease susceptibility and immunotherapy," Tissue Antigens 61:189-202, 2003.

Vely et al., 1997, "A new set of monoclonal antibodies against human Fc gamma RII (CD32) and Fc gamma RIII (CD16): characterization and use in various assays." Hybridoma 16(6):519-28.

Veri, M.C. et al. (2007) "Monoclonal antibodies capable of discriminating the human inhibitory Fcgamma-receptor IIB (CD32B) from the activating Fcgamma-receptor IIA (CD32A): biochemical, biological and functional characterization," Immunology 121(3):392-404.

Vingerhoeds et al., Immunoliposomes in vivo. Immunomethods. Jun. 1994;4(3):259-72.

Vidarte, "Serine 132 is the C3 covalent attachment point on the CH1 domain of human IgG1," J Biol Chem 276:38217-38233, 2001.

Vitetta, E.S. et al. (2006) "Immunology. Cnsidering Therapeutic Antibodies," Science 313:308-309.

Vuist et al. (1990) "Two distinct mechanisms of antitumor activity mediated by the combination of interleukin 2 and monoclonal antibodies," Canc. Res. 50:5767-5772.

Wallick et al., Glycosylation of a VH residue of a monoclonal antibody against {acute over(.alpha.)} (1.fwdarw.6) dextran increases its affinity for antigen. J Exp Med. Sep. 1, 1988;168(3):1099-109.

Ward et al. (1989) Building Activities of a repertoire of single immunoglobulin variable domains secreted from *Escherichia coli*, Nature 341:544-546 (1989).

Ward and Ghetie, "The effector functions of immunoglobulins: implications for therapy," Therapeutic Immunology 2:77-94, 1995.

Warmerdam et al., Molecular basis for a polymorphism of human Fc gamma receptor II (CD32). J Exp Med. Jul. 1, 1990;172(1):19-25.

Warren, HS et al.(1999) "NK cells and apoptosis," Immunol. Cell Biol. 77(1):64-75.

Weng and Levy, "Two immunoglobulin G fragment C receptor polymorphisms independently predict response to rituximab in patients with follicular lymphoma," J Clin Oncol 21:3940-3947, 2003.

Wheeler, "Preventive Vaccines for Cervical Cancer," Salud Publica d Mexico, 1997, vol. 39, pp. 1-9.

Wiener, E. et al. "Differences between the activities of human monoclonal IgG1 and IgG3 anti-D antibodies of the Rh blood group system in their abilities to mediate effector functions of monocytes," Immunol. 65:159-163 (1988).

Weinrich, V. et al. "Epitope Mapping of New Monoclonal Antibodies Recognizing Distinct Human FCRII (CD32) Isoforms," Hybridoma 15(2):109-116, 1996.

Wing et al., "Mechanism of first-dose cytokine-release syndrome by CAMPATH 1-H: Involvement of CD16 (FcγRIII) and CD11a/CD18 (LFA-1) on NK cells," J Clin Invest 98 :2819-2826, 1996.

Wingren et al., "Comparison of surface properties of human IgA, IgE, IgG and IgM antibodies with identical and different specificities," Scand J Immunol 44:430-436, 1996.

Wittrup, "The single cell as a microplate well," Nat Biotechnol 18:1039-1040, 2000.

Witttrup, "Protein engineering by cell-surface display," Curr, Opin. Biotechnol. 12:395-399, 2001.

Woof et al., "Localisation of the monocyte-binding region on human immunoglobulin G," Mol Immunol 23 :319-330, 1986.

Wright and Morrison, Effect of glycosylation on antibody function: implications for genetic engineering. Trends Biotechnol. Jan. 1997;15(1):26-32.

Wu et al., "A novel polymorphism of FcγRIIIa (CD16) alters receptor function and predisposes to autoimmune disease," J Clin Invst 100 :1059-1070, 1997.

Wu et al., "Humanization of a Murine Monoclonal Antibody by Simultaneous Optimization of Framework and CDR Residues," Journal of Molecular Biology, 1999, vol. 294, pp. 151-162.

Xu et al., Fc.gamma.Rs Modulate Cytotoxicity of Anti-Fas Antibodies: Implications for Agonistic Antibody Based Therapeutics. J Immunol. 2003;171:562-68.

Xu et al. (1993) "Antibody-induced growth inhibition is mediated through immunochemically and functionally distinct epitopes on the extracellular domain of the c-erbB-2 (HER-2/neu) gene product p185," Int. J. Cancer. 53(3):401-8.

Xu et al., "Residue at position 331 in the IgG1 and IgG4 CH2 domains contributes to their differential ability to bind and activate complement," J Biol Chem 269 :3469-3474, 1994.

Yeung and Wittrup, "Quantitative screening of yeast surface-displayed polypeptide libraries by magnetic bead capture," Biotechnol Prog 18:212-220, 2002.

Zeidler et al., "The Fc-region of a new class of intact bispecific antibody mediates activation of accessory cells and NK cells and induces direct phagocytosis of tumour cells," British J Cancer 83:261-266, 2000.

Zola et al., 2000, "CD32 (FcgammaRII)." J Biol Regul Homeost Agents 14(4):311-6.

Zuckier et al., "Chimeric human-mouse IgG antibodies with shuffled constant region exons demonstrate that multiple domains contribute to in vivo half-life," Cancer Res 58 :3905-3908, 1998.

Extended Search Report EP 05857521.8 (WO 06/088494) (2009) (6 pages).

International Search Report; PCT/US04/000643 (WO04/063351) (2004) (4 pages).

International Preliminary Report on Patentability PCT/US04/000643 (WO04/063351) (2007)(5 pages).

International Search Report; PCT/US05/024645 (WO06/088494) (2007) (3 pages).

International Preliminary Report on Patentability PCT/US05/024645(WO06/088494) (2007) (5 pages).

International Search Report; PCT/US06/031201 (WO07/021841) (2008) (2 pages).

International Preliminary Report on Patentability PCT/US06/031201(WO07/021841) (2008)(8 pages).

International Search Report; PCT/US07/086793 (WO08/140603) (2008) (5 pages).

International Preliminary Report on Patentability PCT/US07/086793 (WO08/140603) (2008)(9 pages).

European Search Report (EP 05778285) Apr. 14, 2008 (2 pages).

Singapore Search Report SG 200607186-4 Nov. 5, 2008 (2 pages).

International Search Report; PCT/US05/12798 (WO05/115452) (2005) (2 pages).

International Preliminary Report on Patentability PCT/US05/12798 (WO05/115452) (2005)(5 pages).

International Search Report; PCT/US07/72153 (WO08/019199) (2008) (4 pages).

International Preliminary Report on Patentability PCT/US07/72153 (WO08/019199) (2008)(11 pages).

Extended Search Report EP 05854332.2 (PCT/US2005/045586) (2009) (4 pages).

Extended Search Report EP 07758130.4 (PCT/US2007/063548) (2009) (6 pages).

Extended Search Report EP 07812341.1 (PCT/US2007/72153) (2009) (9 pages).

Extended Search Report EP 07873826.7 (PCT/US2007/069767) (2009) 8 pages).

International Search Report; PCT/US09/38201 (WO09/123894) (2009) (11 pages).

International Search Report; PCT/US07/069767 (WO08/105886) (2008) (4pages).

International Preliminary Report on Patentability PCT/US07/069767 (WO08/105886) (2008)(7 pages).

International Search Report and Written Opinion PCT/US09/38171 (WO 2009/151717) (13 pages).

US 6,331,391, 12/2001, Wittrup et al. (withdrawn)

* cited by examiner

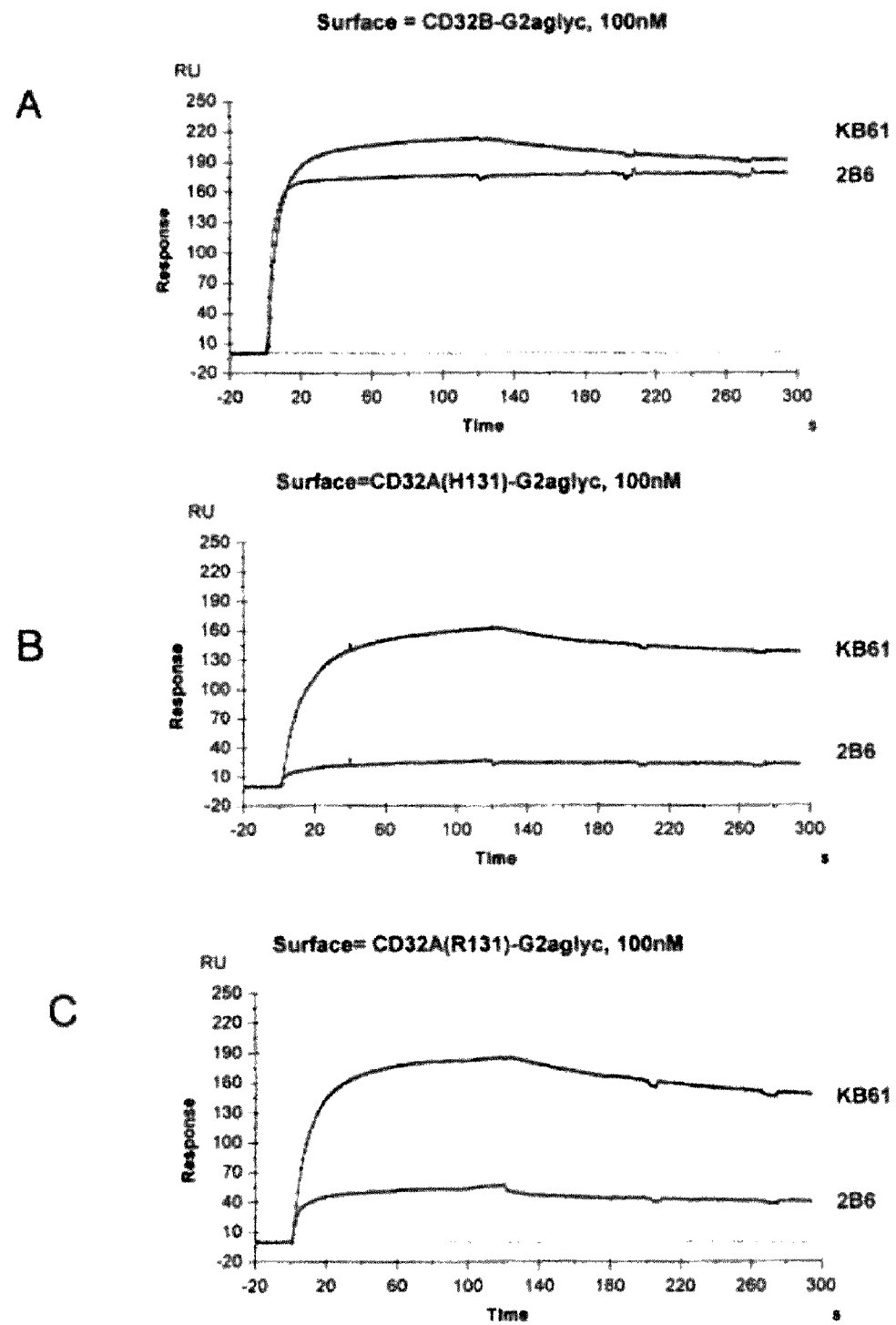
Figs. 8A-C

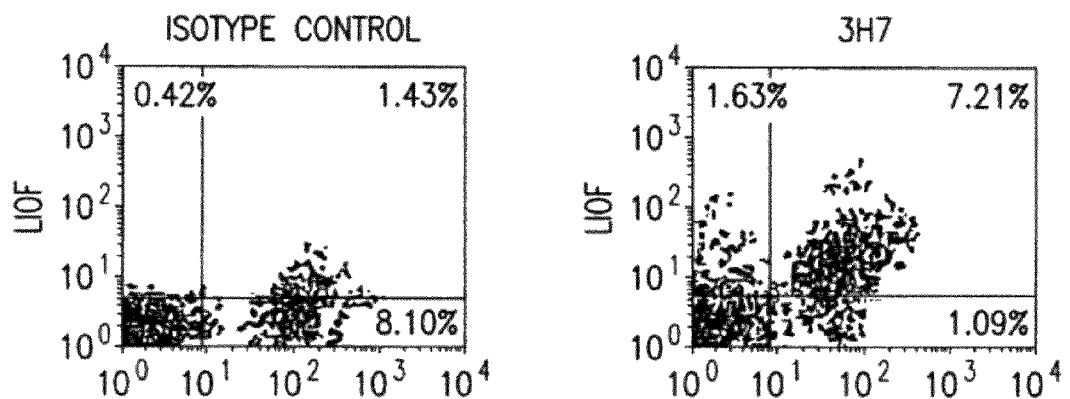
FIG. 9A  FIG. 9B
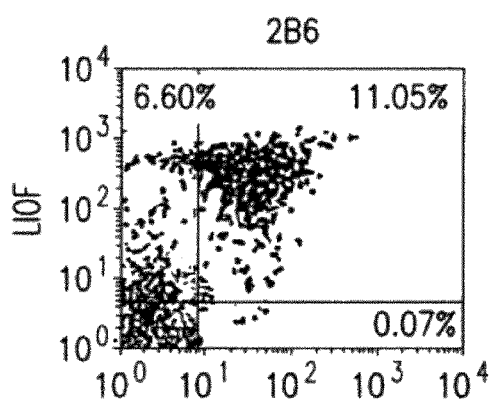
FIG. 9C

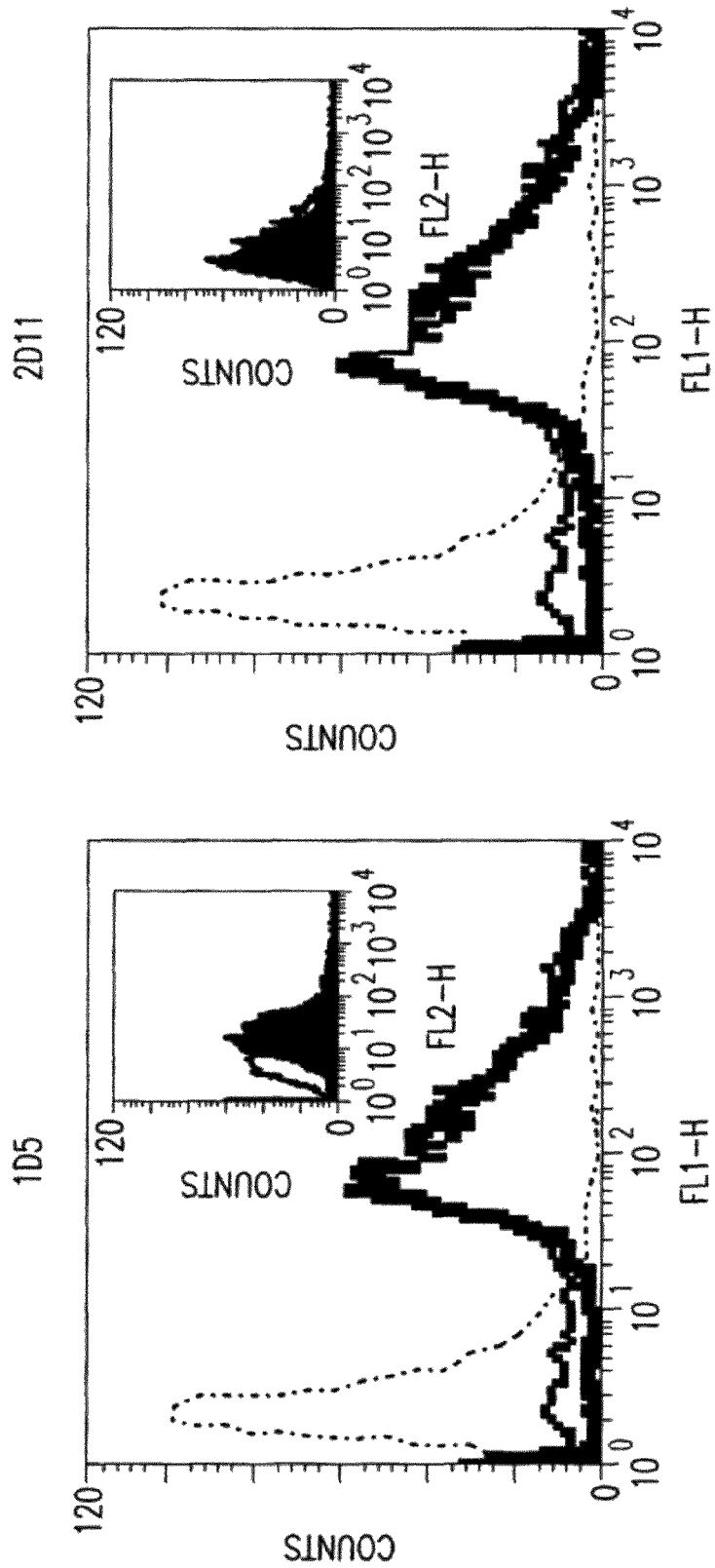

A
Cross-linking of activating receptors
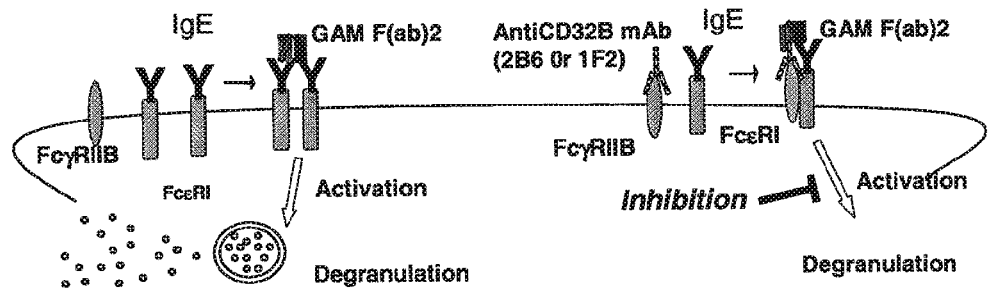
B
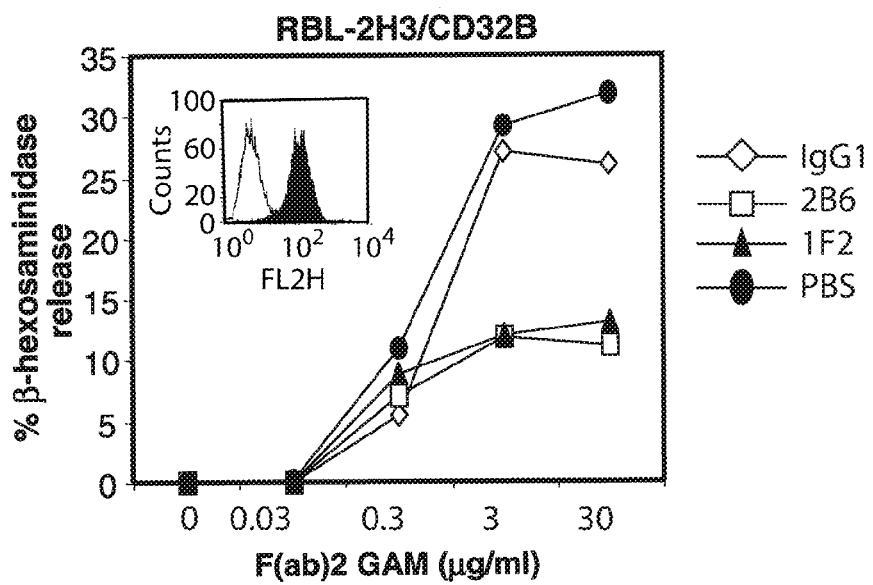
FIGS. 14A and B

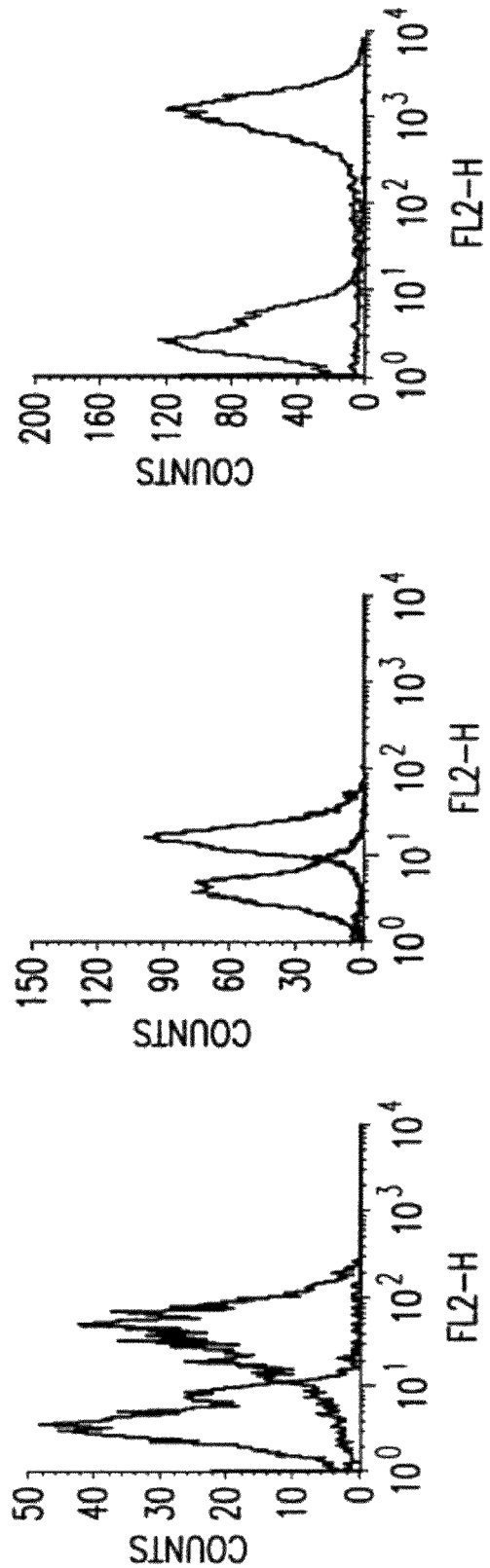

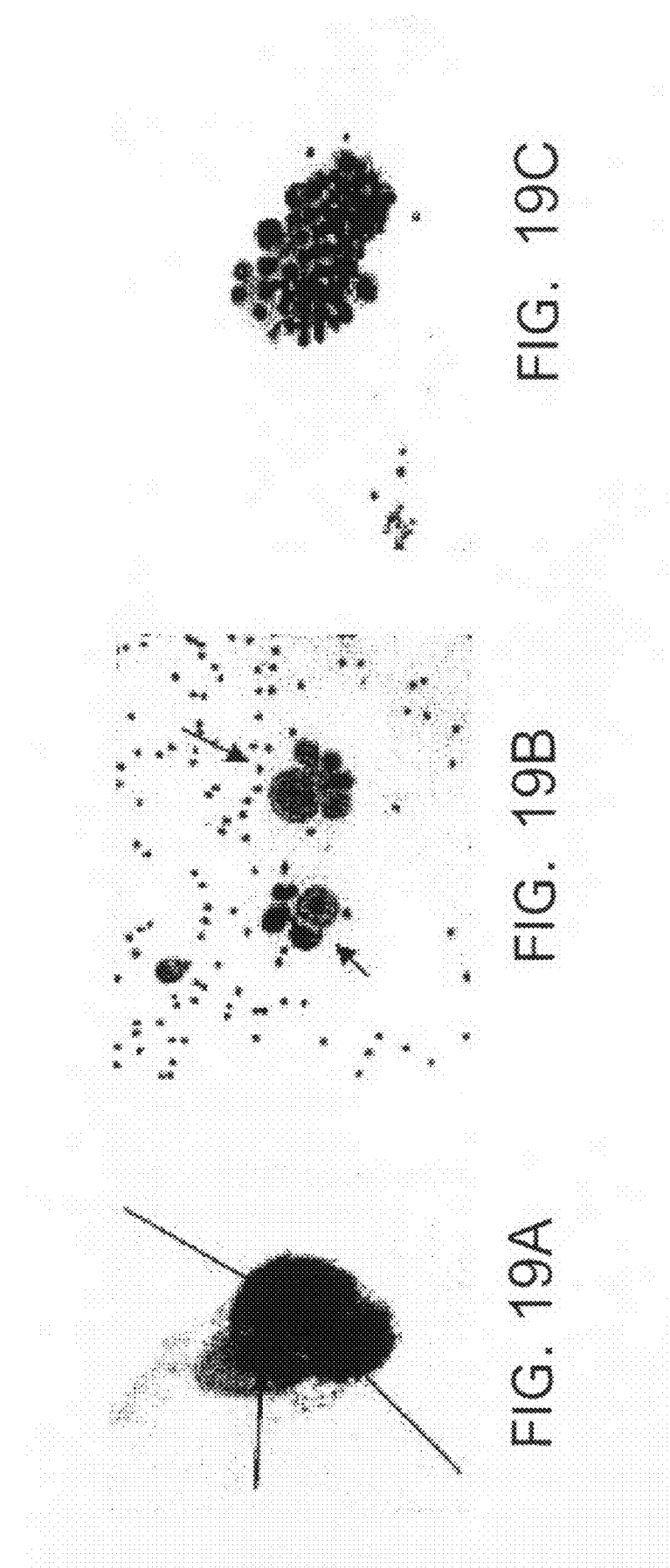

Tonsils
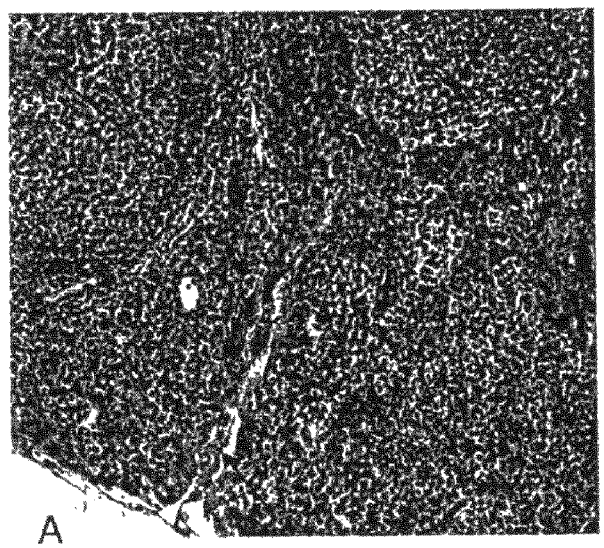
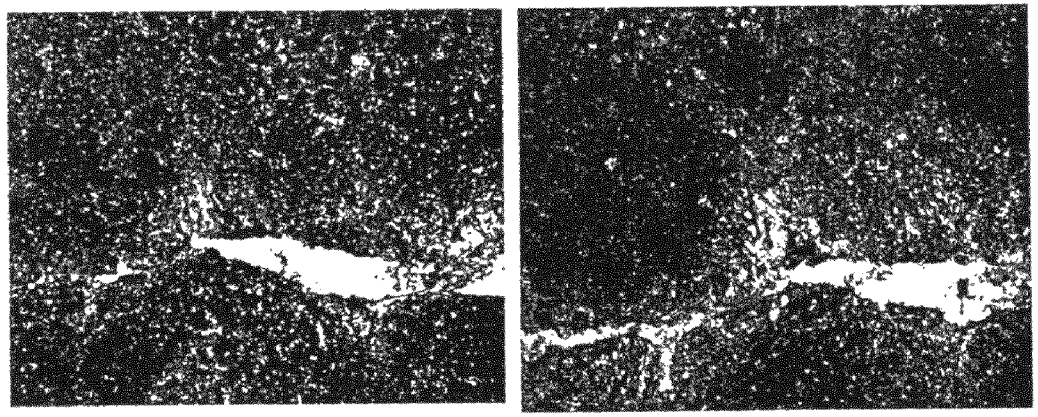
Anti CD32B, 40x
Anti CD20, 40x
FIG. 28

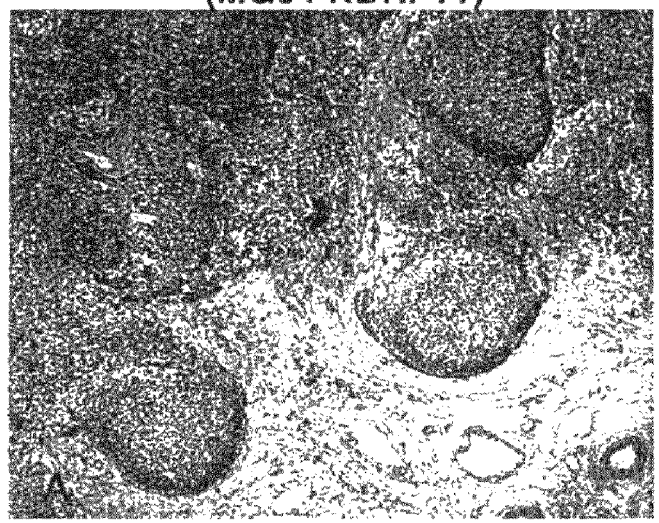
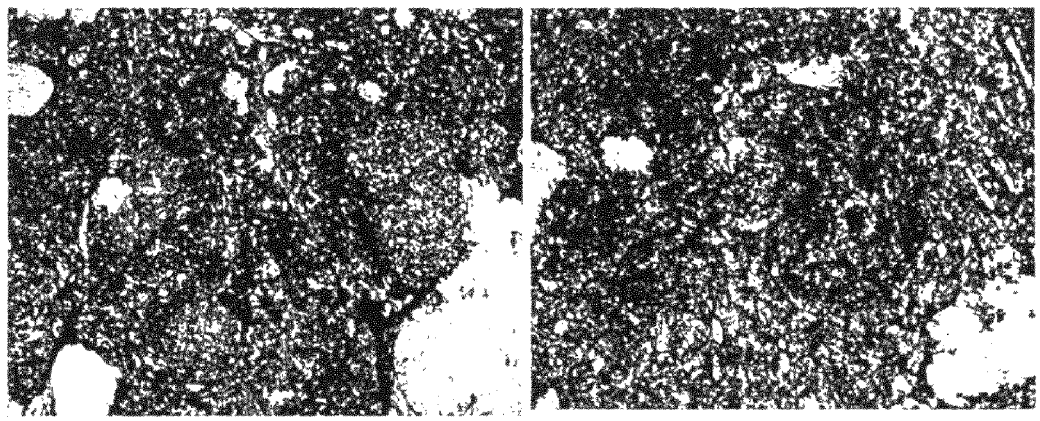
Anti CD32B, 4x  Anti CD20, 4x
FIG. 29

Diffuse Large B Cell Lymphoma
Lymph node (MG04-CHTN-19)
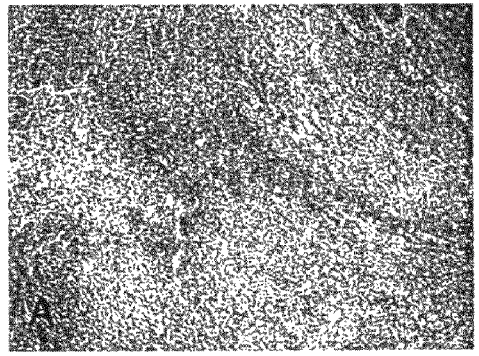
H&E, 4x
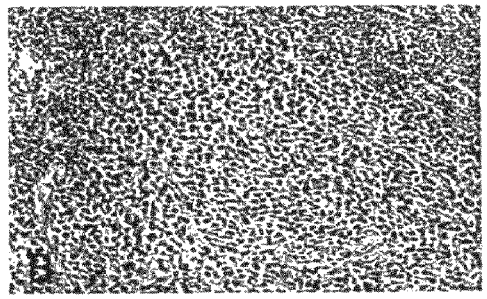
H&E, 20X
FIG. 30
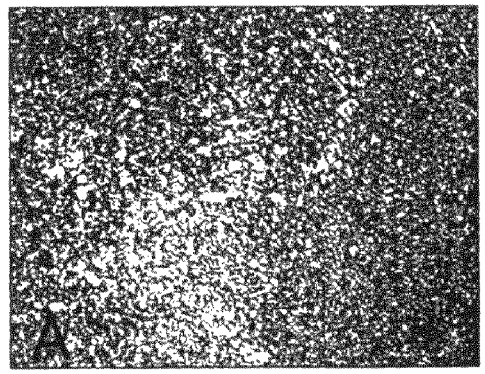
Anti CD32B, 4x
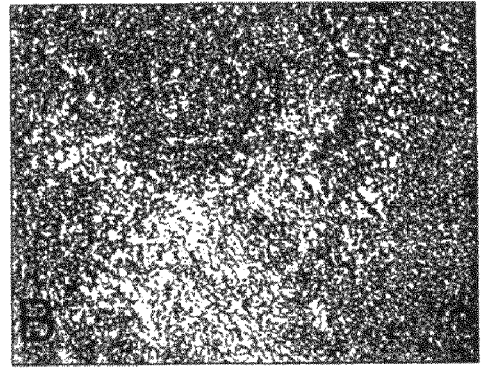
Anti CD20, 4x
FIG. 31

Diffuse Large B Cell Lymphoma
Lymph node (MG04-CHTN-19)
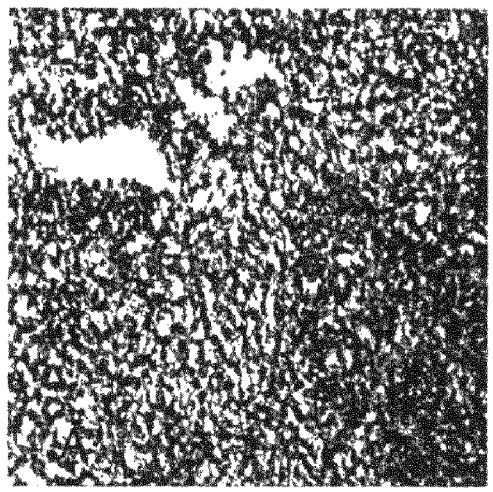
Iso-control (IgG1)
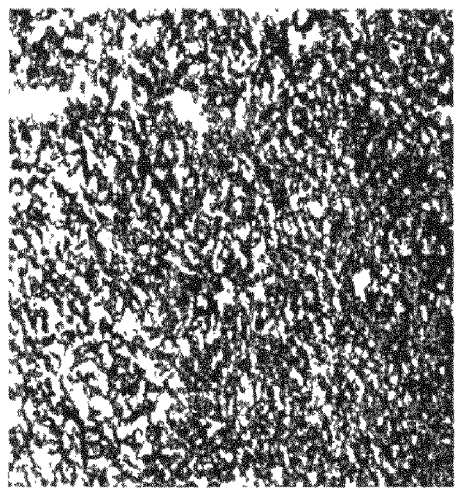
CD32B
(m2B6)
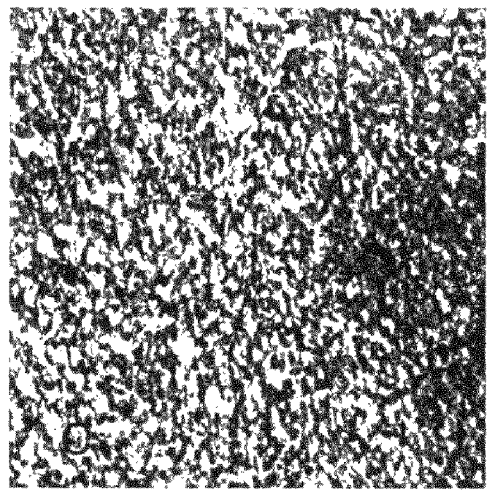
Iso-control (IgG2a)
10x.
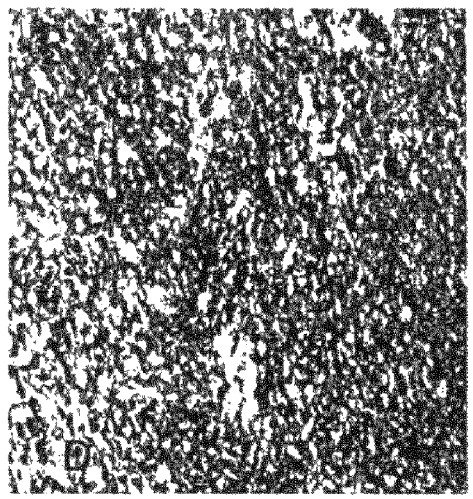
CD20 (1F5)
FIG. 32

Diffuse Large B Cell Lymphoma
Lymph node (MG04-CHTN-22)
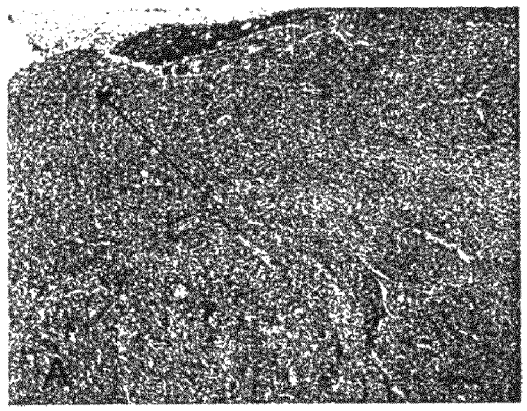
H&E, 4x
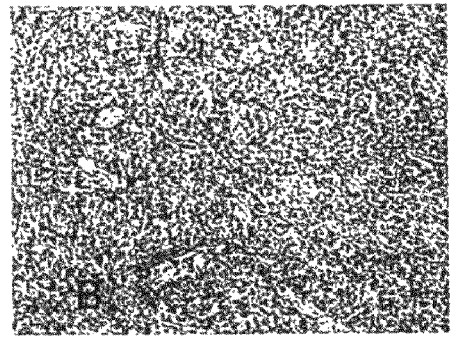
H&E, 10x
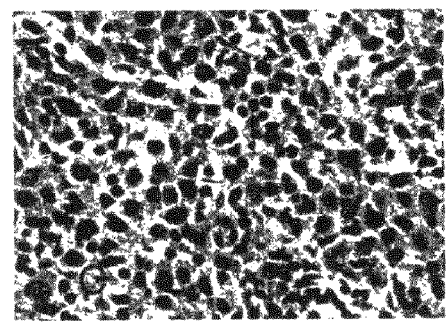
H&E, 20X
FIG. 33
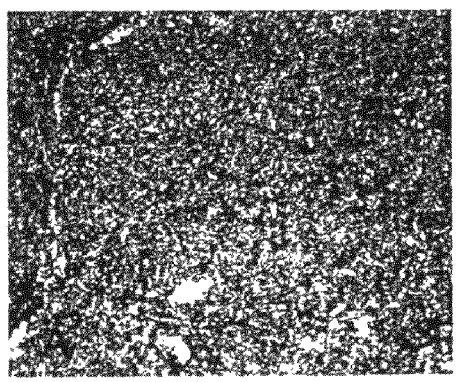
Anti CD32B, 4x
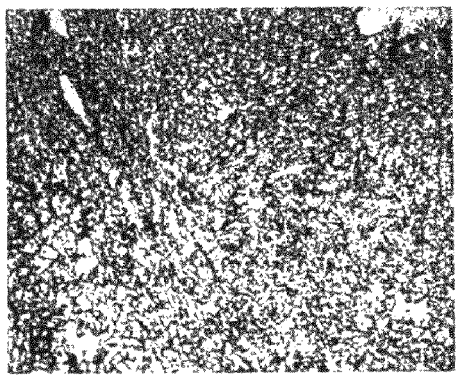
Anti CD20, 4x
FIG. 34

Diffuse Large B Cell Lymphoma
Lymph node (MG04-CHTN-22)
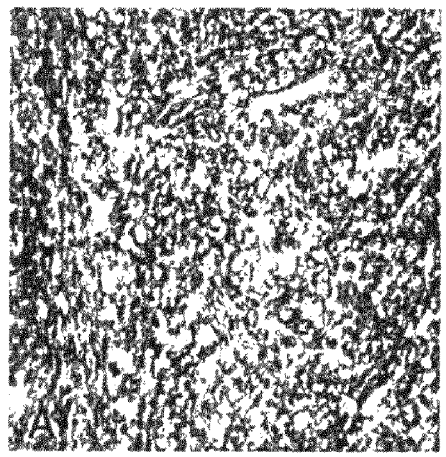
Iso-control (IgG1)
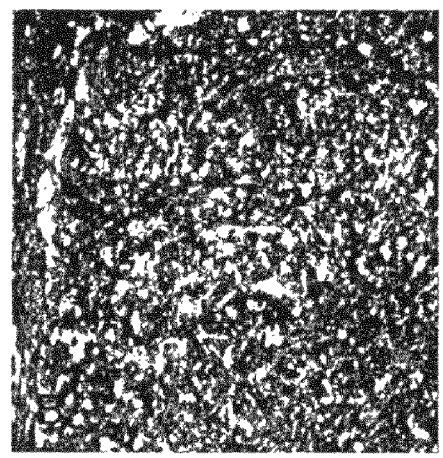
CD32B
(m2B6)
Iso-control (IgG2a)
10x.
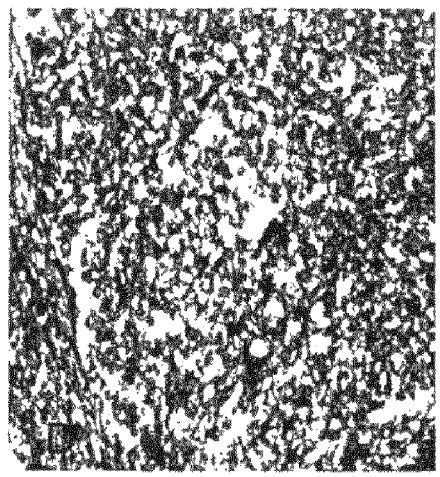
CD20 (1F5)
FIG. 35

Follicular Lymphoma With Areas Of Diffuse Large B Cell Lymphoma
Lymph node (MG04-CHTN-26)
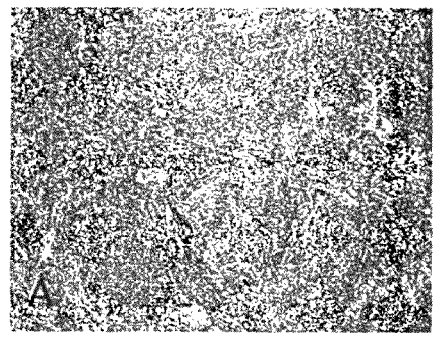
H&E, 4x
H&E, 10x
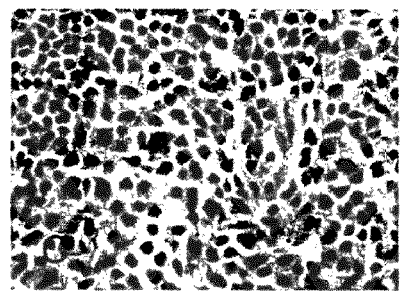
H&E, 20X
FIG. 36
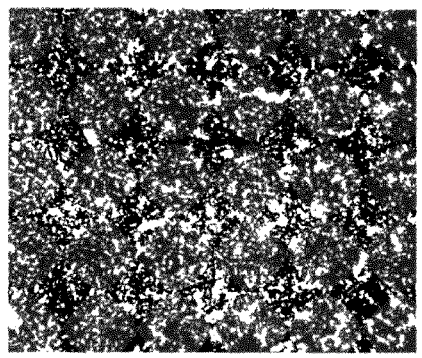
Anti CD32B, 4x
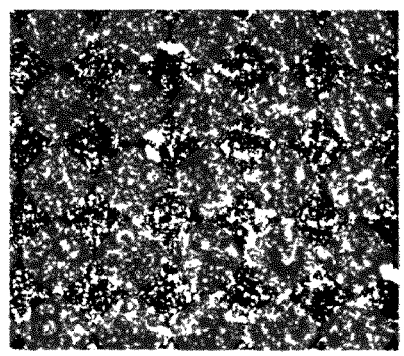
Anti CD20, 4x
FIG. 37

Follicular Lymphoma With Areas Of Diffuse Large B
Cell Lymphoma
Lymph node (MG04-CHTN-26)
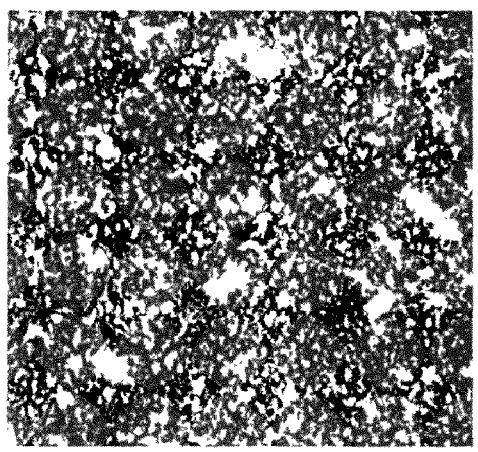
Iso-control (IgG1)
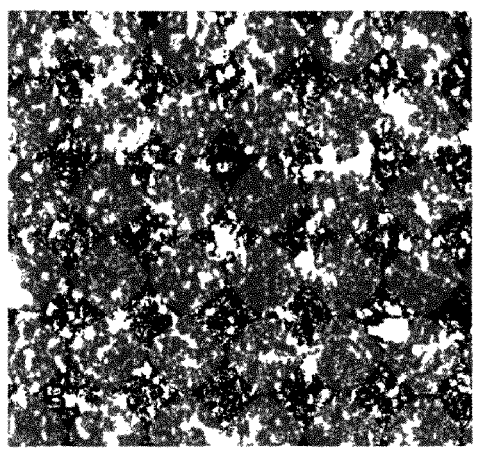
CD32B
(m2B6)
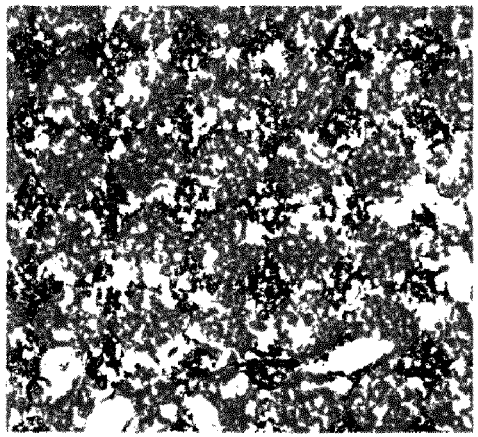
Iso-control (IgG2a)
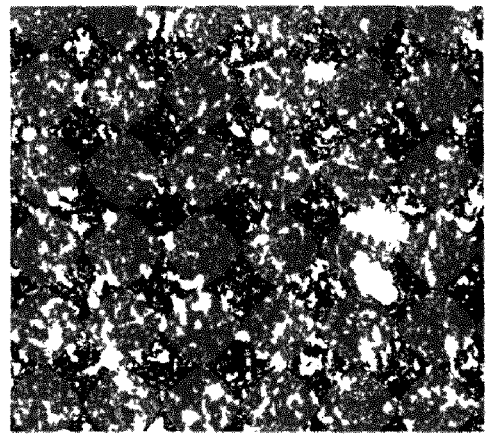
CD20 (1F5)
FIG. 38

Diffuse Large B Cell Lymphoma
Lymph node (MG04-CHTN-27)
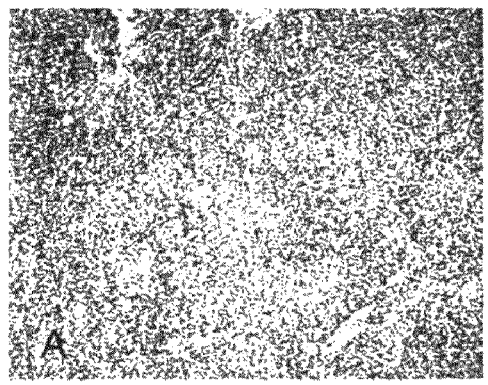
H&E, 4x
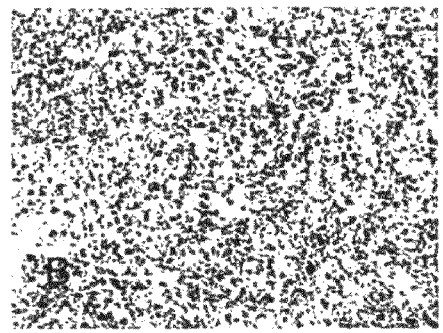
H&E, 10x
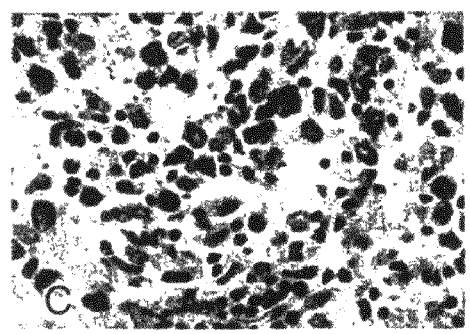
H&E, 20X
FIG. 39
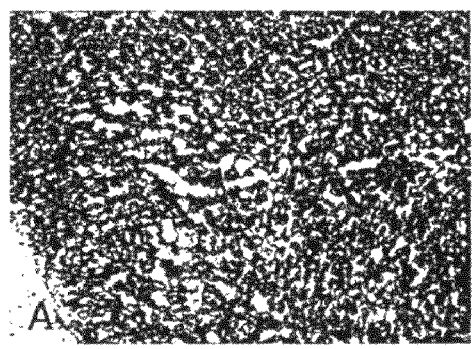
Anti CD32B, 4x
Anti CD20, 4x
FIG. 40

Diffuse Large B Cell Lymphoma
Lymph node (MG04-CHTN-27)
Iso-control (IgG1), 10x
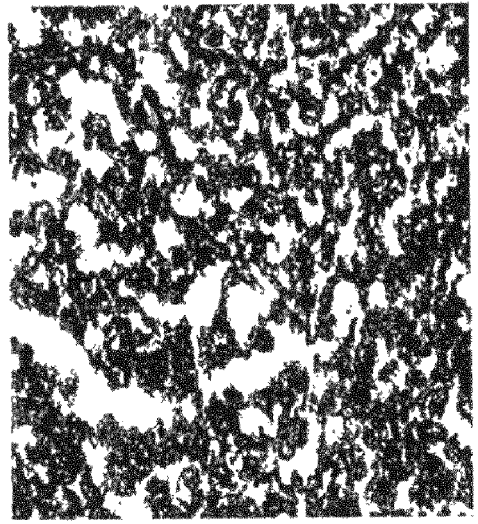
CD32B (m2B6), 10x
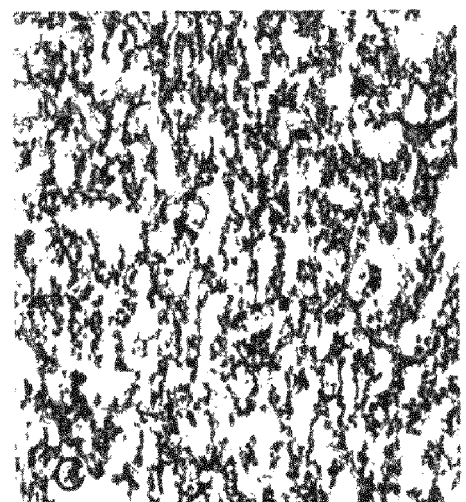
Iso-control (IgG2a), 10x
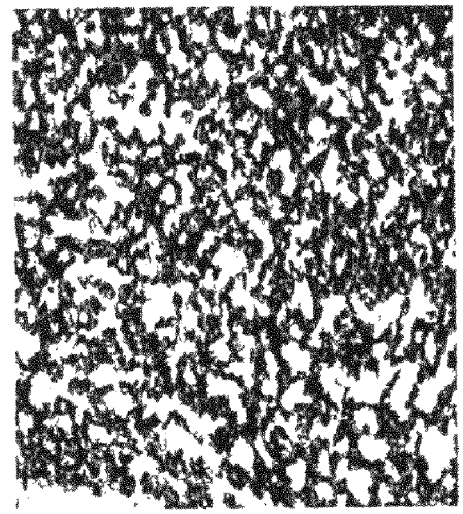
CD20 (1F5), 10x
FIG. 41

Diffuse B Cell Lymphoma
Lymph node (MG05-CHTN-03)
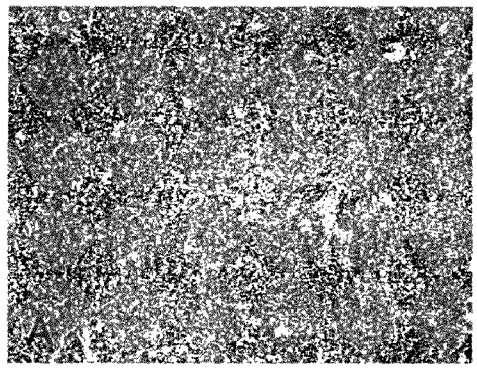
H&E, 4x
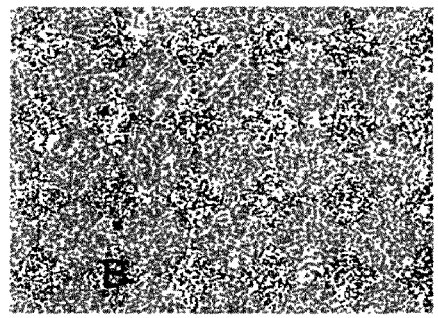
H&E, 10x
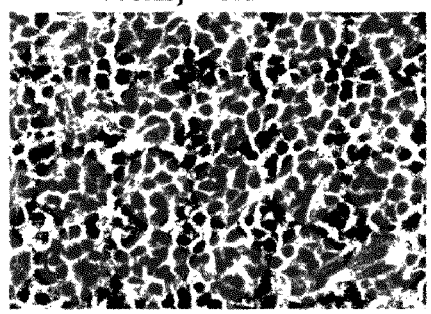
H&E, 20X
FIG. 42
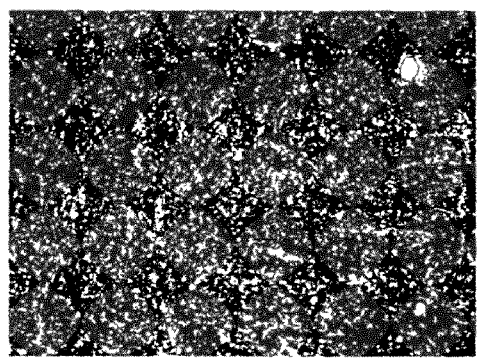
Anti CD32B, 4x
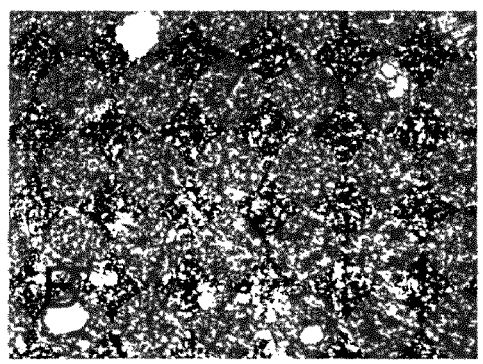
Anti CD20, 4x
FIG. 43

Diffuse Large B Cell Lymphoma
Lymph node (MG05-CHTN-03)
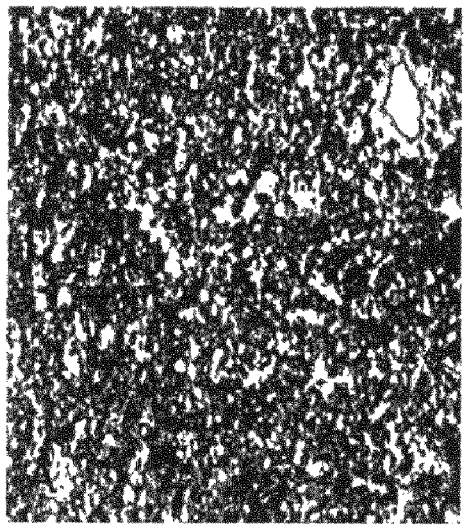
Iso-control (IgG1)
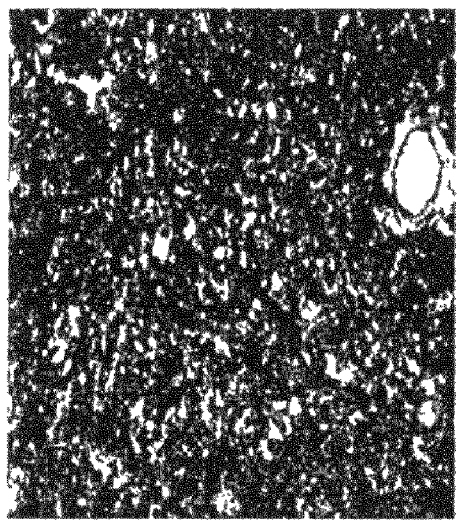
CD32B (m2B6)
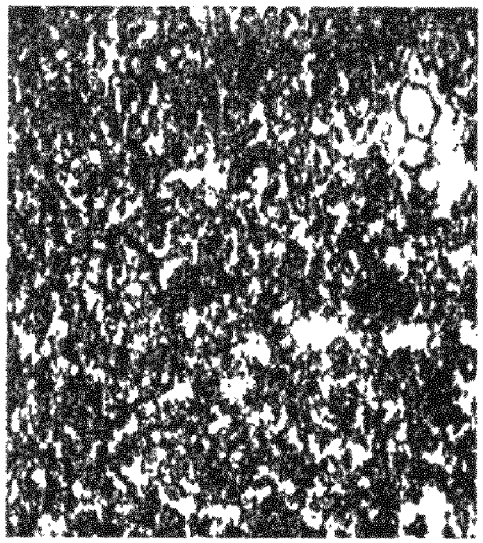
Iso-control (IgG2a)
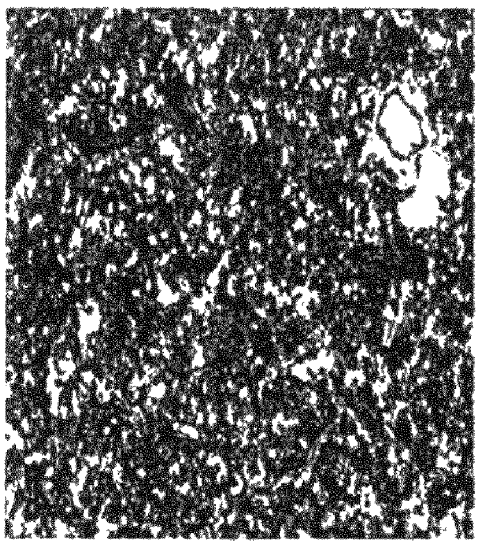
CD20 (1F5)
FIG. 44

Diffuse Large B Cell Lymphoma
Lymph node (MG05-CHTN-05)
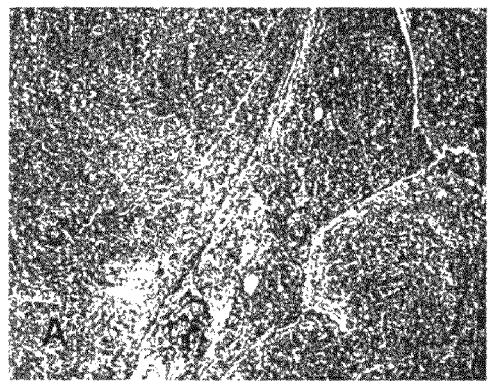
H&E, 4x
FIG. 45
H&E, 10x
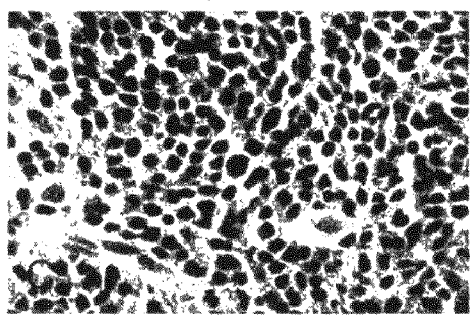
H&E, 20X
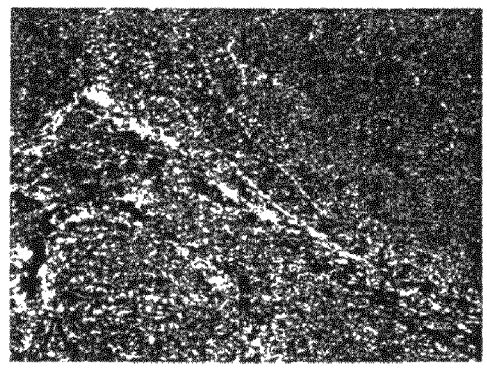
Anti CD32B, 4x
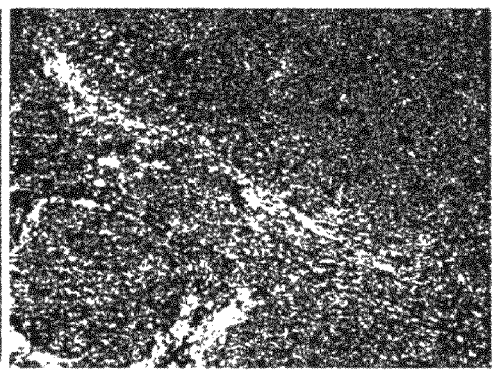
Anti CD20, 4x
FIG. 46

Diffuse Large B Cell Lymphoma
Lymph node (MG05-CHTN-05)
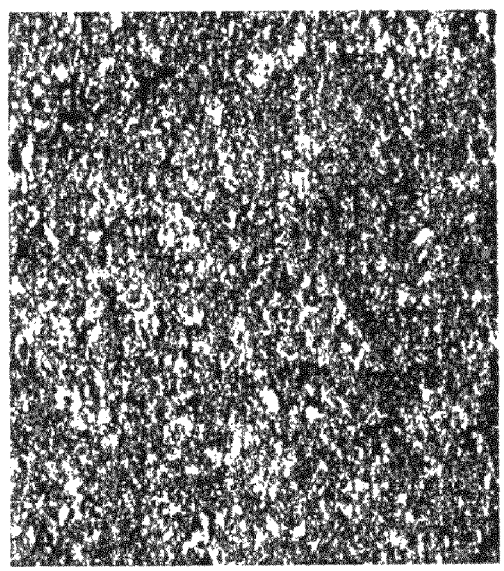
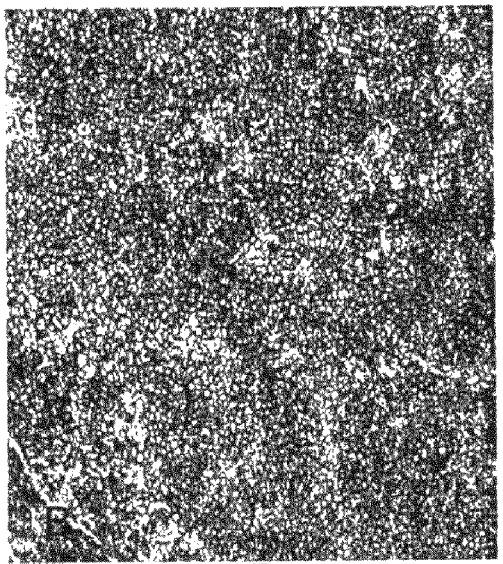
Iso-control (IgG1)
CD32B (m2B6)
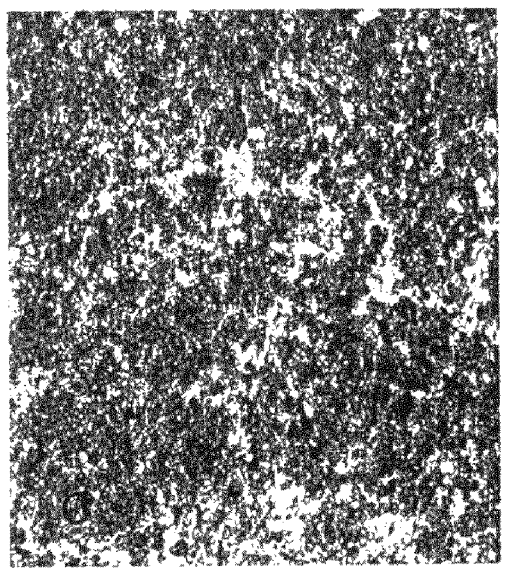
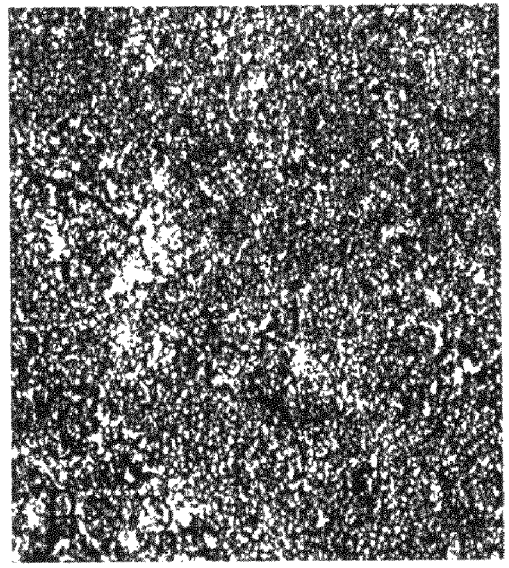
Iso-control (IgG2a)
CD20 (1F5)
FIG. 47

Small Lymphocytic Lymphoma
Lymph node (MG04-CHTN-30)
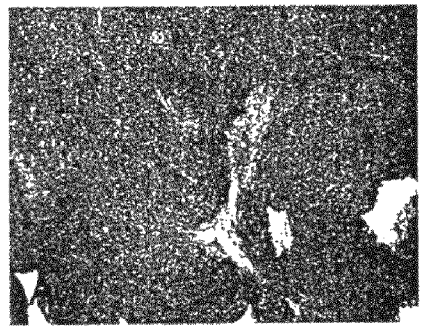
H&E, 4x
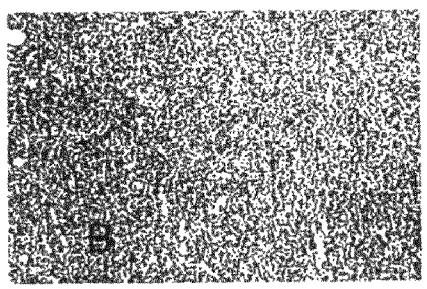
H&E, 10x
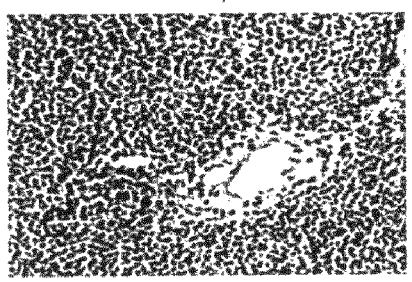
H&E, 20X
FIG. 48
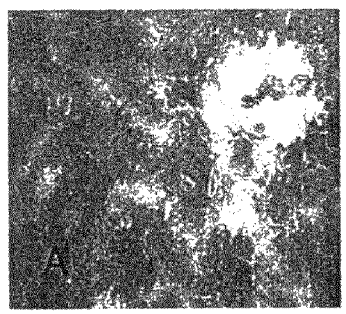
Iso-control (IgG1)
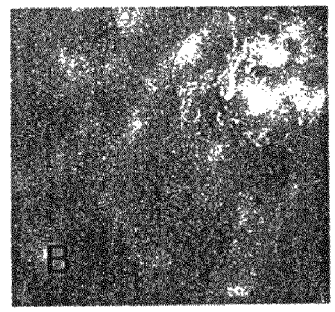
CD32B (m2B6)
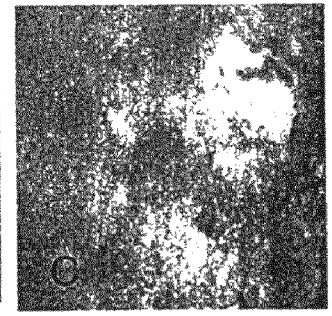
Iso-control (IgG2a)
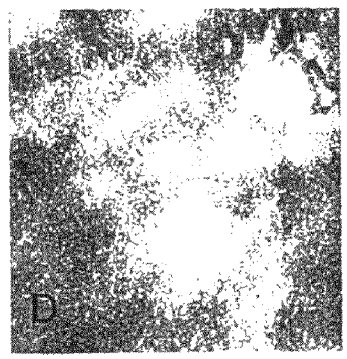
CD20 (1F5)
FIG. 49

Diffuse Large B Cell Lymphoma
Lymph node (MG04-CHTN-31)
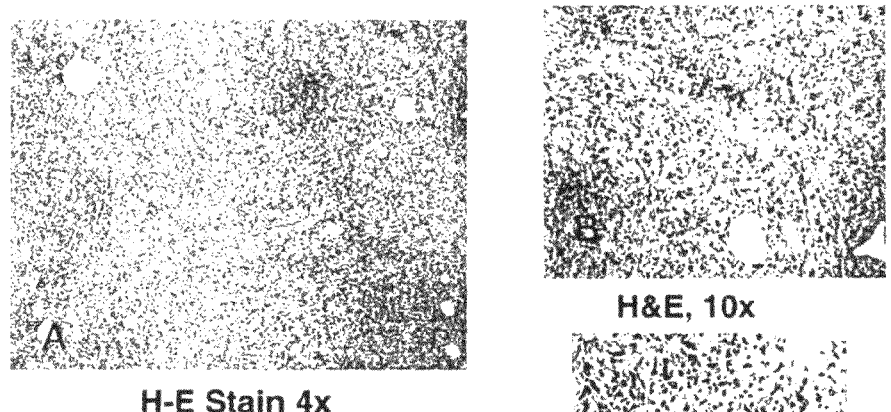
H-E Stain 4x
H&E, 10x
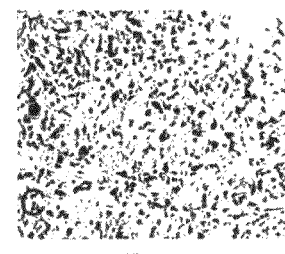
H&E, 20X
FIG. 50
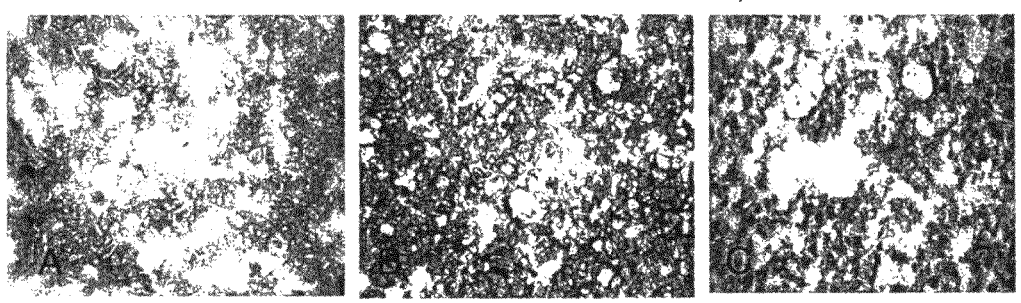
Iso-control (IgG1)
CD32B (m2B6)
Iso-control (IgG2a)
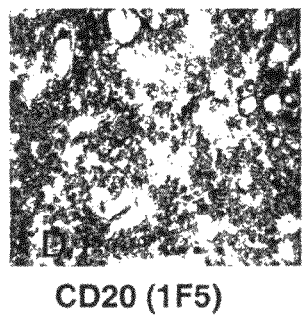
FIG. 51
CD20 (1F5)

Diffuse Large B Cell Lymphoma
Spleen (MG04-CHTN-36)
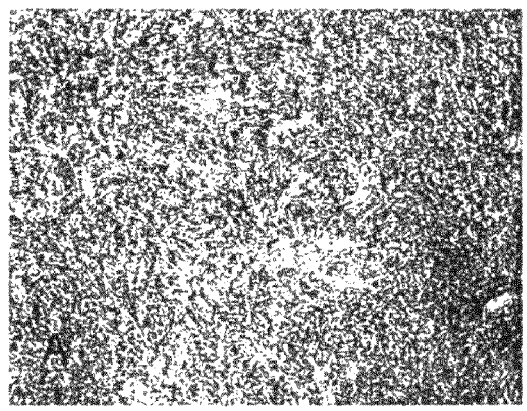
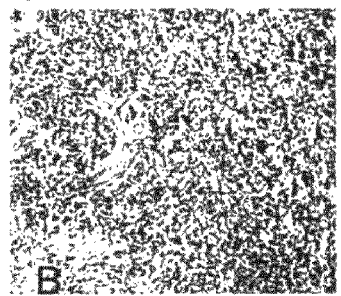
H&E, 10x
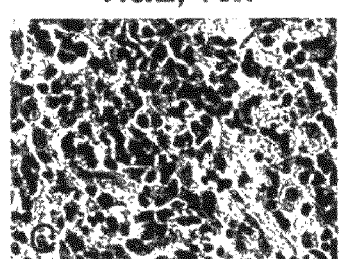
H&E, 40X
H-E Stain 4x
FIG. 52
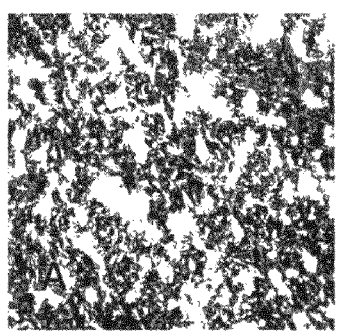
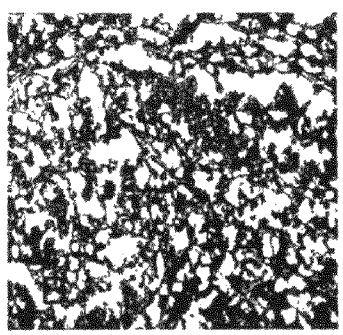
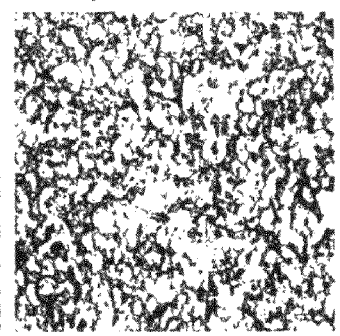
Iso-control (IgG1)　　CD32B　　Iso-control (IgG2a)
　　　　　　　　　　(m2B6)
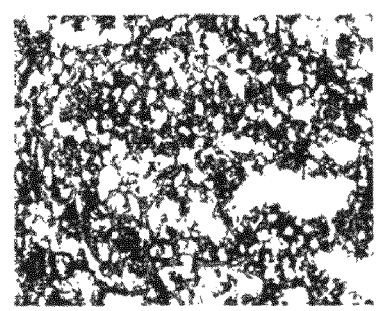
CD20 (1F5)
FIG. 53

Mantle Cell Lymphoma/Diffuse Small Cleaved Cell Lymphoma
Lymph node (MG04-CHTN-41)
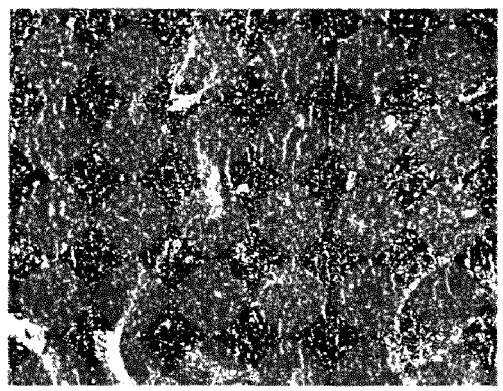
H-E Stain 4x
H&E, 10x
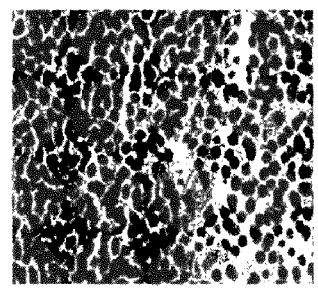
H&E, 20X
FIG. 54
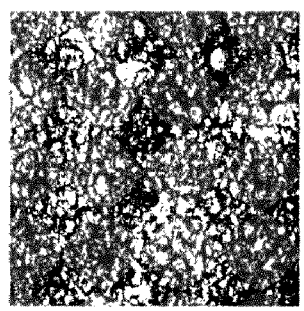
Iso-control (IgG1)
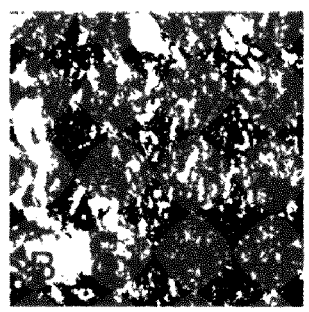
CD32B (m2B6)
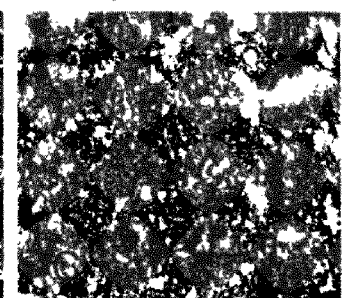
Iso-control (IgG2a)
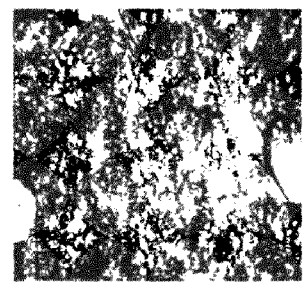
CD20 (1F5)
FIG. 55

Diffuse Large B Cell Lymphoma
Lymph Node (MG04-CHTN-05)
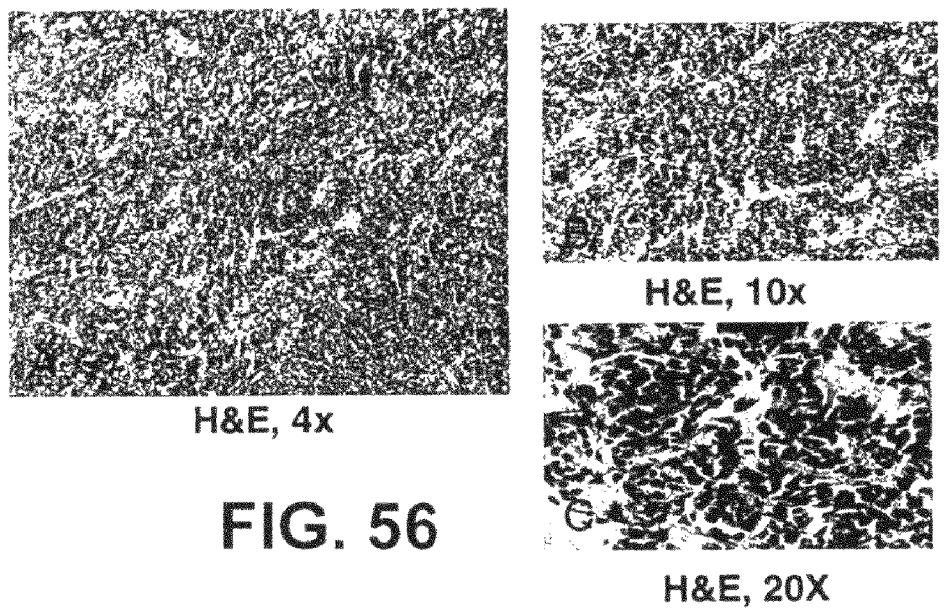
FIG. 56
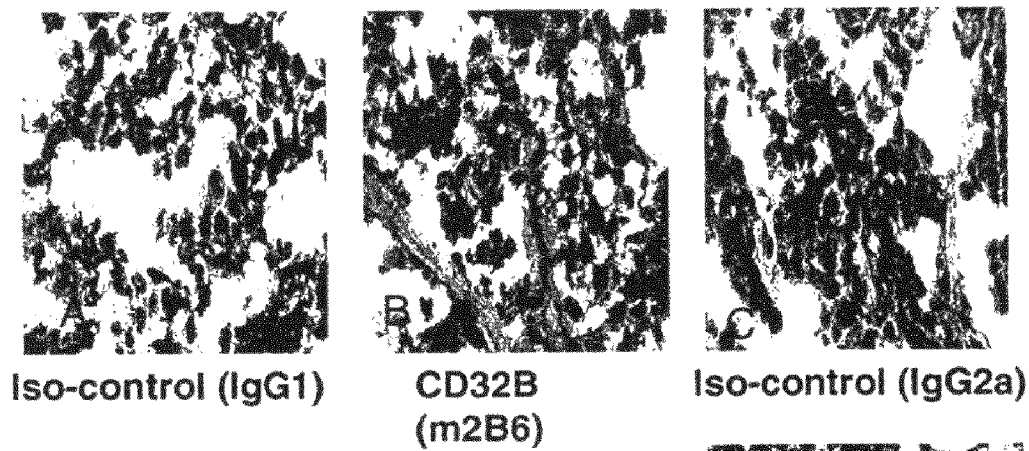
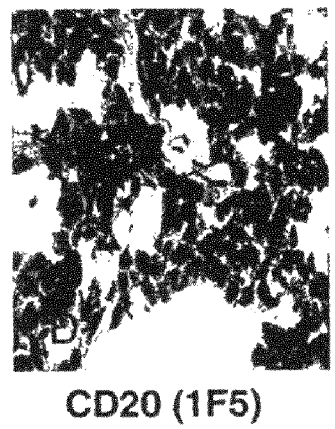
FIG. 57

FCγRIIB SPECIFIC ANTIBODIES AND METHODS OF USE THEREOF

CROSS-REFERENCE TO RELATED APPLICATIONS

This application is a continuation-in-part of U.S. patent application Ser. No. 11/108,135, filed on Apr. 15, 2005, now abandoned, which claims priority to U.S. Provisional Patent Application Ser. Nos. 60/562,804, 60/582,044, 60/582,045 and 60/654,713, filed on Apr. 16, 2004, Jun. 21, 2004, Jun. 21, 2004 and Feb. 18, 2005 respectively. This application is also a continuation-in-part of U.S. patent application Ser. No. 10/524,134 filed on Feb. 11, 2005, which issued as U.S. Pat. No. 7,425,619, which is a National Stage Application under 35 U.S.C. §371 of PCT Application Serial No. PCT/US03/25399, filed on Aug. 14, 2003, which claims priority to U.S. Provisional Application Ser. No. 60/403,266, filed on Aug. 14, 2002. This application is also a continuation-in-part of U.S. patent application Ser. No. 10/643,857 filed on Aug. 14, 2003, which issued as U.S. Pat. No. 7,425,620, which claims priority to U.S. Provisional Application Ser. No. 60/403,266, filed on Aug. 14, 2002. This application is also a continuation-in-part of U.S. patent application Ser. No. 11/305,787, filed on Dec. 15, 2005, now abandoned, which claims priority to U.S. Provisional Application Ser. No. 60/636,663, filed on Dec. 15, 2004. All of the above-identified applications are incorporated herein by reference in their entireties.

FIELD OF THE INVENTION

The present invention relates to antibodies or fragments thereof that specifically bind FcγRIIB, particularly human FcγRIIB, more particularly the extracellular domain of FcγRIIB with greater affinity than said antibodies or fragments thereof bind FcγRIIA, particularly human FcγRIIA, and block the Fc binding site of FcγRIIB. The present invention also encompasses the use of an anti-FcγRIIB antibody or an antigen-binding fragment thereof, as a single agent therapy for the treatment, prevention, management, or amelioration of a cancer, preferably a B-cell malignancy, particularly, B-cell chronic lymphocytic leukemia or non-Hodgkin's lymphoma, an autoimmune disorder, an inflammatory disorder, an IgE-mediated allergic disorder, or one or more symptoms thereof. The present invention also encompasses the use of an anti-FcγRIIB antibody or an antigen-binding fragment thereof, in combination with other cancer therapies. The present invention provides pharmaceutical compositions comprising an anti-FcγRIIB antibody or an antigen-binding fragment thereof, in amounts effective to prevent, treat, manage, or ameliorate a cancer, such as a B-cell malignancy, an autoimmune disorder, an inflammatory disorder, an IgE-mediated allergic disorder, or one or more symptoms thereof. The invention further provides methods of enhancing the therapeutic effect of therapeutic antibodies by administering the antibodies of the invention to enhance the effector function of the therapeutic antibodies. The invention also provides methods of enhancing efficacy of a vaccine composition by administering the antibodies of the invention with a vaccine composition. The invention further provides methods of treating cancer and/or regulating immune complex-mediated cell activation by administering the antibodies of the invention to enhance an immune response. The invention also provides methods of breaking tolerance to an antigen by administering an antigen-antibody complex and an antibody of the invention.

BACKGROUND OF THE INVENTION

I. Fc Receptors and their Roles in the Immune System

The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the A-chain of the Fc receptor. Fc receptors are defined by their specificity for immunoglobulin subtypes. Fc receptors for IgG are referred to as FcγR, for IgE as FcεR, and for IgA as FcαR. Different accessory cells bear Fc receptors for antibodies of different isotype, and the isotype of the antibody determines which accessory cells will be engaged in a given response (reviewed by Ravetch J. V. et al. (1991) "*Fc Receptors*," Annu. Rev. Immunol. 9: 457-92; Gerber et al. (2001) "*Stimulatory And Inhibitory Signals Originating From The Macrophage Fcgamma Receptors*," Microbes and Infection, 3: 131-139; Billadeau et al. (2002), "*ITAMs Versus ITIMs: Striking A Balance During Cell Regulation*," The Journal of Clinical Investigation, 2(109): 161-168; Ravetch et al. (2000) "*Immune Inhibitory Receptors*," Science, 290: 84-89; Ravetch et al., (2001) "*IgG Fc Receptors*," Annu. Rev. Immunol. 19:275-290; Ravetch (1994) "*Fc Receptors: Rubor Redux*," Cell, 78(4): 553-560). The different Fc receptors, the cells that express them, and their isotype specificity is summarized in Table 1 (adapted from IMMUNOBIOLOGY: THE IMMUNE SYSTEM IN HEALTH AND DISEASE, 4$^{th}$ ed. 1999, Elsevier Science Ltd/Garland Publishing, New York).

A. Fcγ Receptors

Each member of this family is an integral membrane glycoprotein, possessing extracellular domains related to a C2-set of immunoglobulin-related domains, a single membrane-spanning domain and an intracytoplasmic domain of variable length. There are three known FcγRs, designated FcγRI(CD64), FcγRII(CD32), and FcγRIII(CD16). The three receptors are encoded by distinct genes; however, the extensive homology among the three family members suggests they arose from a common progenitor, perhaps by gene duplication. This invention specifically focuses on FcγRII(CD32).

B. FcγRII(CD32)

FcγRII proteins are 40 KDa integral membrane glycoproteins that bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRIIA (CD32A) and FcγRIIB (CD32B) create two functionally heterogenous responses to receptor ligation. The fundamental difference is that the A isoform initiates intracellular signaling leading to cell activation, resulting in events such as phagocytosis and respiratory burst, whereas the B isoform initiates inhibitory signals, e.g., inhibiting B-cell activation.

C. Signaling Through FcγRs

Both activating and inhibitory signals are transduced through the FcγRs following ligation. These diametrically opposing functions result from structural differences among the different receptor isoforms. Two distinct domains within the cytoplasmic signaling domains of the receptor called Immunoreceptor Tyrosine based Activation Motifs (ITAMs) or Immunoreceptor Tyrosine based Inhibitory Motifs (ITIMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express FcγRIIA. FcγRIIA clustering via immune complexes or specific antibody cross-linking serves to aggregate ITAMs along with receptor-associated kinases that facilitate ITAM phosphorylation. ITAM phosphorylation serves as a docking site for Syk kinase, activation of which results in activation of downstream substrates (e.g., PI3K). Cellular activation leads to release of pro-inflammatory mediators.

FcγRIIB is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When colligated along with an activating FcγR, the ITIM in FcγRIIB becomes phosphorylated and attracts the SH2 domain of the inositol polyphosphate 5'-phosphatase (SHIP), which hydrolyzes phosphoinositol messengers that are released as a consequence of ITAM-containing FcγR-mediated tyrosine kinase activation, thus preventing the influx of intracellular Ca++. In this manner, crosslinking of FcγRIIB dampens the activating response to FcγR ligation and inhibits cellular responsiveness. B cell activation, B cell proliferation and antibody secretion is aborted.

TABLE 1

Receptors for the Fc Regions of Immunoglobulin Isotypes

| Receptor | Binding | Cell Type | Effect of Ligation |
|---|---|---|---|
| FcγRI (CD64) | IgG1 $10^8 M^{-1}$ | Macrophages, Neutrophils, Eosinophils, Dendritic cells | Uptake Stimulation Activation of respiratory burst Induction of killing |
| FcγRII-A (CD32) | IgG1 $2 \times 10^6 M^{-1}$ | Macrophages, Neutrophils, Eosinophils, Dendritic cells, Platelets, Langerhan cells | Uptake Granule release |
| FcγRII-B2 (CD32) | IgG1 $2 \times 10^6 M^{-1}$ | Macrophages, Neutrophils, Eosinophils | Uptake Inhibition of Stimulation |
| FcγRII-BI (CD32) | IgG1 $2 \times 10^6 M^{-1}$ | B cells, Mast cells | No uptake Inhibition of Stimulation |
| FcγRIII (CD16) | IgG1 $5 \times 10^5 M^{-1}$ | NK cells, Eosinophil macrophages, Neutrophils, Mast Cells | Induction of Killing |
| FcεRI | IgG1 $10^{10} M^{-1}$ | Mast cells, Eosinophil Basophils | Secretion of granules |
| FcαRI (CD89) | IgG1, IgA2 $10^7 M^{-1}$ | Macrophages, Neutropils Eosinophils | Uptake Induction killing of |

II. Diseases of Relevance

A. Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, BASIC PATHOLOGY, $2^{nd}$ Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime. A cure for cancer has yet to be found. Current treatment options, such as surgery, chemotherapy and radiation treatment, are often either ineffective or present serious side effects.

Currently, cancer therapy may involve surgery, chemotherapy, hormonal therapy and/or radiation treatment to eradicate neoplastic cells in a patient (See, for example, Stockdale, 1998, "Principles of Cancer Patient Management," in SCIENTIFIC AMERICAN: MEDICINE, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly, by inhibiting the biosynthesis of the deoxyribonucleotide triphosphate precursors, to prevent DNA replication and concomitant cell division (See, for example, Gilman et al., GOODMAN AND GILMAN'S: THE PHARMACOLOGICAL BASIS OF THERAPEUTICS, 8th Ed., (Pergamom Press, New York, 1990). These agents, which include alkylating agents, such as nitrosourea, anti-metabolites, such as methotrexate and hydroxyurea, and other agents, such as etoposides, camptothecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management," in SCIENTIFIC AMERICAN MEDICINE, vol. 3, Rubenstein and Federman, eds., Ch. 12, Sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

B. B Cell Malignancies

B cell malignancies, including, but not limited to, B-cell lymphomas and leukemias, are neoplastic diseases with significant incidence in the United States. There are approximately 55,000 new lymphoma cases of per year in the U.S. (1998 data), with an estimated 25,000 deaths per year. This represents 4% of cancer incidence and 4% of all cancer-related deaths in the U.S. population. The revised European-American classification of lymphoid neoplasms (1994 REAL classification, modified 1999) grouped lymphomas based on their origin as either B cell lineage lymphoma, T cell lineage lymphoma, or Hodgkin's lymphoma. Lymphoma of the B cell lineage is the most common type of non-Hodgkin's lymphoma (HL) diagnosed in the U.S. (Williams, HEMATOLOGY, 6$^{th}$ ed. Beutler et al. eds., McGraw Hill, 2001).

Chronic lymphocytic leukemia (CLL) is a neoplastic disease characterized by the accumulation of small, mature-appearing lymphocytes in the blood, marrow, and lymphoid tissues. CLL has an incidence of 2.7 cases per 100,000 in the U.S. The risk increases progressively with age, particularly in men. It accounts for 0.8% of all cancers and is the most common adult leukemia, responsible for 30% of all leukemias. In nearly all cases (>98%) the diseased cells belong to the B lymphocyte lineage. A non-leukemic variant, small lymphocytic lymphoma, constitutes 5-10% of all lymphomas, has histological, morphological and immunological features indistinguishable from that of involved lymph nodes in patients with B-CLL (Williams, HEMATOLOGY, 6$^{th}$ ed. Beutler et al. eds., McGraw Hill, 2001).

The natural history of chronic lymphocytic leukemia falls into several phases. In the early phase, chronic lymphocytic leukemia is an indolent disease, characterized by the accumulation of small, mature, functionally incompetent malignant B-cells having a lengthened life span. Eventually, the doubling time of the malignant B-cells decreases and patients become increasingly symptomatic. While treatment with chemotherapeutic agents can provide symptomatic relief, the overall survival of the patients is only minimally extended. The late stages of chronic lymphocytic leukemia are characterized by significant anemia and/or thrombocytopenia. At this point, the median survival is less than two years (Foon et al. (1990) "Chronic Lymphocytic Leukemia: New Insights Into Biology And Therapy," Annals Int. Medicine 113:525-539). Due to the very low rate of cellular proliferation, chronic lymphocytic leukemia is resistant to treatment with chemotherapeutic agents.

Recently, gene expression studies have identified several genes that may be up-regulated in lymphoproliferative disorders. One molecule thought to be over-expressed in patients with B-cell chronic lymphocytic leukemia (B-CLL) and in a large fraction of non-Hodgkin lymphoma patients is CD32B (Alizadeh et al. (2000) "Distinct Types Of Diffuse Large B-Cell Lymphoma Identified By Gene Expression Profiling," Nature 403:503-511; Rosenwald et al. (2001) "Relation Of Gene Expression Phenotype To Immunoglobulin Mutation Genotype In B Cell Chronic Lymphocytic Leukemia," J. Exp. Med. 184:1639-1647). However, the role of CD32B is B-CLL is unclear since one report demonstrates that CD32B was expressed on a low percentage of B-CLL cells and at a low density (Damle et al. (2002) "B-Cell Chronic Lymphocytic Leukemia Cells Express A Surface Membrane Phenotype Of Activated, Antigen-Experienced B Lymphocytes," Blood 99:4087-4093). CD32B is a B cell lineage surface antigen, whose over-expression in B cell neoplasia makes it a suitable target for therapeutic antibodies. In addition, CD32B belongs to the category of inhibitory receptors, whose ligation delivers a negative signal. Therefore, antibodies directed against CD32B could function to eliminate tumor cells by mechanisms that include complement dependent cytotoxicity (CDC), antibody-dependent cellular cytotoxicity (ADCC), but also triggering an apoptotic signal. The high homology of CD32B with its counterpart, CD32A, an activating Fcγ receptor, has thus far hampered the generation of antibodies that selectively recognize one but not the other form of the molecule.

B cell malignancy is generally treated with single agent chemotherapy, combination chemotherapy and/or radiation therapy. These treatments can reduce morbidity and/or improve survival, albeit they carry significant side effects. The response of B-cell malignancies to various forms of treatment is mixed. For example, in cases in which adequate clinical staging of non-Hodgkin's lymphoma is possible, field radiation therapy can provide satisfactory treatment. Certain patients, however, fail to respond and disease recurrence with resistance to treatment ensues with time, particularly with the most aggressive variants of the disease. About one-half of the patients die from the disease (Devesa et al. (1987) "Cancer Incidence And Mortality Trends Among Whites In The United States, 1947-84," J. Nat'l Cancer Inst. 79:701-770).

Investigational therapies for the treatment of refractory B cell neoplasia include autologous and allogeneic bone marrow or stem cell transplantation and gene therapies. Recently, immunotherapy using monoclonal antibodies to target B-cell specific antigens has been introduced in the treatment of B cell neoplasia. The use of monoclonal antibodies to direct radionuclides, toxins, or other therapeutic agents offers the possibility that such agents can be delivered selectively to tumor sites, thus limiting toxicity to normal tissues.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response; for example, hybridoma technology has enabled the development of tumor selective monoclonal antibodies (See Green et al. (2000) "*Monoclonal Antibody Therapy For Solid Tumors,*" Cancer Treat Rev., 26: 269-286; Weiner L M (1999) "*Monoclonal Antibody Therapy Of Cancer,*" Semin Oncol. 26(suppl. 14):43-51), and in the past few years, the Food and Drug Administration has approved the first mAbs for cancer therapy: RITUXAN® (rituximab) (anti-CD20) for non-Hodgkin's Lymphoma, CAMPATH® (alemtuzumab) (anti-CD52) for B-cell chronic lymphocytic leukemia (B-CLL) and HERCEPTIN® (trastuzumab) [anti-(c-erb-2/HER-2)] for metastatic breast cancer (S. A. Eccles (2001) "*Monoclonal Antibodies Targeting Cancer: 'Magic Bullets' Or Just The Trigger?,*" Breast Cancer Res., 3: 86-90). These antibodies have demonstrated clinical efficacy, but their use is not without side effects. The potency of antibody effector function, e.g., to mediate antibody dependent cellular cytotoxicity ("ADCC") is an obstacle to such treatment. Furthermore, with RITUXAN® (rituximab) and CAMPATH® (alemtuzumab), at least half the patients fail to respond and a fraction of responders may be refractory to subsequent treatments.

C. Inflammatory Diseases and Autoimmune Diseases

Inflammation is a process by which white blood cells and other cellular chemicals protect the body from infection by foreign substances such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders that affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just upon the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and disability, as well as costing millions of dollars in healthcare expenses and lost wages.

Currently, available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

D. Allergy

Immune-mediated allergic (hypersensitivity) reactions are classified into four types (I-IV) according to the underlying mechanisms leading to the expression of the allergic symptoms. Type I allergic reactions are characterized by IgE-mediated release of vasoactive substances such as histamine from mast cells and basophils. The release of these substances and the subsequent manifestation of allergic symptoms are initiated by the cross-linking of allergen-bound IgE to its receptor on the surface of mast cells and basophils. In individuals suffering from type I allergic reactions, exposure to an allergen for a second time leads to the production of high levels of IgE antibodies specific for the allergen as a result of the involvement of memory B and T cells in the 3-cell interaction required for IgE production. The high levels of IgE antibodies produced cause an increase in the cross-linking of IgE receptors on mast cells and basophils by allergen-bound IgE, which in turn leads to the activation of these cells and the release of the pharmacological mediators that are responsible for the clinical manifestations of type I allergic diseases.

Two receptors with differing affinities for IgE have been identified and characterized. The high affinity receptor (FcεRI) is expressed on the surface of mast cells and basophils. The low affinity receptor (FcεRII/CD23) is expressed on many cell types, including B cells, T cells, macrophages, eosinophils and Langerhan cells. The high affinity IgE receptor consists of three subunits (alpha, beta and gamma chains). Several studies demonstrate that only the alpha chain is involved in the binding of IgE, whereas the beta and gamma chains (which are either transmembrane or cytoplasmic proteins) are required for signal transduction events. The identification of IgE structures required for IgE to bind to the FcεRI on mast cells and basophils is of utmost importance in devising strategies for treatment or prevention of IgE-mediated allergies. For example, the elucidation of the IgE receptor-binding site could lead to the identification of peptides or small molecules that block the binding of IgE to receptor-bearing cells in vivo.

Currently, IgE-mediated allergic reactions are treated with drugs such as antihistamines and corticosteroids which attempt to alleviate the symptoms associated with allergic reactions by counteracting the effects of the vasoactive substances released from mast cells and basophils. High doses of antihistamines and corticosteroids have deleterious side effects (e.g., central nervous system disturbance, constipation, etc). Thus, other methods for treating type I allergic reactions are needed.

One approach to the treatment of type I allergic disorders has been the production of monoclonal antibodies which react with soluble (free) IgE in serum, block IgE from binding to its receptor on mast cells and basophils, and do not bind to receptor-bound IgE (i.e., they are non-anaphylactogenic). Two such monoclonal antibodies are in advanced stages of clinical development for treatment of IgE-mediated allergic reactions (see, e.g., Chang, T. W. (2000) "*The Pharmacological Basis Of Anti-IgE Therapy*," Nature Biotechnology 18:157-162).

One of the most promising treatments for IgE-mediated allergic reactions is the active immunization against appropriate non-anaphylactogenic epitopes on endogenous IgE. Stanworth et al. (U.S. Pat. No. 5,601,821) described a strategy involving the use of a peptide derived from the CεH4 domain of the human IgE coupled to a heterologous carrier protein as an allergy vaccine. However, this peptide has been shown not to induce the production of antibodies that react with native soluble IgE. Further, Hellman (U.S. Pat. No. 5,653,980) proposed anti-IgE vaccine compositions based on fusion of full-length CεH2-CεH3 domains (approximately 220 amino acids long) to a foreign carrier protein. However, the antibodies induced by the anti-IgE vaccine compositions proposed in Hellman will most likely it result in anaphylaxis, since antibodies against some portions of the CεH2 and CεH3 domains of the IgE molecule have been shown to cross-link the IgE receptor on the surface of mast cell and basophils and lead to production of mediators of anaphylaxis (See, e.g., Stadler et al. (1993) "*Biological Activities Of Anti-IgE Antibodies*," Int. Arch. Allergy and Immunology 102:121-126). Therefore, a need remains for treatment of IgE-mediated allergic reactions which do not induce anaphylactic antibodies.

The significant concern over induction of anaphylaxis has resulted in the development of another approach to the treatment of type I allergic disorders consisting of mimotopes that could induce the production of anti-IgE polyclonal antibodies when administered to animals (See, e.g., Rudolf, et al. (1998) "*Epitope-Specific Antibody Response To IgE By Mimotope Immunization*," Journal of Immunology 160:3315-3321). Kricek et al. (International Publication No. WO 97/31948) screened phage-displayed peptide libraries with the monoclonal antibody BSW17 to identify peptide mimotopes that could mimic the conformation of the IgE receptor binding. These mimotopes could presumably be used to induce polyclonal antibodies that react with free native IgE, but not with receptor-bound IgE as well as block IgE from binding to its receptor. Kriek et al. disclosed peptide mimotopes that are not homologous to any part of the IgE molecule and are thus different from peptides disclosed in the present invention.

As evidenced by a survey of the art, there remains a need for enhancing the therapeutic efficacy of current methods of treating or preventing disorders such as cancer, autoimmune disease, inflammatory disorder, or allergy. In particular, there is a need for enhancing the effector function, particularly, the cytotoxic effect of therapeutic antibodies used in treatment of cancer. The current state of the art is also lacking in treating or preventing allergy disorders (e.g., either by antibody therapy or vaccine therapy).

SUMMARY OF THE INVENTION

The extracellular domains of FcγRIIA and FcγRIIB are 95% identical and thus share numerous epitopes. However, FcγRIIA and FcγRIIB exhibit very different activities. The fundamental difference is that the FcγRIIA initiates intracellular signaling leading to cell activation such as phagocytosis and respiratory burst, whereas the FcγRIIB initiates inhibitory signaling. Prior to this invention, to the knowledge of the inventors, antibodies known to distinguish between native human FcγRIIA and native human FcγRIIB have not been identified. In view of their distinctive activities and role in modulating immune responses, antibodies that recognize native FcγRIIB and not native FcγRIIA are needed. The present invention is based, in part, on the discovery of such FcγRIIB-specific antibodies.

The invention relates to an isolated antibody or a fragment thereof that specifically binds FcγRIIB, particularly human FcγRIIB, more particularly native human FcγRIIB, with a greater affinity than said antibody or a fragment thereof binds FcγRIIA, particularly human FcγRIIA, more particularly native human FcγRIIA, and blocks the Fc binding domain of FcγRIIB. Preferably, the antibodies of the invention bind the extracellular domain of native human FcγRIIB. In certain embodiments of the invention, the antibody or a fragment thereof binds FcγRIIB with at least 2 times greater affinity than said antibody or a fragment thereof binds FcγRIIA. In other embodiments of the invention, the antibody or a fragment thereof binds FcγRIIB with at least 4 times, at least 6 times, at least 8 times, at least 10 times, at least 100 times, at least 1000 times, at least $10^4$, at least $10^5$, at least $10^6$, at least $10^7$, or at least $10^8$ times greater affinity than said antibody or a fragment thereof binds FcγRIIA. In a preferred embodiment, said antibody or a fragment thereof binds FcγRIIB with 100 times, 1000 times, $10^4$ times, $10^5$ times, $10^6$ times, $10^7$ times, or $10^8$ times greater affinity than said antibody or a fragment thereof binds FcγRIIA. Preferably, these binding affinities are determined with the monomeric IgG, and not the aggregated IgG, and binding is via the variable domain (e.g., Fab fragments of the antibodies have binding characteristics similar to the full immunolobulin molecule).

In a preferred embodiment, the antibody or fragment thereof blocks crosslinking of FcγRIIB to an immunoreceptor tyrosine-based activation motif (ITAM) containing activating receptor, preferably enhancing the activity of an activating receptor. ITAM-containing receptors include Fc receptors, and BCR-associated Igα. In certain embodiments, the blocking leads to B cell, mast cell, dendritic cell, or macrophage activation.

In certain embodiments, the Fc receptor is a FcεR or a FcγR, preferably FcεRI. Preferably, an FcεRI dependent activity is modulated, for example, modulation of calcium mobilization and/or modulation of degranulation.

In one embodiment, the FcγRIIB-specific antibody in accordance with the invention is not the monoclonal antibody designated KB61, as disclosed in Pulford et al. (1986) "*A New Monoclonal Antibody (KB61) Recognizing A Novel Antigen Which Is Selectively Expressed On A Subpopulation Of Human B Lymphocytes*," Immunology 57:71-76, or the monoclonal antibody designated MAbII8D2 as disclosed in Weinrich et al. (1996) "Epitope Mapping Of *New Monoclonal Antibodies Recognizing Distinct Human FcRII (CD32) Isoforms*," Hybridoma 15: 109-116. In a specific embodiment, the FcγRIIB-specific antibody of the invention does not bind to the same epitope and/or does not compete for binding with the monoclonal antibody KB61 or the monoclonal antibody MAbII8D2. Preferably, the FcγRIIB-specific antibody of the invention does not bind the amino acid sequence SDPNFSI (SEQ ID NO:59), corresponding to amino acid positions 176 to 182 of the FcγRIIB2 isoform (SEQ ID NO:60).

```
SEQ ID NO: 60:
MGILSFLPVL ATESDWADCK SPQPWGHMLL WTAVLFLAPV AGTPAPPKAV    50

LKLEPQWINV LQEDSVTLTC RGTHSPESDS IQWFHNGNLI PTHTQPSYRF   100

KANNNDSGEY TCQTGQTSLS DPVHLTVLSE WLVLQTPHLE FQEGETIVLR   150

CHSWKDKPLV KVTFFQNGKS KKFSRSDPNF SIPQANHSHS GDYHCTGNIG   200

YTLYSSKPVT ITVQAPSSSP MGIIAVVTG IAVAAIVAAV VALIYCRKKR   250

ISANPTNPDE ADKVGAENTI TYSLLMHPDA LEEPDDQNRI              290
```

The invention relates to an isolated antibody or a fragment thereof that specifically binds FcγRIIB with a greater affinity than said antibody or a fragment thereof binds FcγRIIA, as determined by any standard method known in the art for assessing specificities. The invention relates to an isolated antibody or a fragment thereof that specifically binds FcγRIIB with a greater affinity than said antibody or a fragment thereof binds FcγRIIA, as determined, for example, by Western blot, BIAcore or radioimmunoassay. The invention relates to an isolated antibody, or a fragment thereof, that specifically binds FcγRIIB with a greater affinity than said antibody or a fragment thereof binds FcγRIIA, as determined in an ELISA assay, in the linear range for FcγRIIB binding. In one embodiment of the invention, the invention relates to an isolated antibody, or a fragment thereof, that specifically binds FcγRIIB, produced in either a bacterial or mammalian system, with a greater affinity than said antibody or a fragment thereof binds FcγRIIA, as determined in an ELISA assay.

In a particular embodiment, the invention relates to an isolated antibody or a fragment thereof that specifically binds FcγRIIB with a greater affinity than said antibody or a fragment thereof binds FcγRIIA, and the constant domain of said antibody further has an enhanced affinity for at least one or more Fc activation receptors. In yet another specific embodiment, said Fc activation receptor is FcγRIII.

In one embodiment of the invention, said antibody, or a fragment thereof, blocks the IgG binding site of FcγRIIB and blocks the binding of aggregated labeled IgGs to FcγRIIB in, for example, a blocking ELISA assay. In one particular embodiment, said antibody or a fragment thereof blocks the binding of aggregated labeled IgGs in an ELISA blocking assay by at least 50%, 60%, 70%, 80%, 90%, 95%, 99%, or 99.9%. In yet another particular embodiment, the antibody or a fragment thereof completely blocks the binding of said aggregated labeled IgG in said ELISA assay.

In another embodiment of the invention, said antibody or a fragment thereof blocks the IgG binding site of FcγRIIB and blocks the binding of aggregated labeled IgG to FcγRIIB, as determined by a double-staining FACS assay.

The invention encompasses the use of antibodies that modulate (i.e., agonize or antagonize) the activity of FcγRIIB. In one embodiment of the invention, the antibodies of the invention agonize at least one activity of FcγRIIB, i.e., elicit signaling. Although not intending to be bound by any mechanism of action, agonistic antibodies of the invention may mimic clustering of FcγRIIB leading to dampening of the activating response to FcγR ligation and inhibition of cellular responsiveness.

In another embodiment of the invention, the antibodies of the invention antagonize at least one activity of FcγRIIB, i.e., block signaling. For example, the antibodies of the invention block the binding of aggregated IgGs to FcγRIIB.

The invention provides antibodies that inhibit FcεRI-induced mast cell activation. The invention further provides anti-FcγRIIB antibodies that inhibit FcγRIIA-mediated macrophage activation in monocytic cells. The invention also provides anti-FcγRIIB antibodies that inhibit B-cell receptor mediated signaling.

In certain embodiments, the Fc region comprises at least one amino acid modification relative to a wild-type Fc region, such that the modified Fc region has an altered binding affinity to an Fc receptor. Preferably, the antibody or fragment thereof has an increased binding affinity to FcγRIIB or FcγRIII. Preferred amino acid modifications comprise a substitution at position 265 or 297. More preferably, the amino acid modification is a substitution at position 265 with alanine or a substitution at position 297 with glutamine.

In one particular embodiment, the anti-FcγRIIB antibodies block the ligand binding site of FcγRIIB. In a further specific embodiment, the blocking activity can block the negative regulation of immune-complex-triggered activation and consequently enhance the immune response. In a further specific embodiment, the enhanced immune response is an increase in antibody-dependent cellular response. In another specific embodiment, the anti-FcγRIIB antibodies of the invention block crosslinking of FcγRIIB receptors to B cell and/or Fc receptors, leading to B cell, mast cell, dendritic cell, or macrophage activation.

The present invention encompasses methods for the production of antibodies of the invention or fragments thereof, particularly for the production of novel monoclonal antibodies with specificities for FcγRIIB relative to FcγRIIA. The antibodies of the invention or fragments thereof can be produced by any method known in the art for the production of antibodies, in particular, by secretion from cultured hybridoma cells, chemical synthesis or by recombinant expression techniques known in the art. In one specific embodiment, the invention relates to a method for recombinantly producing a FcγRIIB-specific antibody, said method comprising:
 (i) culturing under conditions suitable for the expression of said antibody in a medium, a host cell containing a first nucleic acid molecule, operably linked to a heterologous promoter, and a second nucleic acid operably linked to the same or a different heterologous promoter, said first nucleic acid and second nucleic acid encoding a heavy chain and a light chain, respectively, of an antibody or a fragment thereof that specifically binds FcγRIIB with greater affinity than said antibody or a fragment thereof binds FcγRIIA; and
 (ii) recovery of said antibody from said medium.

In another embodiment, the invention provides a method for producing FcγRIIB monoclonal antibodies that specifically bind FcγRIIB, particularly human FcγRIIB, with a greater affinity than said monoclonal antibodies bind FcγRIIA, particularly human FcγRIIA, said method comprising:
 (A) immunizing one or more FcγRIIA transgenic mice with purified FcγRIIB or an immunogenic fragment thereof;
 (B) producing hybridoma cells lines from spleen cells of said one or more mice; and
 (C) screening said hybridoma cell lines for one or more hybridoma cell lines that produce antibodies that specifically bind FcγRIIB with a greater affinity than the antibodies bind FcγRIIA.

The invention encompasses any antibody produced by said method.

In one specific embodiment, the invention provides a method for producing FcγRIIB monoclonal antibodies that specifically bind FcγRIIB, particularly human FcγRIIB, with a greater affinity than said monoclonal antibodies bind FcγRIIA, particularly human FcγRIIA, said method comprising:
 (A) immunizing one or more FcγRIIA transgenic mice with purified FcγRIIB or an immunogenic fragment thereof;
 (B) booster immunizing said mice for a time sufficient to elicit an immune response;
 (C) producing hybridoma cells lines from spleen cells of said one or more mice; and
 (D) screening said hybridoma cell lines for one or more hybridoma cell lines that produce antibodies that specifically bind FcγRIIB with a greater affinity than the antibodies bind FcγRIIA.

In a preferred embodiment, said mice are booster immunized at least four times over a period of four months. In one embodiment of the invention, said mice are immunized with purified FcγRIIB, which has been mixed with adjuvants known in the art to enhance immune response in said mice. In one particular embodiment of the invention, said immunogenic fragment is the soluble extracellular domain of FcγRIIB. The hybridoma cell lines can be screened using standard techniques known in the art (e.g., ELISA).

In certain embodiments of the invention, the anti-FcγRIIB antibodies are monoclonal antibodies, synthetic antibodies, recombinantly produced antibodies, multispecific antibodies, human antibodies, chimeric antibodies, camelized antibodies, single-chain Fvs (scFv), single chain antibodies, Fab fragments, F(ab') fragments, disulfide-linked Fvs (sdFv), intrabodies, or epitope-binding fragments of any of the above.

Preferably, the antibodies of the invention are monoclonal antibodies, and more preferably, humanized or human antibodies. In one specific preferred embodiment, the antibodies of the invention bind to the extracellular domain of human FcγRIIB, particularly native human FcγRIIB. In another specific embodiment, the antibodies of the invention specifically or selectively recognize one or more epitopes of FcγRIIB, particularly native human FcγRIIB. Another embodiment of the invention encompasses the use of phage display technology to increase the affinity of the antibodies of the invention for FcγRIIB. Any screening method known in the art can be used to identify mutant antibodies with increased avidity for FcγRIIB (e.g., ELISA). In another specific embodiment, antibodies of the invention are screened using antibody screening assays well known in the art (e.g., BIACORE assays) to identify antibodies with $K_{off}$ rate less than $3\times10-3\ s^{-1}$.

In a preferred embodiment, the invention provides a monoclonal antibody produced by clone 2B6 or 3H7, having ATCC accession numbers PTA-4591 and PTA-4592, respectively, or chimeric, humanized or other engineered versions thereof. In another preferred embodiment, the invention provides a monoclonal antibody produced by clone 1D5, 2E1, 2H9, 2D11, and 1F2 having ATCC Accession numbers, PTA-5958, PTA-5961, PTA-5962, PTA-5960, and PTA-5959, respectively, or chimeric, humanized or other engineered versions thereof. In another embodiment, the invention provides an isolated antibody, or a fragment thereof, that competes for binding with the monoclonal antibody produced by clone 2B6 or 3H7 and binds FcγRIIB, preferably native human FcγRIIB with a greater affinity than said antibody or a fragment thereof binds FcγRIIA, preferably native human FcγRIIA and/or binds to the same epitope of FcγRIIB as the monoclonal antibody produced from clone 2B6 or 3H7 and binds FcγRIIB with a greater affinity than said antibody or a fragment thereof binds FcγRIIA. Furthermore, the invention provides hybridoma cell line 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively. In one specific embodiment, the invention provides the use of a 2B6, 3H7, 1D5, 2E1, 2H9, 2D11, or 1F2 antibody, or chimeric, humanized or other engineered versions thereof, to prevent, treat, manage or ameliorate a B-cell malignancy, or one or more symptoms thereof. In one particular embodiment, an engineered version comprises one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof. In a preferred embodiment, a humanized 2B6 comprises a heavy chain variable domain having the following amino acid sequence:

```
SEQ ID NO: 24:
QVQLVQSGAE VKKPGASVKV SCKASGYTFT NYWIHWVRQA PGQGLEWMGV      50

IDPSDTYPNY NKKFKGRVTM TTDTSTSTAY MELRSLRSDD TAVYYCARNG     100

DSDYYSGMDY WGQGTTVTVS S;                                   121
``` and a light chain variable domain having the amino acid sequence of:

```
SEQ ID NO: 18:
EIVLTQSPDF QSVTPKEKVT ITCRTSQSIG TNIHWYQQKP DQSPKLLIKN      50

VSESISGVPS RFSGSGSGTD FTLTINSLEA EDAATYYCQQ SNTWPFTFGG     100

GTKVEIK;                                                   107
``` or a light chain variable domain having the amino acid sequence of:

```
SEQ ID NO: 20:
EIVLTQSPDF QSVTPKEKVT ITCRTSQSIG TNIHWYQQKP DQSPKLLIKY      50

VSESISGVPS RFSGSGSGTD FTLTINSLEA EDAATYYCQQ SNTWPFTFGG     100

GTKVEIK;                                                   107
``` or a light chain variable region having the amino acid sequence of:

```
SEQ ID NO: 22:
EIVLTQSPDF QSVTPKEKVT ITCRTSQSIG TNIHWYQQKP DQSPKLLTKY      50

ASESISGVPS RFSGSGSGTD FTLTINSLEA EDAATYCQQS NTWPFTFGGG     100

TKVEIK;                                                    106
```

In another preferred embodiment, the Fc domain of the heavy chain of the humanized 2B6 or humanized 3H7 antibody is engineered to comprise at least one amino acid substitution at position 240, 243, 247, 255, 270, 292, 300, 316, 370, 392, 396, 416, 419, or 421 with another amino acid at that position. In a more preferred embodiment, the Fc domain of the heavy chain of the humanized 2B6 has:
(1) a leucine at position 247, a lysine at position 421, a glutamic acid at position 270, a threonine at position 392, a leucine at position 396 and a glutamic acid at position 270; or
(2) a glutamic acid at position 270, an aspartic acid at position 316 and a glycine at position 416.

In certain embodiments of the invention, the antibody is not a monoclonal antibody produced by clone 2B6 or 3H7, or chimeric, humanized or other engineered versions thereof.

In certain embodiments of the invention, humanized 2B6 antibodies are provided, said humanized 2B6 antibodies comprising a heavy chain variable domain having the amino acid sequence of SEQ ID NO:24 and a light chain variable domain having the amino acid sequence of SEQ ID NO:20, wherein the Fc domain of the heavy chain of the humanized 2B6 has:
(1) a leucine at position 247, a lysine at position 421, a glutamic acid at position 270, a threonine at position 392, a leucine at position 396 and a glutamic acid at position 270; or
(2) a glutamic acid at position 270, an aspartic acid at position 316 and a glycine at position 416.

The invention also encompasses polynucleotides that encode the antibodies of the invention. In one embodiment, the invention provides an isolated nucleic acid sequence encoding a heavy chain or a light chain of an antibody or a fragment thereof that specifically binds FcγRIIB with greater affinity than said antibody or a fragment thereof binds FcγRIIA. The invention also relates to a vector comprising said nucleic acid. The invention further provides a vector comprising a first nucleic acid molecule encoding a heavy chain and a second nucleic acid molecule encoding a light chain, said heavy chain and light chain being of an antibody or a fragment thereof that specifically binds FcγRIIB with greater affinity than said antibody or a fragment thereof binds FcγRIIA. In one specific embodiment, said vector is an expression vector. The invention further provides host cells containing the vectors of or polynucleotides encoding the antibodies of the invention. Preferably, the invention encompasses polynucleotides encoding heavy and light chains of the antibodies produced by the deposited hybridoma clones, 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively, or portions thereof, e.g., CDRs, variable domains, and humanized versions thereof, etc.

The invention encompasses the use of the antibodies of the invention to detect the presence of FcγRIIB specifically (i.e., FcγRIIB and not FcγRIIA) in a biological sample.

Activating and inhibitory Fc receptors, e.g., FcγRIIA and FcγRIIB, are critical for the balanced function of these receptors and proper cellular immune responses. The invention encompasses the use of the antibodies of the invention for the treatment of any disease related to loss of such balance and regulated control in the Fc receptor signaling pathway. Thus, the FcγRIIB antibodies of the invention have uses in regulating the immune response, e.g., in inhibiting immune response in connection with autoimmune or inflammatory disease, or allergic response. The FcγRIIB antibodies of the invention can also be used to alter certain effector functions to enhance, for example, therapeutic antibody-mediated cytotoxicity.

The antibodies of the invention are useful for prevention or treatment of cancer, for example, in one embodiment, as a single agent therapy. In one embodiment of the invention, the antibodies of the invention are useful for prevention or treatment of B-cell malignancies, particularly non-Hodgkin's lymphoma or chronic lymphocytic leukemia. In a preferred embodiment, the antibodies of the invention are used for the treatment and/or prevention of melanoma. In another embodiment, the antibodies are useful for prevention or treatment of cancer, particularly in potentiating the cytotoxic activity of cancer antigen-specific therapeutic antibodies with cytotoxic activity to enhance tumor cell killing and/or enhancing antibody dependent cytotoxic cellular ("ADCC") activity, complement dependent cytotoxic ("CDC") activity, or phagocytosis of the therapeutic antibodies. The invention provides a method of treating cancer in a patient having a cancer characterized by a cancer antigen, said method comprising administering to said patient a therapeutically effective amount of a first antibody or a fragment thereof that specifically binds FcγRIIB with greater affinity than said antibody or a fragment thereof binds FcγRIIA, and a second antibody that specifically binds said cancer antigen and is cytotoxic. The invention also provides a method of treating cancer in a patient having a cancer characterized by a cancer antigen, said method comprising administering to said patient a therapeutically effective amount of an antibody or a fragment thereof that specifically binds FcγRIIB, particularly native human FcγRIIB with greater affinity than said antibody or a fragment thereof binds FcγRIIA, preferably native human FcγRIIA, and the constant domain of which further has an increased affinity for one or more Fc activation receptors, when the antibody is monomeric, such as FcγRIIIA, and an antibody that specifically binds said cancer antigen and is cytotoxic. In one particular embodiment, said Fc activation receptor is FcγRIIIA. In particular embodiments, the antibody of the invention is administered at a dose such that the antibody does not detectably bind to neutrophils.

The invention also provides a method of treating cancer in a patient having a cancer characterized by a cancer antigen, said method comprising administering to said patient a therapeutically effective amount of an antibody or a fragment thereof that specifically binds said cancer antigen and a therapeutically effective amount of an antibody or fragment thereof that specifically binds the extracellular domain of human FcγRIIB and blocks the Fc binding site of human FcγRIIB.

In another preferred embodiment of the invention, the antibodies of the invention are useful for prevention or treatment of B-cell malignancies, particularly non-Hodgkin's lymphoma or chronic lymphocytic leukemia. Accordingly, the present invention provides methods of treating, managing, preventing, or ameliorating a B-cell malignancy by administering, either alone or in combination with one or more other therapeutics, antibodies that specifically bind FcγRIIB, and, preferably, do not specifically bind FcγRIIA, as well as derivatives, analogs and antigen binding fragments of such antibodies. In particular embodiments, the cancer of the subject is refractory to one or more standard or experimental therapies, particularly, to RITUXAN® (rituximab) treatment. The methods of the invention may be used for the treatment, management, prevention, or amelioration of B-cell diseases, such as, B-cell chronic lymphocytic leukemia (B-CLL), non-Hodgkin's lymphoma, diffuse large B cell lymphoma, follicular lymphoma with areas of diffuse large B cell lymphoma, small lymphocytic lymphoma, mantle cell lymphoma, and diffuse small cleaved cell lymphoma.

In another embodiment, the invention provides for the use of a FcγRIIB-specific antibody conjugated to a therapeutic agent or drug. Examples of therapeutic agents that may be conjugated to an anti-FcγRIIB antibody or an antigen-binding fragment thereof include, but are not limited to, cytokines, toxins, radioactive elements, and antimetabolites.

In one embodiment, the invention provides for the use of an FcγRIIB-specific antibody in combination with a standard or experimental treatment regimen for B-cell malignancies (e.g., chemotherapy, radioimmunotherapy, or radiotherapy). Such combination therapy may enhance the efficacy of standard or experimental treatment. Examples of therapeutic agents that are particularly useful in combination with a FcγRIIB-specific antibody or an antigen-binding fragment thereof, for the prevention, treatment, management, or amelioration of B-cell malignancies, include, but are not limited to, RITUXAN® (rituximab), interferon-alpha, and anti-cancer agents. Chemotherapeutic agents that can be used in combination with an FcγRIIB-specific antibody or an antigen-binding fragment thereof, include, but are not limited to alkylating agents, antimetabolites, natural products, and hormones. The combination therapies of the invention enable lower dosages of an anti-FcγRIIB antibody or an antigen-binding fragment thereof and/or less frequent administration of anti-FcγRIIB antibody or an antigen-binding fragment thereof to a subject with a B-cell malignancy, to achieve a therapeutic or prophylactic effect.

In another embodiment, the use of an anti-FcγRIIB antibody or an antigen-binding fragment thereof prolongs the survival of a subject diagnosed with a B-cell malignancy.

In another embodiment, the invention provides a method of enhancing an antibody mediated cytotoxic effect in a subject being treated with a cytotoxic antibody, said method comprising administering to said patient an antibody of the invention or a fragment thereof, in an amount sufficient to enhance the cytotoxic effect of said cytotoxic antibody. In yet another embodiment, the invention provides a method of enhancing an antibody-mediated cytotoxic effect in a subject being treated with a cytotoxic antibody, said method comprising administering to said patient an antibody of the invention or a fragment thereof, further having an enhanced affinity for an Fc activation receptor, when monomeric, in an amount sufficient to enhance the cytotoxic effect of said cytotoxic antibody. In yet another embodiment, the invention provides a method further comprising the administration of one or more additional cancer therapies.

In yet another embodiment, the invention provides a method of regulating immune-complex mediated cell activation in a patient, said method comprising administering to said patient a therapeutically effective amount of an antibody or fragment thereof that specifically binds the extracellular domain of human FcγRIIB and blocks the Fc binding site of human FcγRIIB. In a preferred embodiment, administration of the antibody or fragment thereof results in an enhanced immune response, such as an increase in an antibody-dependent cellular response. In another preferred embodiment, the immune complex mediated cell activation is B cell activation, mast cell activation, dendritic cell activation or macrophage activation.

In another embodiment, the invention provides a method of breaking tolerance to an antigen in a patient, said method comprising administering to a patient in need thereof:
(A) an antigen-antibody complex comprising said antigen; and
(B) an antibody or fragment thereof that specifically binds the extracellular domain of human FcγRIIB and blocks the Fc binding site of human FcγRIIB, thereby breaking tolerance in said patient to said antigen.

The antibody or fragment thereof can be administered before, concurrently with, or after administration of said antigen-antibody complex.

The invention further provides a pharmaceutical composition comprising:
(i) a therapeutically effective amount of an antibody or fragment thereof that specifically binds the extracellular domain of human FcγRIIB and blocks the Fc binding site of human FcγRIIB;
(ii) a cytotoxic antibody that specifically binds a cancer antigen; and
(iii) a pharmaceutically acceptable carrier.

In a preferred embodiment, the antibody or fragment thereof is a human or humanized antibody. In another preferred embodiment, the antibody or fragment thereof that specifically binds the extracellular domain of human FcγRIIB and blocks the Fc binding site of human FcγRIIB blocks crosslinking of FcγRIIB to an Fc receptor. In yet another preferred embodiment, the antibody or fragment thereof that specifically binds the extracellular domain of human FcγRIIB and blocks the Fc binding site of human FcγRIIB comprises a Fc region comprising at least one amino acid modification relative to a wild-type Fc region, such that the modified Fc region has an altered binding affinity to a Fc receptor. In a preferred embodiment, the amino acid modification comprises a substitution at position 265 or 297, preferably a substitution at position 265 with alanine or a substitution at position 297 with glutamine. In certain embodiments, the cytotoxic antibody is HERCEPTIN® (trastuzumab), RITUXAN® rituximab, IC14, PANOREX® (edrecolomab), IMC-225, VITAXIN™, CAMPATH® (alemtuzumab) 1H/LDP-03, LYMPHOCIDE® (epratuzumab), or ZEVLIN® (ibritumomab tiuxetan).

The invention encompasses the use of the antibodies of the invention in combination with any therapeutic antibody that mediates its therapeutic effect through cell killing to potentiate the antibody's therapeutic activity. In one particular embodiment, the antibodies of the invention potentiate the antibody's therapeutic activity by enhancing antibody-mediated effector function. In another embodiment of the invention, the antibodies of the invention potentiate the cytotoxic antibody's therapeutic activity by enhancing phagocytosis and opsonization of the targeted tumor cells. In yet another embodiment of the invention, the antibodies of the invention potentiate the antibody's therapeutic activity by enhancing antibody-dependent cell-mediated cytotoxicity ("ADCC") in destruction of the targeted tumor cells. In certain embodiments, the antibodies of the invention are used in combination with Fc fusion proteins to enhance ADCC.

In some embodiments, the invention encompasses use of the antibodies of the invention in combination with a therapeutic antibody that does not mediate its therapeutic effect through cell killing to potentiate the antibody's therapeutic activity. In a specific embodiment, the invention encompasses use of the antibodies of the invention in combination with a therapeutic apoptosis inducing antibody with agonistic activity, e.g., anti-Fas antibody. Therapeutic apoptosis-inducing antibodies may be specific for any death receptor known in the art for the modulation of apoptotic pathway, e.g., TNFR receptor family member or a TRAIL family member.

The invention encompasses using the antibodies of the invention to block macrophage mediated tumor cell progression and metastasis. The antibodies of the invention are particularly useful in the treatment of solid tumors, where macrophage infiltration occurs. The antagonistic antibodies of the invention are particularly useful for controlling, e.g., reducing or eliminating, tumor cell metastasis, by reducing or eliminating the population of macrophages that are localized at the tumor site. The invention further encompasses antibodies that effectively deplete or eliminate immune effector cells other than macrophages that express FcγRIIB, e.g., dendritic cells. Effective depletion or elimination of immune effector cells using the antibodies of the invention may range from a reduction in population of the effector cells by 50%, 60%, 70%, 80%, preferably 90%, and most preferably 99%. In particular embodiments, the antibody of the invention is administered at a dose such that the antibody does not detectably bind to neutrophils.

In some embodiments, the agonistic antibodies of the invention are particularly useful for the treatment of tumors of non-hematopoietic origin, including tumors of melanoma cells.

In some embodiments, the invention encompasses use of the antibodies of the invention in combination with therapeutic antibodies that immunospecifically bind to tumor antigens that are not expressed on the tumor cells themselves, but rather on the surrounding reactive and tumor supporting, non-malignant cells comprising the tumor stroma. In a preferred embodiment, an antibody of the invention is used in combination with an antibody that immunospecifically binds a tumor antigen on a fibroblast cell, e.g., fibroblast activation protein (FAP).

The invention provides a method of treating an autoimmune disorder in a patient in need thereof, said method comprising administering to said patient a therapeutically effective amount of one or more antibodies of the invention. The invention also provides a method of treating an autoimmune disorder in a patient in need thereof, said method further comprising administering to said patient a therapeutically effective amount of one or more anti-inflammatory agents, and/or one or more immunomodulatory agents.

The invention also provides a method of treating an inflammatory disorder in a patient in need thereof, said method comprising administering to said patient a therapeutically effective amount of one or more antibodies of the invention. The invention also provides a method of treating an inflammatory disorder in a patient in need thereof, said method further comprising administering to said patient a therapeutically effective amount of one or more anti-inflammatory agents, and/or one or more immunomodulatory agents.

The invention provides a method of enhancing an immune response to a vaccine composition in a subject, said method comprising administering to said subject an antibody or an antigen-binding fragment thereof that specifically binds FcγRIIB with greater affinity than said antibody or a fragment thereof binds FcγRIIA, and a vaccine composition, such that said antibody or a fragment thereof is administered in an amount effective to enhance the immune response to said vaccine composition in said subject. The antibodies of the invention may be used to enhance a humoral and/or cell mediated response against the antigen(s) of the vaccine composition. The antibodies of the invention may be used in combination with any vaccines known in the art. The invention encompasses the use of the antibodies of the invention to either prevent or treat a particular disorder, where an enhanced immune response against a particular antigen or antigens is effective to treat or prevent the disease or disorder.

The invention further provides a method for treating or preventing an IgE-mediated allergic disorder in a patient in need thereof, comprising administering to said patient a therapeutically effective amount of the agonistic antibodies of the invention. The invention also provides a method for treating or preventing an IgE-mediated allergic disorder in a patient in need thereof, comprising administering to said patient the antibodies of the invention in combination with other therapeutic antibodies or vaccine compositions used for the treatment or prevention of IgE-mediated allergic disorders.

The invention also provides a method for enhancing immune therapy for an infectious agent wherein the antibodies of the invention are administered to a patient that is already infected by a pathogen, such as HIV, HCV or HSV, to enhance opsonization and phagocytosis of infected cells.

The invention provides a method of treating diseases with impaired apoptotic mediated signaling, e.g., cancer, autoimmune disease. In a specific embodiment, the invention encompasses a method of treating a disease with deficient Fas-mediated apoptosis, said method comprising administering an antibody of the invention in combination with an anti-Fas antibody.

In another embodiment, the invention provides a method of diagnosis of an autoimmune disease in a subject comprising:
(i) contacting a biological sample from said subject with an effective amount of an antibody of the invention; and
(ii) detecting binding of said antibody or a fragment thereof, wherein detection of said detectable marker above a background or standard level indicates that said subject has an autoimmune disease.

The invention further provides a pharmaceutical composition comprising:
(A) a therapeutically effective amount of the antibody or a fragment thereof that specifically binds FcγRIIB with greater affinity than said antibody or a fragment thereof binds FcγRIIA; and
(B) a pharmaceutically acceptable carrier.

The invention additionally provides a pharmaceutical composition comprising:
(A) a therapeutically effective amount of the antibody or fragment thereof that specifically binds FcγRIIB with greater affinity than said antibody or fragment thereof binds FcγRIIA;
(B) a cytotoxic antibody that specifically binds a cancer antigen; and
(C) a pharmaceutically acceptable carrier.

In certain embodiments of the invention, pharmaceutical compositions are provided for use in accordance with the methods of the invention, said pharmaceutical compositions comprising an anti-FcγRIIB antibody or an antigen-binding fragment thereof, in an amount effective to prevent, treat, manage, or ameliorate a B-cell malignancy, or one or more symptoms thereof, and a pharmaceutically acceptable carrier. The invention also provides pharmaceutical compositions for use in accordance with the methods of the invention, said pharmaceutical compositions comprising an anti-FcγRIIB antibody or an antigen-binding fragment thereof, a prophylactic or therapeutic agent other than a FcγRIIB antagonist, and a pharmaceutically acceptable carrier.

I. DEFINITIONS

As used herein, the term "specifically binds to FcγRIIB" and analogous terms refer to antibodies or fragments thereof (or any other FcγRIIB binding molecules) that specifically bind to FcγRIIB or a fragment thereof and do not specifically bind to other Fc receptors, in particular to FcγRIIA. Further, it is understood to one skilled in the art that an antibody that specifically binds to FcγRIIB may bind through the variable domain or the constant domain of the antibody. If the antibody that specifically binds to FcγRIIB binds through its variable domain, it is understood to one skilled in the art that it is not aggregated, i.e., is monomeric. An antibody that specifically binds to FcγRIIB may bind to other peptides or polypeptides with lower affinity as determined by, e.g., immunoassays, BIAcore, or other assays known in the art. Preferably, antibodies or fragments that specifically bind to FcγRIIB or a fragment thereof do not cross-react with other antigens. Antibodies or fragments that specifically bind to FcγRIIB can be identified, for example, by immunoassays, BIAcore, or other techniques known to those of skill in the art. An antibody or a fragment thereof binds specifically to a FcγRIIB when it binds to FcγRIIB with higher affinity than to any cross-reactive antigen as determined using experimental techniques, such as western blots, radioimmunoassays (RIA) and enzyme-linked immunosorbent assays (ELISAs). See, e.g., FUNDAMENTAL IMMUNOLOGY $2^{nd}$ Edition, (1989) Paul, ed., Raven Press, New York, at pages 332-336 for a discussion regarding antibody specificity.

As used herein, the term "native FcγRIIB" refers to FcγRIIB that is endogenously expressed and present on the surface of a cell. In some embodiments, "native FcγRIIB" encompasses a protein that is recombinantly expressed in a mammalian cell. Preferably, the native FcγRIIB is not expressed in a bacterial cell, i.e., *E. coli*. Most preferably, the native FcγRIIB is not denatured, i.e., it is in its biologically active conformation.

As used herein, the term "native FcγRIIA" refers to FcγRIIA that is endogenously expressed and present on the surface of a cell. In some embodiments, "native FcγRIIA" encompasses a protein that is recombinantly expressed in a mammalian cell. Preferably, the native FcγRIIA is not expressed in a bacterial cell, i.e., *E. coli*. Most preferably, the native FcγRIIA is not denatured, i.e., it is in its biologically active conformation.

As used herein, the term "analog" in the context of proteinaceous agents (e.g., proteins, polypeptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following:

(A) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent;

(B) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (C) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent.

A proteinaceous agent with similar structure to a second proteinaceous agent refers to a proteinaceous agent that has a similar secondary, tertiary or quaternary structure to the second proteinaceous agent. The structure of a polypeptide can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin et al. (1990) "*Methods For Assessing The Statistical Significance Of Molecular Sequence Features By Using General Scoring Schemes*," Proc. Natl. Acad. Sci. U.S.A. 87:2264-2268, modified as in Karlin et al. (1993) "*Applications And Statistics For Multiple High-Scoring Segments In Molecular Sequences*," Proc. Natl. Acad. Sci. U.S.A. 90:5873-5877. Such an algorithm is incorporated into the NBLAST and XBLAST programs of Altschul et al. (1990) "*Basic Local Alignment Search Tool*," J. Mol. Biol. 215:403-410. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al. (1997) "*Gapped BLAST And PSI-BLAST. A New Generation Of Protein Database Search Programs*," Nucleic Acids Res. 25:3389-3402. Alternatively, PSI-BLAST can be used to perform an iterated search that detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers et al. (1988) "*Optimal Alignments In Linear Space*," Comput. Appl. Biosci. 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous agent refers to a second organic or inorganic molecule which possesses a similar or identical function as a first organic or inorganic molecule and is structurally similar to the first organic or inorganic molecule.

As used herein, the terms "antagonist" and "antagonists" refer to any protein, polypeptide, peptide, antibody, antibody fragment, large molecule, or small molecule (less than 10 kD) that blocks, inhibits, reduces or neutralizes a function, activity and/or expression of another molecule, such as that of FcγRIIB. In various embodiments, an antagonist reduces a function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

As used herein, the terms "antibody" and "antibodies" refer to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the terms "B-cell malignancies" and "B-cell malignancy" refer to any B-cell lymphoproliferative disorder. B-cell malignancies include tumors of B-cell origin. B-cell malignancies include, but are not limited to, lymphomas, chronic lymphocytic leukemias, acute lymphoblastic leukemias, multiple myeloma, Hodgkin's and non-Hodgkin's disease, diffuse large B cell lymphoma, follicular lymphoma with areas of diffuse large B cell lymphoma, small lymphocytic lymphoma, mantle cell lymphoma, and diffuse small cleaved cell lymphoma.

As used herein, the term "cancer" refers to a neoplasm or tumor resulting from abnormal uncontrolled growth of cells. As used herein, cancer explicitly includes leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen.

As used herein, the term "derivative" in the context of polypeptides or proteins, including antibodies, refers to a polypeptide or protein that comprises an amino acid sequence that has been altered by the introduction of amino acid residue substitutions, deletions or additions. The term "derivative" as used herein also refers to a polypeptide or protein that has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

The term "derivative" as used herein, in conjunction with FcγRIIB refers to a polypeptide that comprises an amino acid sequence of a FcγRIIB polypeptide, a fragment of a FcγRIIB polypeptide, an antibody that immunospecifically binds to a FcγRIIB polypeptide, or an antibody fragment that immunospecifically binds to a FcγRIIB polypeptide, that has been altered by the introduction of amino acid residue substitutions, deletions or additions (i.e., mutations). In some embodiments, an antibody derivative or fragment thereof comprises amino acid residue substitutions, deletions or additions in one or more CDRs. The antibody derivative may have substantially the same binding, better binding, or worse binding when compared to a non-derivative antibody. In specific embodiments, one, two, three, four, or five amino acid residues of the CDR have been substituted, deleted or added (i.e., mutated). The term "derivative" as used herein, in conjunction with FcγRIIB also refers to a FcγRIIB polypeptide, a fragment of a FcγRIIB polypeptide, an antibody that immunospecifically binds to a FcγRIIB polypeptide, or an antibody fragment that immunospecifically binds to a FcγRIIB polypeptide which has been modified, i.e., by the covalent attachment of any type of molecule to the polypeptide. For example, but not by way of limitation, a FcγRIIB polypeptide, a fragment of a FcγRIIB polypeptide, an antibody, or antibody fragment may be modified, e.g., by glycosylation, acetylation, pegylation, phosphorylation, amidation, derivatization by known protecting/blocking groups, proteolytic cleavage, linkage to a cellular ligand or other protein, etc. A derivative of an FcγRIIB polypeptide, a fragment of an FcγRIIB polypeptide, an antibody, or antibody fragment may be modified by chemical modifications using techniques known to those of skill in the art, including, but not limited to, specific chemical cleavage, acetylation, formulation, metabolic synthesis of tunicamycin, etc. Further, a derivative of an FcγRIIB polypeptide, a fragment of an FcγRIIB polypeptide, an antibody, or antibody fragment may contain one or more non-classical amino acids. In one embodiment, a derivative of an FcγRIIB polypeptide, a fragment of an FcγRIIB polypeptide, an antibody, or antibody fragment possesses a similar or identical function as the parent antibody, or antibody fragment described herein. In another embodiment, a derivative of an FcγRIIB polypeptide, a fragment of an FcγRIIB polypeptide, an antibody, or antibody fragment has an altered activity when compared to an unaltered antibody. For example, a derivative antibody or fragment thereof can bind to its epitope more tightly or be more resistant to proteolysis.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "epitope" refers to a fragment of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide. Preferably, antibody fragments are epitope binding fragments.

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody, because the entire variable region of a chimeric antibody is non-human. One says that the donor antibody has been "humanized", by the process of "humanization", because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan (1991) "*A Possible Procedure For Reducing The Immunogenicity Of Antibody Variable Domains While Preserving Their Ligand-Binding Properties*," Molecular Immunology 28(4/5):489-498; Studnicka et al. (1994) "*Human-Engineered Monoclonal Antibodies Retain Full Specific Binding Activity By Preserving Non-CDR Complementarity-Modulating Residues*," Protein Engineering 7(6):805-814; Roguska et al. (1994) "*Humanization Of Murine Monoclonal Antibodies Through Variable Domain Resurfacing*," Proc. Nat. Acad. Sci. 91:969-973; Tan et al. (2002) "'*Superhumanized' Antibodies: Reduction Of Immunogenic Potential By Complementarity-Determining Region Grafting With Human Germ line Sequences: Application To An Anti-CD28*," J. Immunol. 169:1119-1125; Caldas et al. (2000) "*Design And Synthesis Of Germ line-Based Hemi-Humanized Single-Chain Fv Against The CD18 Surface Antigen*," Protein Eng. 13:353-360; Morea et al. (2000) "*Antibody Modeling: Implications For Engineering And Design*," Methods 20:267-279; Baca et al. (1997) "*Antibody Humanization Using Monovalent Phage Display*," J. Biol. Chem. 272: 10678-10684; Roguska et al. (1996) "*A Comparison Of Two Murine Monoclonal Antibodies Humanized By CDR-Grafting And Variable Domain Resurfacing*," Protein Eng. 9:895-904; Couto et al. (1995) "*Designing Human Consensus Antibodies With Minimal Positional Templates*," Cancer Res. 55 (23 Supp):5973s-5977s; Couto et al. (1995) "*Anti-BA46*

*Monoclonal Antibody Mc3: Humanization Using A Novel Positional Consensus And In Vivo And In Vitro Characterization,*" Cancer Res. 55:1717-1722; Sandhu (1994) "*A Rapid Procedure For The Humanization Of Monoclonal Antibodies,*" Gene 150:409-410; Pedersen et al. (1994) "*Comparison Of Surface Accessible Residues In Human And Murine Immunoglobulin Fv Domains: Implication For Humanization Of Murine Antibodies,*" J. Mol. Biol. 235:959-973; Jones et al. (1986) "*Replacing The Complementarity-Determining Regions In A Human Antibody With Those From A Mouse,*" Nature 321:522-525; Riechmann et al. (1988) "*Reshaping Human Antibodies For Therapy,*" Nature 332:323-327; and Presta (1992) "*Antibody Engineering,*" Curr. Op. Biotech. 3:394-398.

As used herein, the term "hypervariable region" refers to the amino acid residues of an antibody that are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, $5^{th}$ Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia et al. (1987) "*Canonical Structures For The Hypervariable Regions Of Immunoglobulins,*" J. Mol. Biol. 196:901-917). CDR residues for Eph099B-208.261 and Eph099B-233.152 are listed in Table 1 of WO/2003/094859. "Framework Region" or "FR" residues are those variable domain residues other than the hypervariable region residues as herein defined.

As used herein, the term "immunomodulatory agent" and variations thereof including, but not limited to, immunomodulatory agents, refer to an agent that modulates a host's immune system. In certain embodiments, an immunomodulatory agent is an immunosuppressant agent. In certain other embodiments, an immunomodulatory agent is an immunostimulatory agent. Immunomodulatory agents include, but are not limited to, small molecules, peptides, polypeptides, fusion proteins, antibodies, inorganic molecules, mimetic agents, and organic molecules.

As used herein, the terms "manage," "managing" and "management" refer to the beneficial effects that a subject derives from administration of a prophylactic or therapeutic agent, which does not result in a cure of disease. In certain embodiments, a subject is administered one or more prophylactic or therapeutic agents to "manage" a disease so as to prevent the progression or worsening of the disease.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the terms "prevent", "preventing" and "prevention" refer to the prevention of occurrence and/or recurrence or onset of one or more symptoms of a disorder in a subject resulting from the administration of prophylactic or therapeutic agent.

As used herein, the terms "prophylactic agent" and "prophylactic agents" refer to any agent(s) that can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease. Used in connection with an amount of an FcγRIIB antibody of the invention, the term can encompass an amount that improves overall prophylaxis or enhances the prophylactic efficacy of or synergies with another prophylactic agent, such as but not limited to a therapeutic antibody. In certain embodiments, the term "prophylactic agent" refers to an agonistic FcγRIIB-specific antibody. In other embodiments, the term "prophylactic agent" refers to an antagonistic FcγRIIB-specific antibody. In certain other embodiments, the term "prophylactic agent" refers to cancer chemotherapeutics, radiation therapy, hormonal therapy, biological therapy (e.g., immunotherapy), and/or FcγRIIB antibodies of the invention. In other embodiments, more than one prophylactic agent may be administered in combination.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful uncomfortable or risky. Side effects from chemotherapy include, but are not limited to, gastrointestinal toxicity such as, but not limited to, early and late-forming diarrhea and flatulence, nausea, vomiting, anorexia, leukopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art, see, e.g., the PHYSICIANS' DESK REFERENCE ($56^{th}$ ed., 2002), which is incorporated herein by reference in its entirety.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains that enables the scFv to form the desired structure for antigen binding. For a review of sFv, see Pluckthun in THE PHARMACOLOGY OF MONOCLONAL ANTIBODIES, vol. 113, (1994) Rosenburg and Moore eds., pp. 269-315. In specific embodiments, scFvs include bi-specific scFvs and humanized scFvs.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

As used herein, a "therapeutically effective amount" refers to that amount of the therapeutic agent sufficient to treat or manage a disease or disorder associated with FcγRIIB and any disease related to the loss of regulation in the Fc receptor signaling pathway or to enhance the therapeutic efficacy of another therapy, e.g., therapeutic antibody, vaccine therapy or prophylaxis, etc. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease. Used in connection with an amount of FcγRIIB antibody of the invention, the term can encompass an amount that improves overall therapy, reduces or avoids unwanted effects, or enhances the therapeutic efficacy of or synergies with another therapeutic agent.

As used herein, the terms "treat," "treating" and "treatment" refer to the eradication, reduction or amelioration of symptoms of a disease or disorder related to the loss of regulation in the Fc receptor signaling pathway or to enhance the therapeutic efficacy of another therapy, e.g., a therapeutic antibody, vaccine therapy or prophylaxis. In some embodiments, treatment refers to the eradication, removal, modification, or control of primary, regional, or metastatic cancer tissue that results from the administration of one or more therapeutic agents. In certain embodiments, such terms refer to the minimizing or delaying the spread of cancer resulting from the administration of one or more therapeutic agents to a subject with such a disease. In other embodiments, such terms refer to elimination of disease causing cells.

As used herein, the term "in combination" refers to the use of more than one prophylactic and/or therapeutic agents. The use of the term "in combination" does not restrict the order in which prophylactic and/or therapeutic agents are administered to a subject with a disorder, e.g., hyperproliferative cell disorder, especially cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to a disorder. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

II. BRIEF DESCRIPTION OF THE DRAWINGS

Figure 1B:
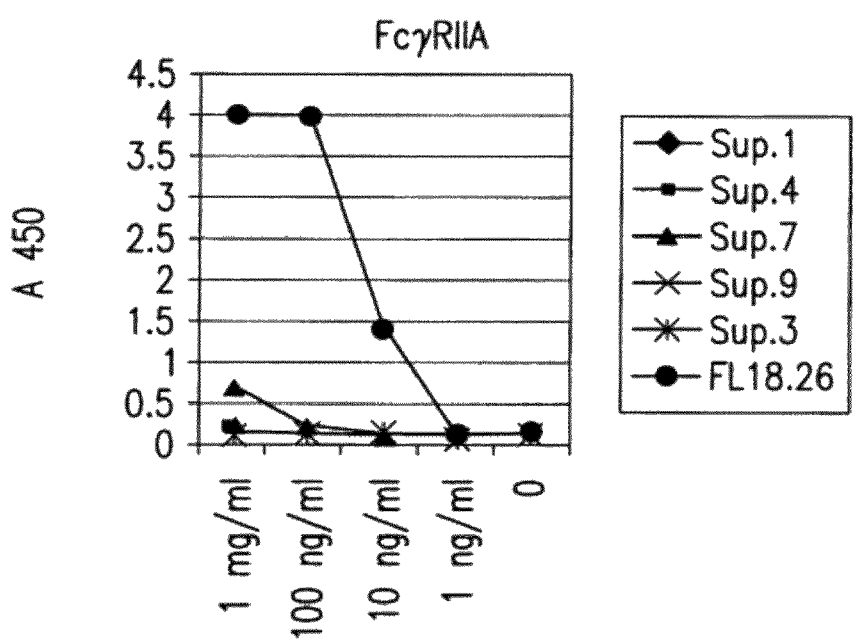

FIGS. 1A and 1B: Direct Binding of the Antibody Produced from the 3H7 Clone to FcγRIIB and FcγRIIA.

FIGS. 1A-1B: The direct binding of antibodies from some of the hybridoma cultures to the FcγRIIs were compared to a commercially available anti-FcγRII antibody in an ELISA assay where the plate was coated with the receptors. Different dilutions (1:10) of the supernatants were incubated on the plate. The bound antibodies were detected with a goat anti-mouse HRP conjugated antibody and the absorbance was monitored at 650 nm.

Figure 1C:
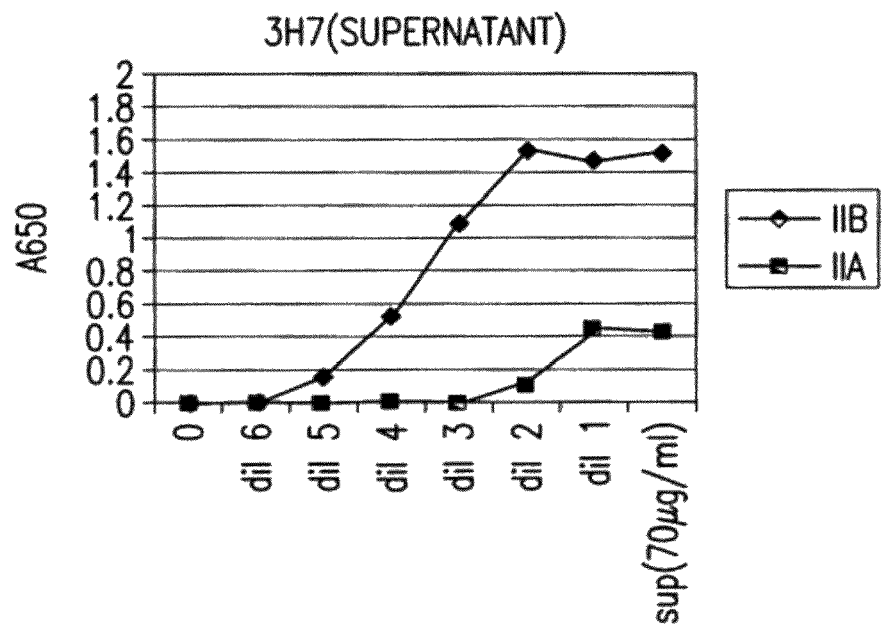
Figure 1D:
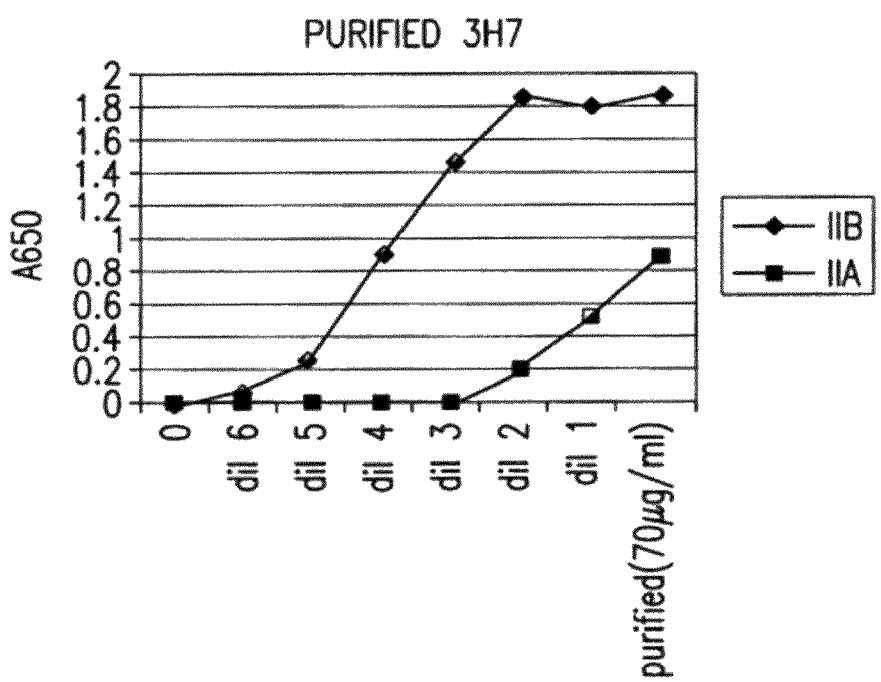

FIGS. 1C-1D: The direct binding of the antibody from the 3H7 hybridoma culture (supernatant n. 7 from the FIGS. 1A-B), in crude (FIG. 1C) and purified form (FIG. 1D), to FcγRIIA and FcγRIIB, were compared using the same ELISA assay as in 1A.

Figure 2:
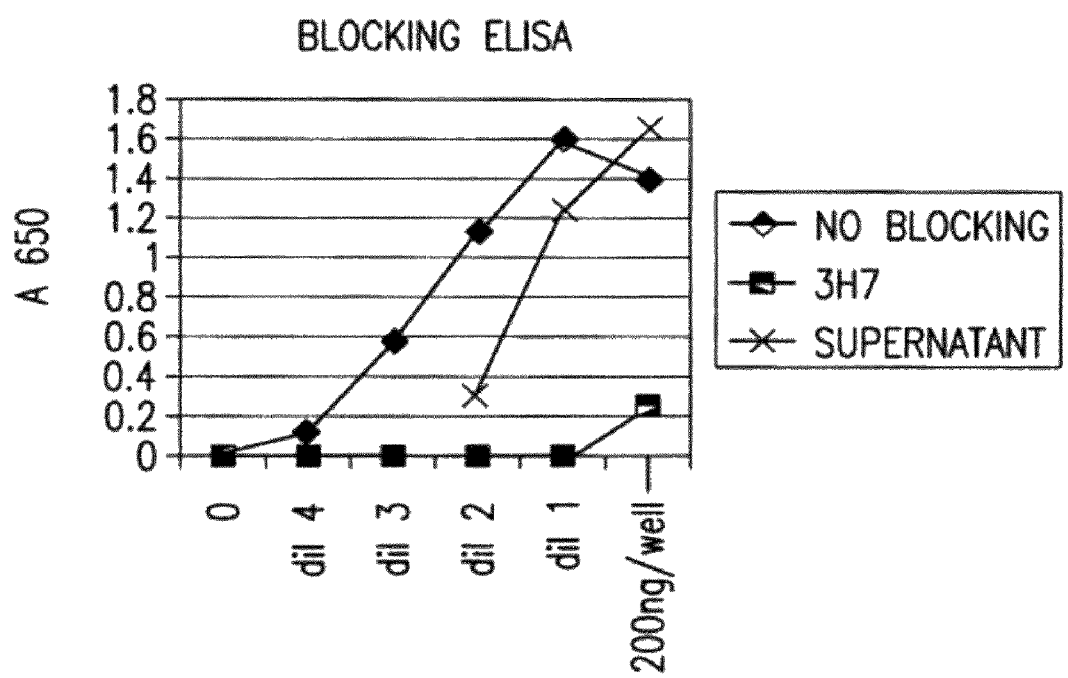

FIG. 2: Competition in Binding to FcγRIIB of the Antibody Produced from the 3H7 Hybridoma and Aggregated Biotinylated Human IgG.

The ability of the 3H7 antibody to compete with aggregated biotinylated human IgG for binding to FcγRIIB was measured using a blocking ELISA experiment. The ELISA plate coated with FcγRIIB was incubated with the supernatant containing the 3H7 antibody and with a supernatant from the same hybridoma cells but not containing antibody (negative control). Different dilutions (1:3) starting from 200 ng/well, of aggregated biotinylated human IgG were then added to the plate and the bound aggregates were detected with Streptavidin-Horse-Radish Peroxidase conjugated, the reaction was developed with TMB and the absorbance was monitored at 650 nm.

Figure 3:
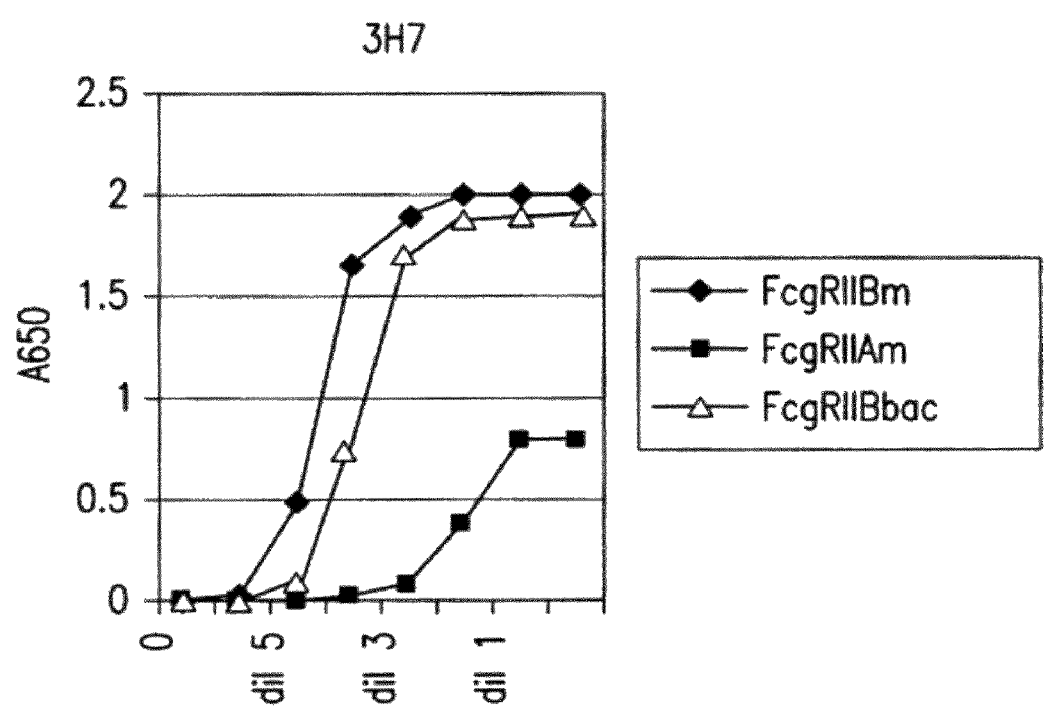

FIG. 3: Comparison of the Direct Binding of the 3H7 Antibody to FcγRIIB Produced in a Bacterial or in a Mammalian System.

Direct binding of the 3H7 antibody to FcγRIIB was measured using an ELISA assay. Binding to the bacterial or mammalian produced FcγRIIB was compared. The antibody titration started from the straight supernatant followed by 1:10 dilutions. The bound antibody was detected with a goat anti-mouse HRP conjugated antibody, the reaction was developed with TMB and the absorbance was monitored at 650 nm.

Figure 4:
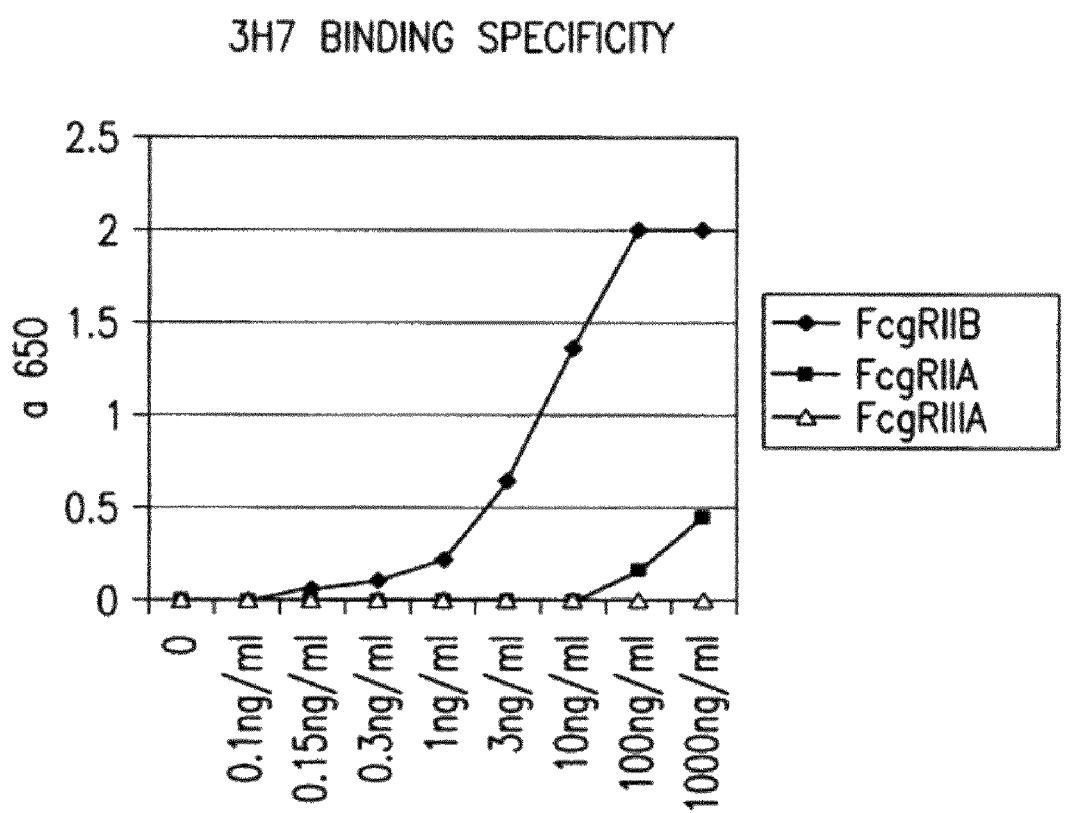

FIG. 4: Direct Binding of the 3H7 Antibody to FcγRIIA, FcγRIIB and FcγRIIIA.

The direct binding of the purified 3H7 antibody to FcγRIIA, FcγRIIB and FcγRIIIA expressed in a mammalian system were compared using the ELISA assay. ELISA plate was coated with the three receptors (100 ng/well). Different dilutions of the purified 3H7 antibody were incubated on the coated plate. A goat anti-mouse-HRP conjugated antibody was used for detection of the bound specific antibody, the reaction was developed with TMB and the absorbance was monitored at 650 nm.

Figure 5A:
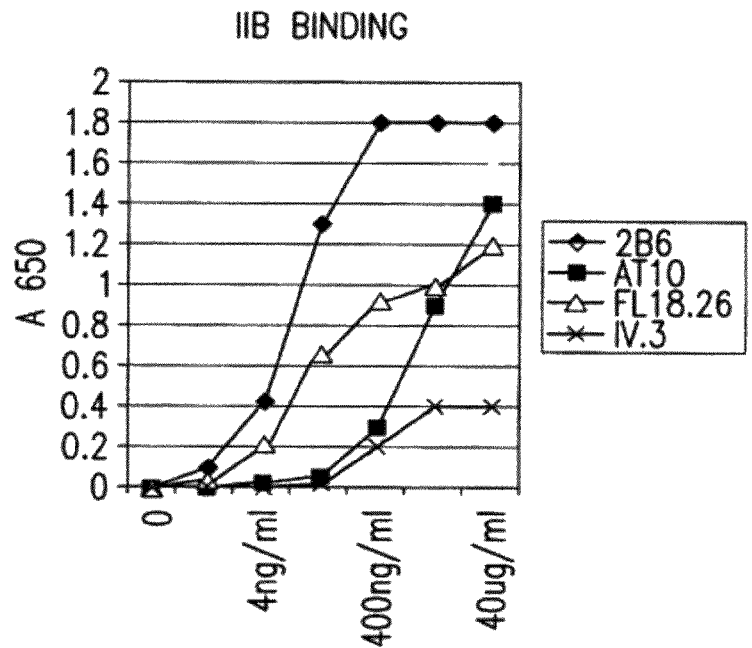
Figure 5B:
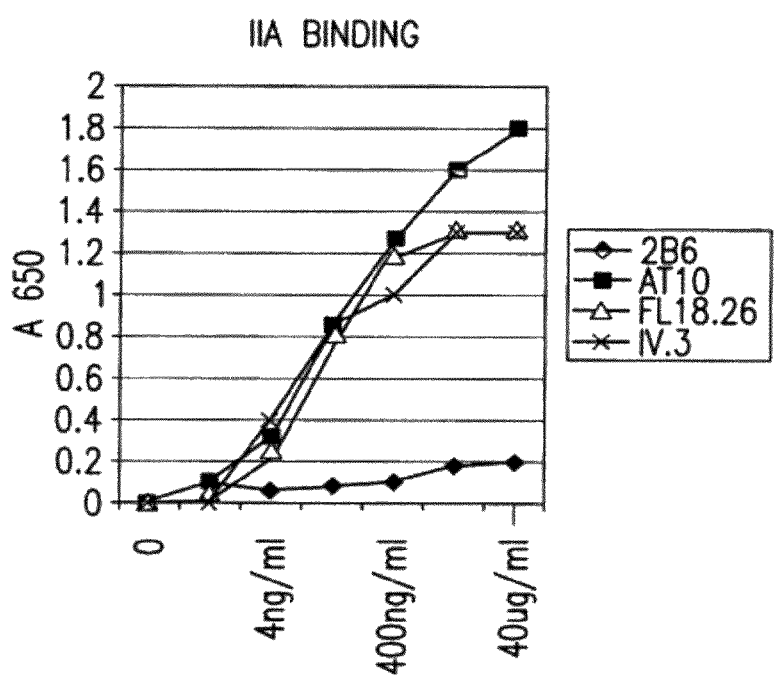
Figure 5C:
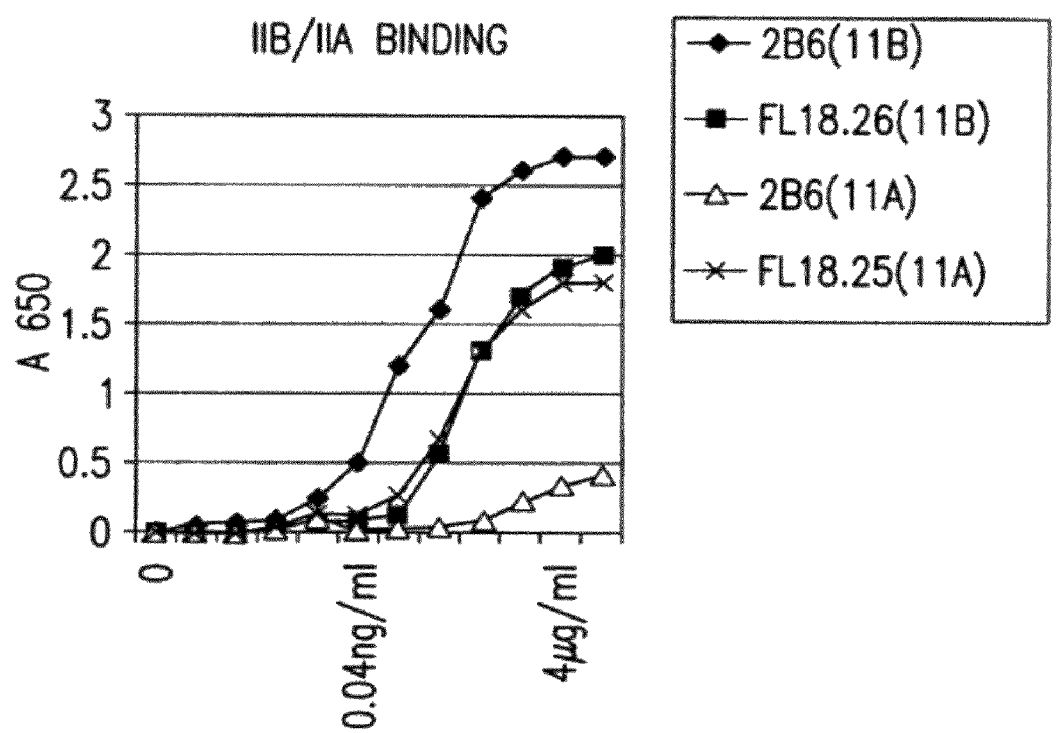

FIGS. 5A-5C: Comparison of the Direct Binding Ability to FcγRIIA and FcγRIIB of the Antibody Purified from Clone 2B6 Compared to Other Three Commercially Available Monoclonal Antibodies Against FcγRII.

The binding of 2B6 antibody to FcγRIIA (FIG. 5B) and FcγRIIB (FIG. 5A) is compared to that of three other commercially available antibodies raised against FcγRII. The ELISA format used is the same described in FIG. 4. FIG. 5C shows IIB/IIA binding of 2B6 and FL18.26.

Figure 6A:
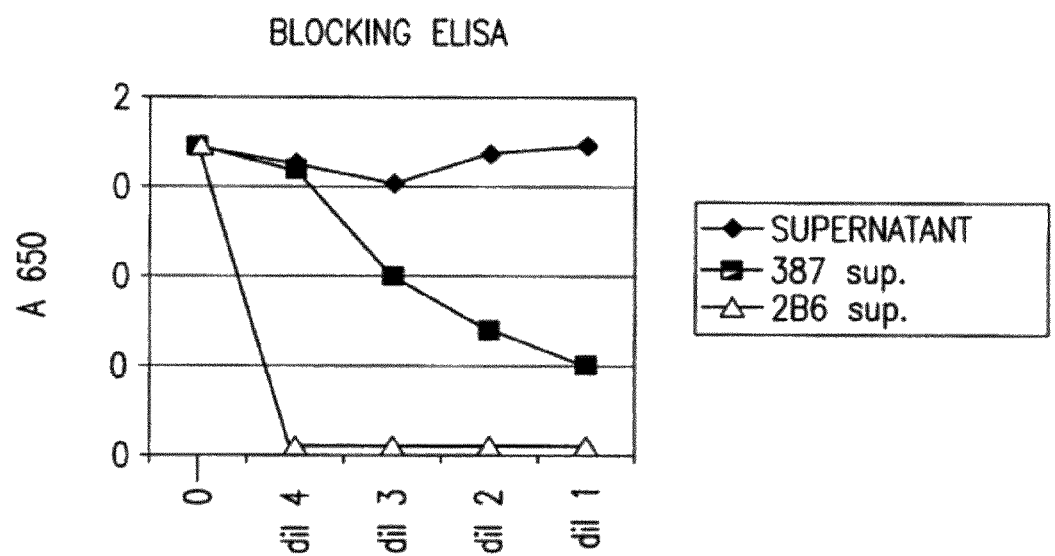
Figure 6B:
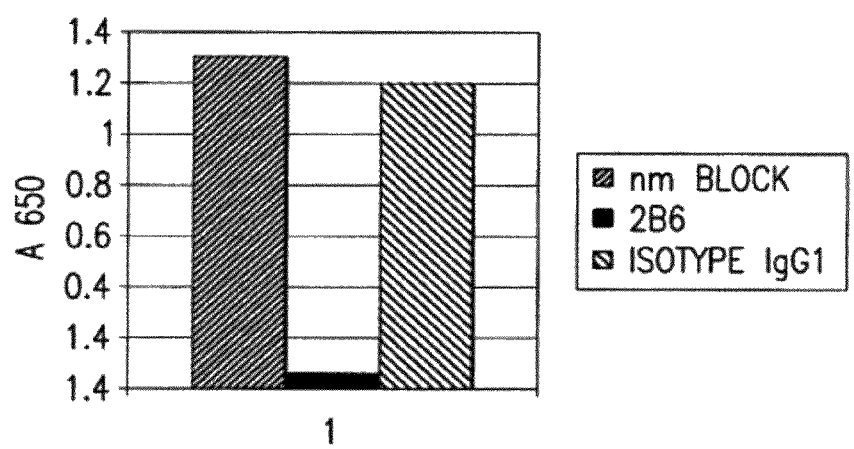

FIGS. 6A and 6B: Competition in Binding of the Antibody Produced from Clone 2B6 and Aggregated Biotinylated Human IgG to FcγRIIB.

FIG. 6A: The ability of the antibody present in the supernatant from the clone 2B6 to compete for binding to FcγRIIB with aggregated biotinylated human IgG was measured using a blocking ELISA experiment. The 2B6 antibody competition ability was compared to that of a negative supernatant from hybridoma and to that of 3H7 antibody.

An ELISA plate coated with FcγRIIB was incubated with different dilutions (1:10) of the supernatants. After washes the plate was incubated with a fixed amount of aggregated biotinylated human IgG (1 mg/well) and the bound aggregates were detected with Streptavidin-HRP conjugated. The reaction was developed with TMB and the absorbance was monitored at 650 nm.

FIG. 6B: The same blocking ELISA described in panel A was performed with purified 2B6 antibody and the data from one concentration of blocking antibody used (4 mg/well) were represented in a bar diagram. The 2B6 ability to block aggregated human IgG binding to FcγRIIB was compared to that of a mouse IgG1 isotype control.

Figure 7A:
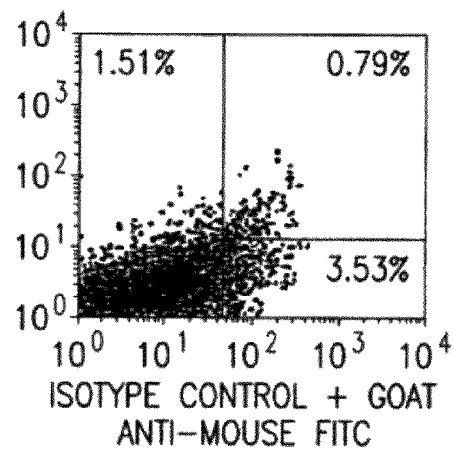
Figure 7B:
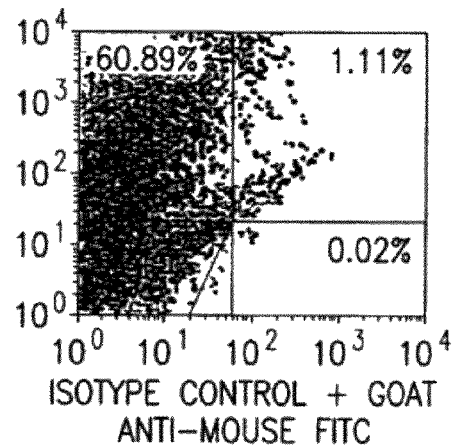
Figure 7C:
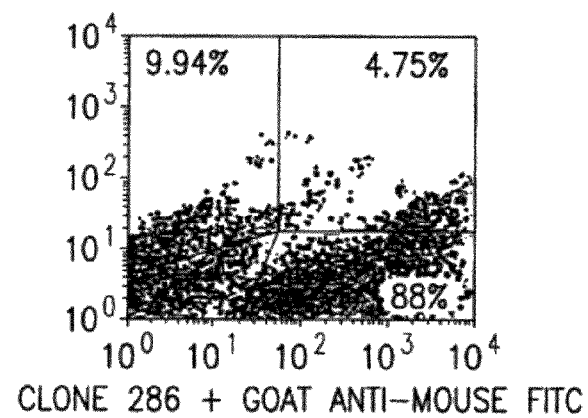

FIGS. 7A-7C: Competition of 2B6 antibody and aggregated biotinylated human IgG in binding to FcγRIIB using a double-staining FACS assay.

A double staining FACS assay was performed to characterize the 2B6 antibody using CHO-K1 cells that had been stably transfected with full-length mammalian FcγRIIB.

FIG. 7A: The transfectant cells were stained with mouse IgG1 isotype control followed by a goat anti-mouse-FITC conjugated antibody and Streptavidin-PE.

FIG. 7B: The transfectant cells were stained with aggregated biotinylated human IgG after being stained with mouse IgG1 isotype control and labeled with a goat anti-mouse-FITC conjugated antibody to detect the bound monoclonal antibody and with Streptavidin-PE conjugated to detect the bound aggregates.

FIG. 7C: The cells were stained with 2B6 antibody, the antibody was removed by washes and the cells were incubated with aggregated biotinylated human IgG. Cells were washed and labeled with a goat anti-mouse-FITC conjugated antibody to detect the bound monoclonal antibody and with Streptavidin-PE conjugated to detect the bound aggregates.

FIGS. 8A-8C: Biacore Analysis of 2B6 and KB6.1 Antibody Binding.

Binding of 2B6 antibody and KB6.1 antibody to surface linked CD32B (FIG. 8A), CD32A(H131) (FIG. 8B), and CD32A(R131) (FIG. 8C) were compared.

FIGS. 9A-9C: Monoclonal Anti FcγRIIB Antibodies and CD20 Co-Stain of Human B Lymphocytes.

Cells from human blood ("buffy coat") were stained with anti-CD20-FITC conjugated antibody, to select the B lymphocytes population, as well as 3H7 and 2B6. The bound anti-FcγRIIB antibodies were detected with a goat anti-mouse-PE conjugated antibody.

FIG. 9A. Cells were co-stained with anti-CD20-FITC antibody and mouse IgG1 isotype control.

FIG. 9B. Cells were co-stained with anti-CD20-FITC antibody and 3H7 antibody.

FIG. 9C. Cells were co-stained with anti-CD20-FITC antibody and 2B6 antibody.

Figure 10A:
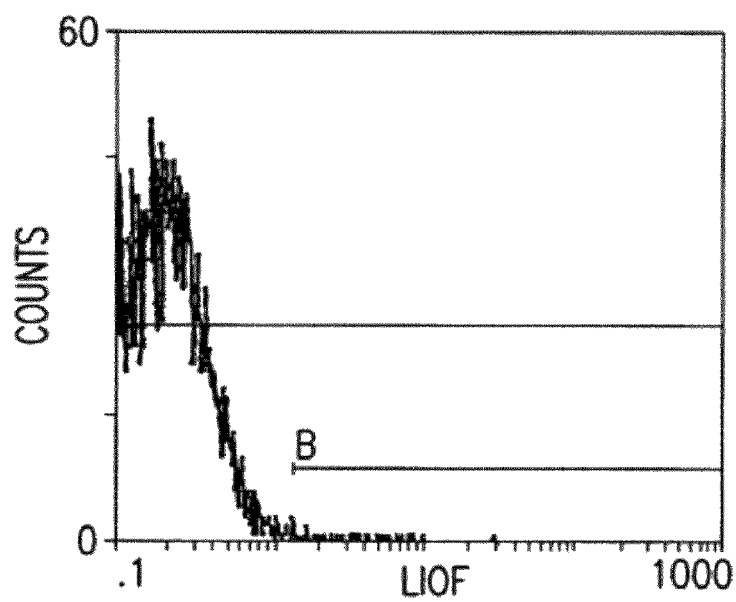
Figure 10B:
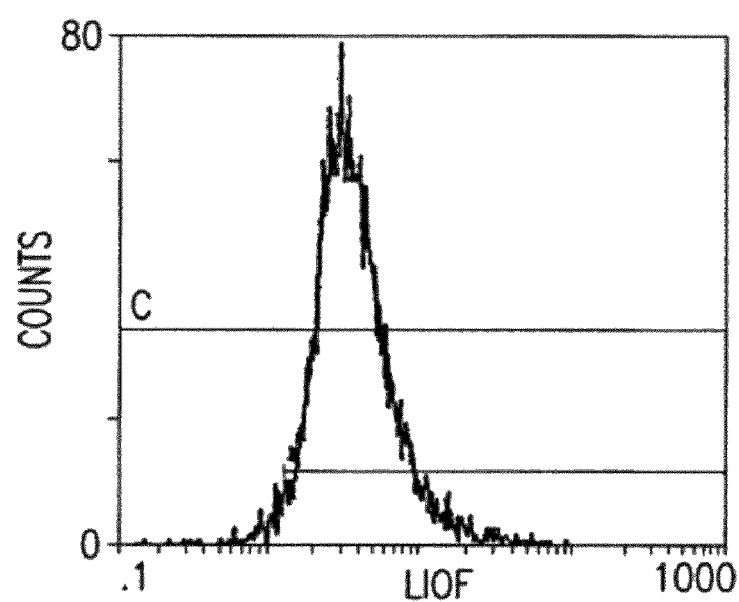

FIGS. 10a and 10b: Staining of Cho Cells Expressing FcγRIIB.

FIGS. 10A-10B. CHO/IIB cells were stained with mouse IgG1 isotype control (FIG. 10A) and 3H7 antibody (FIG. 10B).

Figure 10C:
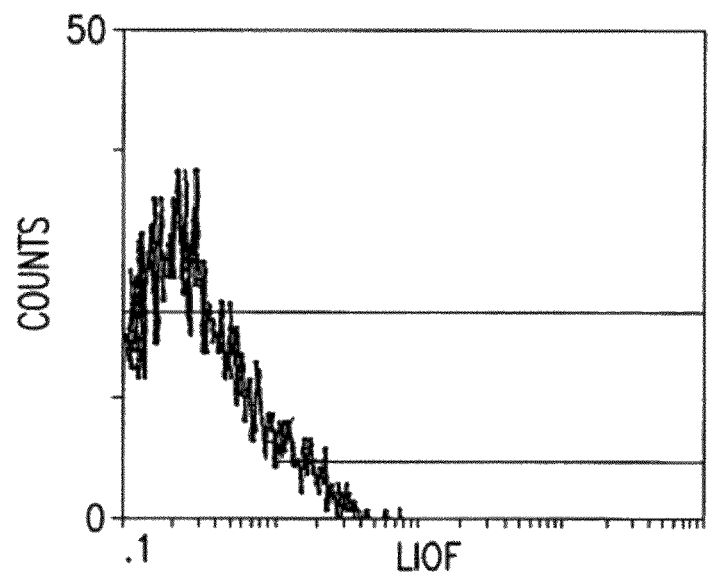
Figure 10D:
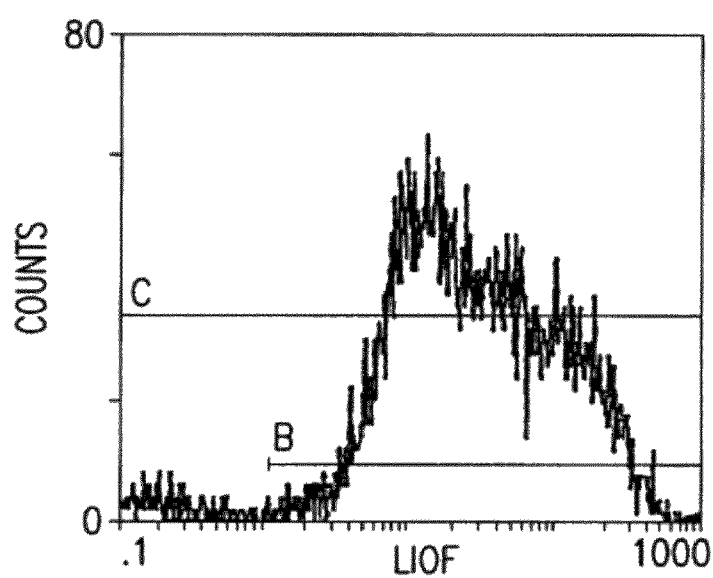

FIGS. 10C-10D. CHO/IIB cells were stained with mouse IgG1 isotype control (FIG. 10C) and 2B6 antibody (FIG. 10D).

FIGS. 11A-11G: Staining of Cho Cells Expressing FcγRIIB.

Figure 11B:
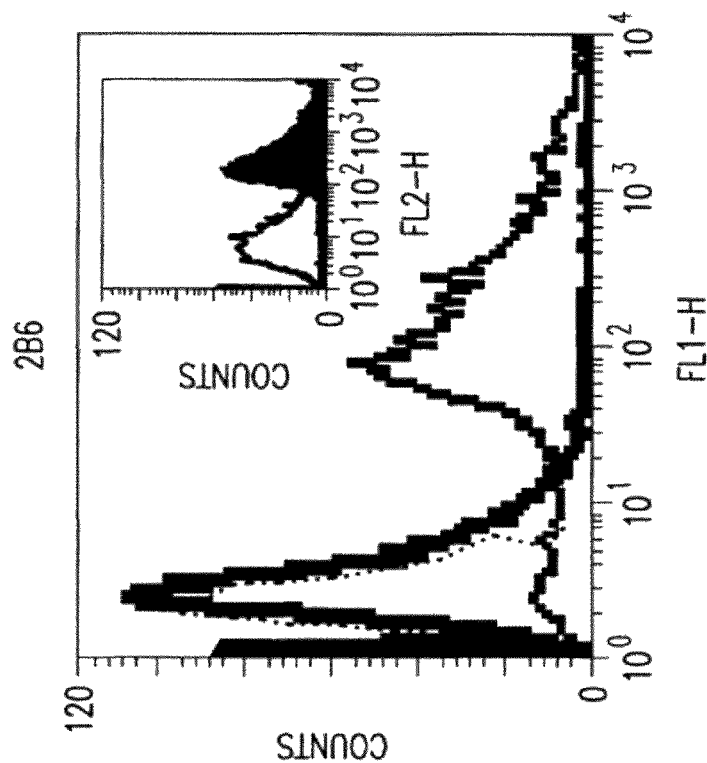
Figure 11A:
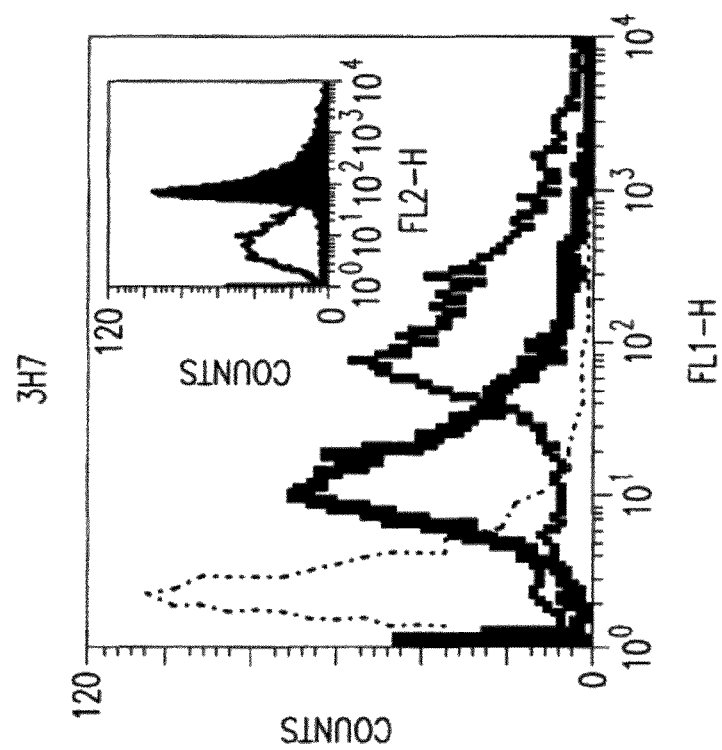
Figure 11C:
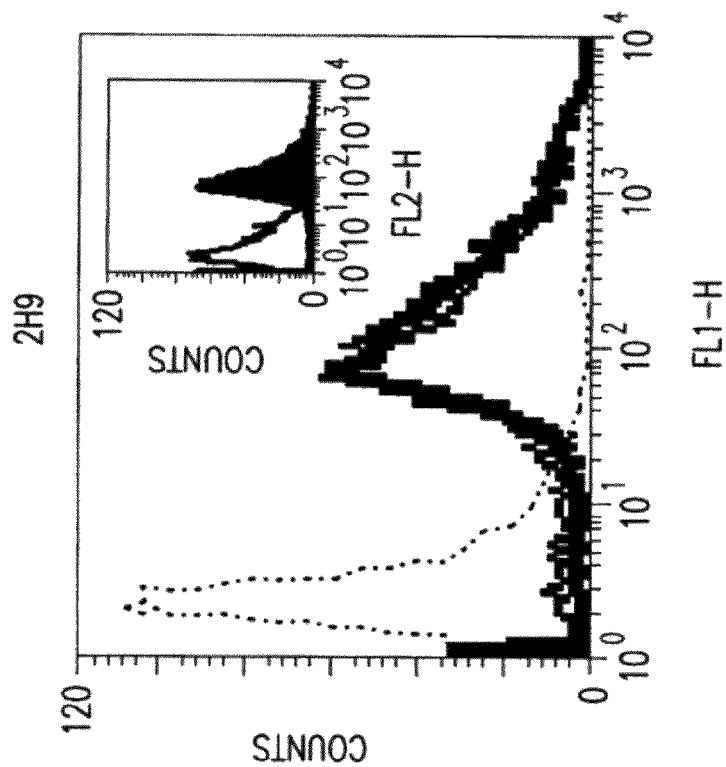
Figure 11D:
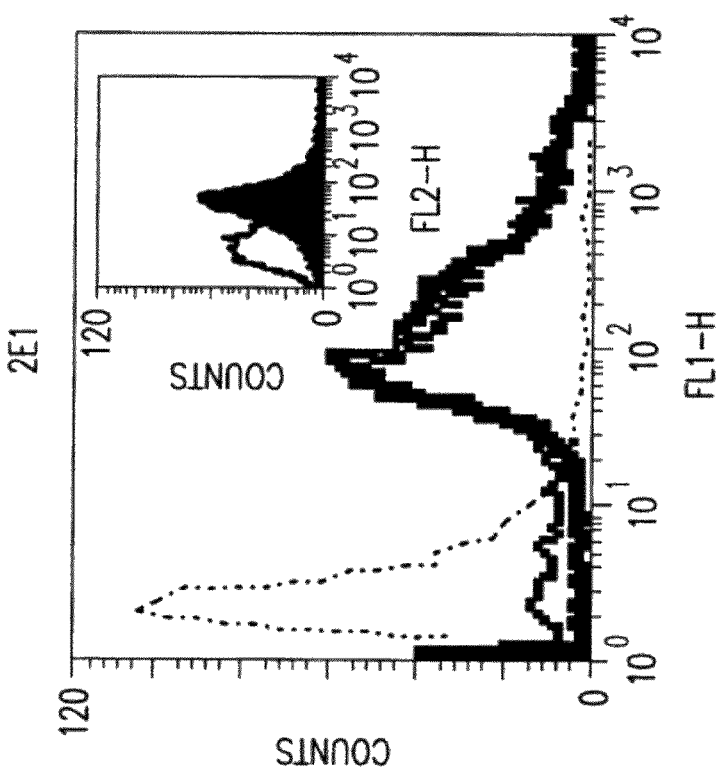
Figure 11G:
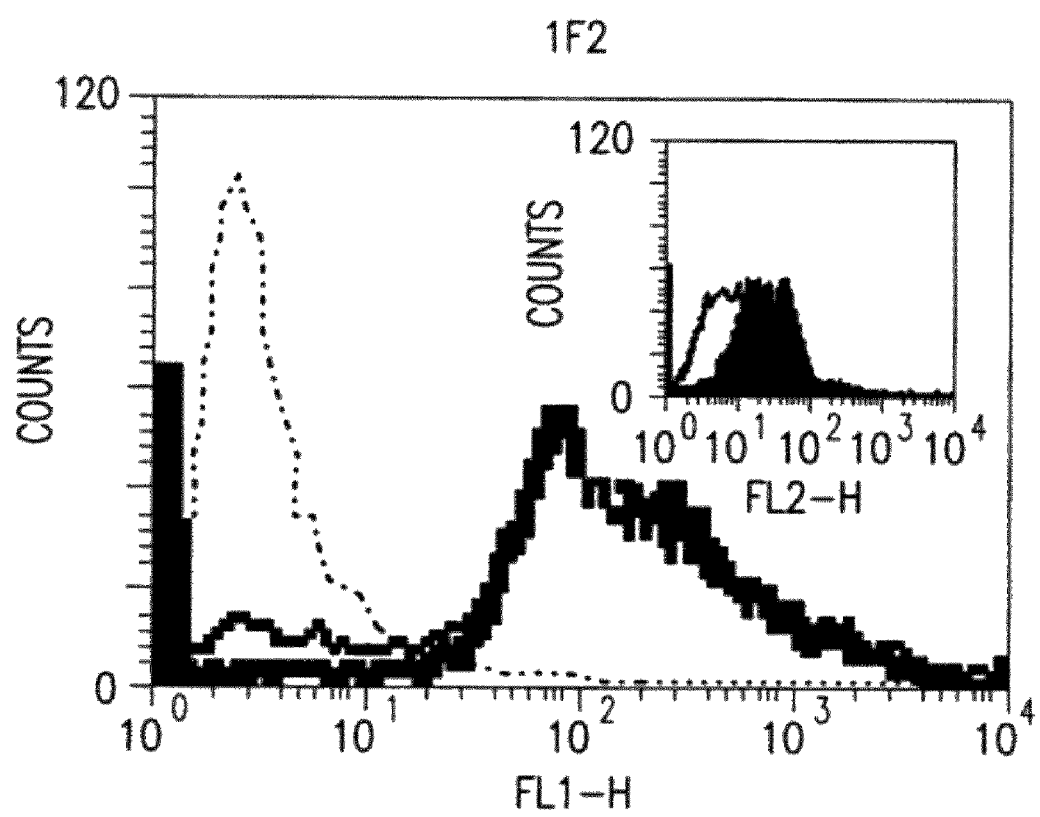

CHO cells expressing huFcγRIIB were incubated with the anti-CD32B antibody 3H7 (FIG. 11A), 2B6 (FIG. 11B), 2E1 (FIG. 11C), 2H9 (FIG. 11D), 1D5 (FIG. 11E), 2D11 (FIG. 11F) and 1F2 (FIG. 11G). Cells were washed and 9 μg/ml of aggregated human IgG were added to the cells on ice. The human aggregated IgG were detected with goat anti-human-IgG FITC conjugated. Samples were analyzed by FACS . . . isotype control+goat anti huIgG-FITC, –isotype control+aggregated humanIgG+goat anti humanIgG-FITC, –anti-CD32B antibody+aggregated humanIgG+goat anti human-IgG-FITC. The amount of each antibody bound to the receptor on the cells was also detected (inset) on a separate set of samples using a goat anti-mouse PE conjugated antibody.

FIGS. 12A-12J: Flow Cytometry Analysis of CD32B Expression in Transformed Cell Lines Using CD32B Specific Antibody, 2B6, and CD32A/B Reactive Antibody, FLI8.26.

Figures 12A, 12B, 12C, 12D, 12E, 12F, 12G, 12H, 12I, 12J:
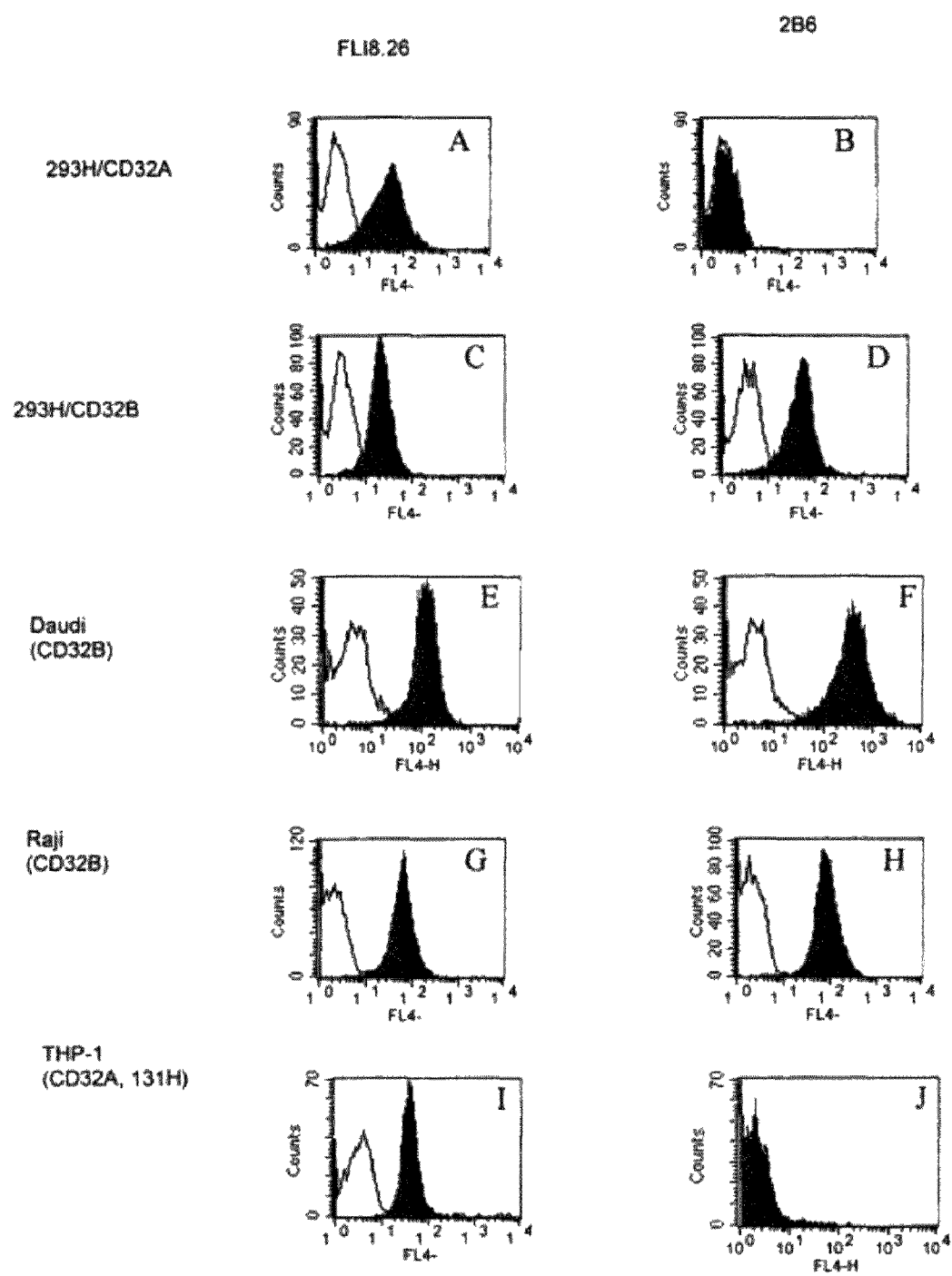

Cell lines: transfected 293H cells expressing CD32A (FIGS. 12A, 12B) or CD32B (FIGS. 12C, 12D), Burkitt's lymphoma cell lines, Daudi (FIGS. 12E, 12F) and Raji (FIGS. 12G, 12H), and the monocytic cell line, THP-1 (FIGS. 12I, 12J).

Figure 13A:
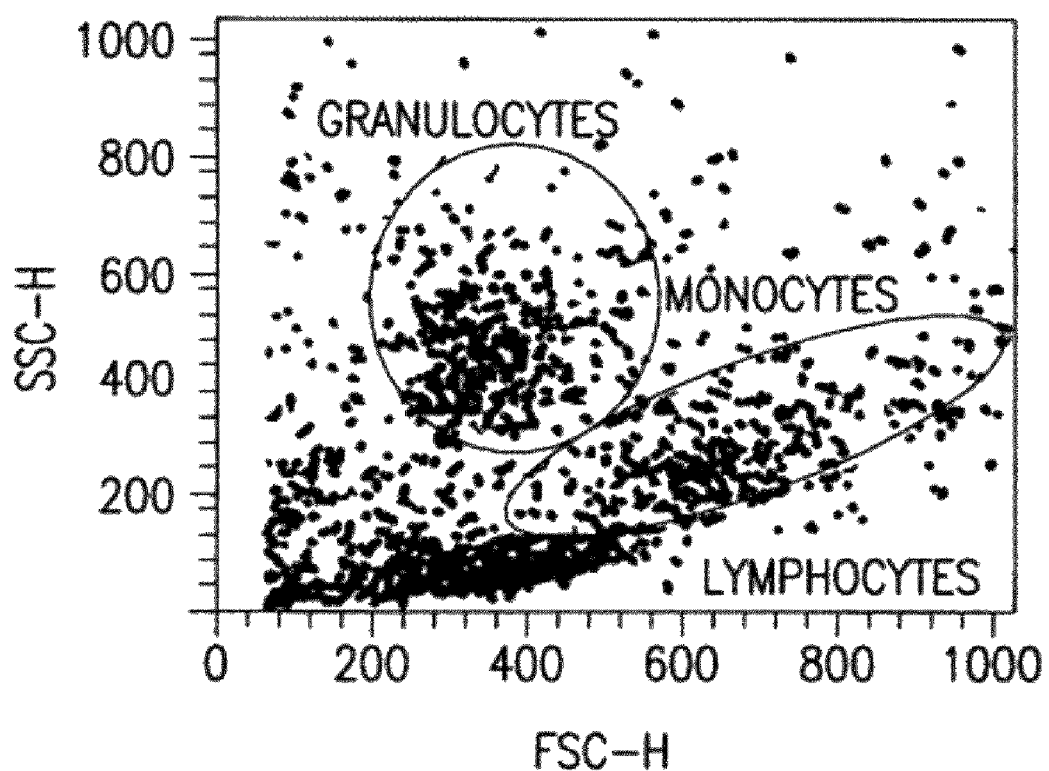
Figure 13B:
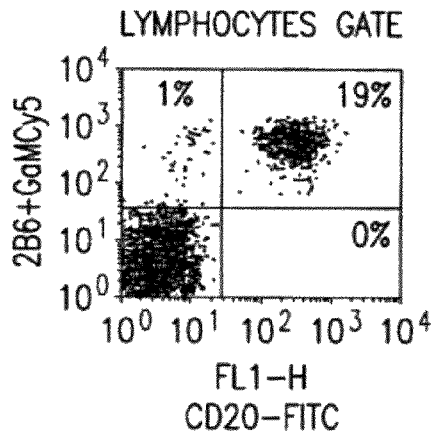
Figure 13C:
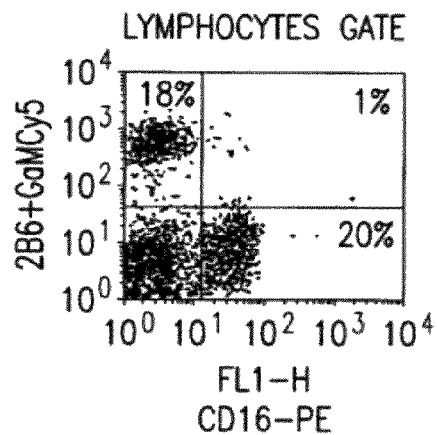
Figure 13D:
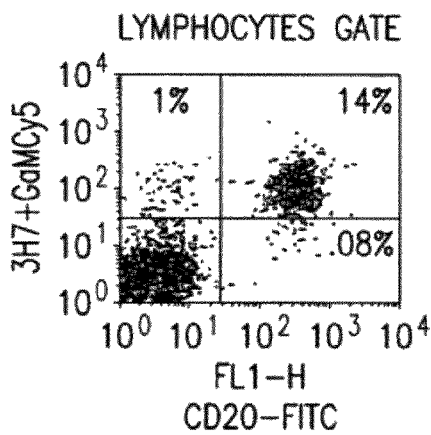
Figure 13E:
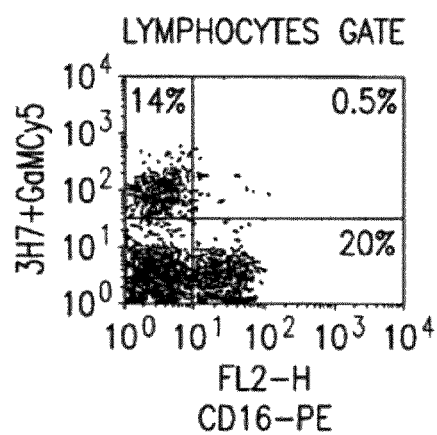
Figure 13F:
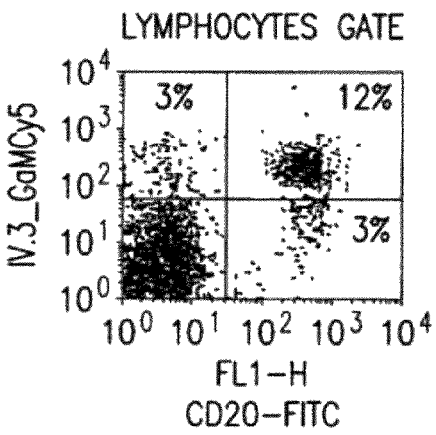
Figure 13G:
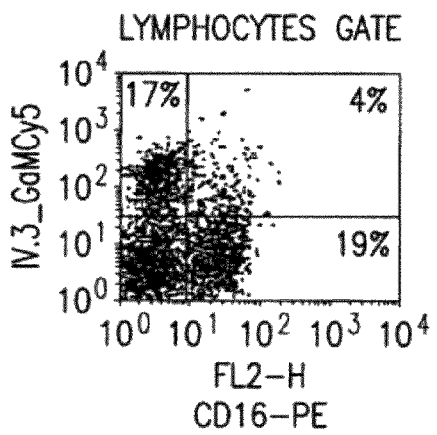
Figure 13H:
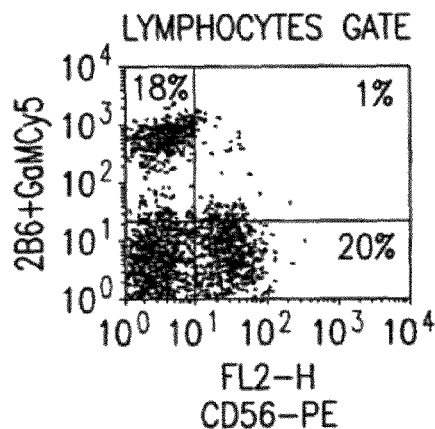
Figure 13I:
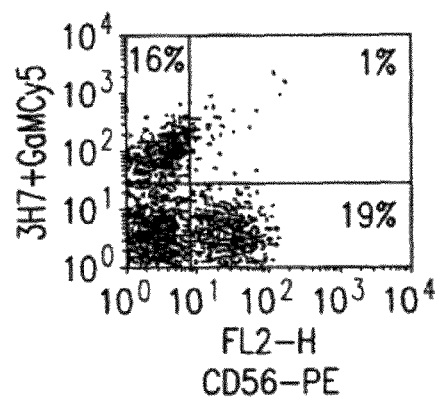
Figure 13J:
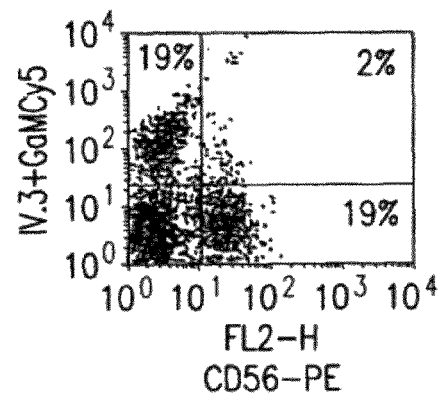
Figure 13K:
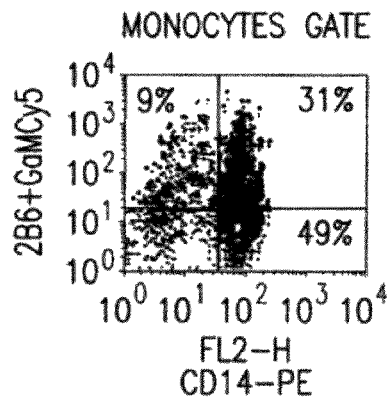
Figure 13L:
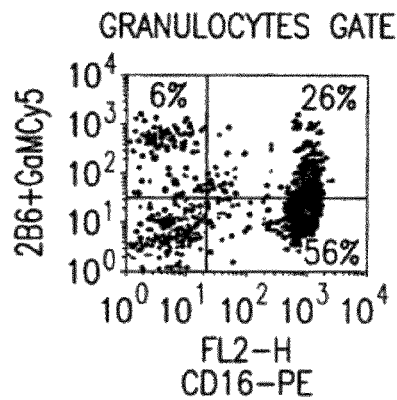
Figure 13M:
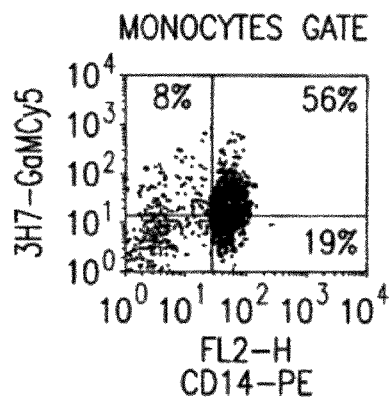
Figure 13N:
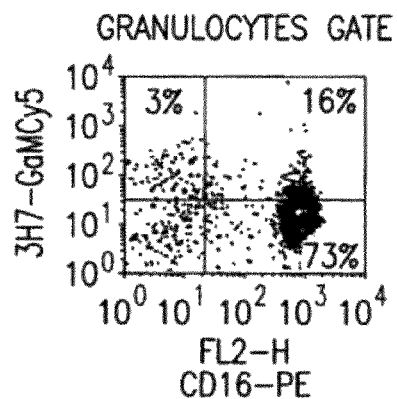
Figure 13O:
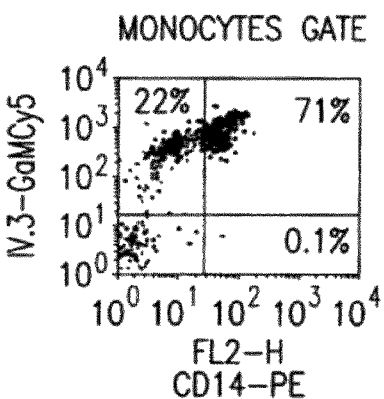
Figure 13P:
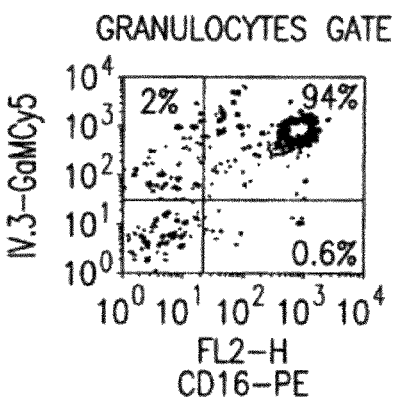

FIGS. 13A-13P: Staining of Human PBMCs with 2B6, 3H7 and Iv.3 Antibodies.

Human PBMCs were stained with 2B6 (FIGS. 13B, 13C, 13H, 13K and 13L), 3H7 (FIGS. 13D, 13E, 13I, 13M and 13N), and 1V.3 (FIGS. 13F, 13G, 13J, 13O and 13P) antibodies, as indicated on the right side of the panel, followed by a goat anti-mouse-Cyanine(Cy5) conjugated antibody (two color staining using anti-CD20-FITC conjugated antibody for B lymphocytes (FIGS. 13B, 13D and 13F), anti-CD14-PE conjugated antibody for monocytes (FIGS. 13K, 13M and 13O), anti-CD56-PE conjugated antibody for NK cells (FIGS. 13H, 13I and 13J) and anti-CD16-PE conjugated antibody for granulocytes (FIGS. 13C, 13E, 13G, 13L, 13N and 13P). FIG. 13A demonstrates staining results for monocytes, B lymphocytes and granulocytes.

FIGS. 14A and 14B: β-Hexaminidase Release Assay.

FIG. 14A. Schematic representation of β-hexaminidase release assay. Transfectants expressing human FcγRIIB were sensitized with mouse IgE and challenged with F(ab')2 fragments of a polyclonal goat anti-mouse IgG to aggregate FcγRI. Crosslinking occurs because of the ability of the polyclonal antibody to recognize the light chain of the murine IgE antibody bound to FcγRI. Transfectants sensitized with murine IgE and preincubated with 2B:6 antibody were also challenged with F(ab')2 fragments of a polyclonal goat anti-mouse IgG to cross link FcεRI to FcγRIIB. FIG. 14B. β-hexosaminidase release induced by goat anti-mouse F(ab)2 fragment (GAM F(ab)2) in RBL-2H3 cells expressing huFcγRIIB. Cells were stimulated with various concentration of GAM F(ab)2 (0.03 μg/ml to 30 μg/ml) after sensitization with mouse IgE (0.01 μg/ml) and IgG1 or with purified 2B6 antibody (3 μg/ml) panel. After 1 hour at 37° C., the supernatant was collected and the cells were lysed. β-hexosaminidase activity released in the supernatant and within the cells was determined by a colorimetric assay using p-nitrophenyl N-acetyl-β-D-glucosaminide. The released β-hexosaminidase activity was expressed as a percentage of the released activity relative to the total activity.

Figures 15A, 15B, 15C:
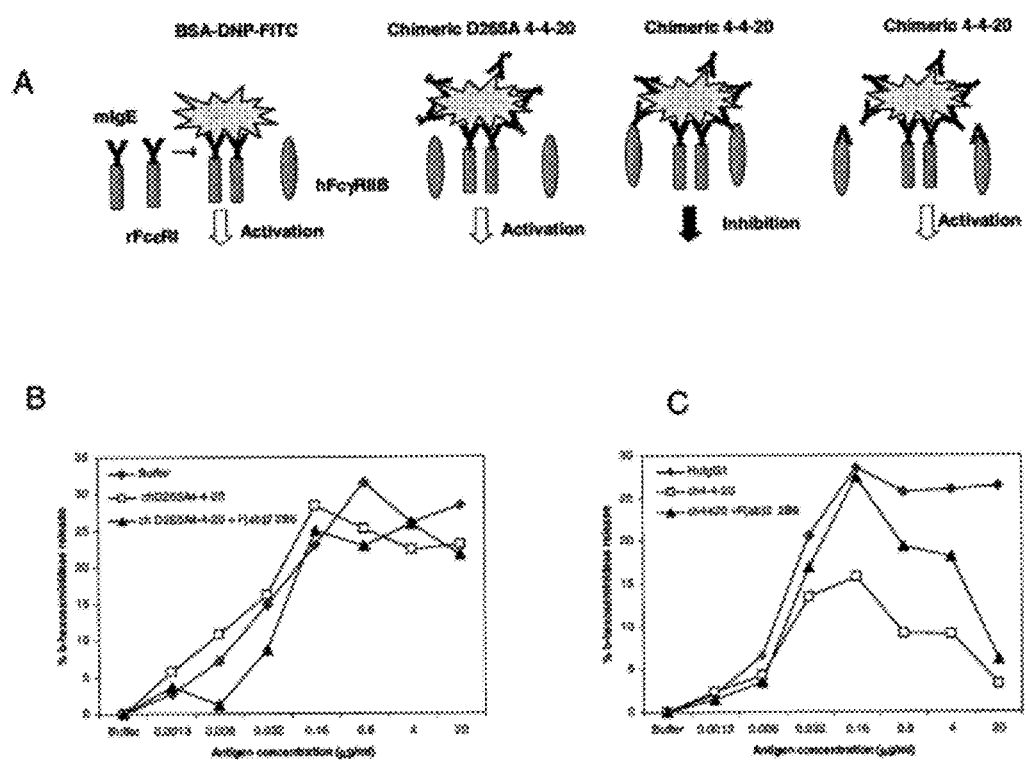

FIGS. 15A-15C: 2B6 is Capable of Functionally Blocking the Fc Binding Site of CD32B and Prevent Co-Ligation of Activating and Inhibitory Receptors.

FIG. 15A. Schematic representation of the experimental model. FIGS. 15B and 15C. RBL-2H3/CD32B cells were stimulated with BSA-DNP-FITC complex in the presence of human IgG1, with BSA-DNP-FITC complexed with chimeric D265A4-4-20 in the presence or not of 3 µg/ml of F(ab)2 fragments of 2B6 (FIG. 15B). Cells were also stimulated with BSA-DNP-FITC complex in the presence of human IgG1, with BSA-DNP-FITC complexed with chimeric 4-4-20 in the presence or not of 3 µg/ml of F(ab)2 fragments of 2B6 (FIG. 15C). After 30 minutes, the supernatant was collected and the cells were lysed. B-hexosaminidase activity released in the supernatant and within the cells was determined by a colorimetric assay using p-nitrophenyl N-acetyl-β-D-glucosaminide. The released β-hexosaminidase activity was expressed as a percentage of the released activity relative to the total activity.

FIGS. 16A-16C: Ovarian and Breast Carcinoma Cell Lines Express Her2/neu to Varying Levels.

Staining of Ovarian IGROV-1 (FIG. 16A) with purified ch4D5, Ovarian OVCAR-8 with purified 4D5 antibody (FIG. 16B), and Breast cancer SKBR-3 cells (FIG. 16C) with purified ch4D5 followed by goat anti-human-conjugated to phycoerythrin (PE). The relevant isotype control IgG1 is indicated the left of the staining with anti-Her2neu antibody.

Figure 17A:
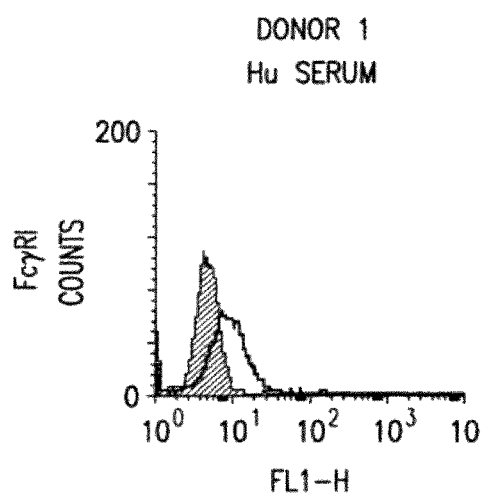
Figure 17B:
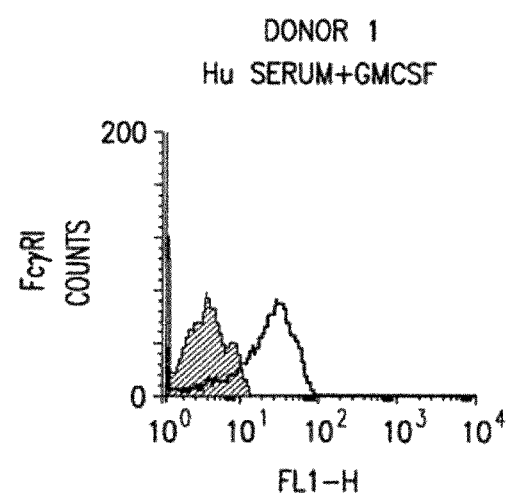
Figure 17C:
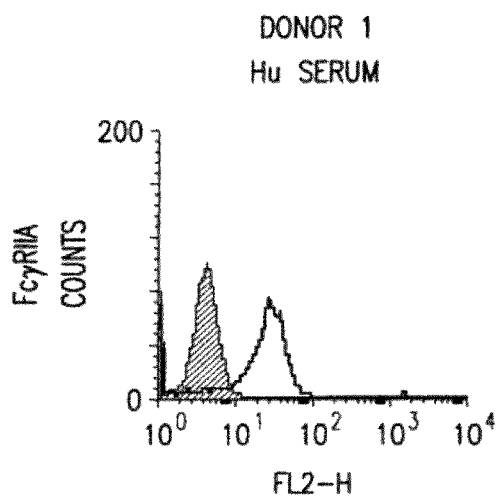
Figure 17D:
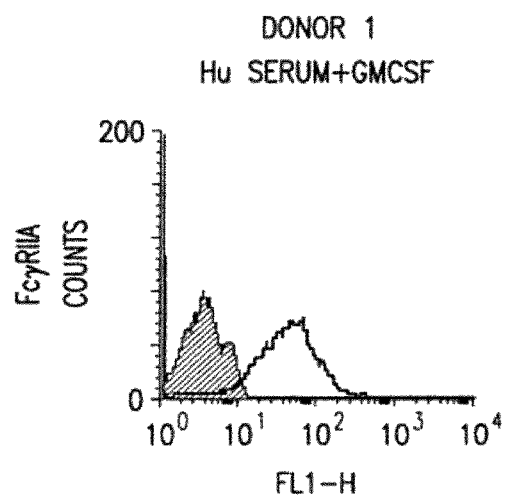
Figure 17E:
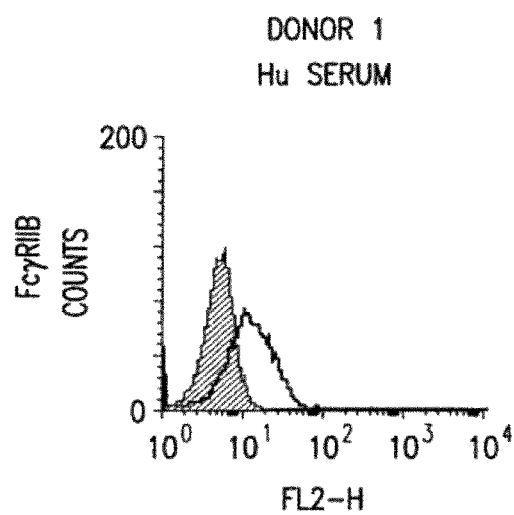
Figure 17F:
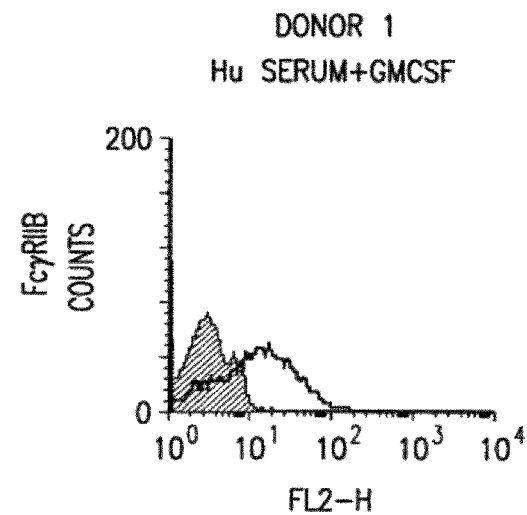
Figure 17G:
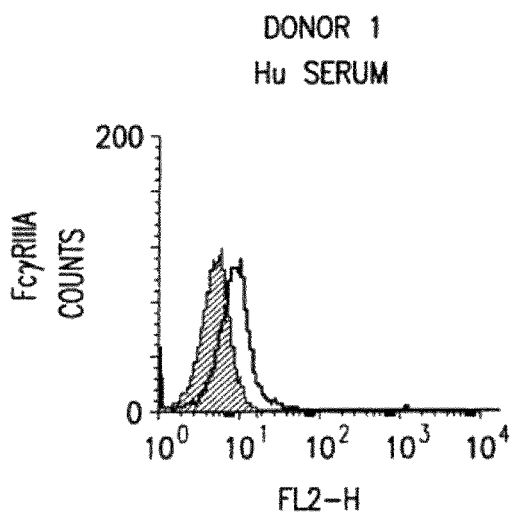
Figure 17H:
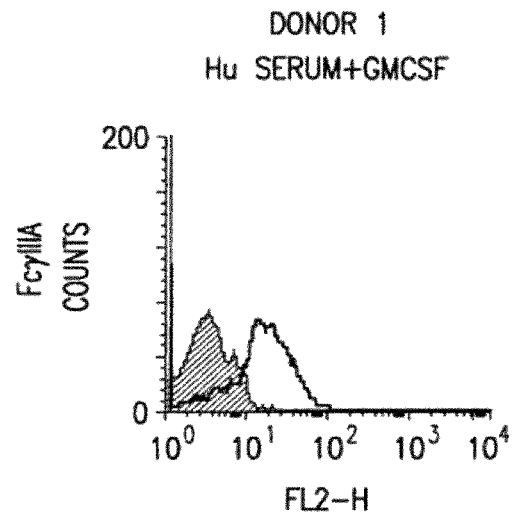
Figure 17I:
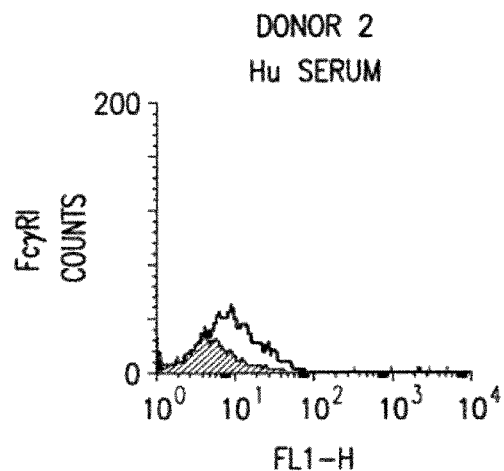
Figure 17J:
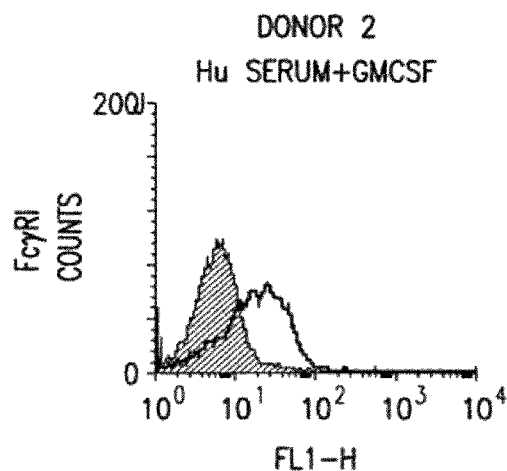
Figure 17K:
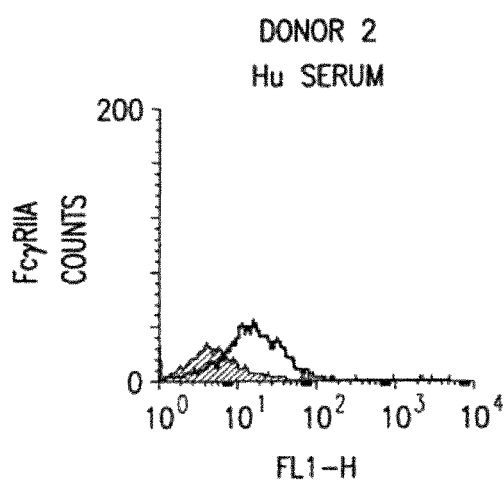
Figure 17L:
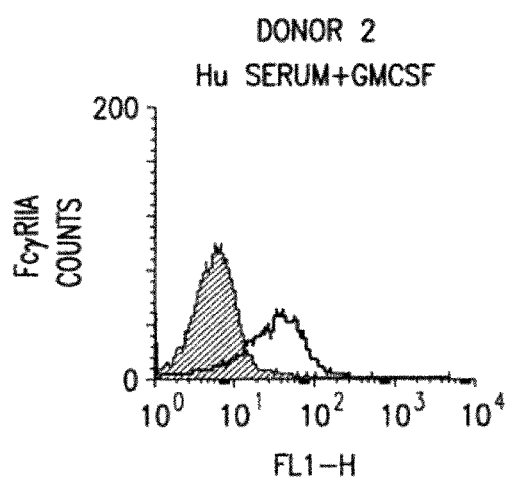
Figure 17M:
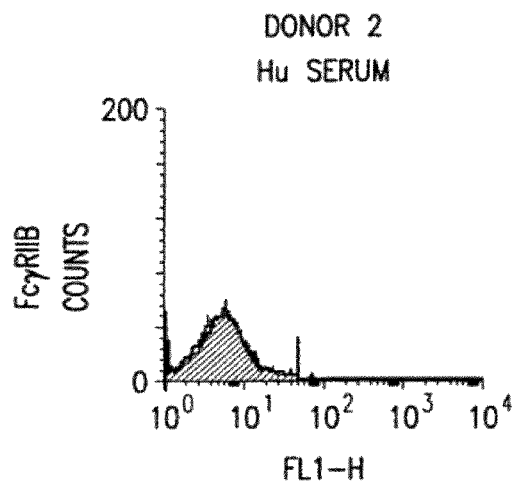
Figure 17N:
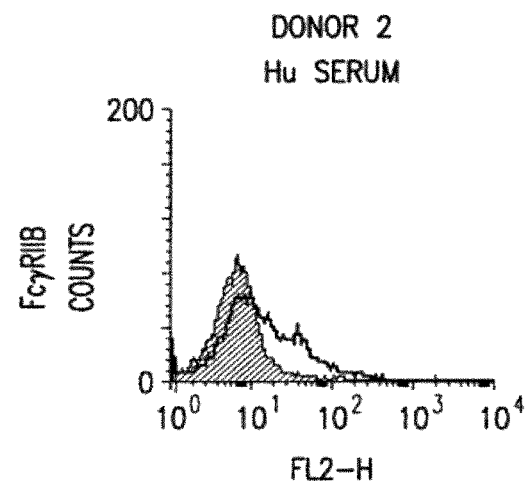
Figure 17O:
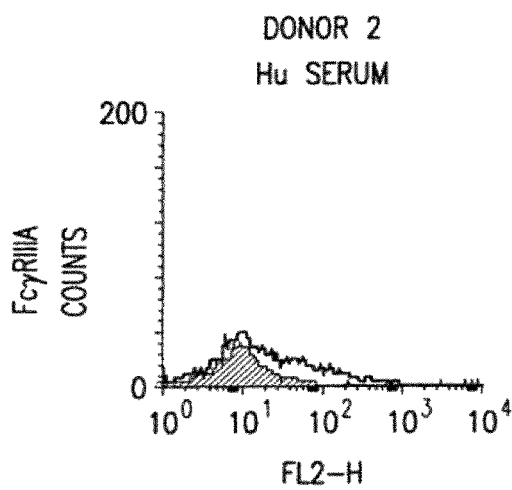
Figure 17P:
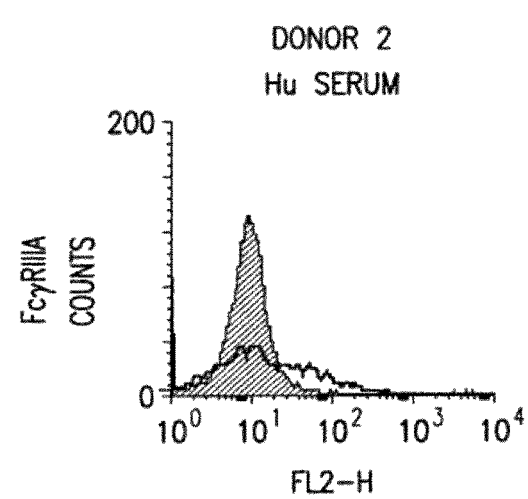
Figure 17Q:
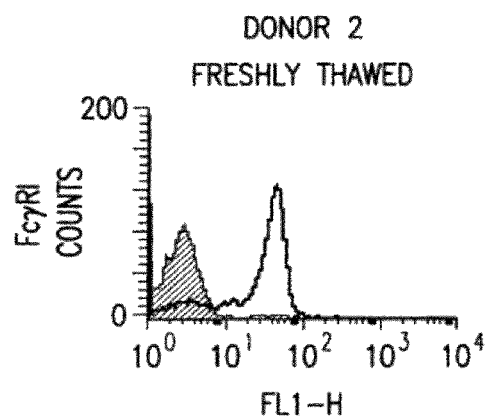
Figure 17R:
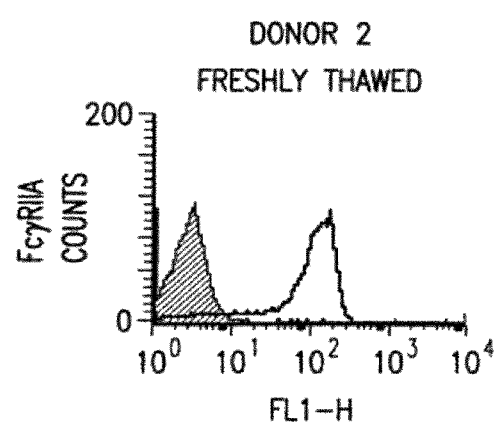
Figure 17S:
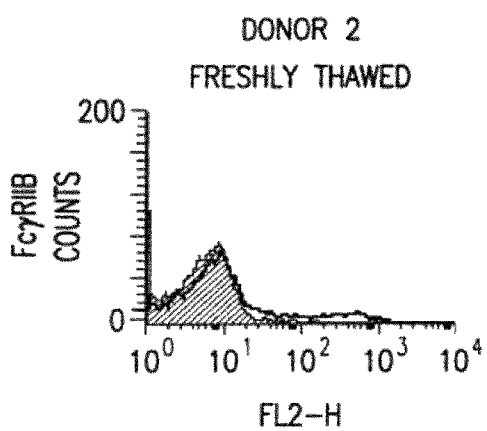
Figure 17T:
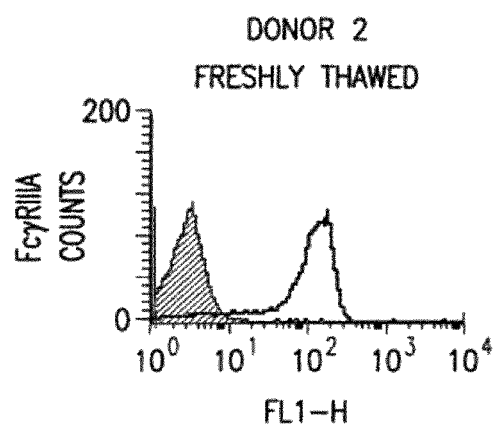

FIGS. 17A-17T: Elutriated Monocytes Express All FcγRs.

MDM obtained from donor 1, propagated in human serum (FIGS. 17A, 17C, 17E and 17G) or human serum and GM-CSF (FIGS. 17B, 17D, 17F and 17H); MDM obtained from donor 2; propagated in human serum (FIGS. 17I, 17K, 17M and 17O) or human serum and GM-CSF (FIGS. 17J, 17L, 17N and 17P); and Monocytes thawed and stained immediately (FIGS. 17Q-17T). Monocyte-derived macrophages were stained with anti-bodies specific for human FcγR receptor. The solid histogram in each plot represents the background staining. The clear histogram within each panel represents the staining with specific anti-human FcγR antibodies.

Figure 18A:
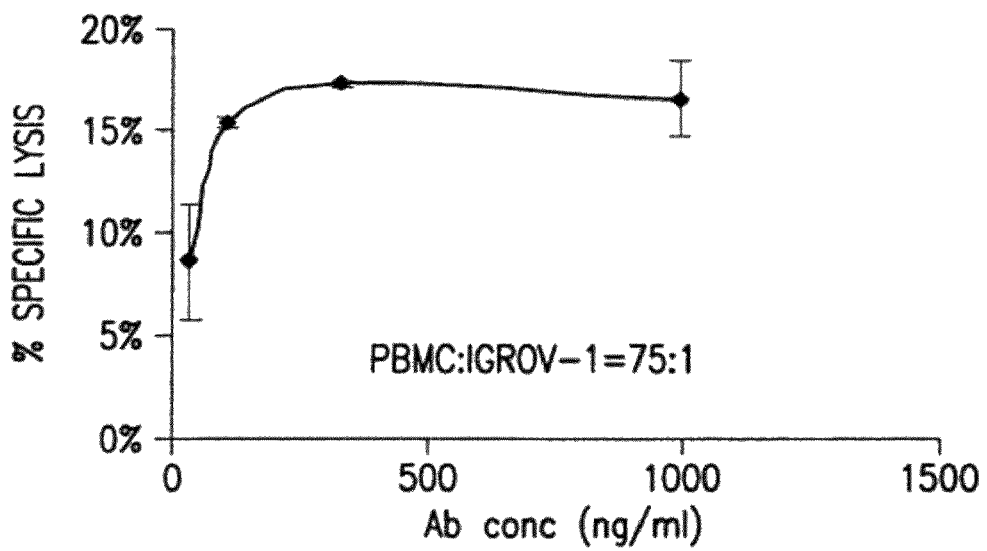
Figure 18B:
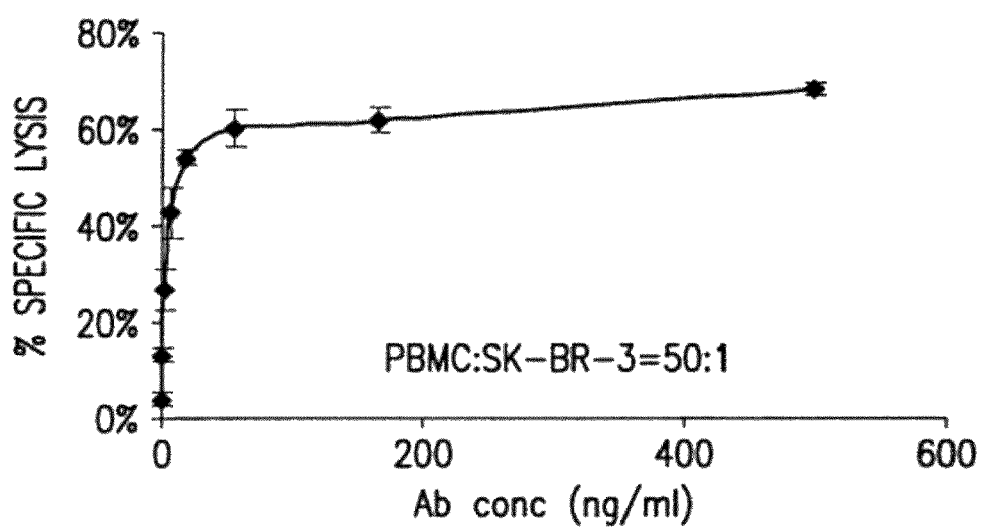

FIGS. 18A and 18B: Ch4D5 Mediates Effective ADCC with Ovarian and Breast Cancer Cell Lines Using PBMC.

Specific lysis subtracted from antibody-independent lysis is shown for Ovarian tumor cell line, IGROV-1 (FIG. 18A) at an effector: target ratio of 75:1, and for Breast tumor cell line SKBR-3 (FIG. 18B) at an effector:target ratio of 50:1 with different concentration of ch4D5 as indicated.

FIGS. 19A-19C: Histochemical Staining of Human Ovarian Ascites Shows Tumors Cells and Other Inflammatory Cells.

FIG. 19A. H & E stain on ascites of a patient with ovarian tumor. Three neoplastic cells can be identified by the irregular size and shape, scattered cytoplasm, and irregular dense nuclei. FIG. 19B. Giemsa stain of unprocessed ascites from a patient with serous tumor of the ovary shows two mesothelial cells placed back to back indicated by short arrows. Also shown is a cluster of five malignant epithelial cells indicated by the long arrow. Erythrocytes are visible in the background. FIG. 19C. Giemsa stain of another patient with serous tumor of the ovary indicating a cluster of cells composed of mesothelial cells, lymphocytes, and epithelial neoplastic cells (arrow).

Figure 20:
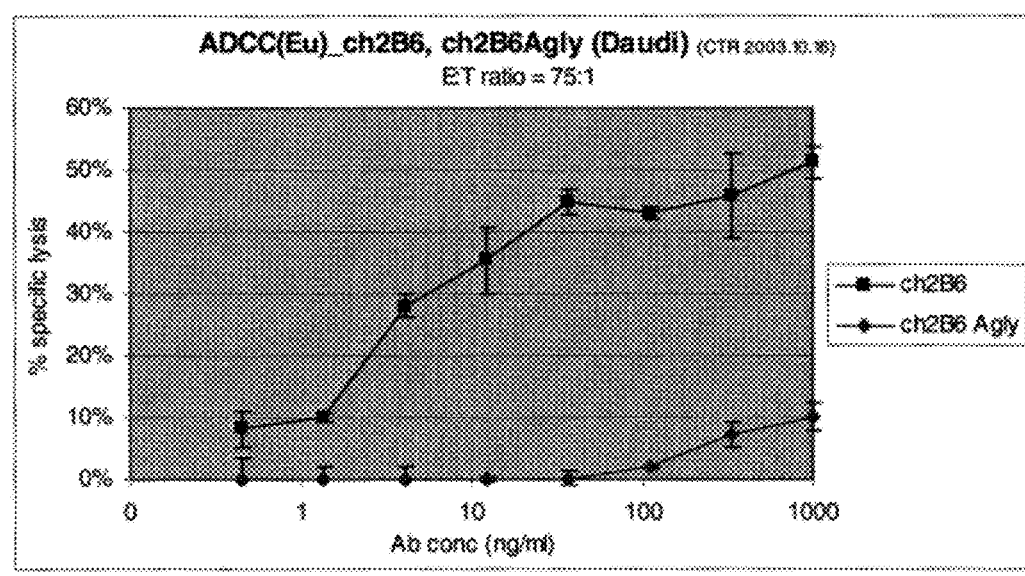

FIG. 20: In Vitro ADCC Assay of Ch2B6 and Aglycosylated Ch2B6 in Daudi Cells.

ch2B6 antibody mediates in vitro ADCC in CD32B expressing Daudi cells.

Figure 21:
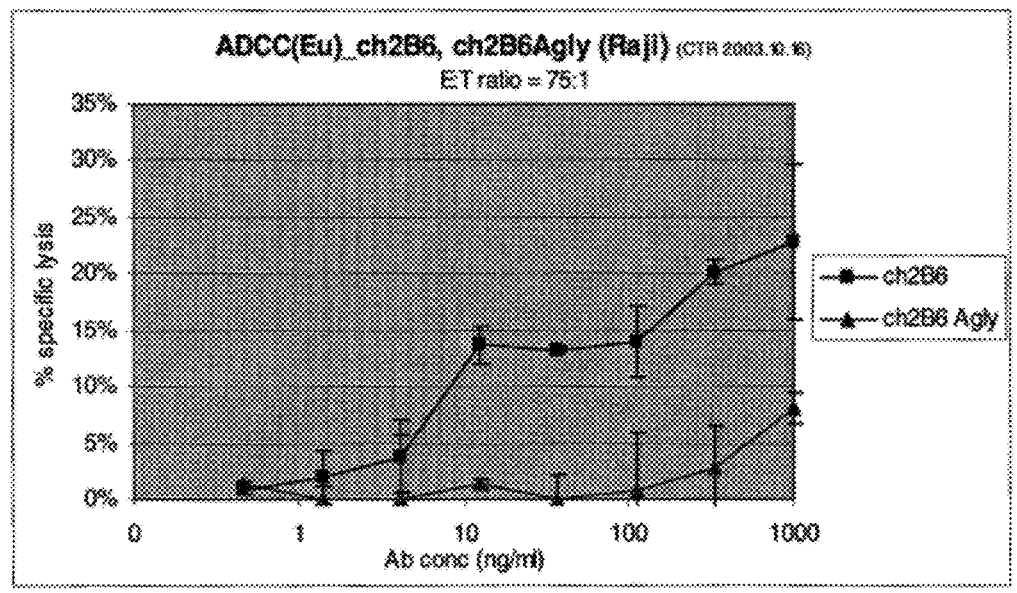

FIG. 21: In Vitro ADCC Assay of Ch2B6 and Aglycosylated Ch2B6 in Raji Cells.

ch2B6 antibody mediates in vitro ADCC in CD32B expressing Raji cells.

Figure 22:
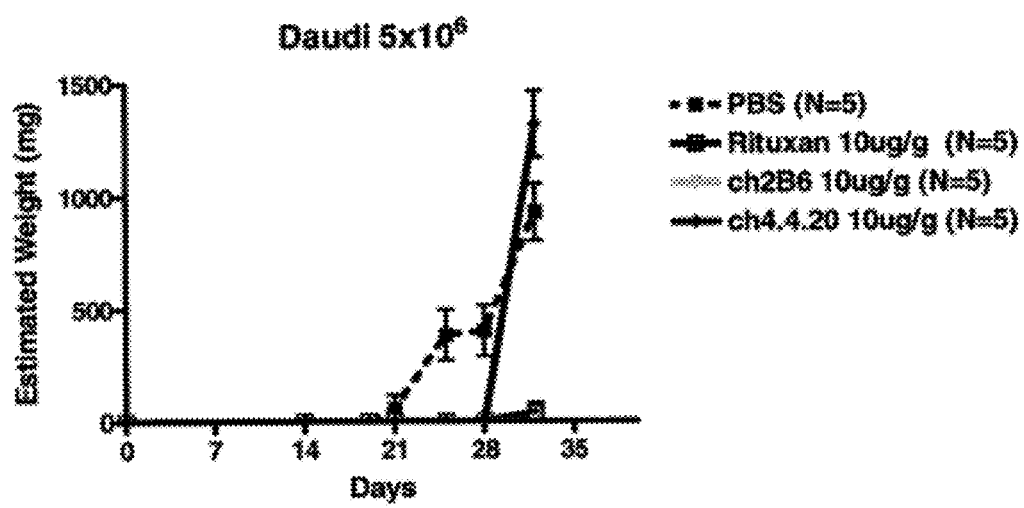

FIG. 22: In Vitro ADCC Activity of Chimeric and Humanized 2B6 Antibodies in Daudi Cells.

Indium-III labeled Daudi cells were opsonized with: ch2B6, ch2B6 N297Q, hu2B6, or hu2B6YA.

Figure 23:
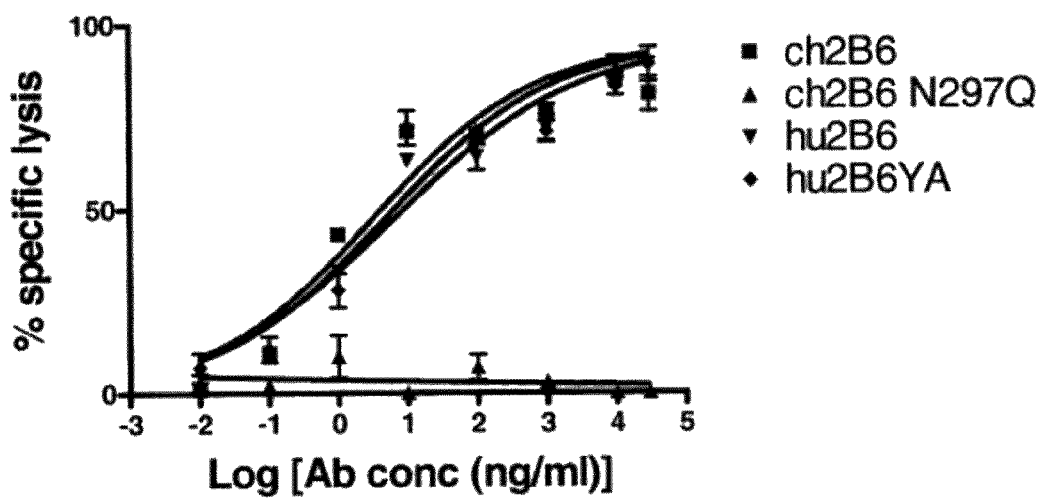

FIG. 23: Estimated Tumor Size in Individual Mice.

Injection days are indicated by arrows.

FIGS. 24A-24G: Effect of RITUXAN® (Rituximab) and 2B6 Variants on Tumor Growth in Mice.

Figures 24A, 24B:
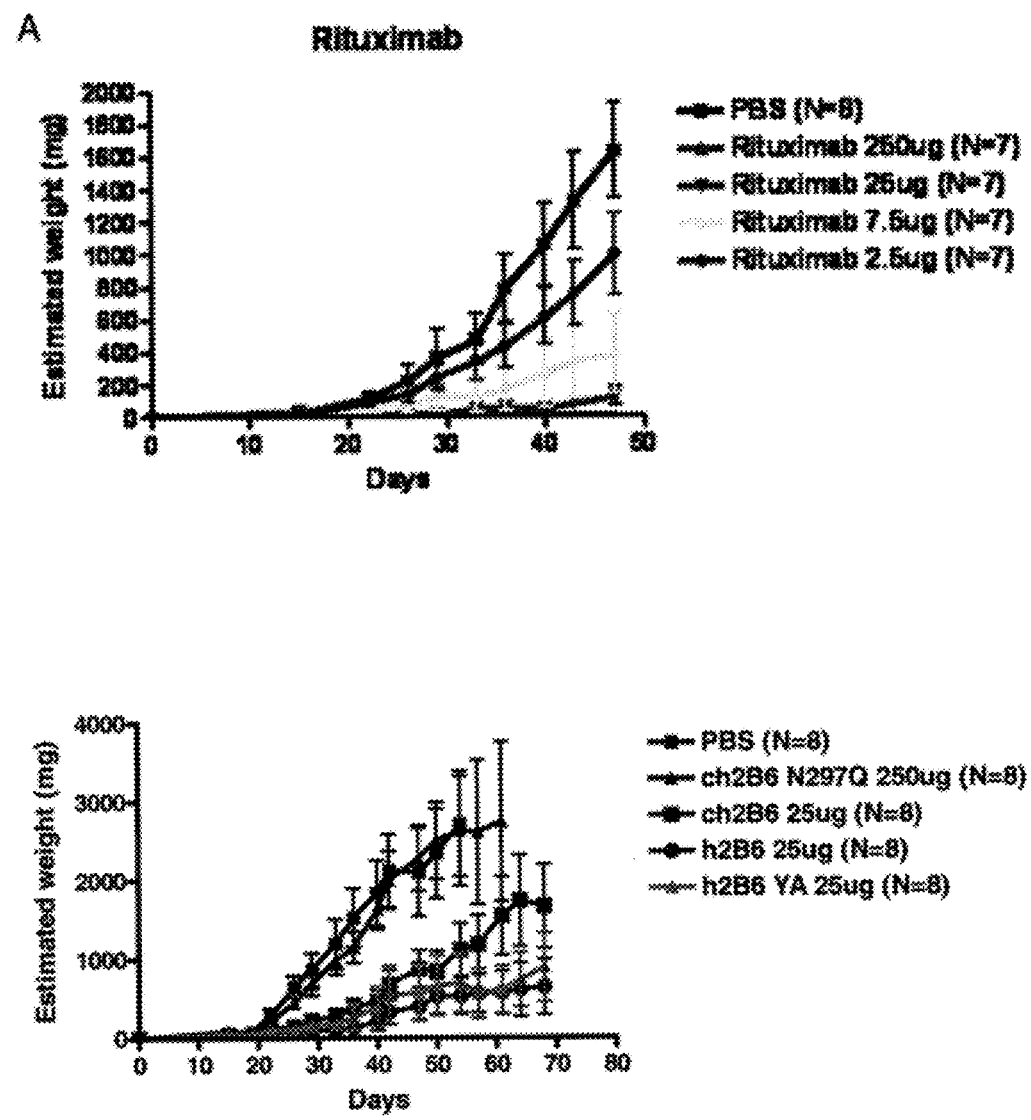
Figures 24C, 24D:
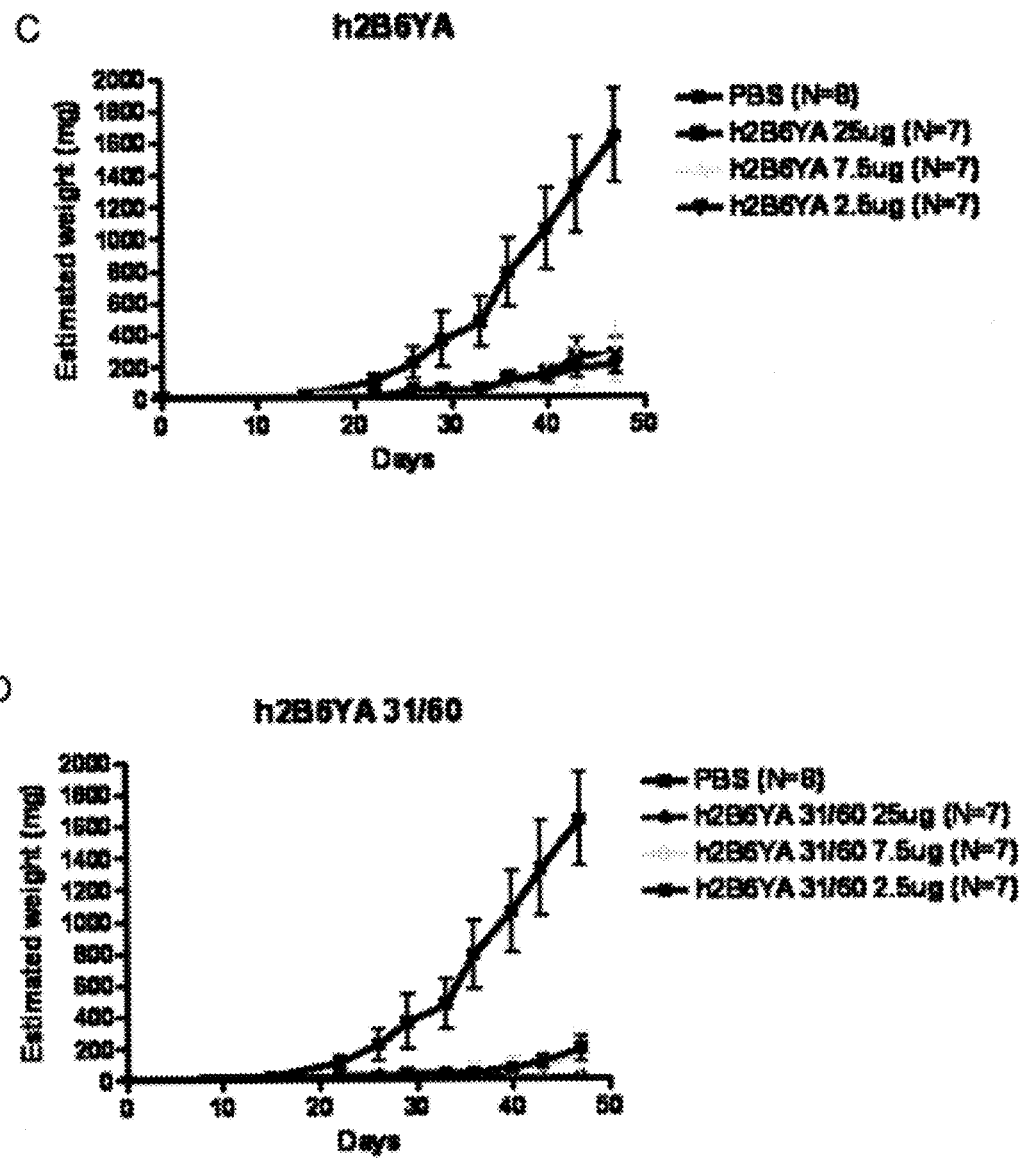
Figure 24E:
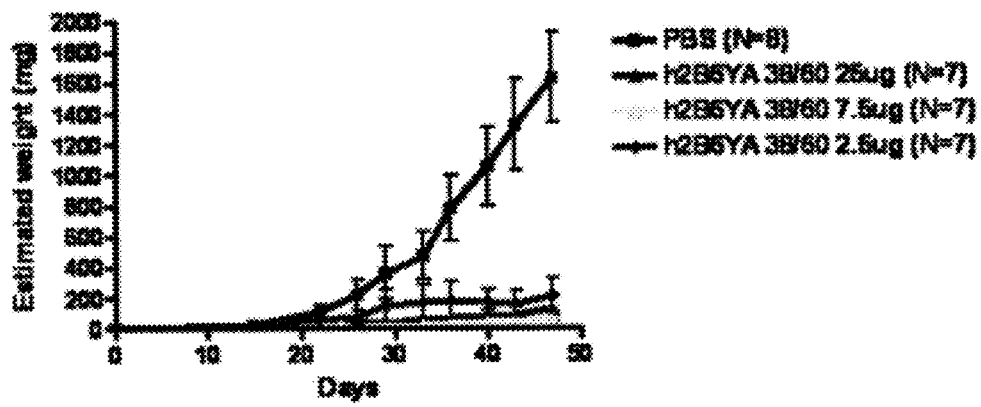
Figure 24F:
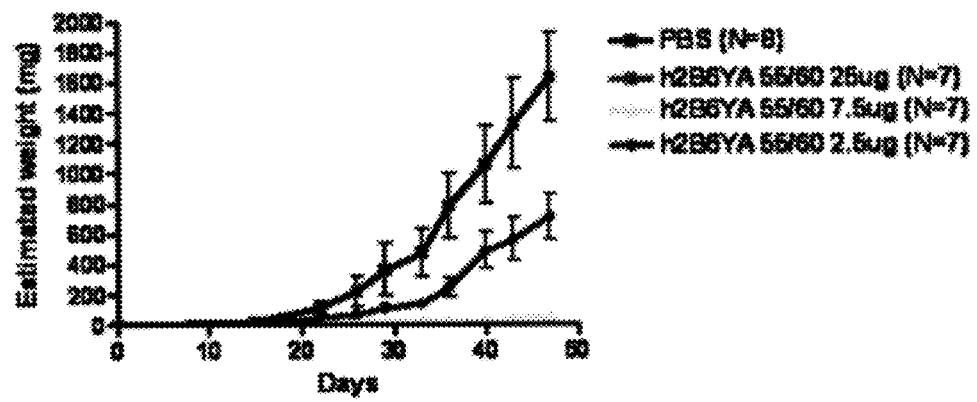
Figure 24G:
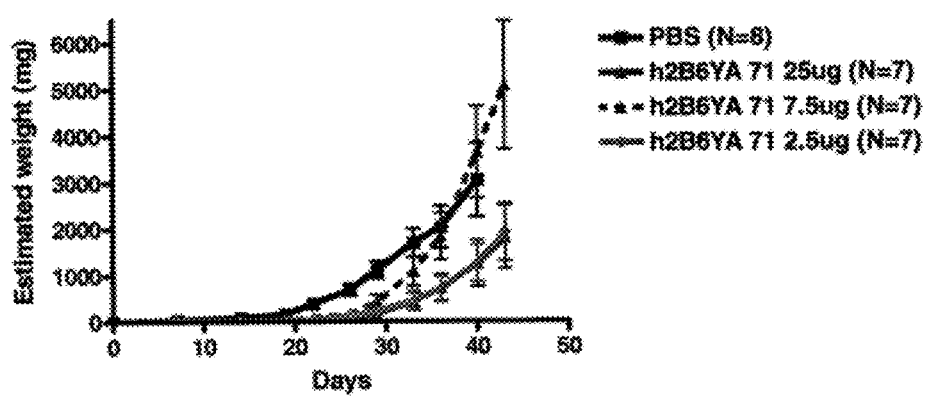

FIG. 24A. Rituximab. FIG. 24B. ch2B6, ch2B6 N297Q, h2B6, and h2B6YA. FIG. 24C. h2B6YA. FIG. 24D. h2B6YA 31/60. FIG. 24E. h2B6YA 38/60. FIG. 24F. h2B6YA 55/60. FIG. 24G. h2B6YA 71.

FIGS. 25A-25I: Ex Vivo Staining of Daudi for CD20 and CD32B.

Figures 25A, 25B, 25C, 25D, 25E, 25F, 25G, 25H, 25I:
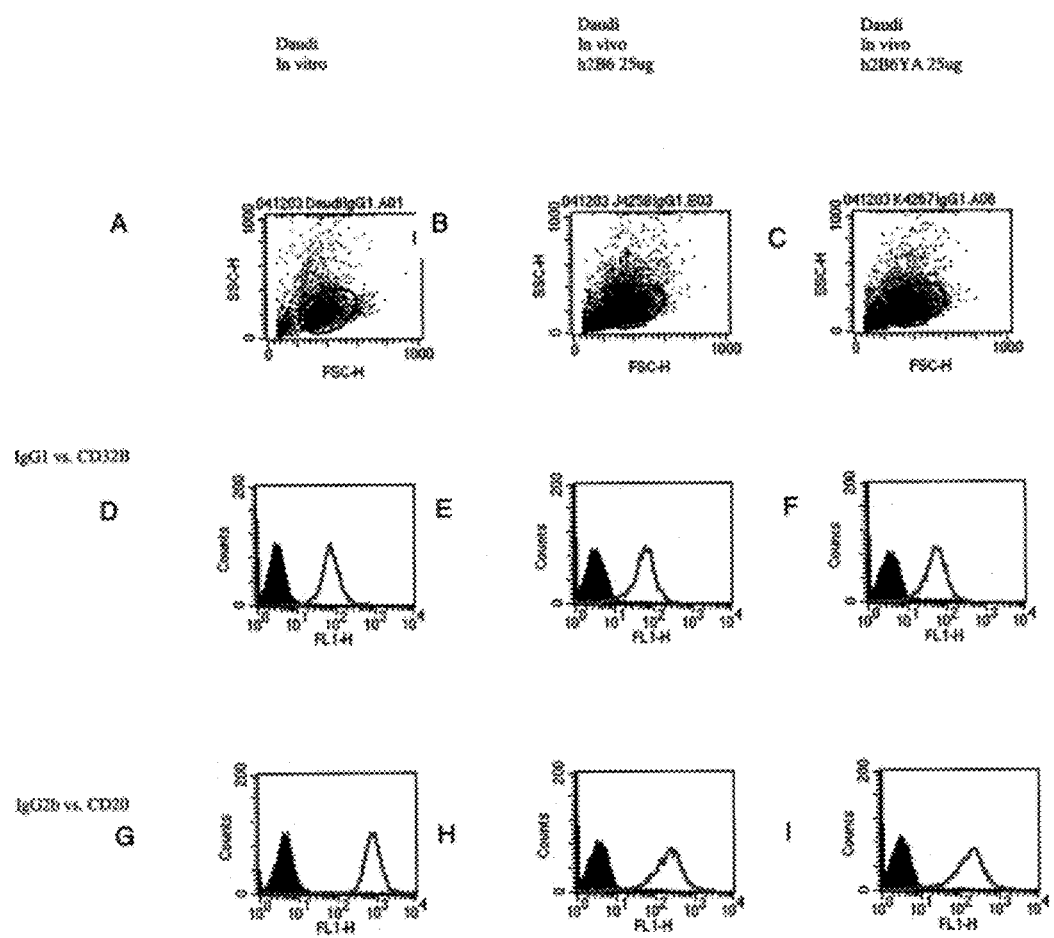

Daudi tumors were collected from mice treated with h2B6 (FIGS. 25B, 25E, 25H) or h2B6YA (FIGS. 25C, 25F, 25I). CD20 (FIGS. 25G, 25H, 25I) and CD32B (FIGS. 25D, 25E, 25F) expression was compared with those of Daudi cells expanded in vitro (FIGS. 25A, 25D, 25G).

Figure 26:
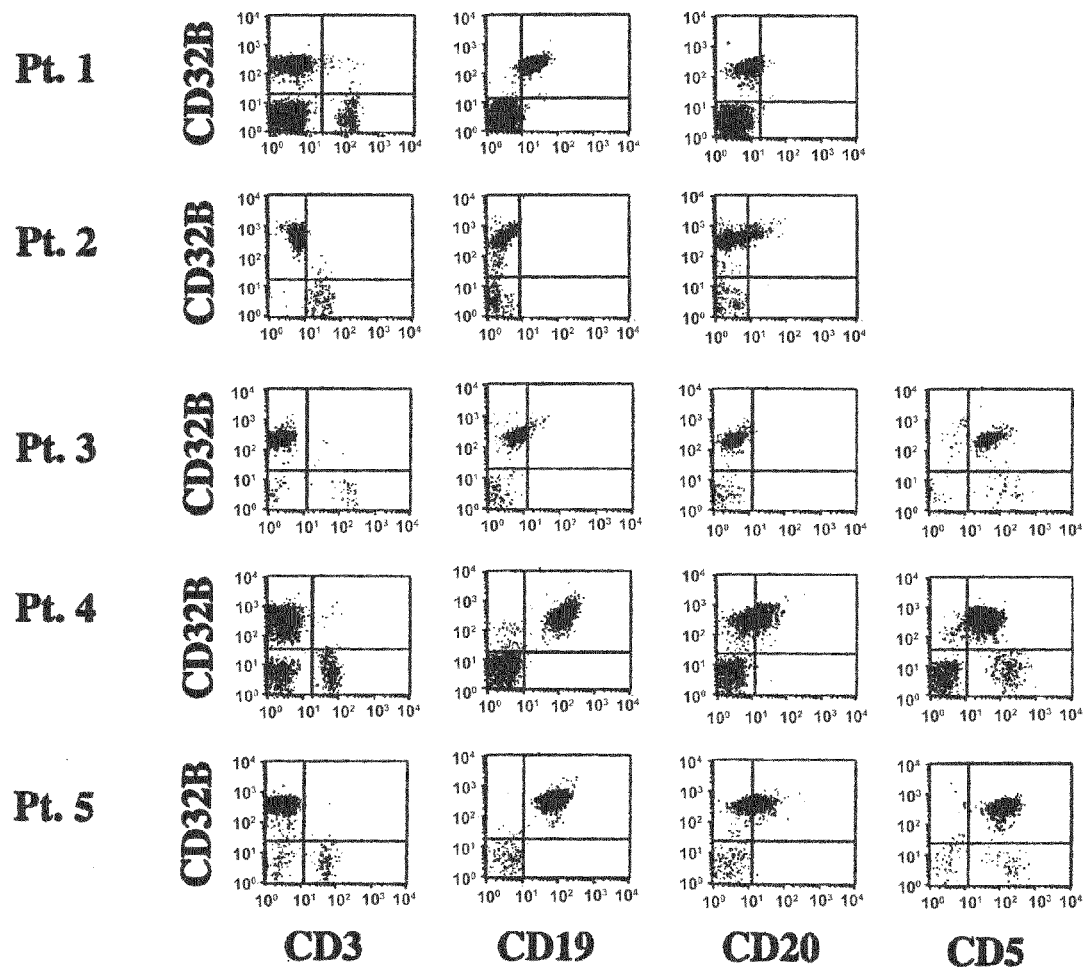

FIG. 26: Expression of Surface Membrane Markers on B-CLL Cells from Five Different Patients.

PBMCs from patients diagnosed with B-CLL were isolated by using Ficoll-Paque density gradient centrifugation and analyzed for expression of CD32B together with CD3, CD19, CD20 or CD5 (last three patients). Cells were stained using 2B6 antibody to detect CD32B followed by F(ab)'2 fragments of Cy5-labeled goat anti mouse IgG, and CD3, and counter-stained with directly FITC or PE-labeled mouse antibodies against CD19, CD20, or CD5. Stained cells were analyzed by FACSCalibur (Becton Dickinson).

Figures 27A, 27B:
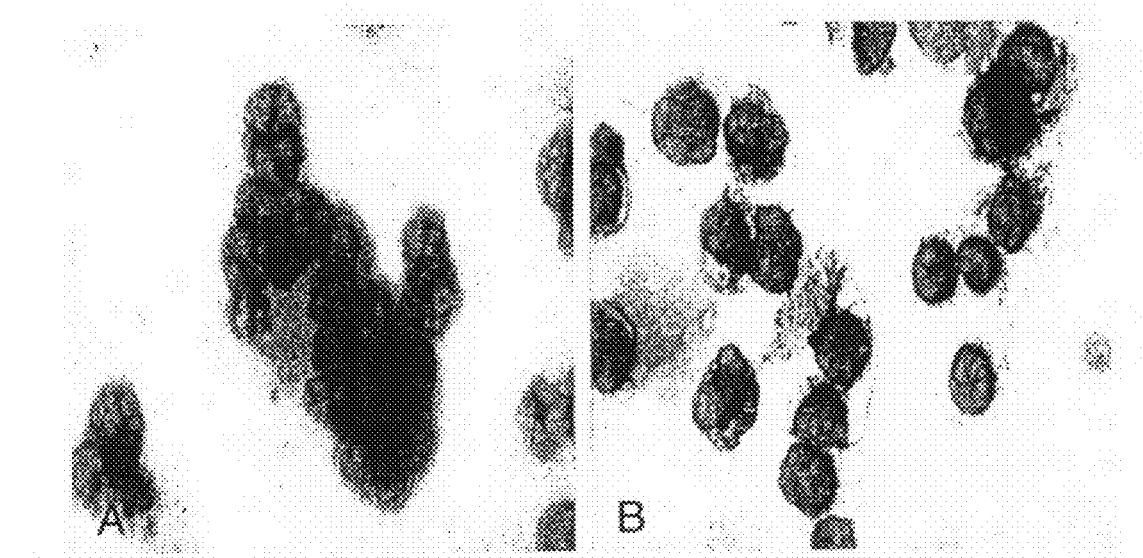

FIGS. 27A-27B: Immunohistochemical Staining of Daudi B Cells.

FIG. 27A. Anti-CD32B antibody; 40× magnification. FIG. 27B. Anti-CD20 antibody; 40× magnification.

FIGS. 28A-28C: Immunohistochemical Staining of Normal Tonsil Tissue.

FIG. 28A. H-E staining; 10× magnification. A portion of a crypt (small arrow) and lymphatic nodules with germinal centers (long arrow) was seen. FIG. 28B. Anti-CD32B; 40× magnification. Positive cells in the follicles surrounding germinal centers. FIG. 28C. Anti-CD20; 40× magnification. Lymphatic follicles showed germinal center cells reacting with anti-CD20.

FIGS. 29A-29C: Immunohistochemical Staining of Normal Lymph Nodes.

FIG. 29A. H-E staining; 4× magnification. Some lymphatic follicles with germinal centers were seen. FIG. 29B. Anti-CD32B; 4× magnification. Germinal centers were circumscribed by a ring of positive cells for CD32B. FIG. 29C. Anti-CD20; 4× magnification. Cells in the germinal centers reacted with antiCD20.

FIGS. 30A-30C: Immunohistochemical Staining of Lymph Nodes from Patient 1 (MG04-CHTN-19).

Evidence of a malignant process with a diffuse type of infiltration changing the architecture of a normal lymph node was seen. This process resulted in sheets of large irregular cells with hyperchromatic nuclei and scan cytoplasm. FIG. 30A. H&E staining; 4× magnification. FIG. 30B. H&E staining; 10× magnification. FIG. 30C. H&E staining; 20× magnification.

FIGS. 31A-31B: Immunohistochemical Staining of Lymph Nodes from Patient 1 (MG04-CHTN-19).

Serial sections at 4× magnification showed differences in the pattern of distribution of cells expressing CD32B (FIG. 31A. anti-CD32B antibody) and CD20 (FIG. 31B. anti-CD20 antibody).

FIGS. 32A-32D: Immunohistochemical Staining of Lymph Nodes from Patient 1 (MG04-CHTN-19).

Isotype controls are to the left of each test antibody. FIG. 32A. Iso-control (IgG1); 10× magnification. FIG. 32B. anti-CD32B antibody (m2B6); 10× magnification. FIG. 32C. Iso-control (IgG2a); 10× magnification. FIG. 32D. anti-CD20 antibody (1F5); 10× magnification.

FIGS. 33A-33C: Immunohistochemical Staining of Lymph Nodes from Patient 2 (MG04-CHTN-22).

Malignant cells were infiltrating and expanding towards areas where normal lymph node tissue (arrow) was still present. No lymphatic follicles were seen. FIG. 33A. H&E staining; 4× magnification. FIG. 33B. H&E staining; 10× magnification. FIG. 33C. H&E staining; 20× magnification.

FIGS. 34A-34B: Immunohistochemical staining of lymph nodes from patient 2 (MG04-CHTN-22).

Differences in cell distribution and number of cells expressing CD32b and CD20 were seen. FIG. 34A. Anti-CD32B antibody; 4× magnification. FIG. 34B. Anti-CD20 antibody; 4× magnification.

FIGS. 35A-35D: Immunohistochemical Staining of Lymph Nodes from Patient 2 (MG04-CHTN-22).

Isotype controls and their corresponding test antibodies to the right. FIG. 35A. Iso-control (IgG1); 10× magnification. FIG. 35B. anti-CD32B antibody (m2B6); 10× magnification. FIG. 35C. Iso-control (IgG2a); 10× magnification. FIG. 35D. anti-CD20 antibody (1F5); 10× magnification.

FIGS. 36A-36C: Immunohistochemical Staining of Lymph Nodes from Patient 3 (MG04-CHTN-26).

Neoplastic cells were distributed in a follicular and diffuse histological pattern. At high power view, large cells with irregular and hyperchromatic nuclei were present. FIG. 36A. H&E staining; 4× magnification. FIG. 36B. H&E staining; 10× magnification. FIG. 36C. H&E staining; 20× magnification.

FIGS. 37A-37B: Immunohistochemical Staining of Lymph Nodes from Patient 3 (MG04-CHTN-26).

More neoplastic cells reacted to anti-CD20 (FIG. 37B) than to anti-CD32b (FIG. 37A). FIG. 37A. Anti-CD32B; 4× magnification. FIG. 37B. Anti-CD20; 4× magnification.

FIGS. 38A-38D: Immunohistochemical Staining of Lymph Nodes from Patient 3 (MG04-CHTN-26).

Isotype control to the left of each test antibody. FIG. 38A. Iso-control (IgG1); 10× magnification. FIG. 38B. anti-CD32B antibody (m2B6); 10× magnification. FIG. 38C. Iso-control (IgG2a); 10× magnification. FIG. 38D. anti-CD20 antibody (1F5); 10× magnification.

FIGS. 39A-39C: Immunohistochemical Staining of Lymph Nodes from Patient 4 (MG04-CHTN-27).

Replacement of the normal lymph node by a diffuse proliferation of cells large in size with hyperchromatic nuclei was seen. FIG. 39A. H&E staining; 4× magnification. FIG. 39B. H&E staining; 10× magnification. FIG. 39C. H&E staining; 20× magnification.

FIGS. 40A-40B: Immunohistochemical Staining of Lymph Nodes from Patient 4 (MG04-CHTN-27).

Neoplastic cells have more affinity for anti CD32B. FIG. 40A. Anti-CD32B antibody; 4× magnification. FIG. 40B. Anti-CD20 antibody; 4× magnification.

FIGS. 41A-41D: Immunohistochemical Staining of Lymph Nodes from Patient 4 (MG04-CHTN-27).

FIG. 41A. Iso-control (IgG1); 10× magnification. FIG. 41B. anti-CD32B antibody (m2B6); 10× magnification. FIG. 41C. Iso-control (IgG2a); 10× magnification. FIG. 41D. anti-CD20 antibody (1F5); 10× magnification.

FIGS. 42A-42C: Immunohistochemical Staining of Lymph Nodes from Patient 5 (MG05-CHTN-03).

This tumor was organized in a diffuse pattern and was composed of intermediate to large cells with hyperchromatic nuclei. FIG. 42A. H&E staining; 4× magnification. FIG. 42B. H&E staining; 10× magnification. FIG. 42C. H&E staining; 20× magnification.

FIGS. 43A-43B: Immunohistochemical Staining of Lymph Nodes from Patient 5 (MG05-CHTN-03).

Tumor cells reacted strongly with anti-CD32B (FIG. 43A). FIG. 43A. Anti-CD32B antibody; 4× magnification. FIG. 43B. Anti-CD20 antibody; 4× magnification.

FIGS. 44A-44D: Immunohistochemical Staining of Lymph Nodes from Patient 5 (MG05-CHTN-03).

FIG. 44A. Iso-control (IgG1); 10× magnification. FIG. 44B. anti-CD32B antibody (m2B6); 10× magnification. FIG. 44C. Iso-control (IgG2a); 10× magnification. FIG. 44D. anti-CD20 antibody (1F5); 10× magnification.

FIGS. 45A-45C: Immunohistochemical Staining of Lymph Nodes from Patient 6 (MG05-CHTN-05).

A predominantly diffuse infiltrate of this lymph node secondary to a proliferation of large cells with round nuclei intermixed with scattered small and normal lymphocytes was seen. FIG. 45A. H&E staining; 4× magnification. FIG. 45B. H&E staining; 10× magnification. FIG. 45C. H&E staining; 20× magnification.

FIGS. 46A-46B: Immunohistochemical Staining of Lymph Nodes from Patient 6 (MG05-CHTN-05).

Anti-CD20 binds strongly to the cells in this lymphoma case (FIG. 46B), while some cells are reacted to anti-CD32B (FIG. 46A) FIG. 46A: Anti-CD32B antibody; 4× magnification. FIG. 46B: Anti-CD20 antibody; 4× magnification.

FIGS. 47A-47D: Immunohistochemical Staining of Lymph Nodes from Patient 6 (MG05-CHTN-05).

FIG. 47A: Iso-control (IgG1); 10× magnification. FIG. 47B: anti-CD32B antibody (m2B6); 10× magnification. FIG. 47C: Iso-control (IgG2a); 10× magnification. FIG. 47D: anti-CD20 antibody (1F5); 10× magnification.

FIGS. 48A-48C: Immunohistochemical Staining of Lymph Nodes from Patient 7 (MG04-CHTN-30).

Lymph node with a diffuse infiltration by small lymphocytes with round and basophilic nuclei and scanty cytoplasm was seen. Cytologic atypia was not present. FIG. 48A: H&E staining; 4× magnification. FIG. 48B: H&E staining; 10× magnification. FIG. 48C: H&E staining; 20× magnification.

FIGS. 49A-49D: Immunohistochemical Staining of Lymph Nodes From Patient 7 (MG04-CHTN-30).

Isotype controls and their corresponding test antibodies to the right. FIG. 49A: Iso-control (IgG1); 10× magnification. FIG. 49B: anti-CD32B antibody (m2B6); 10× magnification. FIG. 49C: Iso-control (IgG2a); 10× magnification. FIG. 49D: anti-CD20 antibody (1F5); 10× magnification.

FIGS. 50A-50C: Immunohistochemical staining of lymph nodes from patient 8 (MG04-CHTN-31).

Lymph node with complete replacement of its normal architecture by large to intermediate cells with round nuclei and scant cytoplasm was seen. FIG. 50A: H&E staining; 4× magnification. FIG. 50B: H&E staining; 10× magnification. FIG. 50C: H&E staining; 20× magnification.

FIGS. 51A-51D: Immunohistochemical Staining of Lymph Nodes from Patient 8 (MG04-CHTN-31).

Isotype controls and their corresponding test antibodies to the right. FIG. 51A: Iso-control (IgG1); 10× magnification. FIG. 51B: anti-CD32B antibody (m2B6); 10× magnification.

FIG. 51C: Iso-control (IgG2a); 10× magnification. FIG. 51D: anti-CD20 antibody (1F5); 10× magnification.

FIGS. 52A-52C: Immunohistochemical Staining of Spleen from Patient 9 (MG04-CHTN-36).

This spleen showed a massive involvement of the red pulp. At high power view, large to intermediate malignant cells with scanty cytoplasm were seen. FIG. 52A: H&E staining; 4× magnification. FIG. 52B: H&E staining; 10× magnification. FIG. 52C: H&E staining; 20× magnification.

FIGS. 53A-53D: Immunohistochemical Staining of Spleen from Patient 9 (MG04-CHTN-36).

FIG. 53A: Iso-control (IgG1); 10× magnification. FIG. 53B: anti-CD32B antibody (m2B6); 10× magnification. FIG. 53C: Iso-control (IgG2a); 10× magnification. FIG. 53D: anti-CD20 antibody (1F5); 10× magnification.

FIGS. 54A-54C: Immunohistochemical Staining of Lymph Nodes from Patient 10 (MG04-CHTN-41).

Although this lymph node presented few structures suggesting the formation of nodules, it was predominantly diffuse. At high power view, these cells were small with slightly irregular nuclei. FIG. 54A: H&E staining; 4× magnification. FIG. 54B: H&E staining; 10× magnification. FIG. 54C: H&E staining; 20× magnification.

FIGS. 55A-55D: Immunohistochemical staining of lymph nodes from patient 10 (MG04-CHTN-41).

FIG. 55A: Iso-control (IgG1); 10× magnification. FIG. 55B: anti-CD32B antibody (m2B6); 10× magnification. FIG. 55C: Iso-control (IgG2a); 10× magnification. FIG. 55D: anti-CD20 antibody (1F5); 10× magnification.

FIGS. 56A-56C: Immunohistochemical Staining of Lymph Nodes from Patient 11 (MG04-CHTN-05).

This lymph node was characterized by a malignant lymphoma of the large cell type. The tumor had a monotonous proliferation of large cells distributed in a diffuse pattern. FIG. 56A: H&E staining; 4× magnification. FIG. 56B: H&E staining; 10× magnification. FIG. 56C: H&E staining; 20× magnification.

FIGS. 57A-57D: Immunohistochemical Staining of Lymph Nodes from Patient 11 (MG04-CHTN-05).

FIG. 57A: Iso-control (IgG1); 10× magnification. FIG. 57B: anti-CD32B antibody (m2B6); 10× magnification. FIG. 57C: Iso-control (IgG2a); 10× magnification. FIG. 57D: anti-CD20 antibody (1F5); 10× magnification.

DESCRIPTION OF THE PREFERRED EMBODIMENTS

I. FcγRIIB-Specific Antibodies

The present invention encompasses antibodies (preferably monoclonal antibodies) or fragments thereof that specifically bind FcγRIIB, preferably human FcγRIIB, more preferably native human FcγRIIB with a greater affinity than said antibodies or fragments thereof bind FcγRIIA, preferably human FcγRIIA, more preferably native human FcγRIIA. Representative antibodies are disclosed in U.S. Provisional Patent Application No. 2004/0185045 and U.S. Provisional Application Ser. No. 60/569,882, herein expressly incorporated by reference in its entirety. The present invention encompasses the use of a FcγRIIB-specific antibody, an analog, derivative or an antigen-binding fragment thereof (e.g., one or more complementarity determining regions ("CDRs") of a FcγRIIB-specific antibody) in the prevention, treatment, management or amelioration of a diseases, such as cancer, in particular, a B-cell malignancy, or one or more symptoms thereof. Preferably, the antibodies of the invention bind the extracellular domain of native human FcγRIIB. In certain embodiments, the antibodies or fragments thereof bind to FcγRIIB with an affinity greater than two-fold, four fold, 6 fold, 10 fold, 20 fold, 50 fold, 100 fold, 1000 fold, $10^4$ fold, $10^5$ fold, $10^6$ fold, $10^7$ fold, or $10^8$ fold than said antibodies or fragments thereof bind FcγRIIA. In yet other embodiments, the invention encompasses the use of FcγRIIB antibodies that bind exclusively to FcγRIIB and have no affinity for FcγRIIA using standard methods known in the art and disclosed herein. In a preferred embodiment, the antibodies are human or humanized.

The invention also encompasses antibodies or fragments thereof that specifically bind FcγRIIB, particularly human FcγRIIB, more particularly native human FcγRIIB, and blocks the Fc binding domain of FcγRIIB, particularly human FcγRIIB, more particularly native human FcγRIIB. Preferably, the antibodies of the invention bind the extracellular domain of native human FcγRIIB. In certain embodiments, the antibody or fragment thereof blocks crosslinking of FcγRIIB to an immunoreceptor tyrosine-based activation motif (ITAM) containing activating receptor. ITAM containing receptors include, but are not limited to Fc Receptors (CD64, CD32A, CD16, CD23, FcεRI, etc.); TCR-associated CD3γ, CD3δ, CD3ε, and ζ chains; BCR-associated Igα (CD79A) and Igβ (CD79B) chains; DAP12; as well as several virally encoded transmembrane molecules. See Billadeau et al. (2002), "*ITAMs Versus ITIMs: Striking A Balance During Cell Regulation*," The Journal of Clinical Investigation, 2(109): 161-168; herein incorporated by reference in its entirety. In preferred embodiments, this blocking enhances the activity of the activating receptor and/or leads to B cell, mast cell, dendritic cell, or macrophage activation. In certain embodiments, the Fc receptor is an FcεR or an FcγR, preferably FcεRI. In preferred embodiments, an FcεRI dependent activity is modulated. In more preferred embodiments, the FcεRI dependent activity is modulation of calcium mobilization and/or modulation of degranulation.

In yet another preferred embodiment, the antibodies of the invention further do not bind Fc activation receptors, e.g., FcγIIA, FcγIIB, etc. In one embodiment, the FcγRIIB-specific antibody in accordance with the invention is not the monoclonal antibody designated KB61, as disclosed in Pulford et al. (1986) "*A New Monoclonal Antibody (KB61) Recognizing A Novel Antigen Which Is Selectively Expressed On A Subpopulation Of Human B Lymphocytes*," Immunology 57:71-76, or the monoclonal antibody designated mAbII8D2 disclosed in Weinrich et al. (1996) "*Epitope Mapping Of New Monoclonal Antibodies Recognizing Distinct Human FcRII (CD32) Isoforms*," Hybridoma 15: 109-116). In a specific embodiment, the FcγRIIB-specific antibody of the invention does not bind to the same epitope and/or does not compete with binding with the monoclonal antibody KB61 or II8D2. Preferably, the FcγRIIB-specific antibody of the invention does not bind the amino acid sequence SDPNFSI (SEQ ID NO:59), corresponding to positions 176-182 of the FcγRIIB2 isoform (SEQ ID NO:60).

SEQ ID NO: 60:
```
MGILSFLPVL ATESDWADCK SPQPWGHMLL WTAVLFLAPV AGTPAPPKAV      50

LKLEPQWINV LQEDSVTLTC RGTHSPESDS IQWFHNGNLI PTHTQPSYRF     100

KANNNDSGEY TCQTGQTSLS DPVHLTVLSE WLVLQTPHLE FQEGETIVLR     150

CHSWKDKPLV KVTFFQNGKS KKFSRSDPNF SIPQANHSHS GDYHCTGNIG     200

YTLYSSKPVT ITVQAPSSSP MGIIVAVVTG IAVAAIVAAV VALIYCRKKR     250

ISANPTNPDE ADKVGAENTI TYSLLMHPDA LEEPDDQNRI                290
```

In a particular embodiment, the antibodies of the invention, or fragments thereof, agonize at least one activity of FcγRIIB. In one embodiment of the invention, said activity is inhibition of B cell receptor-mediated signaling. In another embodiment, the agonistic antibodies of the invention inhibit activation of B cells, B cell proliferation, antibody production, intracellular calcium influx of B cells, cell cycle progression, or activity of one or more downstream signaling molecules in the FcγRIIB signal transduction pathway. In yet another embodiment, the agonistic antibodies of the invention enhance phosphorylation of FcγRIIB or SHIP recruitment. In a further embodiment of the invention, the agonistic antibodies inhibit MAP kinase activity or Akt recruitment in the B cell receptor-mediated signaling pathway. In another embodiment, the agonistic antibodies of the invention agonize FcγRIIB-mediated inhibition of FcεRI signaling. In a particular embodiment, said antibodies inhibit FcεRI-induced mast cell activation, calcium mobilization, degranulation, cytokine production, or serotonin release. In another embodiment, the agonistic antibodies of the invention stimulate phosphorylation of FcγRIIB, stimulate recruitment of SHIP, stimulate SHIP phosphorylation and its association with Shc, or inhibit activation of MAP kinase family members (e.g., Erk1, Erk2, JNK, p38, etc.). In yet another embodiment, the agonistic antibodies of the invention enhance tyrosine phosphorylation of p62dok and its association with SHIP and rasGAP. In another embodiment, the agonistic antibodies of the invention inhibit FcγR-mediated phagocytosis in monocytes or macrophages.

In another embodiment, the antibodies of the invention, or fragments thereof, antagonize at least one activity of FcγRIIB. In one embodiment, said activity is activation of B cell receptor-mediated signaling. In a particular embodiment, the antagonistic antibodies of the invention enhance B cell activity, B cell proliferation, antibody production, intracellular calcium influx, or activity of one or more downstream signaling molecules in the FcγRIIB signal transduction pathway. In yet another particular embodiment, the antagonistic antibodies of the invention decrease phosphorylation of FcγRIIB or SHIP recruitment. In a further embodiment of the invention, the antagonistic antibodies enhance MAP kinase activity or Akt recruitment in the B cell receptor mediated signaling pathway. In another embodiment, the antagonistic antibodies of the invention antagonize FcγRIIB-mediated inhibition of FcεRI signaling. In a particular embodiment, the antagonistic antibodies of the invention enhance FcεRI-induced mast cell activation, calcium mobilization, degranulation, cytokine production, or serotonin release. In another embodiment, the antagonistic antibodies of the invention inhibit phosphorylation of FcγRIIB, inhibit recruitment of SHIP, inhibit SHIP phosphorylation and its association with Shc, enhance activation of MAP kinase family members (e.g., Erk1, Erk2, JNK, p38, etc.). In yet another embodiment, the antagonistic antibodies of the invention inhibit tyrosine phosphorylation of p62dok and its association with SHIP and rasGAP. In another embodiment, the antagonistic antibodies of the invention enhance FcγR-mediated phagocytosis in monocytes or macrophages. In another embodiment, the antagonistic antibodies of the invention prevent phagocytosis, clearance of opsonized particles by splenic macrophages.

In other embodiments, the antibodies of the invention, or fragments thereof can be used to target one population of cells, but not others. Without being bound by any theory, the present inventors have discovered that FcγRIIB is not highly expressed on neutrophils, as previously thought. High concentrations of an anti-FcγRIIB antibody react with neutrophils. However, neutrophil reactivity rapidly disappears with decreasing concentrations of anti-FcγRIIB. At low concentrations of anti-FcγRIIB antibody, reactivity with CD20+ B cells was preserved. Thus, reactivity of an antibody of the invention with neutrophils can be reduced so as to not affect irrelevant populations, such as neutrophils or platelets. Accordingly, in certain embodiments of the invention, an antibody of the invention is employed at levels that fully recognize its target populations, but not other cells.

Antibodies of the invention include, but are not limited to, monoclonal antibodies, synthetic antibodies, recombinantly produced antibodies, multispecific antibodies, human antibodies, humanized antibodies, chimeric antibodies, camelized antibodies, single-chain Fvs (scFv), single chain antibodies, Fab fragments, F(ab') fragments, disulfide-linked Fvs (sdFv), intrabodies, and epitope-binding fragments of any of the above. In particular, antibodies used in the methods of the present invention include immunoglobulin molecules and immunologically active portions of immunoglobulin molecules, i.e., molecules that contain an antigen binding site that immunospecifically binds to FcγRIIB with greater affinity than said immunoglobulin molecule binds FcγRIIA or immunospecifically binds FcγRIIB and blocks the Fc binding domain of FcγRIIB. Antibody analogs may also include FcγRIIB-specific T-cell receptors, for example, chimeric T-cell receptors (see, e.g., U.S. Patent Application Publication No. 2004/0043401), a single-chain T-cell receptor linked to a single-chain antibody (see, e.g., U.S. Pat. No. 6,534,633), and protein scaffolds (see, e.g., U.S. Pat. No. 6,818,418). In certain embodiments, an antibody analog of the invention is not a monoclonal antibody.

The antibodies used in the methods of the invention may be from any animal origin including birds and mammals (e.g., human, non-human primate, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or libraries of synthetic human immunoglobulin coding sequences or from mice that express antibodies from human genes.

The antibodies used in the methods of the present invention may be monospecific, bispecific, trispecific or of greater multispecificity. Multispecific antibodies may immunospecifically bind to different epitopes of FcγRIIB or immunospecifically bind to both an epitope of FcγRIIB as well a heterologous epitope, such as a heterologous polypeptide or solid support material. See, e.g., International Publication Nos. WO 93/17715, WO 92/08802, WO 91/00360, and WO 92/05793; Tutt, et al. (1991) "*Trispecific F(ab)3 Derivatives That Use Cooperative Signaling Via The TCR/CD3 Complex And CD2 To Activate And Redirect Resting Cytotoxic T Cells,*" J. Immunol. 147:60-69; U.S. Pat. Nos. 4,474,893, 4,714,681, 4,925,648, 5,573,920, and 5,601,819; and Kostelny et al. (1992) "*Formation Of A Bispecific Antibody By The Use Of Leucine Zippers,*" J. Immunol. 148:1547-1553; Todorovska et al. (2001) "*Design And Application Of Diabodies, Triabodies And Tetrabodies For Cancer Targeting,*" J. Immunol. Methods, 248:47-66.

In particular embodiments, the antibodies of the invention are multi-specific with specificities for FcγRIIB and for a cancer antigen or any other cell surface marker specific for a cell (e.g., an immune cell such as a T-cell or B-cell) designed to be killed, e.g., in treating or preventing a particular disease or disorder, or for other Fc receptors, e.g., FcγRIIIA, FcγRIIIB, etc.

In one particular embodiment, the antibody is derived from a mouse monoclonal antibody produced by clone 2B6 or 3H7, having ATCC accession numbers PTA-4591 and PTA-4592, respectively. Hybridomas producing antibodies 2B6 and 3H7 have been deposited with the American Type Culture Collection (10801 University Blvd., Manassas, Va. 20110-2209) on Aug. 13, 2002 under the provisions of the Budapest Treaty on the International Recognition of the Deposit of Microorganisms for the Purposes of Patent Procedures, and assigned accession numbers PTA-4591 (for hybridoma producing 2B6) and PTA-4592 (for hybridoma producing 3H7), respectively, and are incorporated herein by reference. In a specific embodiment, the invention encompasses an antibody with the heavy chain variable domain having the following amino acid sequence:

```
SEQ ID NO: 58:
QVQLQQPVTE LVRPGASVML SCKASDYPFT NYWIHWVKQR PGQGLEWIGV      50

IDPSDTYPNY NKKFKGKATL TVVVSSSTAY MQLSSLTSDD SAVYYCARNG     100

DSDYYSGMDY WGQGTSVTVS S;                                   121
``` and the light chain variable domain having the following amino acid sequence:

```
SEQ ID NO: 44:
DILLTQSPAI LSVSPGERVS FSCRTSQSIG TNIHWYQQRT NGFPRLLIKN      50

VSESISGIPS RFSGSGSGTD FILSINSVES EDIADYYCQQ SNTWPFTFGG     100

GTKLEIK.                                                  107
```

In a preferred embodiment, the antibodies of the invention are human or have been humanized, preferably a humanized version of the antibody produced by clone 3H7 or 2B6.

The invention also encompasses the use of other antibodies, preferably monoclonal antibodies or fragments thereof that specifically bind FcγRIIB, preferably human FcγRIIB, more preferably native human FcγRIIB, that are derived from clones including but not limited to 1D5, 2E1, 2H9, 2D11, and 1F2 having ATCC Accession numbers, PTA-5958, PTA-5961, PTA-5962, PTA-5960, and PTA-5959, respectively. Hybridomas producing the above-identified clones were deposited under the provisions of the Budapest Treaty with the American Type Culture Collection (10801 University Blvd., Manassas, Va. 20110-2209) on May 7, 2004, and are incorporated herein by reference. In preferred embodiments, the antibodies described above are chimerized or humanized. Humanized versions of FcγRIIB-specific antibodies are described in U.S. application Ser. No. 11/126,978, filed May 10, 2005, herein incorporated by reference in its entirety.

In a specific embodiment, an antibody used in the methods of the present invention is an antibody or an antigen-binding fragment thereof (e.g., comprising one or more complementarily determining regions (CDRs), preferably all 6 CDRs) of the antibody produced by clone 2B6 or 3H7 with ATCC accession numbers PTA-4591 and PTA-4592, respectively (e.g., the heavy chain CDR3). In a specific embodiment, an antibody used in the methods of the present invention is an antibody or an antigen-binding fragment thereof (e.g., comprising one or more complementarily determining regions (CDRs), preferably all 6 CDRs) of the antibody produced by clone 1D5, 2E1, 2H9, 2D11, and 1F2 having ATCC Accession numbers, PTA-5958, PTA-5961, PTA-5962, PTA-5960, and PTA-5959, respectively (e.g., the heavy chain CDR3). In another embodiment, an antibody used in the methods of the present invention binds to the same epitope as the mouse monoclonal antibody produced from clone 2B6 or 3H7 with ATCC accession numbers PTA-4591 and PTA-4592, respectively and/or competes with the mouse monoclonal antibody produced from clone 2B6 or 3H7 with ATCC accession numbers PTA-4591 and PTA-4592, respectively as determined, e.g., in an ELISA assay or other appropriate competitive immunoassay, and also binds FcγRIIB with a greater affinity than said antibody or a fragment thereof binds FcγRIIA. In another embodiment, an antibody used in the methods of the present invention binds to the same epitope as the mouse monoclonal antibody produced from clone 1D5, 2E1, 2H9, 2D11, and 1F2 having ATCC Accession numbers, PTA-5958, PTA-5961, PTA-5962, PTA-5960, and PTA-5959, respectively, and/or competes with the mouse monoclonal antibody produced from clone 1D5, 2E1, 2H9, 2D11, and 1F2 having ATCC Accession numbers, PTA-5958, PTA-5961, PTA-5962, PTA-5960, and PTA-5959, respectively, as determined, e.g., in an ELISA assay or other appropriate competitive immunoassay, and also binds FcγRIIB with a greater affinity than said antibody or a fragment thereof binds FcγRIIA.

The present invention also encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively. The present invention further encompasses antibodies or fragments thereof that specifically bind FcγRIIB with greater affinity than said antibody or fragment thereof binds FcγRIIA, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively. The determination of percent identity of two amino acid sequences can be determined by any method known to one skilled in the art, including BLAST protein searches.

The present invention also encompasses the use of antibodies or antibody fragments that specifically bind FcγRIIB with greater affinity than said antibodies or fragments thereof binds FcγRIIA, and antibodies or antibody fragments thereof that specifically binds FcγRIIB and block the Fc binding domain of FcγRIIB, wherein said antibodies or antibody fragments are encoded by a nucleotide sequence that hybridizes to the nucleotide sequence of the mouse monoclonal antibody produced by clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively, under stringent conditions. In a preferred embodiment, the invention provides antibodies or fragments thereof that specifically bind FcγRIIB with greater affinity than said antibodies or fragments thereof bind FcγRIIA, and antibodies or a fragments thereof that specifically binds FcγRIIB and block the Fc binding domain of FcγRIIB, said antibodies or antibody fragments comprising a variable light chain and/or variable heavy chain encoded by a nucleotide sequence that hybridizes under stringent conditions to the nucleotide sequence of the variable light chain and/or variable heavy chain of the mouse monoclonal antibody produced by clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively, under stringent conditions. In another preferred embodiment, the invention provides antibodies or fragments thereof that specifically bind FcγRIIB with greater affinity than said antibodies or fragments thereof bind FcγRIIA, and antibodies or a fragments thereof that specifically binds FcγRIIB and block the Fc binding domain of FcγRIIB said antibodies or antibody fragments comprising one or more CDRs encoded by a nucleotide sequence that hybridizes under stringent conditions to the nucleotide sequence of one or more CDRs of the mouse monoclonal antibody produced by clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 CURRENT PROTOCOLS IN MOLECULAR BIOLOGY, vol. 1, Green Publishing Associates, Inc. and John Wiley and Sons, Inc., NY at pages 6.3.1-6.3.6 and 2.10.3, incorporated herein by reference).

The constant domains of the antibodies may be selected with respect to the proposed function of the antibody, in particular with regard to the effector function which may be required. In some embodiments, the constant domains of the antibodies are human IgA, IgE, IgG or IgM domains.

The antibodies used in the methods of the invention include derivatives that are modified, i.e, by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Further, the antibodies of the invention can, in turn, be utilized to generate anti-idiotype antibodies using techniques well known to those skilled in the art. (See, e.g., Greenspan et al. (1989) "*Cooperative Binding Of Two Antibodies To Independent Antigens By An Fc-Dependent Mechanism*," FASEB J. 7:437-444; and Nissinoff (1991) "*Idiotypes: Concepts And Applications*," J. Immunol. 147:2429-2438). The invention provides methods employing the use of polynucleotides comprising a nucleotide sequence encoding an antibody of the invention or a fragment thereof.

The present invention encompasses single domain antibodies, including camelized single domain antibodies (See e.g., Muyldermans et al. (2001) "*Recognition Of Antigens By Single-Domain Antibody Fragments: The Superfluous Luxury Of Paired Domains*," Trends Biochem. Sci. 26:230-235; Nuttall et al. (2000) "*Immunoglobulin VH Domains And Beyond: Design And Selection Of Single-Domain Binding And Targeting Reagents*," Cur. Pharm. Biotech. 1:253-263; Reichmann et al. (1999) "*Single Domain Antibodies: Comparison Of Camel VH And Camelised Human VH Domains*," J. Immunol. Meth. 231:25-38; International Publication Nos. WO 94/04678 and WO 94/25591; U.S. Pat. No. 6,005,079; which are incorporated herein by reference in their entireties). In one embodiment, the present invention provides single domain antibodies comprising two VH domains with modifications such that single domain antibodies are formed.

The methods of the present invention also encompass the use of antibodies or fragments thereof that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The antibodies of the invention may be engineered by methods described in Ward et al. to increase biological half-lives (See U.S. Pat. No. 6,277,375 B1). For example, antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies of the invention may also be modified by the methods and coupling agents described by Davis et al. (See U.S. Pat. No. 4,179,337) in order to provide compositions that can be injected into the mammalian circulatory system with substantially no immunogenic response.

The present invention also encompasses the use of antibodies or antibody fragments comprising the amino acid sequence of any of the antibodies of the invention with mutations (e.g., one or more amino acid substitutions) in the framework or CDR regions. Preferably, mutations in these antibodies maintain or enhance the avidity and/or affinity of the antibodies for FcγRIIIB to which they immunospecifically bind. Standard techniques known to those skilled in the art (e.g., immunoassays) can be used to assay the affinity of an antibody for a particular antigen.

For some uses, including in vivo use of antibodies in humans and in vitro detection assays, it may be preferable to use human, chimeric or humanized antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "*Human Antibodies From Transgenic Mice*," Int. Rev. Immunol. 13:65-93, which is incorporated herein by reference in its entirety. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. (See e.g., Morrison (1985) "*Transfectomas Provide Novel Chimeric Antibodies*," Science 229:1202-1207; Oi et al. (1986) "*Chimeric Antibodies*," BioTechniques 4:214-221; Gillies et al. (1989) "*High-Level Expression Of Chimeric Antibodies Using Adapted cDNA Variable Region Cassettes*," J. Immunol. Methods 125:191-202; Gillies et al. (1989) "*High-Level Expression Of Chimeric Antibodies Using Adapted cDNA Variable Region Cassettes*," J. Immunol. Methods 125:191-202; and U.S. Pat. Nos. 6,311,415, 5,807,715, 4,816,567, and 4,816,397, which are incorporated herein by reference in their entirety.) Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan (1991) "*A Possible Procedure For Reducing The Immunogenicity Of Antibody Variable Domains While Preserving Their Ligand-Binding Properties*," Molecular Immunology 28(4/5):489-498; Studnicka et al. (1994) "*Human-Engineered Monoclonal Antibodies Retain Full Specific Binding Activity By Preserving Non-CDR Complementarity-Modulating Residues*," Protein Engineering 7:805-814; and Roguska et al. (1994) "*Humanization Of Murine Monoclonal Antibodies Through Variable Domain Resurfacing*," Proc. Nat. Acad. Sci. 91:969-973), and chain shuffling (U.S. Pat. No. 5,565,332). Each of the above-identified references is incorporated herein by reference in its entirety.

Often, framework residues in the framework regions will be substituted with the corresponding residue from the CDR donor antibody to alter, preferably improve, antigen binding.

These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al. (1988) "*Reshaping Human Antibodies For Therapy,*" Nature 332:323-327, which are incorporated herein by reference in their entireties.)

II. Humanized Antibodies

In preferred embodiments, the antibodies are humanized antibodies. A humanized antibody is an antibody, a variant or a fragment thereof which is capable of binding to a predetermined antigen and which comprises a framework region having substantially the amino acid sequence of a human immunoglobulin and a CDR having substantially the amino acid sequence of a non-human immunoglobulin. A humanized FcγRIIB specific antibody may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody of the invention also comprises at least a portion of an immunoglobulin constant region (Fc), typically that of a human immunoglobulin. The constant domains of the humanized antibodies of the invention may be selected with respect to the proposed function of the antibody, in particular the effector function which may be required. In some embodiments, the constant domains of the humanized antibodies of the invention are human IgA, IgE, IgG or IgM domains. In a specific embodiment, human IgG constant domains, especially of the IgG1 and IgG3 isotypes are used, when the humanized antibodies of the invention is intended for therapeutic uses and antibody effector functions are needed. In alternative embodiments, IgG2 and IgG4 isotypes are used when the humanized antibody of the invention is intended for therapeutic purposes and antibody effector function is not required. Humanized FcγRIIB specific antibodies are disclosed in U.S. Application Ser. Nos. 60/569,882 and 60/582,043, filed May 10, 2004 and Jun. 21, 2004, respectively.

In some embodiments, the antibody contains both the light chain as well as at least the variable domain of a heavy chain. In other embodiments, the antibody may further comprise one or more of the CHI, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the humanized antibody exhibit cytotoxic activity, and the class is typically IgG1. In other embodiments, where such cytotoxic activity is not desirable, the constant domain may be of the IgG2 class. The humanized antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan (1991) "*A Possible Procedure For Reducing The Immunogenicity Of Antibody Variable Domains While Preserving Their Ligand-Binding Properties,*" Molecular Immunology 28(4/5):489-498; Studnicka et al. (1994) "*Human-Engineered Monoclonal Antibodies Retain Full Specific Binding Activity By Preserving Non-CDR Complementarity-Modulating Residues,*" Protein Engineering 7:805-814; and Roguska et al. (1994) "*Humanization Of Murine Monoclonal Antibodies Through Variable Domain Resurfacing,*" Proc. Nat. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al. (2002) "'*Superhumanized' Antibodies: Reduction Of Immunogenic Potential By Complementarity-Determining Region Grafting With Human Germline Sequences: Application To An Anti-CD28,*" J. Immunol. 169:1119-1125; Caldas et al. (2000) "*Design And Synthesis Of Germ line-Based Hemi-Humanized Single-Chain Fv Against The CD18 Surface Antigen,*" Protein Eng. 13:353-360; Morea et al. (2000) "*Antibody Modeling: Implications For Engineering And Design,*" Methods 20:267-279; Baca et al. (1997) "*Antibody Humanization Using Monovalent Phage Display,*" J. Biol. Chem. 272:10678-10684; Roguska et al. (1996) "*A Comparison Of Two Murine Monoclonal Antibodies Humanized By CDR-Grafting And Variable Domain Resurfacing,*" Protein Eng. 9:895-904; Couto et al. (1995) "*Designing Human Consensus Antibodies With Minimal Positional Templates,*" Cancer Res. 55 (23 Supp):5973s-5977s; Couto et al. (1995) "*Anti-BA46 Monoclonal Antibody Mc3: Humanization Using A Novel Positional Consensus And In Vivo And In Vitro Characterization,*" Cancer Res. 55:1717-22; Sandhu (1994) "*A Rapid Procedure For The Humanization Of Monoclonal Antibodies,*" Gene 150:409-410; Pedersen et al. (1994) "*Comparison Of Surface Accessible Residues In Human And Murine Immunoglobulin Fv Domains. Implication For Humanization Of Murine Antibodies,*" J. Mol. Biol. 235:959-973; Jones et al. (1986) "*Replacing The Complementarity-Determining Regions In A Human Antibody With Those From A Mouse,*" Nature 321:522-525; Riechmann et al. (1988) "*Reshaping Human Antibodies For Therapy,*" Nature 332:323-327; and Presta (1992) "*Antibody Engineering,*" Curr. Op. Biotech. 3:394-398. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al. (1988) "*Reshaping Human Antibodies For Therapy,*" Nature 332:323-327, all of which are incorporated herein by reference in their entireties.).

The present invention provides for the use of humanized antibody molecules specific for FcγRIIB in which one or more regions of one or more CDRs of the heavy and/or light chain variable regions of a human antibody (the recipient antibody) have been substituted by analogous parts of one or more CDRs of a donor monoclonal antibody which specifically binds FcγRIIB, with a greater affinity than FcγRIIA, e.g., a monoclonal antibody produced by clone 2B6 or 3H7, having ATCC accession numbers PTA-4591, and PTA-4592, respectively. In other embodiments, the humanized antibodies bind to the same epitope as 2B6 or 3H7. In a most preferred embodiment, the humanized antibody specifically binds to the same epitope as the donor murine antibody. It will be appreciated by one skilled in the art that the invention encompasses CDR grafting of antibodies in general. Thus, the donor and acceptor antibodies may be derived from animals of the same species and even same antibody class or sub-class. More usually, however, the donor and acceptor antibodies are derived from animals of different species. Typically, the donor antibody is a non-human antibody, such as a rodent mAb, and the acceptor antibody is a human antibody.

In some embodiments, at least one CDR from the donor antibody is grafted onto the human antibody. In other embodiments, at least two and preferably all three CDRs of each of the heavy and/or light chain variable regions are grafted onto the human antibody. The CDRs may comprise the Kabat CDRs, the structural loop CDRs or a combination thereof. In some embodiments, the invention encompasses a humanized FcγRIIB antibody comprising at least one CDR grafted heavy chain and at least one CDR-grafted light chain.

In a preferred embodiment, the CDR regions of the humanized FcγRIIB specific antibody are derived from a murine antibody specific for FcγRIIB. In some embodiments, the humanized antibodies described herein comprise alterations, including but not limited to amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein does not necessarily consist of the precise amino acid sequence of the framework region of a natural occurring human antibody variable region, but contains various alterations, including but not limited to amino acid deletions, insertions, modifications that alter the property of the humanized antibody, for example, improve the binding properties of a humanized antibody region that is specific for the same target as the murine FcγRIIB specific antibody. In most preferred embodiments, a minimal number of alterations are made to the framework region in order to avoid large-scale introductions of non-human framework residues and to ensure minimal immunogenicity of the humanized antibody in humans. The donor monoclonal antibody is preferably a monoclonal antibody produced by clones 2B6 and 3H7 (having ATCC accession numbers PTA-4591, and PTA-4592, respectively) which bind FcγRIIB.

In a specific embodiment, the invention encompasses the use of a CDR-grafted antibody which specifically binds FcγRIIB with a greater affinity than said antibody binds FcγRIIA, wherein the CDR-grafted antibody comprises a heavy chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6 and 3H7. In another specific embodiment, the invention encompasses the use of a CDR-grafted antibody which specifically binds FcγRIIB with a greater affinity than said antibody binds FcγRIIA, wherein the CDR-grafted antibody comprises a light chain variable region domain comprising framework residues of the recipient antibody and residues from the donor monoclonal antibody, which specifically binds FcγRIIB with a greater affinity than said antibody binds FcγRIIA, e.g., monoclonal antibody produced from clones 2B6, 3H7, 1D5, 2E1, 2H9, 2D11, or 1F2.

Preferably the humanized antibodies of the invention bind the extracellular domain of native human FcγRIIB. The humanized anti-FcγRIIB antibodies of the invention may have a heavy chain variable region comprising the following heavy chain CDR1 amino acid sequence: NYWIH (SEQ ID NO:1); or DAWMD (SEQ ID NO:29); and/or the following heavy chain CDR2 amino acid sequence: VIDPSDTYP-NYNKKFKG (SEQ ID NO:2); or EIRNKANNLATYYAES-VKG (SEQ ID NO:30); and/or the following heavy chain CDR3 amino acid sequence: NGDSDYYSGMDY (SEQ ID NO:3); or YSPFAY (SEQ ID NO:31); and/or a light chain variable region comprising the following light chain CDR1 amino acid sequence: RTSQSIGTNIH (SEQ ID NO:8); or RASQEISGYLS (SEQ ID NO:38); and/or the following light chain CDR2 amino acid sequence: NVSESIS (SEQ ID NO:9); or YVSESIS (SEQ ID NO:10); or YASESIS (SEQ ID NO:11); or AASTLDS (SEQ ID NO:39); and/or the following light chain CDR3 amino acid sequence: QQSNTWPFT (SEQ ID NO:12); or LQYVSYPYT (SEQ ID NO:40).

In certain embodiments, the humanized antibodies of the invention comprise a light chain variable regions comprising the amino acid sequence of:

```
SEQ ID NO: 18:
EIVLTQSPDF QSVTPKEKVT ITCRTSQSIG TNIHWYQQKP DQSPKLLIKN      50

VSESISGVPS RFSGSGSGTD FTLTINSLEA EDAATYYCQQ SNTWPFTFGG     100

GTKVEIK;                                                   107
``` a light chain variable region comprising the amino acid sequence of:

```
SEQ ID NO: 20:
EIVLTQSPDF QSVTPKEKVT ITCRTSQSIG TNIHWYQQKP DQSPKLLIKY      50

VSESISGVPS RFSGSGSGTD FTLTINSLEA EDAATYYCQQ SNTWPFTFGG     100

GTKVEIK;                                                   107
``` a light chain variable region comprising the amino acid sequence of:

```
SEQ ID NO: 22:
EIVLTQSPDF QSVTPKEKVT ITCRTSQSIG TNIHWYQQKP DQSPKLLIKY      50

ASESISGVPS RFSGSGSGTD FTLTINSLEA EDAATYCQQS NTWPFTGGG      100

TKVEIK;                                                    106
or
``` a light chain variable region comprising the amino acid sequence of:

```
SEQ ID NO: 46:
DIQMTQSPSS LSASLGERVS LTCRASQEIS GYLSWLQQKP DGTIRRLIYA      50

ASTLDSGVPK RFSGSWSGSD YSLTISSLES EDFADYYCLQ YVSYPYTFGG     100

GTKLEIK;                                                   107
``` and/or a heavy chain variable region comprising the amino acid sequence of:

```
SEQ ID NO: 24:
QVQLVQSGAE VKKPGASVKV SCKASGYTFT NYWIHWVRQA PGQGLEWMGV      50

IDPSDTYPNY NKKFKGRVTM TTDTSTSTAY MELRSLRSDD TAVYYCARNG     100

DSDYYSGMDY WGQGTTVTVS S;                                   121
or
``` a heavy chain variable region comprising the amino acid sequence of:

```
SEQ ID NO: 37:
EVKFEESGGG LVQPGGSMKL SCAASGFTFS DAWMDWVRQG PEKGLEWVAE      50

IRNKANNLAT YYAESVKGRF TIPRDDSKSS VYLHMNSLRA EDTGIYYCYS     100

PFAYWGQGTL VTVSA;                                          115
``` and/or amino acid sequence variants thereof.

In a specific embodiment, the invention encompasses the use of a humanized antibody comprising the CDRs of 2B6 or of 3H7 in the prevention, treatment, management or amelioration of a B-cell malignancy, or one or more symptoms thereof. In particular, an antibody with the heavy chain variable domain having the amino acid sequence of SEQ ID NO:24 and the light chain variable domain having the amino acid sequence of SEQ ID NO:18, SEQ ID NO:20, or SEQ ID NO:22 is used in the prevention, treatment, management or amelioration of a B-cell malignancy, or one or more symptoms thereof. In a specific embodiment, the invention encompasses the use of a humanized antibody with the heavy chain variable domain having the amino acid sequence of SEQ ID NO:37 and the light chain variable domain having the following amino acid sequence:

```
SEQ ID NO: 46:
DIQMTQSPSS LSASLGERVS LTCRASQEIS GYLSWLQQKP DGTIRRLIYA      50

ASTLDSGVPK RFSGSWSGSD YSLTISSLES EDFADYYCLQ YVSYPYTFGG     100

GTKLEIK;                                                   107
``` in the prevention, treatment, management or amelioration of a B-cell malignancy, or one or more symptoms thereof. In yet another preferred embodiment, the humanized antibodies further do not bind Fc activation receptors, e.g., FcγIIIA, FcγIIB, etc.

In one specific embodiment, a humanized 2B6 antibody is provided, wherein the VH region consists of the FR segments from the human germline VH segment VH1-18 (Matsuda et al. (1998) "*The Complete Nucleotide Sequence Of The Human Immunoglobulin Heavy Chain Variable Region Locus*," J. Exp. Med. 188:2151-2162) and JH6 (Ravetch et al. (1981) "*Structure Of The Human Immunoglobulin Mu Locus: Characterization Of Embryonic And Rearranged J And D Genes*," Cell 27(3 Pt. 2): 583-591), and one or more CDR regions of the 2B6 VH, having the amino acid sequence of SEQ ID NO:1, SEQ ID NO:2, or SEQ ID NO:3. In one embodiment, the 2B6 VH has the amino acid sequence of SEQ ID NO:24. In another specific embodiment, the humanized 2B6 antibody further comprises a VL region, which consists of the FR segments of the human germline VL segment VK-A26 (Lautner-Rieske et al. (1992) "*The Human Immunoglobulin Kappa Locus. Characterization Of The Duplicated A Regions*," Eur. J. Immunol. 22:1023-1029) and JK4 (Hieter et al. (1982) "*Evolution Of Human Immunoglobulin Kappa J Region Genes*," J. Biol. Chem. 257:1516-1522), and one or more CDR regions of 2B6VL, having the amino acid sequence of SEQ ID NO:8, SEQ ID NO:9, SEQ ID NO:10, SEQ ID NO:11, and SEQ ID NO:12. In one embodiment, the 2B6 VL has the amino acid sequence of SEQ ID NO:18, SEQ ID NO:20, or SEQ ID NO:22.

In another specific embodiment, a humanized 3H7 antibody is provided, wherein the VH region consists of the FR segments from a human germline VH segment and the CDR regions of the 3H7 VH, having the amino acid sequence of SEQ ID NO:37. In another specific embodiment, the humanized 3H7 antibody further comprises a VL regions, which consists of the FR segments of a human germline VL segment and the CDR regions of 3H7VL, having the amino acid sequence of SEQ ID NO:46.

In particular, a humanized antibody is provided that immunospecifically binds to extracellular domain of native human FcγRIIB, said antibody comprising (or alternatively, consisting of) CDR sequences of 2B6 or 3H7, in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR1, a VL CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

III. Human Antibodies

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring that express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg et al. (1995) "*Human Antibodies From Transgenic Mice*," Int. Rev. Immunol. 13:65-93, which is incorporated herein by reference in its entirety. For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

IV. Chimeric Antibodies

A chimeric antibody is a molecule in which different portions of the antibody are derived from different immunoglobulin molecules such as antibodies having a variable region derived from a non-human antibody and a human immunoglobulin constant region. The present invention provides chimeric antibodies of 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively. Methods for producing chimeric antibodies are known in the art. See e.g., Morrison (1985) "*Transfectomas Provide Novel Chimeric Antibodies*," Science 229:

1202-1207; Oi et al. (1986) "*Chimeric Antibodies*," BioTechniques 4:214-221; Gillies et al. (1989) "*High-Level Expression Of Chimeric Antibodies Using Adapted Cdna Variable Region Cassettes*," J. Immunol. Methods 125:191-202; and U.S. Pat. Nos. 6,311,415, 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan (1991) "*A Possible Procedure For Reducing The Immunogenicity Of Antibody Variable Domains While Preserving Their Ligand-Binding Properties*," Molecular Immunology 28(4/5):489-498; Studnicka et al. (1994) "*Human-Engineered Monoclonal Antibodies Retain Full Specific Binding Activity By Preserving Non-CDR Complementarity-Modulating Residues*," Protein Engineering 7:805-814; and Roguska et al. (1994) "*Humanization Of Murine Monoclonal Antibodies Through Variable Domain Resurfacing*," Proc. Nat. Acad. Sci. 91:969-973), and chain shuffling (U.S. Pat. No. 5,565,332). Each of the above-identified references is incorporated herein by reference in its entirety.

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al. (1988) "*Reshaping Human Antibodies For Therapy*," Nature 332: 323-327, which are incorporated herein by reference in their entireties.

V. Fc Region Modifications

The invention encompasses antibodies with Fc constant domains comprising one or more amino acid modifications that alter antibody effector functions such as those disclosed in U.S. Patent Application Publication Nos. U.S. 2005/0037000 and U.S. 2005/0064514; U.S. Pat. Nos. 5,624,821 and 5,648,260 and European Patent No. EP 0 307 434; all of which are incorporated herein by reference in their entireties. These antibodies may exhibit improved ADCC activity (i.e., 2-fold, 10-fold, 100-fold, 500-fold, etc.) compared to comparable antibodies without amino acid modification.

The present invention encompasses antibodies comprising modifications preferably, in the Fc region that modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821, each of which is incorporated herein by reference in their entirety. The invention encompasses any of the mutations disclosed in U.S. Application Nos. 60/439,498 and 60/456,041, filed Jan. 9, 2003 and Mar. 19, 2003, respectively each of which is incorporated herein by reference in their entirety. In some embodiments, the invention encompasses antibodies that have altered affinity for an activating FcγR, e.g., FcγRIIIA. Preferably, such modifications also have an altered Fc-mediated effector function. Modifications that affect Fc-mediated effector function are known in the art (See U.S. Pat. No. 6,194,551, which is incorporated herein by reference in its entirety). The amino acids that can be modified in accordance with the method of the invention include but are not limited to: Proline 329, Proline 331, and Lysine 322. Proline 329, Proline 331 and Lysine 322 are preferably replaced with alanine, however, substitution with any other amino acid is contemplated. See International Publication No.: WO 00/42072 and U.S. Pat. No. 6,194,551, which are incorporated herein by reference in their entirety.

In one particular embodiment, the modification of the Fc region comprises one or more mutations in the Fc region. The one or more mutations in the Fc region may result in an antibody with an altered antibody-mediated effector function, an altered binding to other Fc receptors (e.g., Fc activation receptors), an altered ADCC activity, or an altered C1q binding activity, or an altered complement dependent cytotoxicity activity, or any combination thereof.

In some embodiments, the invention encompasses molecules comprising a variant Fc region having an amino acid modification at one or more of the following positions: 119, 125, 132, 133, 141, 142, 147, 149, 162, 166, 185, 192, 202, 205, 210, 214, 215, 216, 217, 218, 219, 221, 222, 223, 224, 225, 227, 229, 231, 232, 233, 235, 240, 241, 242, 243, 244, 246, 247, 248, 250, 251, 252, 253, 254, 255, 256, 258, 261, 262, 263, 268, 269, 270, 272, 274, 275, 276, 279, 280, 281, 282, 284, 287, 288, 289, 290, 291, 292, 293, 295, 298, 301, 303, 304, 305, 306, 307, 308, 309, 310, 311, 312, 313, 315, 316, 317, 318, 319, 320, 323, 326, 327, 328, 330, 333, 334, 335, 337, 339, 340, 343, 344, 345, 347, 348, 352, 353, 354, 355, 358, 359, 360, 361, 362, 365, 366, 367, 369, 370, 371, 372, 375, 377, 378, 379, 380, 381, 382, 383, 384, 385, 386, 387, 388, 389, 390, 392, 393, 394, 395, 396, 397, 398, 399, 400, 401, 402, 404, 406, 407, 408, 409, 410, 411, 412, 414, 415, 416, 417, 419, 420, 421, 422, 423, 424, 427, 428, 431, 433, 435, 436, 438, 440, 441, 442, 443, 446, or 447. Preferably, engineering of the Fc portion results in increased cell-mediated killing and/or complement mediated killing of the tumor cells.

The invention encompasses molecules comprising variant Fc regions consisting of or comprising any of the mutations listed in the table below in Table 2.

TABLE 2

EXEMPLARY MUTATIONS

| SINGLE SITE MUTANTS | DOUBLE SITE MUTANTS |
|---|---|
| K392R | Q347H, A339V |
| N315I | S415I, L251F |
| S132I | K290E, L142P |
| P396L | G285E, P247H |
| P396H | K409R, S166N |
| A162V | E334A, K334A |
| R292L | R292L, K334E |
| T359N | K288N, A330S |
| T366S | R255L, E318K |
| V379L | F243L, E318K |
| K288N | V279L, P395S |
| A330S | K246T, Y319F |
| F243L | F243I, V379L |
| E318K | K288M, K334E |
| V379M | K334E, E308D |
| S219Y | E233D, K334E |
| V282M | K246T, P396H |
| D401V | H268D, E318D |
| K222N | K246I, K334N |
| K334I | K320E, K326E |
| K334E | S375C, P396L |
| I377F | K288N, K326N |

TABLE 2-continued

EXEMPLARY MUTATIONS

| SINGLE SITE MUTANTS | DOUBLE SITE MUTANTS |
|---|---|
| P247L | P247L, N421K |
| F372Y | S298N, W381R |
| K326E | R255Q, K326E |
| H224L | V284A, F372L |
| F275Y | T394M, V397M |
| L398V | P247L, E389G |
| K334N | K290T, G371D |
| S400P | P247L, L398Q |
| S407I | P247L, I377F |
| F372Y | K326E, G385E |
| T366N | S298N, S407R |
| K414N | E258D, N384K |
| M352L | F241L, E258G |
| T225S | K370N, S440N |
| I377N | K317N, F423-DELETED |
| K248M | P227S, K290E |
| R292G | K334E, E380D |
| S298N | P291S, P353Q |
| D270E | V240I, V281M |
| E233G | P232S, S304G |
|  | P247L, L406F |
|  | D399E, M428L |
|  | L251F, F372L |
|  | D399E, G402D |
|  | D399E, M428L |
|  | K392T, P396L |
|  | H268N, P396L |
|  | K326I, P396L |
|  | H268D, P396L |
|  | K210M, P396L |
|  | L358P, P396L |
|  | K334N, P396L |
|  | V379M, P396L |
|  | P227S, P396L |
|  | P217S, P396L |
|  | Q419H, P396L |
|  | K370E, P396L |
|  | L242F, P396L |
|  | R255L, P396L |
|  | V240A, P396L |
|  | T250A, P396L |
|  | P247S, P396L |
|  | L410H, P396L |
|  | Q419L, P396L |
|  | V427A, P396L |
|  | E258D, P396L |
|  | N384K, P396L |
|  | V323I, P396L |
|  | P244H, P396L |
|  | V305L, P396L |
|  | S400F, P396L |
|  | V303I, P396L |
|  | A330V, Q419H |
|  | V263Q, E272D |
|  | K326E, A330T |

In yet other embodiments, the invention encompasses molecules comprising variant Fc regions having more than two amino acid modifications. A non-limiting example of such variants is listed in the table below (Table 3). The invention encompasses mutations listed in Table 3 which further comprise one or more amino acid modifications such as those disclosed herein.

TABLE 3

EXEMPLARY COMBINATION VARIANTS

D399E, R292L, V185M
R301C, M252L, S192T
P291S, K288E, H268L, A141V
S383N, N384K, T256N, V262L, K218E, R214I, K205E, F149Y, K133M

TABLE 3-continued

EXEMPLARY COMBINATION VARIANTS

S408I, V215I, V125L
G385E, P247H
V348M, K334N, F275I, Y202M, K147T
H310Y, T289A, Y407V, E258D
R292L, P396L, T359N
F275I, K334N, V348M
F243L, R255L, E318K
K334E, T359N, T366S
T256S, V305I, K334E, N390S
T335N, K370E, A378V, T394M, S424L
K334E, T359N, T366S, Q386R
K288N, A330S, P396L
P244H, L358M, V379M, N384K, V397M
P217S, A378V, S408R
P247L, I253N, K334N
D312E, K327N, I378S
D280E, S354F, A431D, L441I
K218R, G281D, G385R
P247L, A330T, S440G
T355N, P387S, H435Q
P247L, A431V, S442F
P343S, P353L, S375I, S383N
E216D, E345K, S375I
K288N, A330S, P396L
K222N, T335N, K370E, A378V, T394M
G316D, A378V, D399E
N315I, V379M, T394M
K326Q, K334E, T359N, T366S
A378V, N390I, V422I
V282E, V369I, L406F
V397M, T411A, S415N
T223I, T256S, L406F
L235P, V382M, S304G, V305I, V323I
P247L, W313R, E388G
D221Y, M252I, A330G, A339T, T359N, V422I, H433L
F243I, V379L, G420V
A231V, Q386H, V412M
T215P, K274N, A287G, K334N, L365V, P396L
P244A, K326I, C367R, S375I, K447T
R301H, K340E, D399E
C229Y, A287T, V379M, P396L, L443V
E269K, K290N, Q311R, H433Y
E216D, K334R, S375I
T335N, P387S, H435Q
K246I, Q362H, K370E
K334E, E380D, G446V
V303I, V369F, M428L
K246E, V284M, V308A
E293V, Q295E, A327T
Y319F, P352L, P396L
D221E, D270E, V308A, Q311H, P396L, G402D
K290T, N390I, P396L
K288R, T307A, K344E, P396L
V273I, K326E, L328I, P396L
K326I, S408N, P396L
K261N, K210M, P396L
F243L, V305I, A378D, F404S, P396L
K290E, V369A, T393A, P396L
K210N, K222I, K320M, P396L
P217S, V305I, I309L, N390H, P396L
K246N, Q419R, P396L
P217A, T359A, P396L
V215I, K290V, P396L
F275L, Q362H, N384K, P396L
A330V, H433Q, V427M
V263Q, E272D, Q419H
N276Y, T393N, W417R
V282L, A330V, H433Y, T436R
V284M, S298N, K334E, R355W
A330V, G427M, K438R
S219T, T225K, D270E, K360R
K222E, V263Q, S298N
E233G, P247S, L306P
S219T, T225K, D270E
S254F, A330V, N361D, P243L
V284M, S298N, K334E, R355W R416T
D270E, G316D, R416G
K392T, P396L, D270E

TABLE 3-continued

EXEMPLARY COMBINATION VARIANTS

R255L, P396L, D270E
V240A, P396L, D270E
Q419H, P396L, D270E
K370E, P396L, D270E
P247L, N421K, D270E
R292P, V305I
R292P, V305I, F243L
V284M, R292L, K370N

In specific embodiments, the variant Fc region has:
(A) a leucine at position 247, a lysine at position 421, and a glutamic acid at position 270 (MgFc31/60);
(B) a threonine at position 392, a leucine at position 396, and a glutamic acid at position 270 (MgFc38/60);
(C) a threonine at position 392, a leucine at position 396, a glutamic acid at position 270, and a leucine at position 243 (MgFc38/60/F243L);
(D) a histidine at position 419, a leucine at position 396, and a glutamic acid at position 270 (MGFc51/60);
(E) a histidine at position 419, a leucine at position 396, a glutamic acid at position 270, and a leucine at position 243 (MGFc51/60/F243L);
(F) a lysine at position 255 and a leucine at position 396 (MgFc55);
(G) a lysine at position 255, a leucine at position 396, and a glutamic acid at position 270 (MGFc55/60);
(H) a lysine at position 255, a leucine at position 396, a glutamic acid at position 270, and a lysine at position 300 (MGFc55/60/Y300L);
(I) a lysine at position 255, a leucine at position 396, a glutamic acid at position 270, and a leucine at position 243 (MgFc55/60/F243L);
(J) a glutamic acid at position 370, a leucine at position 396, and a glutamic acid at position 270 (MGFc59/60);
(K) a glutamic acid at position 270, an aspartic acid at position 316, and a glycine at position 416 (MgFc71);
(M) a leucine at position 243, a proline at position 292, an isoleucine at position 305, and a leucine at position 396 (MGFc74/P396L);
(N) a glutamine at position 297, or
any combination of the individual substitutions.

VI. Carbohydrate Modifications

The invention also provides antibodies with altered oligosaccharide content. Oligosaccharides as used herein refer to carbohydrates containing two or more simple sugars and the two terms may be used interchangeably herein. Carbohydrate moieties of the instant invention will be described with reference to commonly used nomenclature in the art. For a review of carbohydrate chemistry, see, e.g., Hubbard et al. (1981) "*Synthesis And Processing Of Asparagine-Linked Oligosaccharides*," Ann. Rev. Biochem., 50: 555-583, which is incorporated herein by reference in its entirety. This nomenclature includes for example, Man, which represents mannose; GlcNAc which represents 2-N-acetylglucosamine; Gal which represents galactose; Fuc for fucose and Glc for glucose. Sialic acids are described by the shorthand notation NeuNAc for 5-N-acetylneuraminic acid, and NeuNGc for 5-glycolneuraminic.

In general, antibodies contain carbohydrate moieties at conserved positions in the constant region of the heavy chain, and up to 30% of human IgGs have a glycosylated Fab region. IgG has a single N-linked biantennary carbohydrate structure at Asn 297 which resides in the CH2 domain (Jefferis et al. (1998) "*IgG-Fc-Mediated Effector Functions: Molecular Definition Of Interaction Sites For Effector Ligands And The Role Of Glycosylation*," Immunol. Rev. 163: 59-76; Wright et al. (1997) "*Effect Of Glycosylation On Antibody Function: Implications For Genetic Engineering*," Trends Biotech. 15: 26-32). Human IgG typically has a carbohydrate of the following structure; GlcNAc(Fucose)-GlcNAc-Man-(ManGlcNAc)$_2$. However variations among IgGs in carbohydrate content does occur which leads to altered function, see, e.g., Jassal et al. (2001) "*Sialylation Of Human IgG-Fc Carbohydrate By Transfected Rat Alpha-2,6-Sialyltransferas*," Biochem. Biophys. Res. Commun. 288: 243-249; Groenink et al. (1996) "*On The Interaction Between Agalactosyl IgG And Fc Gamma Receptors*," Eur. J. Immunol. 26: 1404-1407; Boyd et al. (1995) "*The Effect Of The Removal Of Sialic Acid, Galactose And Total Carbohydrate On The Functional Activity Of Campath-1H*," Mol. Immunol. 32: 1311-1318; Kumpel et al. (1994) "*Galactosylation Of Human IgG Monoclonal Anti-D Produced By EBV-Transformed B-Lymphoblastoid Cell Lines Is Dependent On Culture Method And Affects Fc Receptor-Mediated Functional Activity*," Human Antibody Hybridomas, 5: 143-151. The invention encompasses antibodies comprising a variation in the carbohydrate moiety that is attached to Asn 297. In one embodiment, the carbohydrate moiety has a galactose and/or galactose-sialic acid at one or both of the terminal GlcNAc and/or a third GlcNac arm (bisecting GlcNAc).

In some embodiments, the antibodies of the invention are substantially free of one or more selected sugar groups, e.g., one or more sialic acid residues, one or more galactose residues, one or more fucose residues. An antibody that is substantially free of one or more selected sugar groups may be prepared using common methods known to one skilled in the art, including for example recombinantly producing an antibody of the invention in a host cell that is defective in the addition of the selected sugar groups(s) to the carbohydrate moiety of the antibody, such that about 90-100% of the antibody in the composition lacks the selected sugar group(s) attached to the carbohydrate moiety. Alternative methods for preparing such antibodies include for example, culturing cells under conditions that prevent or reduce the addition of one or more selected sugar groups, or post-translational removal of one or more selected sugar groups.

In a specific embodiment, the invention encompasses a method of producing a substantially homogenous antibody preparation, wherein about 80-100% of the antibody in the composition lacks a fucose on its carbohydrate moiety, e.g., the carbohydrate attachment on Asn 297. The antibody may be prepared, for example, by:
(i) use of an engineered host cell that is deficient in fucose metabolism such that it has a reduced ability to fucosylate proteins expressed therein;
(ii) culturing cells under conditions which prevent or reduce fusocylation;
(iii) post-translational removal of fucose, e.g., with a fucosidase enzyme; or
(iv) purification of the antibody so as to select for the product which is not fucosylated.

Most preferably, nucleic acid encoding the desired antibody is expressed in a host cell that has a reduced ability to fucosylate the antibody expressed therein. Preferably the host cell is a dihydrofolate reductase deficient chinese hamster ovary cell (CHO), e.g., a Lec 13 CHO cell (lectin resistant CHO mutant cell line; Ripka et al. (1986) "*Lectin-Resistant CHO Cells: Selection Of Four New Pea Lectin-Resistant Phenotypes*," Somatic Cell & Molec. Gen. 12(1): 51-62; Ripka et al. (1986) "*Two Chinese Hamster Ovary Glycosylation Mutants Affected In The Conversion Of GDP-Mannose To GDP-Fucose*," Arch. Biochem. Biophys. 249(2): 533-545), CHO-K1, DUX-B11, CHO-DP12 or CHO-DG44, which has been modified so that the antibody is not substantially fucosylated. Thus, the cell may display altered expression and/or activity for the fucoysltransferase enzyme, or another enzyme or substrate involved in adding fucose to the N-linked oligosaccharide so that the enzyme has a diminished activity and/or reduced expression level in the cell. For methods to produce antibodies with altered fucose content, see, e.g., WO 03/035835 and Shields et al. (2002) "*Lack Of Fucose On Human IgG1 N-Linked Oligosaccharide Improves Binding To Human Fcgamma RIII And Antibody-Dependent Cellular Toxicity*," J. Biol. Chem. 277(30): 26733-26740; both of which are incorporated herein by reference in their entirety.

In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (see Shields et al. (2002) "*Lack Of Fucose On Human IgG1 N-Linked Oligosaccharide Improves Binding To Human Fcgamma RIII And Antibody-Dependent Cellular Toxicity*," J. Biol. Chem. 277(30): 26733-26740; Davies et al. (2001) "*Expression Of GnTIII In A Recombinant Anti-CD20 CHO Production Cell Line: Expression Of Antibodies With Altered Glycoforms Leads To An Increase In ADCC Through Higher Affinity For FCγRIII*," Biotechnology & Bioengineering, 74(4): 288-294). In another specific embodiment, the altered carbohydrate modifications enhance the binding of antibodies of the invention to FcγRIIB receptor. Altering carbohydrate modifications in accordance with the methods of the invention includes, for example, increasing the carbohydrate content of the antibody or decreasing the carbohydrate content of the antibody. Methods of altering carbohydrate contents are known to those skilled in the art, see, e.g., Wallick et al. (1988) "*Glycosylation Of A VH Residue Of A Monoclonal Antibody Against Alpha* (1----6) *Dextran Increases Its Affinity For Antigen*," Journal of Exp. Med. 168(3): 1099-1109; Tao et al. (1989) "*Studies Of Aglycosylated Chimeric Mouse-Human IgG. Role Of Carbohydrate In The Structure And Effector Functions Mediated By The Human IgG Constant Region*," J. Immunol., 143(8): 2595-2601; Routledge et al. (1995) "*The Effect Of Aglycosylation On The Immunogenicity Of A Humanized Therapeutic CD3 Monoclonal Antibody*," Transplantation, 60(8): 847-853; Elliott et al. (2003) "*Enhancement Of Therapeutic Protein In Vivo Activities Through Glycoengineering*," Nature Biotechnology, 21: 414-421; Shields et al. (2002) "*Lack Of Fucose On Human IgG1 N-Linked Oligosaccharide Improves Binding To Human Fcgamma RIII And Antibody-Dependent Cellular Toxicity*," J. Biol. Chem. 277(30): 26733-26740; all of which are incorporated herein by reference in their entirety.

In some embodiments, the invention encompasses antibodies comprising one or more glycosylation sites, so that one or more carbohydrate moieties are covalently attached to the antibody. In other embodiments, the invention encompasses antibodies comprising one or more glycosylation sites and one or more modifications in the Fc region, such as those disclosed supra and those known to one skilled in the art. In preferred embodiments, the one or more modifications in the Fc region enhance the affinity of the antibody for an activating FcγR, e.g., FcγRIIIA, relative to the antibody comprising the wild type Fc regions. Antibodies of the invention with one or more glycosylation sites and/or one or more modifications in the Fc region have an enhanced antibody mediated effector function, e.g., enhanced ADCC activity. In some embodiments, the invention further comprises antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al. (1995) "*Recognition Sites On Human IgG For Fc Gamma Receptors: The Role Of Glycosylation*," Immunology Letters, 44: 111-117, which is incorporated herein by reference in its entirety.

The invention encompasses antibodies that have been modified by introducing one or more glycosylation sites into one or more sites of the antibodies, preferably without altering the functionality of the antibody, e.g., binding activity to FcγRIIB. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "*In Vitro Mutagenesis*," in RECOMBINANT DNA: A SHORT COURSE, (1983) J. D. Watson, et al. eds. Ch. 8, pp. 106-116, which is incorporated herein by reference in its entirety. An exemplary method for introducing a glycosylation site into an antibody of the invention may comprise modifying or mutating an amino acid sequence of the antibody so that the desired Asn-X-Thr/Ser sequence is obtained.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody.

In some specific embodiments, the invention encompasses the use of modified FcγRIIB antibodies wherein the N-glysosylation consensus site Asn50-Val-Ser of the CDR2 region has been modified, so that the glycosylation site at position 50 is eliminated. Although not intending to be bound by a particular mechanism of action, removal of the glycosylation site may limit potential variation in production of the antibody as well as potential immunogenicity in a pharmaceutical application. In a specific embodiment, the invention encompasses the use of a humanized FcγRIIB antibody wherein the amino acid at position 50 has been modified, e.g., deleted or substituted. In another specific embodiment, the invention further encompasses the use of an antibody with an amino acid modification, e.g., deletion or substitution, at position 51. In one specific embodiment, the invention encompasses the use of a humanized FcγRIIB antibody wherein the amino acid at position 50 has been replaced with tyrosine. In another more specific embodiment, the invention encompasses the use of an FcγRIIB antibody wherein the amino acid at position 50 has been replaced with tyrosine and the amino acid at position 51 has been replaced with alanine.

VII. FcγRIIB Agonists and Antagonists

In addition to the use of a FcγRIIB-specific antibody, an analog, derivative, or an antigen-binding fragment thereof in the methods and compositions of the invention, other FcγRIIB agonist and antagonists may be used in accordance with the methods of the invention. FcγRIIB agonists and antagonists include, but are not limited to, proteinaceous molecules (e.g., proteins, polypeptides (e.g., soluble FcγRIIB polypeptides), peptides, fusion proteins (e.g., soluble FcγRIIB polypeptides conjugated to a therapeutic moiety), nucleic acid molecules (e.g., FcγRIIB antisense nucleic acid molecules, triple helices, dsRNA that mediates RNAi, or nucleic acid molecules encoding proteinaceous molecules), organic molecules, inorganic molecules, small organic molecules, drugs, and small inorganic molecules that block, inhibit, reduce or neutralize a function, an activity and/or the expression of a FcγRIIB polypeptide, expressed by an immune cell, preferably a B-cell. In some embodiments, an FcγRIIB agonist or antagonist used in accordance with the methods of the invention is not a small organic molecule, a drug or an antisense molecule. FcγRIIB agonists and antagonists can be identified using techniques well-known in the art or described herein.

Prophylactic and therapeutic compounds of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

In certain embodiments, FcγRIIB antagonists reduce a function, activity, and/or expression of a FcγRIIB polypeptide in a subject with a B-cell malignancy. In other embodiments, the FcγRIIB antagonists directly bind to an FcγRIIB polypeptide and directly or indirectly modulate an activity and/or function of B-lymphocytes. In particular embodiments, FcγRIIB antagonists inhibit or reduce B-cell proliferation in a subject with a B-cell malignancy as determined by standard in vivo and/or in vitro assays described herein or well-known to those skilled in the art. In a specific embodiment, FcγRIIB antagonists mediate the depletion of lymphocytes, in particular peripheral blood B-cells, in a subject with a B-cell malignancy as determined by standard in vivo and/or in vitro assays described herein or well-known to those skilled in the art. In another embodiment, FcγRIIB antagonists directly or indirectly modulate an activity and/or function of B-lymphocytes by utilizing antibody-dependent cytotoxicity (ADCC).

In a preferred embodiment, proteins, polypeptides or peptides (including antibodies and fusion proteins) that are utilized as FcγRIIB antagonists are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as FcγRIIB antagonists are human or humanized.

Nucleic acid molecules encoding proteins, polypeptides, or peptides that function as FcγRIIB antagonists can be administered to a subject with a B-cell malignancy, in accordance with the methods of the invention. Further, nucleic acid molecules encoding derivatives, analogs, fragments or variants of proteins, polypeptides, or peptides that function as FcγRIIB antagonists can be administered to a subject with a B-cell malignancy in accordance with the methods of the invention. Preferably, such derivatives, analogs, variants and fragments retain the FcγRIIB antagonist activity of the full-length wild-type protein, polypeptide, or peptide.

VIII. Antibody Conjugates

The present invention encompasses antibodies recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Antibodies may be used for example to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., PCT Publication No. WO 93/21232; EP 439,095; Naramura et al. (1994) *"Mechanisms Of Cellular Cytotoxicity Mediated By A Recombinant Antibody-IL2 Fusion Protein Against Human Melanoma Cells,"* Immunol. Lett., 39:91-99; U.S. Pat. No. 5,474,981; Gillies et al. (1992) *"Antibody-Targeted Interleukin 2 Stimulates T-Cell Killing Of Autologous Tumor Cells,"* Proc. Nat. Acad. Sci., 89:1428-1432; and Fell et al. (1991) *"Genetic Construction And Characterization Of A Fusion Protein Consisting Of A Chimeric F(ab) With Specificity For Carcinomas And Human IL-2,"* J. Immunol., 146:2446-2452, each of which is incorporated herein by reference in their entireties.

Further, an antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, e.g., PCT Publication No. WO 97/34911), Fas Ligand (Takahashi et al. (1994) "*Human Fas Ligand. Gene Structure, Chromosomal Location And Species Specificity*," Int. Immunol., 6:1567-1574), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), macrophage colony stimulating factor, ("M-CSF"), or a growth factor (e.g., growth hormone ("GH"); a protease, or a ribonuclease.

Antibodies can be fused to marker sequences, such as a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al. (1989) "*Bioassay For Trans-Activation Using Purified Human Immunodeficiency Virus Tat-Encoded Protein: Trans-Activation Requires mRNA Synthesis*," Proc. Natl. Acad. Sci. USA, 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al. (1984) "*The Structure Of An Antigenic Determinant In A Protein*," Cell, 37:767-778) and the "flag" tag (Knappik et al. (1994) "*An Improved Affinity Tag Based On The FLAG Peptide For The Detection And Purification Of Recombinant Antibody Fragments*," Biotechniques, 17(4):754-761).

The present invention further includes the use of compositions comprising heterologous polypeptides fused or conjugated to antibody fragments. For example, the heterologous polypeptides may be fused or conjugated to a Fab fragment, Fd fragment, Fv fragment, F(ab)$_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; International Publication Nos. WO 96/04388 and WO 91/06570; Ashkenazi et al. (1991) "*Protection Against Endotoxic Shock By A Tumor Necrosis Factor Receptor Immunoadhesin*," Proc. Nat. Acad. Sci. 88: 10535-10539; Zheng et al. (1995) "*Administration Of Noncytolytic IL-10/Fc In Murine Models Of Lipopolysaccharide-Induced Septic Shock And Allogeneic Islet Transplantation*," J. Immunol. 154:5590-5600; and Vie et al. (1992) "*Human Fusion Proteins Between Interleukin 2 And IgM Heavy Chain Are Cytotoxic For Cells Expressing The Interleukin 2 Receptor*," Proc. Nat. Acad. Sci. 89:11337-11341 (said references incorporated by reference in their entirefies).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al. (1997) "*Applications Of DNA Shuffling To Pharmaceuticals And Vaccines*," Curr. Opinion Biotechnol. 8:724-733; Harayama (1998) "*Artificial Evolution By DNA Shuffling*," Trends Biotechnol. 16:76-82; Hansson, et al. (1999) "*Evolution Of Differential Substrate Specificities In Mu Class Glutathione Transferases Probed By DNA Shuffling*," J. Mol. Biol. 287:265-276; and Lorenzo et al. (1998) "*PCR-Based Method For The Introduction Of Mutations In Genes Cloned And Expressed In Vaccinia Virus*," BioTechniques 24:308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to FcγRIIB may be recombined with one or more components, motifs, sections, parts, domains, fragments, etc. of one or more heterologous molecules.

The present invention also encompasses antibodies conjugated to a diagnostic or therapeutic agent or any other molecule for which serum half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium (97Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

An antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al. (1998) "*Comparison Of 1,4,7,10-Tetraazacyclododecane-N, N',N'',N'''-Tetraacetic Acid (DOTA)-Peptide-ChL6, A Novel Immunoconjugate With Catabolizable Linker, To 2-Iminothiolane-2-[p-(bromoacetamido)benzyl]-DOTA-ChL6 In Breast Cancer Xenografts*," Clin. Cancer Res. 4:2483-2490; Peterson et al. (1999) "*Enzymatic Cleavage Of Peptide-Linked Radiolabels From Immunoconjugates*," Bioconjug. Chem. 10:553-557; and Zimmerman et al. (1999) "*A Triglycine Linker Improves Tumor Uptake And Biodistributions Of 67-Cu-Labeled Anti-Neuroblastoma MAb chCE7 F(ab)$_2$ Fragments*," Nucl. Med. Biol. 26:943-950, each of which is incorporated by reference in their entireties.

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-256, Alan R. Liss, Inc.; Hellstrom et al., "*Antibodies For Drug Delivery*", in CONTROLLED DRUG DELIVERY (2$^{nd}$ Ed.), Robinson et al. (eds.), 1987, pp. 623-653, Marcel Dekker, Inc.; Thorpe, "*Antibody Carriers Of Cytotoxic Agents In Cancer Therapy: A Review*", in MONOCLONAL ANTIBODIES: BIOLOGICAL AND CLINICAL APPLICATIONS, Pinchera et al. (eds.), 1985, pp. 475-506; "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates*," Immunol. Rev., 62:119-158.

An antibody or fragment thereof, with or without a therapeutic moiety conjugated to it, administered alone or in combination with cytotoxic factor(s) and/or cytokine(s) can be used as a therapeutic.

Alternatively, an antibody can be conjugated to a second antibody to form an antibody heteroconjugate as described by Segal in U.S. Pat. No. 4,676,980, which is incorporated herein by reference in its entirety.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

IX. Preparation and Characterization of Monoclonal Antibodies of the Invention

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., ANTIBODIES: A LABORATORY MANUAL, (Cold Spring Harbor Laboratory Press, 2 ed. 1988); Hammerling, et al., in: MONOCLONAL ANTIBODIES AND T-CELL HYBRIDOMAS, pp. 563-681 (Elsevier, N.Y., 1981) both of which are incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

In one particular embodiment, the invention provides a method for producing monoclonal antibodies that specifically bind FcγRIIB with greater affinity than said monoclonal antibodies bind FcγRIIA comprising: immunizing one or more FcγRIIA transgenic mice (see U.S. Pat. Nos. 5,877,396 and 5,824,487) with the purified extracellular domain of human FcγRIIB, amino acids 1-180; producing hybridoma cell lines from spleen cells of said mice, screening said hybridoma cells lines for one or more hybridoma cell lines that produce antibodies that specifically bind FcγRIIB with greater affinity than said antibodies bind FcγRIIA. In another specific embodiment, the invention provides a method for producing FcγRIIB monoclonal antibodies that specifically bind FcγRIIB, particularly human FcγRIIB, with a greater affinity than said monoclonal antibodies bind FcγRIIA, said method further comprising: immunizing one or more FcγRIIA transgenic mice with purified FcγRIIB or an immunogenic fragment thereof, booster immunizing said mice sufficient number of times to elicit an immune response, producing hybridoma cells lines from spleen cells of said one or more mice, screening said hybridoma cell lines for one or more hybridoma cell lines that produce antibodies that specifically bind FcγRIIB with a greater affinity than said antibodies bind FcγRIIA. In one embodiment of the invention, said mice are immunized with purified FcγRIIB which has been mixed with any adjuvant known in the art to enhance immune response. Adjuvants that can be used in the methods of the invention include, but are not limited to, protein adjuvants; bacterial adjuvants, e.g., whole bacteria (BCG, *Corynebacterium parvum, Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, iodoacetate and cholesteryl hemisuccinateor; naked DNA adjuvants. Other adjuvants that can be used in the methods of the invention include, Cholera toxin, paropox proteins, MF-59 (Chiron Corporation; See also Bieg et al. (1999) "*GAD65 And Insulin B Chain Peptide (9-23) Are Not Primary Autoantigens In The Type 1 Diabetes Syndrome Of The BB Rat*," Autoimmunity, 31(1): 15-24, which is incorporated herein by reference), MPL® (Corixa Corporation; See also Lodmell et al. (2000) "*DNA Vaccination Of Mice Against Rabies Virus: Effects Of The Route Of Vaccination And The Adjuvant Monophosphoryl Lipid A (MPL)*,"Vaccine, 18: 1059-1066; Johnson et al. (1999) "3-*O*-*Desacyl Monophosphoryl Lipid A Derivatives: Synthesis And Immunostimulant Activities*," Journal of Medicinal Chemistry, 42: 4640-4649; Baldridge et al. (1999) "*Monophosphoryl Lipid A (MPL) Formulations For The Next Generation Of Vaccines*," Methods, 19: 103-107, all of which are incorporated herein by reference), RC-529 adjuvant (Corixa Corporation; the lead compound from Corixa's aminoalkyl glucosaminide 4-phosphate (AGP) chemical library, see also www.corixa.com), and DETOX™ adjuvant (Corixa Corporation; DETOX™ adjuvant includes MPL® adjuvant (monophosphoryl lipid A) and mycobacterial cell wall skeleton; See also Eton et al. (1998) "*Active Immunotherapy With Ultraviolet B-Irradiated Autologous Whole Melanoma Cells Plus DETOX In Patients With Metastatic Melanoma*," Clin. Cancer Res. 4(3):619-627; and Gupta et al. (1995) "*Adjuvants For Human Vaccines— Current Status, Problems And Future Prospects*," Vaccine, 13(14): 1263-1276, both of which are incorporated herein by reference.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and at least a portion of the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al. (1995) "*Phage Display Of Disulfide-Stabilized Fv Fragments*," J. Immunol. Methods, 182:41-50; Ames et al. (1995) "*Conversion Of Murine Fabs Isolated From A Combinatorial Phage Display Library To Full Length Immunoglobulins*," J. Immunol. Methods, 184:177-186; Kettleborough et al. (1994) "*Isolation Of Tumor Cell-Specific Single-Chain Fv From Immunized Mice Using Phage-Antibody Libraries And The Re-Construction Of Whole Antibodies From These Antibody Fragments*," Eur. J. Immunol., 24:952-958; Persic et al. (1997) "*An Integrated Vector System For The Eukaryotic Expression Of Antibodies Or Their Fragments After Selection From Phage Display Libraries*," Gene, 187: 9-18; Burton et al. (1994) "*Human Antibodies From Combinatorial Libraries*," Advances in Immunology, 57:191-280; PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax et al. (1992) "*Expression Of A Heterodimeric Fab Antibody Protein In One Cloning Step*," BioTechniques, 12(6):864-869; and Sawai et al. (1995) "*Direct Production Of The Fab Fragment Derived From The Sperm Immobilizing Antibody Using Polymerase Chain Reaction And cDNA Expression Vectors*," Am. J. Repr. Immunol. 34:26-34; and Better et al. (1988) "*Escherichia coli Secretion Of An Active Chimeric Antibody Fragment*," Science, 240: 1041-1043, each of which references is incorporated by reference in its entirety. Examples of techniques which can be used to produce single-chain Fvs and antibodies include those described in U.S. Pat. Nos. 4,946,778 and 5,258,498; Huston et al. (1991) "*Protein Engineering Of Single-Chain Fv Analogs And Fusion Proteins*," Methods in Enzymology, 203:46-88; Shu et al. (1993) "*Secretion Of A Single-Gene-Encoded Immunoglobulin From Myeloma Cells*," Proc. Nat. Acad. Sci., 90:7995-7999; and Skerra et al. (1988) "*Assembly Of A Functional Immunoglobulin Fv Fragment In Escherichia coli*," Science, 240:1038-1040.

Phage display technology can be used to increase the affinity of an antibody of the invention for FcγRIIB. This technique would be useful in obtaining high affinity antibodies that could be used in the combinatorial methods of the invention. The technology, referred to as affinity maturation, employs mutagenesis or CDR walking and re-selection using FcγRIIB or an antigenic fragment thereof to identify antibodies that bind with higher affinity to the antigen when compared with the initial or parental antibody (See, e.g., Glaser et al. (1992) "*Antibody Engineering By Codon-Based Mutagenesis In A Filamentous Phage Vector System*," J. Immunology 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (See Wu et al. (1998) "*Stepwise in vitro Affinity Maturation Of Vitaxin, An Alphav Beta3-Specific Humanized Ab*," Proc Natl. Acad Sci. USA 95:6037-6042; Yelton et al. (1995) "*Affinity Maturation*

Of The Br96 Anti-Carcinoma Antibody By Codon-Based Mutagenesis," J. Immunology 155:1994-2004). CDR walking, which randomizes the light chain, is also possible (See Schier et al. (1996) "Isolation Of Picomolar Affinity Anti-C-ErbB-2 Single-Chain Fv By Molecular Evolution Of The Complementarity Determining Regions In The Center Of The Antibody Binding Site," J. Mol. Bio. 263:551-567).

Antibodies of the invention may be further characterized by epitope mapping, so that antibodies may be selected that have the greatest specificity for FcγRIIB compared to FcγRIIA. Epitope mapping methods of antibodies are well known in the art and encompassed within the methods of the invention. In certain embodiments fusion proteins comprising one or more regions of FcγRIIB may be used in mapping the epitope of an antibody of the invention. In a specific embodiment, the fusion protein contains the amino acid sequence of a region of an FcγRIIB fused to the Fc portion of human IgG2. Each fusion protein may further comprise amino acid substitutions and/or replacements of certain regions of the receptor with the corresponding region from a homolog receptor, e.g., FcγRIIA, as shown in Table 4 below. pMGX125 and pMGX132 contain the IgG binding site of the FcγRIIB receptor, the former with the C-terminus of FcγRIIB and the latter with the C-terminus of FcγRIIA and can be used to differentiate C-terminus binding. The others have FcγRIIA substitutions in the IgG binding site and either the FcγIIA or FcγIIB N-terminus. These molecules can help determine the part of the receptor molecule where the antibodies bind.

Table 4 shows a list of the fusion proteins that may be used to investigate the epitope of the monoclonal anti-FcγRIIB antibodies. The C-terminus sequence APXXXSSS is SEQ ID NO: 57 and the C-terminus sequence VPSMGSSS is SEQ ID NO: 58.

TABLE 4

| Plasmid | Receptor | N-ter | 172-180 | C-ter |
|---|---|---|---|---|
| pMGX125 | RIIb | IIb | KKFSRSDPN (SEQ ID NO: 5) | APS------SS (IIb) (SEQ ID NO: 11) |
| pMGX126 | RIIa/b | IIa | QKFSRLDPN (SEQ ID NO: 6) | APS------SS (IIb) (SEQ ID NO: 11) |
| pMGX127 | | IIa | QKFSRLDPT (SEQ ID NO: 7) | APS------SS (IIb) (SEQ ID NO: 11) |
| pMGX128 | | IIb | KKFSRLDPT (SEQ ID NO: 8) | APS------SS (IIb) (SEQ ID NO: 11) |
| pMGX129 | | IIa | QKFSHLDPT (SEQ ID NO: 9) | APS------SS (IIb) (SEQ ID NO: 11) |
| pMGX130 | | IIb | KKFSHLDPT (SEQ ID NO: 10) | APS------SS (IIb) (SEQ ID NO: 11) |
| pMGX131 | | IIa | QKFSRLDPN (SEQ ID NO: 6) | VPSMGSSS (IIa) (SEQ ID NO: 12) |
| pMGX132 | | IIb | KKFSRSDPN (SEQ ID NO: 5) | VPSMGSSS (IIa) (SEQ ID NO: 12) |
| pMGX133 | RIIa-131R | IIa | QKFSRLDPT (SEQ ID NO: 7) | VPSMGSSS (IIa) (SEQ ID NO: 12) |
| pMGX134 | RIIa-131H | IIa | QKFSHLDPT (SEQ ID NO: 9) | VPSMGSSS (IIa) (SEQ ID NO: 12) |
| pMGX135 | | IIb | KKFSRLDPT (SEQ ID NO: 8) | VPSMGSSS (IIa) (SEQ ID NO: 12) |
| pMGX136 | | IIb | KKFSHLDPT (SEQ ID NO: 10) | VPSMGSSS (IIa) (SEQ ID NO: 12) |

The fusion proteins may be used in any biochemical assay for determination of binding to an anti-FcγRIIB antibody of the invention, e.g., an ELISA. In other embodiments, further confirmation of the epitope specificity may be done by using peptides with specific residues replaced with those from the FcγRIIA sequence.

The antibodies of the invention may be characterized for specific binding to FcγRIIB using any immunological or biochemical based method known in the art for characterizing including quantitating, the interaction of the antibody to FcγRIIB. Specific binding of an antibody of the invention to FcγRIIB may be determined for example using immunological or biochemical based methods including, but not limited to, an ELISA assay, surface plasmon resonance assays, immunoprecipitation assay, affinity chromatography, and equilibrium dialysis. Immunoassays which can be used to analyze immunospecific binding and cross-reactivity of the antibodies of the invention include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, CURRENT PROTOCOLS IN MOLECULAR BIOLOGY, Vol. 1, John Wiley & Sons, Inc., New York, which is incorporated by reference herein in its entirety).

Antibodies of the invention may also be assayed using any surface plasmon resonance based assays known in the art for characterizing the kinetic parameters of the interaction of the antibody with FcγRIIB. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullett et al. (2000) "Surface Plasmon Resonance-Based Immunoassays," Methods 22: 77-91; Dong et al. (2002) "Some New Aspects In Biosensors," Reviews in Mol. Biotech., 82: 303-323; Fivash et al. (1998) "BIAcore For Macromolecular Interaction," Current Opinions in Biotechnology 9: 97-101; Rich et al. (2000) "Advances In Surface Plasm on Resonance Biosensor Analysis," Current Opinions in Biotechnology 11: 54-61; all of which are incorporated herein by reference in their entirety. Additionally, any of the SPR instruments and SPR-based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR-based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occurs is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CM5, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

Antibodies of the invention may also be assayed using any fluorescence-based assays known in the art for characterizing the interaction of the antibody with FcγRIIB. Specific binding of an antibody of the invention to FcγRIIB may be determined, for example, using fluorescence-based methods including, but not limited to, resonance energy transer assays, anisotropy assays, quenching assays, flow cytometry assays, fluorescence correlation spectroscopy assays, two-photon excited fluorescence microscopy assays, third harmonic generation microscopy assays, coherent anti-stokes raman scattering microscopy assays, confocal scanning microscopy assays and fluorescent immunoassays, including, but not limited to, ELISA, etc. Such assays are routine and well-known in the art (see, e.g., PRINCIPLES OF FLUORESCENCE SPECTROSCOPY, $2^{nd}$ Edition, 1999, Lakowicz (ed.); CONFOCAL SCANNING OPTICAL MICROSCOPY AND RELATED IMAGING SYSTEMS, 1996, Corle et al. (eds.); and OPTICAL IMAGING AND MICROSCOPY: TECHNIQUES AND ADVANCED SYSTEMS, 2003, Torok et al. (eds.), herein incorporated by reference in their entireties).

The invention encompasses characterization of the antibodies produced by the methods of the invention using certain characterization assays for identifying the function of the antibodies of the invention, particularly the activity to modulate FcγRIIB signaling. For example, characterization assays of the invention can measure phosphorylation of tyrosine residues in the ITIM motif of FcγRIIB, or measure the inhibition of B cell receptor-generated calcium mobilization. The characterization assays of the invention can be cell-based or cell-free assays.

It has been well established in the art that in mast cells coaggregation of FcγRIIB with the high affinity IgE receptor, FcεRI, leads to inhibition of antigen-induced degranulation, calcium mobilization, and cytokine production (Metcalfe et al. (1997) "*Mast Cells,*" Physiol. Rev. 77:1033-1079; Long (1999) "*Regulation Of Immune Responses Through Inhibitory Receptors,*" Annu. Rev. Immunol. 17: 875-904). The molecular details of this signaling pathway have been recently elucidated (Ott (2002) "*Downstream Of Kinase, p62 (dok), Is A Mediator Of Fc gamma IIB Inhibition Of Fc Epsilon RI Signaling,*" J. Immunol. 162(9):4430-4439). The molecular details of this signaling pathway have been recently elucidated (Ott (2002) "*Downstream Of Kinase, p62dok, Is A Mediator Of FcRIIB Inhibition Of FcRI Signaling,*" J. Immunol. 168(9):4430-4439). Once coaggregated with FcεRI, FcγRIIB is rapidly phosphorylated on tyrosine in its ITIM motif, and then recruits Src Homology-2 containing inositol-5-phosphatase (SHIP), an SH2 domain-containing inosital polyphosphate 5-phosphatase, which is in turn phosphorylated and associates with Shc and $p62^{dok}$ ($p62^{dok}$ is the prototype of a family of adaptor molecules, which includes signaling domains such as an aminoterminal pleckstrin homology domain (PH domain), a PTB domain, and a carboxy terminal region containing PXXP motifs and numerous phosphorylation sites (Carpino et al. (1997) "*p62(dok): A Constitutively Tyrosine-Phosphorylated, GAP-Associated Protein In Chronic Myelogenous Leukemia Progenitor Cells,*" Cell, 88: 197-204; Yamanashi et al. (1997) "*Identification Of The Abl-And rasGAP-Associated 62 kDa Protein As A Docking Protein, Dok,*" Cell, 88:205-211).

The invention encompasses characterizing the anti-FcγRIIB antibodies of the invention in modulating one or more IgE mediated responses. Preferably, cells lines co-expressing the high affinity receptor for IgE and the low affinity receptor for FcγRIIB will be used in characterizing the anti-FcγRIIB antibodies of the invention in modulating IgE mediated responses. In a specific embodiment, cells from a rat basophilic leukemia cell line (RBL-H23; Barsumian et al. (1981) "*IgE-Induced Histamine Release From Rat Basophilic Leukemia Cell Lines: Isolation Of Releasing And Nonreleasing Clones,*" Eur. J. Immunol. 11:317-323, which is incorporated herein by reference in its entirety) transfected with full length human FcγRIIB will be used in the methods of the invention. RBL-2H3 is a well characterized rat cell line that has been used extensively to study the signaling mechanisms following IgE-mediated cell activation. When expressed in RBL-2H3 cells and coaggregated with FcεRI, FcγRIIB inhibits FcεRI-induced calcium mobilization, degranulation, and cytokine production (Malbec et al. (1998) "*Fc Epsilon Receptor I-Associated Lyn-Dependent Phosphorylation Of Fc Gamma Receptor IIB During Negative Regulation Of Mast Cell Activation,*" J. Immunol. 160:1647-1658; Daeron et al. (1995) "*Regulation Of High-Affinity IgE Receptor-Mediated Mast Cell Activation By Murine Low-Affinity IgG Receptors,*" J. Clin. Invest. 95:577-585; Ott et al. (2002) "*Downstream Of Kinase, p62(dok), Is A Mediator Of Fc gamma IIB Inhibition Of Fc Epsilon RI Signaling,*" J. Immunol. 168:4430-4439).

In some embodiments, the invention encompasses characterizing the anti-FcγRIIB antibodies of the invention for inhibition of FcεRI induced mast cell activation. For example, cells from a rat basophilic leukemia cell line (RBL-H23; Barsumian et al. (1981) "*IgE-Induced Histamine Release From Rat Basophilic Leukemia Cell Lines: Isolation Of Releasing And Nonreleasing Clones,*" Eur. J. Immunol. 11:317-323) that have been transfected with FcγRIIB are sensitized with IgE and stimulated either with F(ab')$_2$ fragments of rabbit anti-mouse IgG, to aggregate FcεRI alone, or with whole rabbit anti-mouse IgG to coaggregate FcγRIIB and FcεRI. In this system, indirect modulation of down stream signaling molecules can be assayed upon addition of antibodies of the invention to the sensitized and stimulated cells. For example, tyrosine phosphorylation of FcγRIIB and recruitment and phosphorylation of SHIP, activation of MAP kinase family members, including but not limited to Erk1, Erk2, JNK, or p38; and tyrosine phosphorylation of $p62^{dok}$ and its association with SHIP and RasGAP can be assayed.

One exemplary assay for determining the inhibition of FcεRI induced mast cell activation by the antibodies of the invention can comprise the following: transfecting RBL-H23 cells with human FcγRIIB; sensitizing the RBL-H23 cells with IgE; stimulating RBL-H23 cells with either F(ab')$_2$ of rabbit anti-mouse IgG (to aggregate FcεRI alone and elicit FcεRI-mediated signaling, as a control), or stimulating RBL-H23 cells with whole rabbit anti-mouse IgG to (to coaggregate FcγRIIB and FcεRI, resulting in inhibition of FcεRI-mediated signaling). Cells that have been stimulated with whole rabbit anti-mouse IgG antibodies can be further preincubated with the antibodies of the invention. Measuring FcεRI-dependent activity of cells that have been pre-incubated with the antibodies of the invention and cells that have not been pre-incubated with the antibodies of the invention, and comparing levels of FcεRI-dependent activity in these cells, would indicate a modulation of FcεRI-dependent activity by the antibodies of the invention.

The exemplary assay described above can be for example, used to identify antibodies that block ligand (IgG) binding to FcγRIIB receptor and antagonize FcγRIIB-mediated inhibition of FcεRI signaling by preventing coaggregating of FcγRIIB and FcεRI. This assay likewise identifies antibodies that enhance coaggregation of FcγRIIB and FcεRI and agonize FcγRIIB-mediated inhibition of FcεRI signaling by promoting coaggregating of FcγRIIB and FcεRI.

In a preferred embodiment, FcεRI-dependent activity is at least one or more of the following: modulation of downstream signaling molecules (e.g., modulation of phosphorylation state of FcγRIIB, modulation of SHIP recruitment, modulation of MAP Kinase activity, modulation of phosphorylation state of SHIP, modulation of SHIP and Shc association SHIP and Shc, modulation of the phosphorylation state of $p62^{dok}$, modulation of $p62^{dok}$ and SHIP association, modulation of $p62^{dok}$ and RasGAP association, modulation of calcium mobilization, modulation of degranulation, and modulation of cytokine production. In yet another preferred embodiment, FcεRI-dependent activity is serotonin release and/or extracellular $Ca^{++}$ influx and/or IgE dependent mast cell activation. It is known to one skilled in the art that coaggregation of FcγRIIB and FCεRI stimulates FcγRIIB tyrosine phosphorylation, stimulates recruitment of SHIP, stimulates SHIP tyrosine phosphorylation and association with Shc, and inhibits activation of MAP kinase family members including, but not limited to, Erk1, Erk2, JNK, p38. It is also known to those skilled in the art that coaggregation of FcγRIIB and FcεRI stimulates enhanced tyrosine phosphorylation of $p62^{dok}$ and its association with SHIP and RasGAP.

In some embodiments, the anti-FcγRIIB antibodies of the invention are characterized for their ability to modulate an IgE-mediated response by monitoring and/or measuring degranulation of mast cells or basophils, preferably in a cell-based assay. Preferably, mast cells or basophils for use in such assays have been engineered to contain human FcγRIIB using standard recombinant methods known to one skilled in the art. In a specific embodiment, the anti-FcγRIIB antibodies of the invention are characterized for their ability to modulate an IgE mediated response in a cell-based β-hexosaminidase (enzyme contained in the granules) release assay. β-hexosaminidase release from mast cells and basophils is a primary event in acute allergic and inflammatory condition (Aketani et al. (2001) "*Correlation Between Cytosolic Calcium Concentration And Degranulation In RBL-2H3 Cells In The Presence Of Various Concentrations Of Antigen-Specific IgEs*," Immunol. Lett. 75: 185-189; Aketani et al. (2000) "*A Screening Method For Antigen-Specific IgE Using Mast Cells Based On Intracellular Calcium Signaling*," Anal. Chem. 72: 2653-2658). Release of other inflammatory mediators including but not limited to serotonin and histamine may be assayed to measure an IgE-mediated response in accordance with the methods of the invention. Although not intending to be bound by a particular mechanism of action, release of granules such as those containing β-hexosaminidase from mast cells and basophils is an intracellular calcium concentration dependent process that is initiated by the cross-linking of FcεRIs with multivalent antigen.

One exemplary assay for characterizing the anti-FcγRIIB antibodies of the invention in mediating an IgE mediated response is a β-hexosaminidase release assay comprising the following: transfecting RBL-H23 cells with human FcγRIIB; sensitizing the cells with mouse IgE alone or with mouse IgE and an anti-FcγRIIB antibody of the invention; stimulating the cells with various concentrations of goat anti-mouse F (ab)$_2$, preferably in a range from 0.03 μg/mL to 30 μg/mL for about 1 hour; collecting the supernatant; lysing the cells; and measuring the β-hexosaminidase activity released in the supernatant by a colorometric assay, e.g., using p-nitrophenyl N-acetyl-β-D-glucosaminide. The released β-hexosaminidase activity is expressed as a percentage of the released activity to the total activity. The released β-hexosaminidase activity will be measured and compared in cells treated with antigen alone; IgE alone; IgE and an anti-FcγRIIB antibody of the invention. Although not intending to be bound by a particular mechanism of action, once cells are sensitized with mouse IgE alone and challenged with F(ab)$_2$ fragments of a polyclonal goat anti-mouse IgG, aggregation and cross linking of FcεRI occurs since the polyclonal antibody recognizes the light chain of the murine IgE bound to the FcεRI; which in turn leads to mast cell activation and degranulation. On the other hand, when cells are sensitized with mouse IgE and an anti-FcγRIIB antibody of the invention and challenged with F(ab)$_2$ fragments of a polyclonal goat anti-mouse IgG; cross linking of FcεRI and FcγRIIB occurs, resulting in inhibition of FcεRI-induced degranulation. In either case, goat anti mouse F(ab)$_2$ induces a dose-dependent β-hexoaminidase release. In some embodiments, the anti-FcγRIIB antibodies bound to the FcγRIIB receptor and cross linked to FcεRI do not affect the activation of the inhibitory pathway, i.e., there is no alteration in the level of degranulation in the presence of an anti-FcγRIIB antibody. In other embodiments, the anti-FcγRIIB antibodies mediate a stronger activation of the inhibitory receptor, FcγRIIB, when bound by the anti-FcγRIIB antibody, allowing effective cross-linking to FcεRI and activation of the inhibitory pathway of homo-aggregated FcγRIIB.

The invention also encompasses characterizing the effect of the anti-FcγRIIB antibodies of the invention on IgE mediated cell response using calcium mobilization assays using methodologies known to one skilled in the art. An exemplary calcium mobilization assay may comprise the following: priming basophils or mast cells with IgE; incubating the cells with a calcium indicator, e.g., Fura 2; stimulating cells as described supra; and monitoring and/or quantitating intracellular calcium concentration for example by using flow cytometry. The invention encompasses monitoring and/or quantitating intracellular calcium concentration by any method known to one skilled in the art see, e.g., Aketani et al. (2001) "*Correlation Between Cytosolic Calcium Concentration And Degranulation In RBL-2H3 Cells In The Presence Of Various Concentrations Of Antigen-Specific IgEs*," Immunology Letters 75:185-189; Oka et al. (2002) "*FcRI Cross-Linking-Induced Actin Assembly Mediates Calcium Signalling In RBL-2H3 Mast Cells*," British J. of Pharm. 136:837-845; Ott et al. (2002) "*Downstream Of Kinase, p62dok, Is A Mediator Of FcRIIB Inhibition Of FcRI Signaling*," J. Immunol. 168: 4430-4439 and Mahmoud et al. (2001) "*Microdomains Of High Calcium Are Not Required For Exocytosis In RBL-2H3 Mucosal Mast Cells*," J. Cell Biol., 153(2):339-350; all of which are incorporated herein by reference.

In preferred embodiments, anti-FcγRIIB antibodies of the invention inhibit IgE mediated cell activation. In other embodiments, the anti-FcγRIIB antibodies of the invention block the inhibitory pathways regulated by FcγRIIB or block the ligand binding site on FcγRIIB and thus enhance immune response.

The ability to study human mast cells has been limited by the absence of suitable long term human mast cell cultures. Recently two novel stem cell factor dependent human mast cell lines, designated LAD 1 and LAD2, were established from bone marrow aspirates from a patient with mast cell sarcoma/leukemia. (Kirshenbaum et al. (2003) *"Characterization Of Novel Stem Cell Factor Responsive Human Mast Cell Lines LAD 1 And 2 Established From A Patient With Mast Cell Sarcoma/Leukemia; Activation Following Aggregation Of FcepsilonRI Or FcgammaRI,"* Leukemia research, 27(8): 677-682, which is incorporated herein by reference in its entirety.) Both cell lines have been described to express FcεRI and several human mast cell markers. The invention encompasses using LAD 1 and 2 cells in the methods of the invention for assessing the effect of the antibodies of the invention on IgE mediated responses. In a specific embodiment, cell-based β-hexosaminidase release assays such as those described supra may be used in LAD cells to determine any modulation of the IgE-mediated response by the anti-FcγRIIB antibodies of the invention. In an exemplary assay, human mast cells, e.g., LAD 1, are primed with chimaeric human IgE anti-nitrophenol (NP) and challenged with BSA-NP, the polyvalent antigen, and cell degranulation is monitored by measuring the β-hexosaminidase released in the supernatant (Kirshenbaum et al. (2003) *"Characterization Of Novel Stem Cell Factor Responsive Human Mast Cell Lines LAD 1 And 2 Established From A Patient With Mast Cell Sarcoma/Leukemia; Activation Following Aggregation Of FcepsilonRI Or FcgammaRI,"* Leukemia research, 27(8):677-682, which is incorporated herein by reference in its entirety).

In some embodiments, if human mast cells have a low expression of endogenous FcγRIIB, as determined using standard methods known in the art, e.g., FACS staining, it may be difficult to monitor and/or detect differences in the activation of the inhibitory pathway mediated by the anti-FcγRIIB antibodies of the invention. The invention thus encompasses alternative methods, whereby the FcγRIIB expression may be upregulated using cytokines and particular growth conditions. FcγRIIB has been described to be highly up-regulated in human monocyte cell lines, e.g., THP1 and U937, (Tridandapani et al. (2002) *"Regulated Expression And Inhibitory Function Of FcRIIb In Human Monocytic Cells,"* J. Biol. Chem., 277(7): 5082-5089) and in primary human monocytes (Pricop et al. (2001) *"Differential Modulation Of Stimulatory And Inhibitory Fc Gamma Receptors On Human Monocytes By Th1 And Th2 Cytokines,"* J. Immunol., 166: 531-537) by IL4. Differentiation of U937 cells with dibutyryl cyclic AMP has been described to increase expression of FcγRII (Cameron et al. (2002) *"Differentiation Of The Human Monocyte Cell Line, U937, With Dibutyryl CyclicAMP Induces The Expression Of The Inhibitory Fc Receptor, FcgammaRIIB,"* Immunology Letters 83, 171-179). Thus, the endogenous FcγRIIB expression in human mast cells for use in the methods of the invention may be up-regulated using cytokines, e.g., IL-4, IL-13, in order to enhance sensitivity of detection.

The invention also encompasses characterizing the anti-FcγRIIB antibodies of the invention for inhibition of B-cell receptor (BCR)-mediated signaling. BCR-mediated signaling can include at least one or more down stream biological responses, such as activation and proliferation of B cells, antibody production, etc. Coaggregation of FcγRIIB and BCR leads to inhibition of cell cycle progression and cellular survival. Further, coaggregation of FcγRIIB and BCR leads to inhibition of BCR-mediated signaling.

Specifically, BCR-mediated signaling comprises at least one or more of the following: modulation of down stream signaling molecules (e.g., phosphorylation state of FcγRIIB, SHIP recruitment, localization of Btk and/or PLCγ, MAP kinase activity, recruitment of Akt (anti-apoptotic signal), calcium mobilization, cell cycle progression, and cell proliferation.

Although numerous effector functions of FcγRIIB-mediated inhibition of BCR signaling are mediated through SHIP, recently it has been demonstrated that lipopolysaccharide (LPS)-activated B cells from SHIP deficient mice exhibit significant FcγRIIB-mediated inhibition of calcium mobilization, $Ins(1,4,5)P_3$ production, and Erk and Akt phosphorylation (Brauweiler et al (2001) *"Partially Distinct Molecular Mechanisms Mediate Inhibitory FcgammaRIIB Signaling In Resting And Activated B Cells,"* J. Immunol. 167(1): 204-211). Accordingly, ex vivo B cells from SHIP deficient mice can be used to characterize the antibodies of the invention. One exemplary assay for determining FcγRIIB-mediated inhibition of BCR signaling by the antibodies of the invention can comprise the following: isolating splenic B cells from SHIP deficient mice, activating said cells with lipopolysaccharide, and stimulating said cells with either $F(ab')_2$ anti-IgM to aggregate BCR or with anti-IgM to coaggregate BCR with FcγRIIB. Cells that have been stimulated with intact anti-IgM to coaggregate BCR with FcγRIIB can be further pre-incubated with the antibodies of the invention. FcγRIIB-dependent activity of cells can be measured by standard techniques known in the art. Comparing the level of FcγRIIB-dependent activity in cells that have been pre-incubated with the antibodies of the invention and cells that have not been pre-incubated, and comparing the levels would indicate a modulation of FcγRIIB-dependent activity by the antibodies of the invention.

Measuring FcγRIIB-dependent activity can include, for example, measuring intracellular calcium mobilization by flow cytometry, measuring phosphorylation of Akt and/or Erk, measuring BCR-mediated accumulation of $PI(3,4,5)P_3$, or measuring FcγRIIB-mediated proliferation B cells.

The assays can be used, for example, to identify antibodies that modulate FcγRIIB-mediated inhibition of BCR signaling by blocking the ligand (IgG) binding site to FcγRIIB receptor and antagonizing FcγRIIB-mediated inhibition of BCR signaling by preventing coaggregation of FcγRIIB and BCR. The assays can also be used to identify antibodies that enhance coaggregation of FcγRIIB and BCR and agonize FcγRIIB-mediated inhibition of BCR signaling.

The invention relates to characterizing the anti-FcγRIIB antibodies of the invention for FcγRII-mediated signaling in human monocytes/macrophages. Coaggregation of FcγRIIB with a receptor bearing the immunoreceptor tyrosine-based activation motif (ITAM) acts to down-regulate FcγR-mediated phagocytosis using SHIP as its effector (Tridandapani et al. (2002) *"Regulated Expression And Inhibitory Function Of FcRIIb In Human Monocytic Cells,"* J. Biol. Chem. 277(7): 5082-5089). Coaggregation of FcγRIIA with FcγRIIB results in rapid phosphorylation of the tyrosine residue on FcγRIIB's ITIM motif, leading to an enhancement in phosphorylation of SHIP, association of SHIP with Shc, and phosphorylation of proteins having the molecular weight of 120 and 60-65 kDa. In addition, coaggregation of FcγRIIA with FcγRIIB results in down-regulation of phosphorylation of Akt, which is a serine-threonine kinase that is involved in cellular regulation and serves to suppress apoptosis.

The invention further encompasses characterizing the anti-FcγRIIB antibodies of the invention for their inhibition of FcγR-mediated phagocytosis in human monocytes/macrophages. For example, cells from a human monocytic cell line, THP-1 can be stimulated either with Fab fragments of mouse monoclonal antibody IV.3 against FcγRII and goat anti-mouse antibody (to aggregate FcγRIIA alone), or with whole IV.3 mouse monoclonal antibody and goat anti-mouse antibody (to coaggregate FcγRIIA and FcγRIIB). In this system, modulation of down stream signaling molecules, such as tyrosine phosphorylation of FcγRIIB, phosphorylation of SHIP, association of SHIP with Shc, phosphorylation of Akt, and phosphorylation of proteins having the molecular weight of 120 and 60-65 kDa can be assayed upon addition of antibodies of the invention to the stimulated cells. In addition, FcγRIIB-dependent phagocytic efficiency of the monocyte cell line can be directly measured in the presence and absence of the antibodies of the invention.

Another exemplary assay for determining inhibition of FcγR-mediated phagocytosis in human monocytes/macrophages by the antibodies of the invention can comprise the following: stimulating THP-1 cells with either Fab of IV.3 mouse anti-FcγRII antibody and goat anti-mouse antibody (to aggregate FcγRIIA alone and elicit FcγRIIA-mediated signaling); or with mouse anti-FcγRII antibody and goat anti-mouse antibody (to coaggregate FcγRIIA and FcγRIIB and inhibiting FcγRIIA-mediated signaling. Cells that have been stimulated with mouse anti-FcγRII antibody and goat anti-mouse antibody can be further pre-incubated with the antibodies of the invention. Measuring FcγRIIA-dependent activity of stimulated cells that have been pre-incubated with antibodies of the invention and cells that have not been pre-incubated with the antibodies of the invention and comparing levels of FcγRIIA-dependent activity in these cells would indicate a modulation of FcγRIIA-dependent activity by the antibodies of the invention.

The exemplary assay described can be used for example, to identify antibodies that block ligand binding of FcγRIIB receptor and antagonize FcγRIIB-mediated inhibition of FcγRIIA signaling by preventing coaggregation of FcγRIIB and FcγRIIA. This assay likewise identifies antibodies that enhance coaggregation of FcγRIIB and FcγRIIA and agonize FcγRIIB-mediated inhibition of FcγRIIA signaling.

In another embodiment of the invention, the invention relates to characterizing the function of the antibodies of the invention by measuring the ability of THP-1 cells to phagocytose fluoresceinated IgG-opsonized sheep red blood cells (SRBC) by methods previously described (Tridandapani et al. (2000) "*The Adapter Protein LAT Enhances Fc Receptor-Mediated Signal Transduction In Myeloid Cells*," J. Biol. Chem. 275: 20480-20487). For example, an exemplary assay for measuring phagocytosis comprises of: treating THP-1 cells with the antibodies of the invention or with a control antibody that does not bind to FcγRII, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate a modulation of FcγRIIA-dependent activity by the antibodies of the invention. This assay can be used to identify, for example, antibodies that block ligand binding of FcγRIIB receptor and antagonize FcγRIIB-mediated inhibition of phagocytosis. This assay can also identify antibodies that enhance FcγRIIB-mediated inhibition of FcγRIIA signaling.

In a preferred embodiment, the antibodies of the invention modulate FcγRIIB-dependent activity in human monocytes/macrophages in at least one or more of the following ways: modulation of downstream signaling molecules (e.g., modulation of phosphorylation state of FcγRIIB, modulation of SHIP phosphorylation, modulation of SHIP and Shc association, modulation of phosphorylation of Akt, modulation of phosphorylation of additional proteins around 120 and 60-65 kDa) and modulation of phagocytosis.

The invention encompasses characterization of the antibodies of the invention using assays known to those skilled in the art for identifying the effect of the antibodies on effector cell function of therapeutic antibodies, e.g., their ability to enhance tumor-specific ADCC activity of therapeutic antibodies. Therapeutic antibodies that may be used in accordance with the methods of the invention include but are not limited to anti-tumor antibodies, anti-viral antibodies, anti-microbial antibodies (e.g., bacterial and unicellular parasites), examples of which are disclosed herein. In particular, the invention encompasses characterizing the antibodies of the invention for their effect on FcγR-mediated effector cell function of therapeutic antibodies, e.g., tumor-specific monoclonal antibodies. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al. (2000) "*Assays For Antibody-Dependent Cell-Mediated Cytotoxicity (ADCC) And Reverse ADCC (redirected cytotoxicity) In Human Natural Killer Cells*," Methods Mol. Biol. 121: 179-192; Lehmann et al. (2000) "*Phagocytosis: Measurement By Flow Cytometry*," J. Immunol. Methods, 243(1-2): 229-242; Brown (1994) "*In Vitro Assays Of Phagocytic Function Of Human Peripheral Blood Leukocytes: Receptor Modulation And Signal Transduction*," Methods Cell Biol., 45: 147-164; Munn et al. (1990) "*Phagocytosis Of Tumor Cells By Human Monocytes Cultured In Recombinant Macrophage Colony-Stimulating Factor*," J. Exp. Med., 172: 231-237, Abdul-Majid et al. (2002) "*Fc Receptors Are Critical For Autoimmune Inflammatory Damage To The Central Nervous System In Experimental Autoimmune Encephalomyelitis*," Scand. J. Immunol. 55: 70-81; Ding et al. (1998) "*Two Human T Cell Receptors Bind In A Similar Diagonal Mode To The HLA-A2/Tax Peptide Complex Using Different TCR Amino Acids*," Immunity 8:403-411, each of which is incorporated by reference herein in its entirety).

Antibodies of the invention can be assayed for their effect on FcγR-mediated ADCC activity of therapeutic antibodies in effector cells, e.g., natural killer cells, using any of the standard methods known to those skilled in the art (See e.g., Perussia et al. (2000) "*Assays For Antibody-Dependent Cell-Mediated Cytotoxicity (ADCC) And Reverse ADCC (redirected cytotoxicity) In Human Natural Killer Cells*," Methods Mol. Biol. 121: 179-192). "Antibody-dependent cell-mediated cytotoxicity" and "ADCC" as used herein carry their ordinary and customary meaning in the art and refer to an in vitro cell-mediated reaction in which nonspecific cytotoxic cells that express FcγRs (e.g., monocytic cells such as Natural Killer (NK) cells and macrophages) recognize bound antibody on a target cell and subsequently cause lysis of the target cell. In principle, any effector cell with an activating FcγR can be triggered to mediate ADCC. The primary cells for mediating ADCC are NK cells which express only FcγRIII, whereas monocytes, depending on their state of activation, localization, or differentiation, can express FcγRI, FcγRII, and FcγRIII. For a review of FcγR expression on hematopoietic cells see, e.g., Ravetch et al. (1991) "*Fc Receptors*," Annu. Rev. Immunol., 9:457-492, which is incorporated herein by reference in its entirety.

Effector cells are leukocytes which express one or more FcγRs and perform effector functions. Preferably, the cells express at least FcγRIII and perform ADCC effector function. Effector cells that may be used in the methods of the invention include but are not limited to peripheral blood mononuclear cells (PBMC), natural killer (NK) cells, monocytes, and neutrophils; with PBMCs and NK cells being preferred. The effector cells may be isolated from a native source thereof, e.g., from blood or PBMCs as described herein. Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. For example, PBMCs may be isolated by layering whole blood onto Ficoll-Hypaque and spinning the cells at 500 g, at room temperature for 30 minutes. The leukocyte layer can be harvested as effector cells. Other effector cells that may be used in the ADCC assays of the invention include but are not limited to monocyte-derived macrophages (MDMs). MDMs that are used as effector cells in the methods of the invention, are preferably obtained as frozen stocks or used fresh, (e.g., from Advanced Biotechnologies, MD). In most preferred embodiments, elutriated human monocytes are used as effector cells in the methods of the invention. Elutriated human monocytes express activating receptors, FcγRIIIA and FcγRIIA and the inhibitory receptor, FcγRIIB. Human monocytes are commercially available and may be obtained as frozen stocks, thawed in basal medium containing 10% human AB serum or in basal medium with human serum containing cytokines. Levels of expression of FcγRs in the cells may be directly determined; e.g. using FACS analysis. Alternatively, cells may also be allowed to mature to macrophages in culture. The level of FcγRIIB expression may be increased in macrophages. Antibodies that may be used in determining the expression level of FcγRs include but are not limited to anti-human FcγRIIA antibodies, e.g., IV.3-FITC; anti-FcγRI antibodies, e.g., 32.2 FITC; and anti-FcγRIIIA antibodies, e.g., 3G8-PE.

Target cells used in the ADCC assays of the invention include, but are not limited to, breast cancer cell lines, e.g., SK-BR-3 with ATCC accession number HTB-30 (see, e.g., Tremp et al. (1976) "*Human Breast Cancer In Culture*," Recent Results Cancer Res. 57:33-41); B-lymphocytes; cells derived from Burkitts lymphoma, e.g., Raji cells with ATCC accession number CCL-86 (see, e.g., Epstein et al. (1965) "*Characteristics And Mode Of Growth Of Tissue Culture Strain (EB1) Of Human Lymphoblasts From Burkitt's Lymphoma*," J. Natl. Cancer Inst. 34: 231-240), Daudi cells with ATCC accession number CCL-213 (see, e.g., Klein et al. (1968) "*Surface IgM-Kappa Specificity On A Burkitt Lymphoma Cell In Vivo And In Derived Culture Lines*," Cancer Res. 28: 1300-1310); ovarian carcinoma cell lines, e.g., OVCAR-3 with ATCC accession number HTB-161 (see, e.g., Hamilton et al. (1983) "*Characterization Of A Human Ovarian Carcinoma Cell Line (NIH:OVCAR-3) With Androgen And Estrogen Receptors*," Cancer Res. 43(11):5379-5389), SK-OV-3, PA-1, CAOV3, OV-90, and IGROV-1, available from the NCI repository. (See, Benard et al. (1985) "*Characterization Of A Human Ovarian Adenocarcinoma Line, IGROV1, In Tissue Culture And In Nude Mice*," Cancer Research, 45:4970-4979; which is incorporated herein by reference in its entirety.) The target cells must be recognized by the antigen binding site of the antibody to be assayed. The target cells for use in the methods of the invention may have low, medium, or high expression level of a cancer antigen. The expression levels of the cancer antigen may be determined using common methods known to one skilled in the art, e.g., FACS analysis. For example, the invention encompasses the use of ovarian cancer cells such as IGROV-1, wherein Her2/neu is expressed at different levels, or OV-CAR-3 (ATCC Assession Number HTB-161; characterized by a lower expression of Her2/neu than SK-BR-3, the breast carcinoma cell line). Other ovarian carcinoma cell lines that may be used as target cells in the methods of the invention include OVCAR-8 (Hamilton et al. (1983) "*Characterization Of A Human Ovarian Carcinoma Cell Line (NIH:OVCAR-3) With Androgen And Estrogen Receptors*," Cancer Res. 43(11): 5379-5389, which is incorporated herein by reference in its entirety); SK-OV-3 (ATCC Accession Number HTB-77); Caov-3 (ATCC Accession Number HTB-75); PA-1 (ATCC Accession Number CRL-1572); OV-90 (ATCC Accession Number CRL-11732); and OVCAR-4. Other breast cancer cell lines that may be used in the methods of the invention include BT-549 (ATCC Accession Number HTB-122), MCF7 (ATCC Accession Number HTB-22), and Hs578T (ATCC Accession Number HTB-126), all of which are available from the NCI repository and ATCC and incorporated herein by reference. Other cell lines that may be used in the methods of the invention include, but are not limited to: CCRF-CEM (leukemia); HL-60 (TB, leukemia); MOLT-4 (leukemia); RPMI-8226 (leukemia); SR (leukemia); A549 (Non-small cell lung); EKVX (Non-small cell lung); HOP-62 (Non-small cell lung); HOP-92 (Non-small cell lung); NCl-H226 (Non-small cell lung); NCl-H23 (Non-small cell lung); NCl-H322M (Non-small cell lung); NCl-H460 (Non-small cell lung); NCl-H522 (Non-small cell lung); COLO 205 (Colon); HCC-2998 (Colon); HCT-116 (Colon); HCT-15 (Colon); HT29 (Colon); KM12 (Colon); SW-620 (Colon); SF-268 (CNS); SF-295 (CNS); SF-539 (CNS); SNB-19 (CNS); SNB-75 (CNS); U251 (CNS); LOX 1MV1 (Melanoma); MALME-3M (Melanoma); M14 (Melanoma); SK-MEL-2 (Melanoma); SK-MEL-28 (Melanoma); SK-MEL-5 (Melanoma); UACC-257 (Melanoma); UACC-62 (Melanoma); IGR-OV1 (Ovarian); OVCAR-3, 4, 5, 8 (Ovarian); SK-OV-3 (Ovarian); 786-0 (Renal); A498 (Renal); ACHN (Renal); CAK1-1 (Renal); SN12C(Renal); TK-10 (Renal); UO-31 (Renal); PC-3C (Prostate); DU-145 (Prostate); NCl/ADR-RES (Breast); MDA-MB-231/ATCC (Breast); MDA-MB-435 (Breast); DMS 114 (Small-cell lung); and SHP-77 (Small-cell lung); all of which are available from the NCI and incorporated herein by reference.

An exemplary assay for determining the effect of the antibodies of the invention on the ADCC activity of therapeutic antibodies is based on a $^{51}$Cr release assay comprising: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell lysis); preferably, the target cells express one or more tumor antigens, osponizing the target cells with one or more antibodies that immunospecifically bind the tumor antigens expressed on the cell surface of the target cells, in the presence and absence of an antibody of the invention, e.g., 2B6, 3H7, combining the opsonized radiolabeled target cells with effector cells in a microtitre plate at an appropriate ratio of target cells to effector cells; incubating the mixture of cells preferably for 16-18 hours, preferably at 37° C.; collecting supernatants; and analyzing the radioactivity in the supernatant samples. The cytotoxicity of the therapeutic antibodies in the presence and absence of the antibodies of the invention can then be determined, for example using the following formula: Percent specific lysis=(Experimental lysis-antibody-independent lysis/maximal lysis—antibody independent lysis)×100%. A graph can be generated by varying either the target: effector cell ratio or antibody concentration.

In yet another embodiment, the antibodies of the invention are characterized for antibody dependent cellular cytotoxicity (ADCC) in accordance with the method described earlier, see, e.g., Ding et al. (1998) "*Two Human T Cell Receptors Bind In A Similar Diagonal Mode To The HLA-A2/Tax Peptide Complex Using Different TCR Amino Acids*," Immunity 8:403-411; which is incorporated herein by reference in its entirety.

In some embodiments, the invention encompasses characterizing the function of the antibodies of the invention in enhancing ADCC activity of therapeutic antibodies in an in vitro based assay and/or in an animal model.

In a specific embodiment, the invention encompasses determining the function of the antibodies of the invention in enhancing tumor specific ADCC using an ovarian cancer model and/or breast cancer model.

Preferably, the ADCC assays of the invention are performed using more than one cancer cell line, characterized by the expression of at least one cancer antigen, wherein the expression level of the cancer antigen is varied among the cancer cell lines used. Although not intending to be bound by a particular mechanism of action, performing ADCC assays in more than one cell line wherein the expression level of the cancer antigen is varied, will allow determination of stringency of tumor clearance of the antibodies of the invention. In one embodiment, the ADCC assays of the invention are done using cancer cell lines with different levels of expression of a cancer antigen.

In an exemplary assay, OVCAR3, an ovarian carcinoma cell line can serve as the tumor target expressing the tumor antigens, Her2/neu and TAG-72; human monocytes, that express the activating FcγRIIIA and FcγRIIA and inhibitory FcγRIIB, can be used as effectors; and tumor specific murine antibodies, ch4D5 and chCC49, can be used as the tumor specific antibodies. OVCAR-3 cells are available from ATCC (Accession Number HTB-161). Preferably, OVCAR-3 cells are propagated in medium supplemented with 0.01 mg/ml bovine insulin. $5 \times 10^6$ viable OVCAR-3 cells may be injected subcutaneously (s.c) into age and weight matched nude athymic mice with Matrigel (Becton Dickinson). The estimated weight of the tumor can be calculated by the formula: length·(width)$^2$/2, and preferably does not exceed 3 grams. Anchorage-dependent tumor can be isolated after 6-8 weeks, and the cells can be dissociated by adding 1 μg of Collagenase (Sigma) per gram of tumor and a 5 mg/mL RNase, passed through a cell strainer and nylon mesh to isolate cells. Cells can then be frozen for long-term storage for s.c. injection for establishment of the xenograft model.

Hybridomas secreting CC49 and 4D5 antibodies are available with ATCC Accession Numbers HB-9459 and CRL-3D463 and the heavy chain and light chain nucleotide sequences are in the public domain (Murray et al. (1994) "*Phase II Radioimmunotherapy Trial With* 131*I-CC49 In Colorectal Cancer*," Cancer 73 (35):1057-1066, Yamamoto et al. (1986) "*Similarity Of Protein Encoded By The Human c-erb-B-2 Gene To Epidermal Growth Factor Receptor*," Nature, 319:230-234; both of which are incorporated herein by reference in their entirety). Preferably, the 4D5 and CC49 antibodies are chimerized using standard methods known to one skilled in the art so that the human Fc sequence, e.g., human constant region of IgG1, is grafted onto the variable region of the murine antibodies in order to provide the effector function. The chimeric 4D5 and CC49 antibodies bind via their variable region to the target cell lines and via their Fc region to FcγRs expressed on human effector cells. CC49 is directed to TAG-72; a high molecular weight mucin that is highly expressed on many adenocarcinoma cells and ovarian carcinoma (Lottich et al. (1985) "*Tumor-Associated Antigen TAG-72: Correlation Of Expression In Primary And Metastatic Breast Carcinoma Lesions*," Breast Cancer Res. Treat. 6(1):49-56; Mansi et al. (1989) "*Diagnosis Of Ovarian Cancer With Radiolabelled Monoclonal Antibodies: Our Experience Using* 131I-B72.3," Int. J. Rad. Appl. Instrum B. 16(2): 127-135; Colcher et al. (1991) "*In vivo And In Vitro Clinical Applications Of Monoclonal Antibodies Against TAG-72*," Int. J. Rad. Appl. Instrum B. 18:395-441; all of which are incorporated herein by reference in their entirety). 4D5 is directed to human epidermal growth factor receptor 2 (Carter et al. (1992) "*Humanization Of An Anti-p*185*HER2 Antibody For Human Cancer Therapy*," Proc. Natl. Acad. Sci. USA, 89: 4285-4289 which is incorporated herein by reference). Antibodies of the invention can then be utilized to investigate the enhancement of ADCC activity of the tumor specific antibodies, by blocking the inhibitory FcγRIIB. Although not intending to be bound by a particular mechanism of action, upon activation of effector cells that express at least one activating FcγR, e.g., FcγRIIA, the expression of the inhibitory receptor (FcγRIIB) is enhanced and this limits the clearance of tumors as the ADCC activity of FcγRIIA is suppressed. However, antibodies of the invention can serve as a blocking antibody, i.e., an antibody that will prevent the inhibitory signal from being activated and thus the activation signal, e.g., ADCC activity, will be sustained for a longer period and may result in potent tumor clearance.

Preferably, the antibodies of the invention for use in enhancement of ADCC activity have been modified to comprise at least one amino acid modification, so that their binding to FcγR has been diminished, most preferably abolished. In some embodiments, the antibodies of the invention have been modified to comprise at least one amino acid modification that reduces the binding of the constant domain to an activating FcγR, e.g., FcγRIIIA, FcγRIIA, as compared to a wild type antibody of the invention while retaining maximal FcγRIIB blocking activity. Antibodies of the invention may be modified in accordance with any method known to one skilled in the art or disclosed herein. Any amino acid modification which is known to disrupt effector function may be used in accordance with the methods of the invention such as those disclosed in U.S. Application Ser. Nos. 60/439,498 (filed Jan. 9, 2003); and 60/456,041 (filed Mar. 19, 2003); both of which are incorporated herein by reference in their entireties. In some embodiments, antibodies of the invention are modified so that position 265 is modified, e.g., position 265 is substituted with alanine. In preferred embodiments, the murine constant region of an antibody of the invention is swapped with the corresponding human constant region comprising a substitution of the amino acid at position 265 with alanine, so that the effector function is abolished while FcγRIIB blocking activity is maintained. A single amino acid change at position 265 of IgG1 heavy chain has been shown to significantly reduce binding to FcγR based on ELISA assays and has resulted in tumor mass reduction. (Shields et al. (2001) "*High Resolution Mapping Of The Binding Site On Human IgG*1 *For Fc gamma RI, Fc gamma RII, Fc gamma RIII, And FcRn And Design Of IgG*1 *Variants With Improved Binding To The Fc gamma R*," J. Biol. Chem. 276(9):6591-604; and Clynes et al. (2000) "*Inhibitory Fc Receptors Modulate In Vivo Cytoxicity Against Tumor Targets*," Nature Medicine 6(4):443-446; which is incorporated herein by reference in its entirety.) In other embodiments, antibodies of the invention are modified so that position 297 is modified, e.g., position 297 is substituted with glutamine, so that the N-linked glycosylation site is eliminated (see, e.g., Jefferis et al. (1995) "*Recognition Sites On Human Igg For Fc Gamma Receptors: The Role Of Glycosylation*," Immunol. Lett. 44(2-3):111-117; Lund et al. (1996) "*Multiple Interactions Of Igg With Its Core Oligosaccharide Can Modulate Recognition By Complement And Human Fc Gamma Receptor I And Influence The Synthesis Of Its Oligosaccharide Chains*," J. Immunol., 157:4963-4969; Wright et al. (1994) "*Effect Of Altered CH2-Associated Carbohydrate Structure On The Functional Properties And In Vivo Fate Of Chimeric Mouse-Human Immunoglobulin G1*," J. Exp. Med. 180:1087-1096; White et al. (1997) "*Ig N-glycan Orientation Can Influence Interactions With The Complement System*," J. Immunol. 158:426-435; all of which are incorporated herein by reference in their entireties. Modification at this site has been reported to abolish all interaction with FcγRs. In preferred embodiments, the murine constant region of an antibody of the invention is swapped with the corresponding human constant region comprising a substitution of the amino acid at position 265 and/or 297, so that the effector function is abolished while FcγRIIB blocking activity is maintained.

An exemplary assay for determining the ADCC activity of the tumor specific antibodies in the presence and absence of the antibodies of the invention is a non-radioactive europium based fluorescent assay (BATDA, Perkin Elmer) and may comprise the following: labeling the targets cells with an acteoxylmethyl ester of fluorescence-enhancing ester that forms a hydrophilic ligand (TDA) with the membrane of cells by hydrolysis of the esters; this complex is unable to leave the cell and is released only upon lysis of the cell by the effectors; adding the labeled targets to the effector cells in presence of anti-tumor antibodies and an antibody of the invention; incubating the mixture of the target and effector cells a for 6 to 16 hours, preferably at 37° C. The extent of ADCC activity can be assayed by measuring the amount of ligand that is released and interacts with europium (DELFIA® reagent; PerkinElmer). The ligand and the europium form a very stable and highly fluorescent chelate (EuTDA) and the measured fluorescence is directly proportional to the number of cells lysed. Percent specific lysis can be calculated using the formula: (Experimental lysis-antibody-independent lysis/maximal lysis antibody-independent lysis×100%).

In some embodiments, if the sensitivity of the fluorescence-based ADCC assay is too low to detect ADCC activity of the therapeutic antibodies, the invention encompasses radioactive-based ADCC assays, such as $^{51}$Cr release assay. Radioactive-based assays may be done instead of or in combination with fluorescent-based ADCC assays.

An exemplary $^{51}$Cr release assay for characterizing the antibodies of the invention can comprise the following: labeling 1-2×10$^6$ target cells such as OVCAR-3 cells with $^{51}$Cr; opsonizing the target cells with antibodies 4D5 and CC49 in the presence and absence of an antibody of the invention and adding 5×10$^3$ cells to 96 well plate. Preferably 4D5 and CC49 are at a concentration varying from 1-15 µg/mL; adding the opsonized target cells to monocyte-derived macrophages (MDM) (effector cells); preferably at a ratio varying from 10:1 to 100:1; incubating the mixture of cells for 16-18 hours at 37° C.; collecting supernatants; and analyzing the radioactivity in the supernatant. The cytotoxicity of 4D5 and CC49 in the presence and absence of an antibody of the invention can then be determined, for example using the following formula percent specific lysis=(experimental lysis–antibody independent lysis/maximal lysis–antibody independent lysis)×100%.

In some embodiments, the in vivo activity of the FcγRIIB antibodies of the invention is determined in xenograft human tumor models. Tumors may be established using any of the cancer cell lines described supra. In some embodiments, the tumors will be established with two cancer cell lines, wherein the first cancer cell line is characterized by a low expression of a cancer antigen and a second cancer cell line, wherein the second cancer cell line is characterized by a high expression of the same cancer antigen. Tumor clearance may then be determined using methods known to one skilled in the art, using an anti-tumor antibody which immunospecifically binds the cancer antigen on the first and second cancer cell line, and an appropriate mouse model, e.g., a Balb/c nude mouse model (e.g., Jackson Laboratories, Taconic), with adoptively transferred human monocytes and MDMs as effector cells. Any of the antibodies described supra may then be tested in this animal model to evaluate the role of anti-FcγRIIB antibody of the invention in tumor clearance. Mice that may be used in the invention include, for example, FcγRIII–/– (where FcγRIIIA is knocked out); Fcγ–/–nude mice (where FcγRI and FcγRIIIA are knocked out); or human FcγRIIB knock in mice or a transgenic knock-in mice, where mouse fcgr2 and fcgr3 loci on chromosome 1 are inactivated and the mice express human FcγRIIA, human FcγRIIA human FcγRIIB, human FcγRIIC, human FcγRIIIA, and human FcγRIIIB.

An exemplary method for testing the in vivo activity of an antibody of the invention may comprise the following: establishing a xenograft murine model using a cancer cell line characterized by the expression of a cancer antigen and determining the effect of an antibody of the invention on an antibody specific for the cancer antigen expressed in the cancer cell line in mediating tumor clearance. Preferably, the in vivo activity is tested parallel using two cancer cell lines, wherein the first cancer cell line is characterized by a first cancer antigen expressed at low levels and a second cancer cell line, characterized by the same cancer antigen expressed at a higher level relative to the first cancer cell line. These experiments will thus increase the stringency of the evaluation of the role of an antibody of the invention in tumor clearance. For example, tumors may be established with the IGROV-1 cell line and the effect of an anti-FcγRIIB antibody of the invention in tumor clearance of a Her2/neu specific antibody may be assessed. In order to establish the xenograft tumor models, 5×10$^6$ viable cells, e.g., IGROV-1, SKBR3, may be injected, e.g., s.c. into mice, e.g., 8 age and weight matched femal nude athymic mice using for example Matrigel (Becton Dickinson). The estimated weight of the tumor may be determined by the formula: length×(width)$^2$/2; and preferably does not exceed 3 grams. Injection of IGROV-1 cells s.c. gives rise to fast growing tumors while the i.p. route induces a peritoneal carcinomatosis which kills mice in 2 months (Benard et al. (1985) "*Characterization Of A Human Ovarian Adenocarcinoma Line, IGROV1, In Tissue Culture And In Nude Mice*," Cancer Research, 45:4970-4979). Since the IGROV-1 cells form tumors within 5 weeks, at day 1 after tumor cell injection, monocytes as effectors are co-injected i.p. along with a therapeutic antibody specific for Her2/neu, e.g., Ch4D5, and an antibody of the invention; e.g. chimeric 2B6 or 3H7 as described supra. Preferably, the antibodies are injected at 4 µg each per gram of mouse body weight (mbw). The initial injection will be followed by weekly injections of antibodies for 4-6 weeks thereafter at 2 µg/wk. Human effector cells will be replenished once in 2 weeks. A group of mice will receive no therapeutic antibody but will be injected with a chimeric 4D5 comprising a N297A mutation and human IgG1 as isotype control antibodies for the anti-tumor and anti-FcγRIIB antibodies, respectively. Mice may be placed in groups of 4 and monitored three times weekly.

Table 5 below is an exemplary setup for tumor clearance studies in accordance with the invention. As shown in Table 5, six groups of 8 mice each will be needed for testing the role of an antibody of the invention in tumor clearance, wherein one target and effector cell combination is used and wherein two different combinations of the antibody concentration are used. In group A, only tumor cells are injected; in group B tumor cells and monocytes are injected; in group C, tumor cells, monocytes, an anti-tumor antibody (ch4D5) are injected; in group D, tumor cells, monocytes, anti-tumor antibody, and an anti-FcγRII antibody are injected; in group E, tumor cells, monocytes and an anti-FcγRIIB antibody are injected; in group F, tumor cells, monocytes, Ch4D5 (297Q), and human IgG1 are injected. It will be appreciated by one skilled in the art that various antibody concentrations of various antibody combinations may be tested in the tumor models described. Preferably, studies using a breast cancer cell line, e.g., SKBR3, is carried out in parallel to the above-described experiment.

TABLE 5

Exemplary Experimental Set Up In Mice

| 8 mice per group | Tumor cell s.c day 0 | Monocytes i.p at day 1 | ch4D5 (4 μg/gm of mbw day 1 i.p.) | ch4D5 (N297Q at 4 μg/gm of mbw day 1 i.p.) | ch2B6 (N297Q at 4 μg/gm of mbw day 1 i.p.) | Human (IgG1 4 μg/gm of mbw day 1 i.p.) |
|---|---|---|---|---|---|---|
| A | + | − | − | − | − | − |
| B | + | + | − | − | − | − |
| C | + | + | + | − | − | − |
| D | + | + | + | − | + | − |
| E | + | + | − | − | + | − |
| F | + | + | − | + | − | + |

The endpoint of the xenograft tumor models is determined based on the size of the tumors, weight of mice, survival time and histochemical and histopathological examination of the cancer, using methods known to one skilled in the art. Each of the groups of mice in Table 5 will be evaluated. Mice are preferably monitored three times a week. Criteria for tumor growth may be abdominal distention, presence of palpable mass in the peritoneal cavity. Preferably, estimates of tumor weight versus days after inoculation will be calculated. A comparison of the aforementioned criteria of mice in Group D compared to those in other groups will define the role of an antibody of the invention in enhancement of tumor clearance. Preferably, antibody-treated animals will be under observation for an additional 2 months after the control group.

In alternative embodiments, human FcγRIIB "knock in" mice expressing human FcγRIIB on murine effector cells may be used in establishing the in vivo activity of the antibodies of the invention, rather than adoptively transferring effector cells. Founder mice expressing the human FcγRIIB may be generated by "knocking in" the human FcγRIIB onto the mouse FcγRIIB locus. The founders can then be backcrossed onto the nude background and will express the human FcγRIIB receptor. The resulting murine effector cells will express endogenous activating FcγRI and FcγRIIIA and inhibitory human FcγRIIB receptors.

The in vivo activity of the antibodies of the invention may be further tested in a xenograft murine model with human primary tumor derived cells, such as human primary ovarian and breast carcinoma derived cells. Ascites and pleural effusion samples from cancer patients may be tested for expression of Her2/neu, using methods known to one skilled in the art. Samples from ovarian carcinoma patients may be processed by spinning down the ascites at 6370 g for 20 minutes at 4° C., lysing the red blood cells, and washing the cells with PBS. Once the expression of Her2/neu in tumor cells is determined, two samples, a median and a high expressor may be selected for s.c. inoculation to establish the xenograft tumor model. The isolated tumor cells will then be injected i.p. into mice to expand the cells. Approximately 10 mice may be injected i.p. and each mouse ascites further passaged into two mice to obtain ascites from a total of 20 mice which can be used to inject a group of 80 mice. Pleural effusion samples may be processed using a similar method as ascites. The Her2/neu+ tumor cells from pleural effusion samples may be injected into the upper right & left mammary pads of the mice.

In some embodiments, if the percentage of neoplastic cells in the ascites or pleural effusion samples is low compared to other cellular subsets, the neoplastic cells may be expanded in vitro. In other embodiments, tumor cells may be purified using CC49 antibody (anti-TAG-72)-coated magnetic beads as described previously, see, e.g., Barker et al. (2001) "*An Immunomagnetic-Based Method For The Purification Of Ovarian Cancer Cells From Patient-Derived Ascites*," Gynecol. Oncol. 82:57-63, which is incorporated herein by reference in its entirety. Briefly, magnetic beads coated with CC49 antibody can be used to separate the ovarian tumor cells that will be detached from the beads by an overnight incubation at 37° C. In some embodiments, if the tumor cells lack the TAG-72 antigen, negative depletion using a cocktail of antibodies, such as those provided by Stem Cell Technologies, Inc., Canada, may be used to enrich the tumor cells.

In other embodiments, other tumors markers besides Her2/neu may be used to separate tumor cells obtained from the ascites and pleural effusion samples from non-tumor cells. In the case of pleural effusion or breast tissue, it has been recently reported that CD44 (an adhesion molecule), B38.1(a breast/ovarian cancer-specific marker), CD24 (an adhesion molecule) may be used as markers, see, e.g., Al Hajj, et al. (2003) "*Prospective Identification Of Tumorigenic Breast Cancer Cells*," Proc. Natl. Acad. Sci. USA 100:3983-3988; which is incorporated herein by reference in its entirety. Once tumor cells are purified they may be injected s.c. into mice for expansion.

Preferably, immunohistochemistry and histochemistry is performed on ascites and pleural effusion of patients to analyze structural characteristics of the neoplasia. Such methods are known to one skilled in the art and encompassed within the invention. The markers that may be monitored include for example cytokeratin (to identify ovarian neoplastic and mesothelial cells from inflammatory and mesenchymal cells); calretinin (to separate mesothelial from Her2neu positive neoplastic cells); and CD45 (to separate inflammatory cells from the rest of the cell population in the samples).

Additional markers that may be followed include CD3 (T cells), CD20 (B cells), CD56 (NK cells), and CD14 (monocytes). It will be appreciated by one skilled in the art that the immunohistochemistry and histochemistry methods described supra, are analogously applied to any tumor cell for use in the methods of the invention. After s.c. inoculation of tumor cells, mice are followed for clinical and anatomical changes. As needed, mice may be necropsied to correlate total tumor burden with specific organ localization.

In a specific embodiment, tumors are established using carcinoma cell lines such as IGROV-1, OVCAR-8, SK-B, and OVCAR-3 cells and human ovarian carcinoma ascites and pleural effusion from breast cancer patients. The ascites preferably contain both the effectors and the tumor targets for the antibodies being tested. Human monocytes will be transferred as effectors.

The in vivo activity of the antibodies of the invention may also be tested in an animal model, e.g., Balb/c nude mice, injected with cells expressing Fc FcγRIIB, including but not limited to SK-BR-3 with ATCC accession number HTB-30 (see, e.g., Tremp et al. (1976) "*Human Breast Cancer In Culture*," Recent Results Cancer Res. 57:33-41); B-lymphocytes; cells derived from Burkitts lymphoma, e.g., Raji cells with ATCC accession number CCL-86 (see, e.g., Epstein et al. (1965) "*Characteristics And Mode Of Growth Of Tissue Culture Strain (EB1) Of Human Lymphoblasts From Burkitt's Lymphoma,*" J. Natl. Cancer Inst. 34: 231-240), Daudi cells with ATCC accession number CCL-213 (see, e.g., Klein et al. (1968) "*Surface IgM-Kappa Specificity On A Burkitt Lymphoma Cell In Vivo And In Derived Culture Lines*," Cancer Res. 28: 1300-1310); ovarian carcinoma cell lines, e.g., OVCAR-3 with ATCC accession number HTB-161 (see, e.g., Hamilton et al. (1983) "*Characterization Of A Human Ovarian Carcinoma Cell Line (NIH:OVCAR-3) With Androgen And Estrogen Receptors*," Cancer Res. 43(11):5379-5389), SK-OV-3, PA-1, CAOV3, OV-90, and IGROV-1 (available from the NCI repository; Benard et al. (1985) "*Characterization Of A Human Ovarian Adenocarcinoma Line, IGROV1, In Tissue Culture And In Nude Mice*," Cancer Research, 45:4970-4979; which is incorporated herein by reference in its entirety.

An exemplary assay for measuring the in vivo activity of the antibodies of the invention may comprise the following: Balb/c Nude female mice (Taconic, Md.) are injected at day 0 with cells expressing FcγRIIB such as $5 \times 10^6$ Daudi cells for example by the subcutaneous route. Mice (e.g., 5 mice per group) also receive i.p. injection of PBS (negative control), ch 4.4.20 (anti-FITC antibody) as a negative control, and as a positive control another therapeutic cancer antibody such as those disclosed herein, e.g., RITUXAN° (rituximab), (e.g., at 10 µg/g) or 10 µg/g ch2B6 once a week starting at day 0. Mice are observed, e.g., twice a week following injection, and tumor size (length and width) is determined using, for example, a caliper. Tumor weight in mg is estimated using the formula: (length×width$^2$)/2.

Preferably, the antibodies of the invention have an enhanced efficacy in decreasing tumor relative to a cancer therapeutic antibody when administered at the same dose, e.g., 10 µg/g, over a time period of at least 14 days, at least 21 days, at least 28 days, or at least 35 days. In most preferred embodiments, the antibodies of the invention reduce tumor size by at least 10 fold, at least 100 fold, at least 1000 fold relative to administration of a cancer therapeutic antibody at the same dose. In yet another preferred embodiment, the antibodies of the invention completely abolish the tumor.

X. Polynucleotides Encoding an Antibody

The present invention also includes polynucleotides that encode the antibodies of the invention (e.g., mouse monoclonal antibody produced from clone 2B6, 3H7, 1D5, 2E1, 2H9, 2D11, or 1F2 having ATCC accession numbers PTA-4591, PTA-4592, PTA-5958, PTA-5961, PTA-5962, PTA-5960, and PTA-5959, respectively), or other monoclonal antibodies produced by immunization methods of the invention, and humanized versions thereof, and methods for producing same.

The present invention encompasses the polynucleotide encoding the heavy chain of the 2B6 antibody, with ATCC accession number PTA-4591, as disclosed in SEQ ID NO:57. The present invention also encompasses the polynucleotide encoding the light chain of the 2B6 antibody with ATCC accession number PTA-4591, as disclosed in SEQ ID NO:25.

```
SEQ ID NO: 57:
caggtccaat tgcagcagcc tgtgactgag ctggtgaggc cggggcttc      50 agtgatgttg tcctgcaagg cttctgacta ccccttcacc aactactgga    100
tacactgggt aaagcagagg cctggacaag gcctggagtg gatcggagtg    150
attgatcctt ctgatactta tccaaattac aataaaaagt tcaagggcaa    200
ggccacattg actgtagtcg tatcctccag cacagcctac atgcagctca    250
gcagcctgac atctgacgat tctgcggtct attactgtgc aagaaacggt    300
gattccgatt attactctgg tatggactac tggggtcaag gaacctcagt    350
caccgtctcc tca                                              363

SEQ ID NO: 25
gacatcttgc tgactcagtc tccagccatc ctgtctgtga gtccaggaga     50
gagagtcagt ttttcctgca ggaccagtca gagcattggc acaaacatac    100
actggtatca gcaaagaaca aatggttttc caaggcttct cataaagaat    150
gtttctgagt ctatctctgg gatccctccc aggtttagtg gcagtggatc    200
agggacagat tttattctta gcatcaacag tgtggagtct gaagatattg    250
```

```
                       -continued
cagattatta ttgtcaacaa agtaatacct ggccgttcac gttcggaggg      300
gggaccaagc tggaaataaa a                                     321
```

The methods of the invention also encompass polynucleotides that hybridize under various stringency, e.g., high stringency, intermediate or lower stringency conditions, to polynucleotides that encode an antibody of the invention. The hybridization can be performed under various conditions of stringency. By way of example and not limitation, procedures using conditions of low stringency are as follows (see also Shilo et al. (1981) "*DNA Sequences Homologous To Vertebrate Oncogenes Are Conserved In Drosophila Melanogaster*," Proc. Natl. Acad. Sci. U.S.A 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20× $10^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations). By way of example and not limitation, procedures using conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. Selection of appropriate conditions for such stringencies is well known in the art (see e.g., Sambrook et al., 1989, MOLECULAR CLONING, A LABORATORY MANUAL, $2_{nd}$ Ed., Cold Spring Harbor Laboratory Press, New York; see also, Ausubel et al., eds., CURRENT PROTOCOLS IN MOLECULAR BIOLOGY series of laboratory technique manuals, Current Protocols, ©1994-1997 John Wiley and Sons, Inc.; see especially, Dyson, 1991, *"Immobilization of nucleic acids and hybridization analysis,"* In: ESSENTIAL MOLECULAR BIOLOGY: A PRACTICAL APPROACH, Vol. 2, T. A. Brown, ed., pp. 111-156, IRL Press at Oxford University Press, Oxford, UK).

The polynucleotides may be obtained, and the nucleotide sequence of the polynucleotides determined, by any method known in the art.

A polynucleotide encoding an antibody may be generated from nucleic acid from a suitable source (e.g., a cDNA library generated from, or nucleic acid, preferably poly A+ RNA, isolated from, any tissue or cells expressing the antibody, such as hybridoma cells selected to express an antibody of the invention, e.g., 2B6 or 3H7) by hybridization with Ig specific probes and/or PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, MOLECULAR CLONING, A LABORATORY MANUAL, $2^{nd}$ Ed., Cold Spring Harbor Laboratory, Cold Spring Harbor, N.Y. and Ausubel et al., eds., 1998, CURRENT PROTOCOLS IN MOLECULAR BIOLOGY, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs are inserted within framework regions using routine recombinant DNA techniques. The framework regions may be naturally occurring or consensus framework regions, and preferably human framework regions (see, e.g., Chothia et al. (1998) "*Structural Determinants In The Sequences Of Immunoglobulin Variable Domain*," J. Mol. Biol. 278: 457-479 for a listing of human framework regions). Preferably, the polynucleotide generated by the combination of the framework regions and CDRs encodes an antibody that specifically binds to FcγRIIB with greater affinity than said antibody binds FcγRIIA. Preferably, as discussed supra, one or more amino acid substitutions may be made within the framework regions, and, preferably, the amino acid substitutions improve binding of the antibodies of the invention to FcγRIIB. Representative plasmids, pMGx608 (pCI-neo [Invitrogen, Inc.] containing a humanized 2B6 heavy chain with human VH1-18 and JH6 germline sequences as frameworks, 2B6 mouse CDRs and human IgG1 Fc constant region) and pMGx611 (pCI-neo containing a humanized 2B6 light chain with human VK-A26 and JK4 as frameworks, human kappa as constant region, and mouse 2B6 light chain CDRs with $N_{50}{\rightarrow}Y$ and $V_{51}{\rightarrow}A$ in CDR2), having ATCC Accession numbers PTA-5963 and PTA-5964, respectively, were deposited under the provisions of the Budapest Treaty with the American Type Culture Collection (10801 University Blvd., Manassas, Va. 20110-2209) on May 7, 2004, respectively, and are incorporated herein by reference. The antibody formed by these heavy and light chains is designated h2B6YA.

In another embodiment, human libraries or any other libraries available in the art, can be screened by standard techniques known in the art, to clone the nucleic acids encoding the antibodies of the invention.

XI. Recombinant Expression of Antibodies

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. (See, for example, the techniques described in Sambrook et al., 1990, MOLECULAR CLONING, A LABORATORY MANUAL, 2$^{nd}$ Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibodies of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Cockett et al. (1990) "*High Level Expression Of Tissue Inhibitor Of Metalloproteinases In Chinese Hamster Ovary Cells Using Glutamine Synthetase Gene Amplification*," Biotechnology 8:662-667).

A variety of host-expression vector systems may be utilized to express the antibodies of the invention. Such host-expression systems represent vehicles by which the coding sequences of the antibodies may be produced and subsequently purified, but also represent cells which may, when transformed or transfected with the appropriate nucleotide coding sequences, express the antibodies of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells, lymphotic cells (see U.S. Pat. No. 5,807,715), Per C.6 cells (rat retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al. (1983) "*Easy Identification Of cDNA Clones*," EMBO J. 2:1791-1794), in which the antibody coding sequence may be ligated individually into the vector in frame with the lac Z coding region so that a fusion protein is produced; pIN vectors (Inouye et al. (1985) "*Up-Promoter Mutations In The Lpp Gene Of Escherichia coli*," Nucleic Acids Res. 13:3101-3110; Van Heeke et al. (1989) "*Expression Of Human Asparagine Synthetase In Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (e.g., see Logan et al. (1984) "*Adenovirus Tripartite Leader Sequence Enhances Translation Of mRNAs Late After Infection*," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "*Expression And Secretion Vectors For Yeast*," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al. (1977) "*Transfer Of Purified Herpes Virus Thymidine Kinase Gene To Cultured Mouse Cells*," Cell 11:223-232), hypoxanthine-guanine phosphoribosyltransferase (Szybalska et al. (1962) "*Genetics Of Human Cess Line. IV. DNA-Mediated Heritable Transformation Of A Biochemical Trait*," Proc. Natl. Acad. Sci. USA 48:2026-2034), and adenine phosphoribosyltransferase (Lowy et al. (1980) "*Isolation Of Transforming DNA: Cloning The Hamster aprt Gene*," Cell 22:817-823) genes can be employed in tk–, hgprt– or aprt– cells, respectively. Also, antimetabolite resistance can be used as the basis of selection for the following genes: dhfr, which confers resistance to methotrexate (Wigler et al. (1980) "*Transformation Of Mammalian Cells With An Amplifiable Dominant-Acting Gene*," Proc. Natl. Acad. Sci. USA 77:3567-3570; O'Hare et al. (1981) "*Transformation Of Mouse Fibroblasts To Methotrexate Resistance By A Recombinant Plasmid Expressing A Prokaryotic Dihydrofolate Reductase*," Proc. Natl. Acad. Sci. USA 78:1527-1531); gpt, which confers resistance to mycophenolic acid (Mulligan et al. (1981) "*Selection For Animal Cells That Express The Escherichia coli Gene Coding For Xanthine-Guanine Phosphoribosyltransferase*," Proc. Natl. Acad. Sci. USA 78:2072-2076); neo, which confers resistance to the aminoglycoside G-418 (Tachibana et al. (1991) "*Altered Reactivity Of Immunoglobulin Produced By Human-Human Hybridoma Cells Transfected By pSV2-Neo Gene*," Cytotechnology 6(3):219-226; Tolstoshev (1993) "*Gene Therapy, Concepts, Current Trials And Future Directions*," Ann. Rev. Pharmacol. Toxicol. 32:573-596; Mulligan (1993) "*The Basic Science Of Gene Therapy*," Science 260:926-932; and Morgan et al. (1993) "*Human gene therapy*," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Chapters 12 and 13, Dracopoli et al. (eds), 1994, Stockton Press, NY; and in CURRENT PROTOCOLS IN HUMAN GENETICS, John Wiley & Sons, NY.; Colbere-Garapin et al. (1981) "*A New Dominant Hybrid Selective Marker For Higher Eukaryotic Cells*," J. Mol. Biol. 150:1-14; and hygro, which confers resistance to hygromycin (Santerre et al. (1984) "*Expression Of Prokaryotic Genes For Hygromycin B And G418 Resistance As Dominant-Selection Markers In Mouse L Cells*," Gene 30: 147-156).

The expression levels of an antibody of the invention can be increased by vector amplification (for a review, see Bebbington and Hentschel, "*The Use Of Vectors Based On Gene Amplification For The Expression Of Cloned Genes In Mammalian Cells*," in DNA CLONING, Vol. 3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al. (1983) "*Expression And Amplification Of Engineered Mouse Dihydrofolate Reductase Minigenes*," Mol. Cell. Biol. 3:257-266).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "*Expression And Amplification Of Engineered Mouse Dihydrofolate Reductase Minigenes*," Nature 322:562-565; Kohler (1980) "*Immunoglobulin Chain Loss In Hybridoma Lines*," Proc. Natl. Acad. Sci. USA 77:2197-2199). The coding sequences for the heavy and light chains may comprise cDNA or genomic DNA.

Once the antibody of the invention has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

XII. Prophylactic and Therapeutic Methods

The present invention encompasses antibody-based therapies which involve administering one or more of the antibodies of the invention to an animal, preferably a mammal, and most preferably a human, for preventing, treating, or ameliorating symptoms associated with a disease, disorder, or infection, associated with aberrant levels or activity of FcγRIIB and/or treatable by altering immune function associated with FcγRIIB activity or enhancing cytotoxic activity of a second therapeutic antibody or enhancing efficacy of a vaccine composition or breaking tolerance to an antigen. In some embodiments, therapy by administration of one or more antibodies of the invention is combine with administration of one or more therapies such as, but not limited to, chemotherapies, radiation therapies, hormonal therapies, and/or biological therapies/immunotherapies.

Prophylactic and therapeutic compounds of the invention include, but are not limited to, proteinaceous molecules, including, but not limited to, peptides, polypeptides, proteins, including post-translationally modified proteins, antibodies, etc.; small molecules (less than 1000 daltons), inorganic or organic compounds; nucleic acid molecules including, but not limited to, double-stranded or single-stranded DNA, double-stranded or single-stranded RNA, as well as triple helix nucleic acid molecules. Prophylactic and therapeutic compounds can be derived from any known organism (including, but not limited to, animals, plants, bacteria, fungi, and protista, or viruses) or from a library of synthetic molecules.

Antibodies may be provided in pharmaceutically acceptable compositions as known in the art or as described herein. As detailed below, the antibodies of the invention can be used in methods of treating cancer (particularly to enhance passive immunotherapy or efficacy of a cancer vaccine), autoimmune disease, inflammatory disorders or allergies (e.g., to enhance efficacy of a vaccine for treatment of allergy).

FcγRIIB (CD32B) has been found to be expressed in the following tissue types: adipose, b-cell, bone, brain, cartilage, colon, endocrine, eye, fetus, gastrointestinal tract, genitourinary, germ cell, head and neck, kidney, lung, lymph node, lymphoreticular, mammary gland, muscle, nervous, ovary, pancreas, pancreatic islet, pituitary gland, placenta, retina, skin, soft tissue, synovium, and uterus (data collected from the Cancer Genome Anatomy Project of the National Cancer Institute). Thus, the antibodies of the invention can be used to agonize or antagonize the activity of FcγRIIB in any of these tissues. For example, FcγRIIB is expressed in the placenta and may play a role in transport of IgG to the fetus and also in scavenging immune complexes (Lyden et al. (2001) "*The Fc Receptor For IgG Expressed In The Villus Endothelium Of Human Placenta Is Fc Gamma RIIB2*," J. Immunol. 166: 3882-3889). In certain embodiments of the invention, an anti-FcγRIIB antibody can used as an abortifacient.

The present inventors have found that neutrophils surprisingly do not express significant levels of FCγRIIB. Accordingly, the invention provides methods and pharmaceutical compositions for use in these methods, comprising an amount of CD32-specific antibody that binds to and has activity on tumor cells or non-neutrophil cell types, such as macrophages, but does not detectably bind or have detectable activity on neutrophils. In certain embodiments, the antibodies of the invention can be used to deplete CD32B+ cells, such as macrophages or CD32B-expressing tumor cells.

Antibodies of the present invention that function as a prophylactic and or therapeutic agent of a disease, disorder, or infection can be administered to an animal, preferably a mammal, and most preferably a human, to treat, prevent or ameliorate one or more symptoms associated with the disease, disorder, or infection. Antibodies of the invention can be administered in combination with one or more other prophylactic and/or therapeutic agents useful in the treatment, prevention or management of a disease, disorder, or infection associated with aberrant levels or activity of FcγRIIB and/or treatable by altering immune function associated with FcγRIIB activity. In certain embodiments, one or more antibodies of the invention are administered to a mammal, preferably a human, concurrently with one or more other therapeutic agents useful for the treatment of cancer. The term "concurrently" is not limited to the administration of prophylactic or therapeutic agents at exactly the same time, but rather it is meant that antibodies of the invention and the other agent are administered to a subject in a sequence and within a time interval such that the antibodies of the invention can act together with the other agent to provide an increased benefit than if they were administered otherwise. For example, each prophylactic or therapeutic agent may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route.

In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the PHYSICIAN'S DESK REFERENCE ($56^{th}$ ed., 2002).

The antibodies of this invention may also be advantageously utilized in combination with other monoclonal or chimeric antibodies, Fc fusion proteins, or with lymphokines, cytokines or hematopoietic growth factors (such as, e.g., IL-2, IL-3, IL-4, IL-7, IL-10 and TGF-β), which enhance FcγRIIB, for example, serve to increase the number or activity of effector cells which interact with the antibodies and, increase immune response. In certain embodiments, a cytokine is conjugated to an anti-FcγRIIB antibody.

The antibodies of this invention may also be advantageously utilized in combination with one or more drugs used to treat a disease, disorder, or infection such as, for example anti-cancer agents, anti-inflammatory agents or anti-viral agents, e.g., as detailed below.

XIII. Cancers

Antibodies of the invention can be used alone or in combination with other therapeutic antibodies known in the art to prevent, inhibit or reduce the growth of primary tumors or metastasis of cancerous cells. In one embodiment, antibodies of the invention can be used in combination with antibodies used in cancer immunotherapy. The invention encompasses the use of the antibodies of the invention in combination with another therapeutic antibody to enhance the efficacy of such immunotherapy by increasing the potency of the therapeutic antibody's effector function, e.g., ADCC, CDC, phagocytosis, opsonization, etc. Although not intending to be bound by a particular mechanism of action antibodies of the invention block FcγRIIB, preferably on monocytes and macrophages and thus enhance the therapeutic benefits a clinical efficacy of tumor specific antibodies by, for example, enhancing clearance of the tumors mediated by activating FcγRs. Accordingly, the invention provides methods of preventing or treating cancer characterized by a cancer antigen, when administered in combination with another antibody that specifically binds a cancer antigen and is cytotoxic. The antibodies of the invention are useful for prevention or treatment of cancer, particularly in potentiating the cytotoxic activity of cancer antigen-specific therapeutic antibodies with cytotoxic activity to enhance tumor cell killing by the antibodies of the invention and/or enhancing for example, ADCC activity or CDC activity of the therapeutic antibodies. In certain embodiments of the invention, antibodies of the invention are administered with Fc fusion proteins. In a specific embodiment, an antibody of the invention, when administered alone or in combination with a cytotoxic therapeutic antibody, inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in absence of said antibody of the invention. In a preferred embodiment, antibodies of the invention in combination with a cytotoxic therapeutic antibody inhibit or reduce the growth of primary tumor or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said antibodies.

The transition from a normal to a malignant state is a multistep process involving genetic and epigenetic changes. In fact, numerous alterations occur in the cellular regulatory circuits that facilitate this progression which enables tumor cells to evade the commitment to terminal differentiation and quiescence that normally regulate tissue homeostasis. Certain genes have been implicated in invasiveness and metastatic potential of cancer cells such as CSF-1 (colony stimulating factor 1 or macrophage colony stimulating factor). Although not intending to be bound by a particular mechanism of action, CSF-1 may mediate tumor progression and metastasis by recruiting macrophages to the tumor site where they promote progression of tumor. It is believed that macrophages have a trophic role in mediating tumor progression and metastasis perhaps by the secretion of angiogenic factors, e.g., thymidine phosphorylase, vascular endothelial-derived growth factor; secretion of growth factors such as epidermal growth factor that could act as a paracrine factor on tumor cells, and thus promoting tumor cell migration and invasion into blood vessels. (See, e.g., Lin et al. (2001) "*Colony-Stimulating Factor* 1 *Promotes Progression Of Mammary Tumors To Malignancy*," J. Exp. Med. 193(6): 727-739; Lin et al. (2002) "*The Macrophage Growth Factor CSF-*1 *In Mammary Gland Development And Tumor Progression*," Journal of Mammary Gland Biology and Neoplasm 7(2): 147-162; Scholl et al. (1993) "*Is Colony-Stimulating Factor-*1 *A Key Mediator Of Breast Cancer Invasion And Metastasis?*" Molecular Carcinogenesis, 7: 207-211; Clynes et al. (2000) "*Inhibitory Fc Receptors Modulate In Vivo Cytoxicity Against Tumor Targets*," Nature Medicine, 6(4): 443-446; Fidler et al. (1985) "*Macrophages And Metastasis—A Biological Approach To Cancer Therapy*," Cancer Research, 45: 4714-4726).

The invention encompasses using the antibodies of the invention to block macrophage mediated tumor cell progression and metastasis. The antibodies of the invention are particularly useful in the treatment of solid tumors, where macrophage infiltration occurs. The antagonistic antibodies of the invention are particularly useful for controlling, e.g., reducing or eliminating, tumor cell metastasis, by reducing or eliminating the population of macrophages that are localized at the tumor site. In some embodiments, the antibodies of the invention are used alone to control tumor cell metastasis. Although not intending to be bound by a particular mechanism of action the antagonistic antibodies of the invention, when administered alone bind the inhibitory FcγRIIB on macrophages and effectively reduce the population of macrophages and thus restrict tumor cell progression. The antagonistic antibodies of the invention reduce, or preferably eliminate macrophages that are localized at the tumor site, since FcγRIIB is preferentially expressed on activated monocytes and macrophages including tumor-infiltrating macrophages. In some embodiments, the antibodies of the invention are used in the treatment of cancers that are characterized by the overexpression of CSF-1, including but not limited to breast, uterine, and ovarian cancers.

The invention further encompasses antibodies that effectively deplete or eliminate immune cells other than macrophages that express FcγRIIB, e.g., dendritic cells and B-cells. Effective depletion or elimination of immune cells using the antibodies of the invention may range from a reduction in population of the immune cells by 50%, 60%, 70%, 80%, preferably 90%, and most preferably 99%. Thus, the antibodies of the invention have enhanced therapeutic efficacy either alone or in combination with a second antibody, e.g., a therapeutic antibody such as anti-tumor antibodies, anti-viral antibodies, and anti-microbial antibodies. In some embodiments, the therapeutic antibodies have specificity for a cancer cell or an inflammatory cell. In other embodiments, the second antibody binds a normal cell. Although not intending to be bound by a particular mechanism of action, when the antibodies of the invention are used alone to deplete FcγRIIB-expressing immune cells, the population of cells is redistributed so that effectively the cells that are remaining have the activating Fc receptors and thus the suppression by FcγRIIB is alleviated. When used in combination with a second antibody, e.g., a therapeutic antibody the efficacy of the second antibody is enhanced by increasing the Fc-mediated effector function of the antibody.

The antibodies and fragments thereof of the invention and methods of treatment are believed to be effective for the treatment of both liquid and solid cancers. By liquid cancers it is meant cancers of the bone marrow, such as leukemias. Solid cancers generally refer to cancers of organs and/or tissues. Cancers and related disorders that can be treated or prevented by methods and compositions of the present invention include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma, gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, superficial spreading melanoma, nodular melanoma, lentigo malignant melanoma, acral lentiginous melanoma; kidney cancers including but not limited to, renal cell cancer, adenocarcinoma, hypemephroma, fibrosarcoma, transitional cell cancer (renal pelvis and/or uterer); Wilms' tumor; bladder cancers including but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, MEDICINE, $2^{nd}$ Ed., J.B. Lippincott Co., Philadelphia; and Murphy et al., 1997, INFORMED DECISIONS: THE COMPLETE BOOK OF CANCER DIAGNOSIS, TREATMENT AND RECOVERY, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

Cancers associated with the cancer antigens may be treated or prevented by administration of the antibodies of the invention in combination with an antibody that binds the cancer antigen and is cytotoxic. In one particular embodiment, the antibodies of the invention enhance the antibody mediated cytotoxic effect of the antibody directed at the particular cancer antigen. For example, but not by way of limitation, cancers associated with the following cancer antigen may be treated or prevented by the methods and compositions of the invention. KS 1/4 pan-carcinoma antigen (Perez et al. (1989) "*Isolation And Characterization Of A cDNA Encoding The Ks1/4 Epithelial Carcinoma Marker*," J. Immunol. 142:3662 3667; Möller et al. (1991) "*Bispecific-Monoclonal-Antibody-Directed Lysis Of Ovarian Carcinoma Cells By Activated Human T Lymphocytes*," Cancer Immunol. Immunother. 33(4):210-216), ovarian carcinoma antigen (CA125) (Yu et al. (1991) "*Coexpression Of Different Antigenic Markers On Moieties That Bear CA 125 Determinants*," Cancer Res. 51(2):468 475), prostatic acid phosphate (Tailor et al. (1990) "*Nucleotide Sequence Of Human Prostatic Acid Phosphatase Determined From A Full-Length cDNA Clone*," Nucl. Acids Res. 18(16):4928), prostate specific antigen (Henttu et al. (1989) "*cDNA Coding For The Entire Human Prostate Specific Antigen Shows High Homologies To The Human Tissue Kallikrein Genes*," Biochem. Biophys. Res. Comm. 10(2): 903 910; Israeli et al. (1993) "*Molecular Cloning Of A Complementary DNA Encoding A Prostate-Specific Membrane Antigen*," Cancer Res. 53:227 230), melanoma-associated antigen p97 (Estin et al. (1989) "*Transfected Mouse Melanoma Lines That Express Various Levels Of Human Melanoma-Associated Antigen p97*," J. Natl. Cancer Instit. 81(6):445 454), melanoma antigen gp75 (Vijayasardahl et al. (1990) "*The Melanoma Antigen Gp75 Is The Human Homologue Of The Mouse B (Brown) Locus Gene Product*," J. Exp. Med. 171(4):1375 1380), high molecular weight melanoma antigen (HMW-MAA) (Natali et al. (1987) "*Immunohistochemical Detection Of Antigen In Human Primary And Metastatic Melanomas By The Monoclonal Antibody 140.240*

And Its Possible Prognostic Significance," Cancer 59:55 63; Mittelman et al. (1990) "Active Specific Immunotherapy In Patients With Melanoma. A Clinical Trial With Mouse Anti-idiotypic Monoclonal Antibodies Elicited With Syngeneic Anti-High-Molecular-Weight-Melanoma-Associated Antigen Monoclonal Antibodies," J. Clin. Invest. 86:2136-2144), prostate specific membrane antigen, carcinoembryonic antigen (CEA) (Foon et al. (1995) "Immune Response To The Carcinoembryonic Antigen In Patients Treated With An Anti-Idiotype Antibody Vaccine," J. Clin. Invest. 96(1):334-42), polymorphic epithelial mucin antigen, human milk fat globule antigen, Colorectal tumor-associated antigens such as: CEA, TAG-72 (Yokota et al. (1992) "Rapid Tumor Penetration Of A Single-Chain Fv And Comparison With Other Immunoglobulin Forms," Cancer Res. 52:3402-3408), CO17-1A (Ragnhammar et al. (1993) "Effect Of Monoclonal Antibody 17-1A And GM-CSF In Patients With Advanced Colorectal Carcinoma—Long-Lasting, Complete Remissions Can Be Induced," Int. J. Cancer 53:751-758); GICA 19-9 (Herlyn et al. (1982) "Monoclonal Antibody Detection Of A Circulating Tumor-Associated Antigen. I. Presence Of Antigen In Sera Of Patients With Colorectal, Gastric, And Pancreatic Carcinoma," J. Clin. Immunol. 2:135-140), CTA-1 and LEA, Burkitt's lymphoma antigen-38.13, CD19 (Ghetie et al. (1994) "Anti-CD19 Inhibits The Growth Of Human B-Cell Tumor Lines In Vitro And Of Daudi Cells In SCID Mice By Inducing Cell Cycle Arrest," Blood 83:1329-1336), human B-lymphoma antigen-CD20 (Reff et al. (1994) "Depletion Of B Cells In Vivo By A Chimeric Mouse Human Monoclonal Antibody To CD20," Blood 83:435-445), CD33 (Sgouros et al. (1993). "Modeling And Dosimetry Of Monoclonal Antibody M195 (Anti-CD33) In Acute Myelogenous Leukemia," J. Nucl. Med. 34:422-430), melanoma specific antigens such as ganglioside GD2 (Saleh et al. (1993) "Generation Of A Human Anti-Idiotypic Antibody That Mimics The GD2 Antigen," J. Immunol., 151, 3390-3398), ganglioside GD3 (Shiara et al. (1993) "A Mouse/Human Chimeric Anti-(Ganglioside GD3) Antibody With Enhanced Antitumor Activities," Cancer Immunol. Immunother. 36:373-380), ganglioside GM2 (Livingston et al. (1994) "Improved Survival In Stage III Melanoma Patients With GM2 Antibodies: A Randomized Trial Of Adjuvant Vaccination With GM2 Ganglioside," J. Clin. Oncol. 12:1036-1044), ganglioside GM3 (Hoon et al. (1993) "Molecular Cloning Of A Human Monoclonal Antibody Reactive To Ganglioside GM3 Antigen On Human Cancers," Cancer Res. 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellström et al. (1985) "Monoclonal Antibodies To Cell Surface Antigens Shared By Chemically Induced Mouse Bladder Carcinomas," Cancer. Res. 45:2210-2188), differentiation antigen such as human lung carcinoma antigen L6, L20 (Hellström et al. (1986) "Monoclonal Mouse Antibodies Raised Against Human Lung Carcinoma," Cancer Res. 46:3917-3923), antigens of fibrosarcoma, human leukemia T cell antigen-Gp37 (Bhattacharya-Chatterjee et al. (1988) "Idiotype Vaccines Against Human T Cell Leukemia. II. Generation And Characterization Of A Monoclonal Idiotype Cascade (Ab1, Ab2, and Ab3)," J. Immunol. 141(4):1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al. (1992) "Cell Membrane-Associated Mucins And Their Adhesion-Modulating Property," Trends in Biochem. Sci. 17:359-363), malignant human lymphocyte antigen-APO-1 (Trauth et al. (1989) "Monoclonal Antibody-Mediated Tumor Regression By Induction Of Apoptosis," Science 245:301-304), differentiation antigen (Feizi (1985) "Demonstration By Monoclonal Antibodies That Carbohydrate Structures Of Glycoproteins And Glycolipids Are Onco-Developmental Antigens," Nature 314:53-57) such as I antigen found in fetal erthrocytes and primary endoderm, I(Ma) found in gastric adencarcinomas, M18 and M39 found in breast epithelium, SSEA-1 found in myeloid cells, VEP8, VEP9, My1, VIM-D5, and $D_1$56-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma, CO-514 (blood group Le$^a$) found in adenocarcinoma, NS-10 found in adenocarcinomas, CO-43 (blood group Le$^b$), G49, EGF receptor, (blood group ALe$^b$/Le$^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, M1:22:25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson (1998) "Cutaneous T-Cell Lymphoma: A Model For Selective Immunotherapy," Cancer J Sci Am. 4:62-71).

The antibodies of the invention can be used in combination with any therapeutic cancer antibodies known in the art to enhance the efficacy of treatment. For example, the antibodies of the invention can be used with any of the antibodies in Table 7, that have demonstrated therapeutic utility in cancer treatment. The antibodies of the invention enhance the efficacy of treatment of the therapeutic cancer antibodies by enhancing at least one antibody-mediated effector function of said therapeutic cancer antibodies. In one particular embodiment, the antibodies enhance the efficacy of treatment by enhancing the complement dependent cascade of said therapeutic cancer antibodies. In another embodiment of the invention, the antibodies of the invention enhance the efficacy of treatment by enhancing the phagocytosis and opsonization of the targeted tumor cells. In another embodiment of the invention, the antibodies of the invention enhance the efficacy of treatment by enhancing antibody-dependent cell-mediated cytotoxicity ("ADCC") in destruction of the targeted tumor cells.

Antibodies of the invention can also be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of cancer (See also Warren et al. (2002) "Synergism Between Cytosine-Guanine Oligodeoxynucleotides And Monoclonal Antibody In The Treatment Of Lymphoma," Semin. Oncol., 29(1 Suppl 2):93-97; Warren et al. (2000) "CpG Oligodeoxynucleotides Enhance Monoclonal Antibody Therapy Of A Murine Lymphoma," Clin. Lymphoma, 1(1):57-61, which are incorporated herein by reference).

Antibodies of the invention can be used in combination with a therapeutic antibody that does not mediate its therapeutic effect through cell killing to potentiate the antibody's therapeutic activity. In a specific embodiment, the invention encompasses use of the antibodies of the invention in combination with a therapeutic apoptosis inducing antibody with agonistic activity, e.g., an anti-Fas antibody. Anti-Fas antibodies are known in the art and include for example, Jo2 (Ogasawara et al. (1993) "*Lethal Effect Of The Anti-Fas Antibody In Mice*," Nature 364: 806-809) and HFE7 (Ichikawa et al. (2000) "*A Novel Murine Anti-Human Fas mAb Which Mitigates Lymphadenopathy Without Hepatotoxicity*," Int. Immunol. 12: 555-562). Although not intending to be bound by a particular mechanisms of action, FcγRIIB has been implicated in promoting anti-Fas mediated apoptosis, (see, e.g., Xu et al. (2003) "*FcγRs Modulate Cytotoxicity Of Anti-Fas Antibodies: Implications For Agonistic Antibody-Based Therapeutics*," J. Immunol. 171: 562-568). In fact, the extracellular domain of FcγRIIB may serve as a cross-linking agent for Fas receptors, leading to a functional complex and promoting Fas dependent apoptosis. In some embodiments, the antibodies of the invention block the interaction of anti-Fas antibodies and FcγRIIB, leading to a reduction in Fas-mediated apoptotic activity. Antibodies of the invention that result in a reduction in Fas-mediated apoptotic activity are particularly useful in combination with anti-Fas antibodies that have undesirable side effects, e.g., hepatotoxicity. In other embodiments, the antibodies of the invention enhance the interaction of anti-Fas antibodies and FcγRIIB, leading to an enhancement of Fas-mediated apoptotic activity. Combination of the antibodies of the invention with therapeutic apoptosis inducing antibodies with agonisitc activity have an enhanced therapeutic efficacy.

Therapeutic apoptosis inducing antibodies used in the methods of the invention may be specific for any death receptor known in the art for the modulation of apoptotic pathway, e.g., TNFR receptor family.

The invention provides a method of treating diseases with impaired apoptotic mediated signaling, e.g., cancer, autoimmune disease. In a specific embodiment, the invention encompasses a method of treating a disease with deficient Fas-mediated apoptosis, said method comprising administering an antibody of the invention in combination with an anti-Fas antibody.

In some embodiments, the agonistic antibodies of the invention are particularly useful for the treatment of tumors of non-hematopoietic origin, including tumors of melanoma cells. Although not intending to be bound by a particular mechanism of action, the efficacy of the agonistic antibodies of the invention is due, in part, to activation of FcγRIIB inhibitory pathway, as tumors of non-hematopoietic origin, including tumors of melanoma cells express FcγRIIB. Recent experiments have in fact shown that expression of FcγRIIB in melanoma cells modulates tumor growth by direct interaction with anti-tumor antibodies (e.g., by binding the Fc region of the anti-tumor antibodies) in an intracytoplasmic-dependent manner (Cassard et al. (2002) "*Modulation Of Tumor Growth By Inhibitory Fc(Gamma) Receptor Expressed By Human Melanoma Cells*," J. Clin. Invest. 110(10): 1549-1557).

In some embodiments, the invention encompasses use of the antibodies of the invention in combination with therapeutic antibodies that immunospecifically bind to tumor antigens that are not expressed on the tumor cells themselves, but rather on the surrounding reactive and tumor supporting, non-malignant cells comprising the tumor stroma. The tumor stroma comprises endothelial cells forming new blood vessels and stromal fibroblasts surrounding the tumor vasculature. In a specific embodiment, an antibody of the invention is used in combination with an antibody that immunospecifically binds a tumor antigen on an endothelial cell. In a preferred embodiment, an antibody of the invention is used in combination with an antibody that immunospecifically binds a tumor antigen on a fibroblast cell, e.g., fibroblast activation protein (FAP). FAP is a 95 KDa homodimeric type TI glycoprotein which is highly expressed in stromal fibroblasts of many solid tumors, including, but not limited to lung, breast, and colorectal carcinomas. (See, e.g., Scanlan et al. (1994) "*Molecular Cloning Of Fibroblast Activation Protein Alpha, A Member Of The Serine Protease Family Selectively Expressed In Stromal Fibroblasts Of Epithelial Cancers*," Proc. Natl. Acad. USA, 91: 5657-5661; Park et al. (1999) "*Fibroblast Activation Protein, A Dual Specificity Serine Protease Expressed In Reactive Human Tumor Stromal Fibroblasts*," J. Biol. Chem., 274: 36505-36512; Rettig et al. (1988) "*Cell-Surface Glycoproteins Of Human Sarcomas: Differential Expression In Normal And Malignant Tissues And Cultured Cells*," Proc. Natl. Acad. Sci. USA 85: 3110-3114; Garin-Chesa et al. (1990) "*Cell Surface Glycoprotein Of Reactive Stromal Fibroblasts As A Potential Antibody Target In Human Epithelial Cancers*," Proc. Natl. Acad. Sci. USA 87: 7235-7239). Antibodies that immunospecifically bind FAP are known in the art and encompassed within the invention, (see, e.g., Wuest et al. (2001) "*Construction Of A Bispecific Single Chain Antibody For Recruitment Of Cytotoxic T Cells To The Tumour Stroma Associated Antigen Fibroblast Activation Protein*," Journal of Biotechnology, 159-168; Mersmann et al. (2001) "Human Antibody Derivatives Against The Fibroblast Activation Protein For Tumor Stroma Targeting Of Carcinomas," Int. J. Cancer, 92: 240-248; U.S. Pat. No. 6,455,677; all of which are incorporated herein in by reference in their entireties).

Recently, IgEs have been implicated as mediators of tumor growth and, in fact, IgE-targeted immediate hypersensitivity and allergic inflammation reactions have been proposed as possible natural mechanisms involved in anti-tumor responses (For a review see, e.g., Vena et al. (1992) "*Allergy-Related Diseases And Cancer: An Inverse Association*," Am. Journal of Epidemiol. 122: 66-74; Eriksson et al. (1995) "*A Prospective Study Of Cancer Incidence In A Cohort Examined For Allergy*," Allergy 50: 718-722). In fact, a recent study has shown loading tumor cells with IgEs reduces tumor growth, leading in some instances to tumor rejection. According to the study, IgE loaded tumor cells not only possess a therapeutic potential but also confer long term antitumor immunity, including activation of innate immunity effector mechanism and T-cell mediated adaptive immune response, (see Reali et al. (2001) "*IgEs Targeted On Tumor Cells: Therapeutic Activity And Potential In The Design Of Tumor Vaccines*," Cancer Res. 61: 5517-5522; which is incorporated herein by reference in its entirety). The antagonistic antibodies of the invention may be used in the treatment and/or prevention of cancer in combination with administration of IgEs in order to enhance the efficacy of IgE-mediated cancer therapy. Although not intending to be bound by a particular mechanism of action the antibodies of the invention enhance the therapeutic efficacy of IgE treatment of tumors, by blocking the inhibitory pathway. The antagonistic antibodies of the invention may enhance the therapeutic efficacy of IgE mediated cancer therapy by:

(i.) enhancing the delay in tumor growth;
(ii.) enhancing the decrease in the rate of tumor progression;
(iii.) enhancing tumor rejection; or
(iv.) enhancing protective immune relative to treatment of cancer with IgE alone.

Cancer therapies and their dosages, routes of administration and recommended usage are known in the art and have

A. B Cell Malignancies

The present invention encompasses therapies which involve administering an anti-FcγRIIB antibody, to an animal, preferably a mammal, and most preferably a human, to prevent, treat, manage or ameliorate a B-cell malignancy, or one or more symptoms thereof. These therapies are an enhancement over current therapies. In certain cases, patients who are refractory to current therapies can be treated with the methods of the invention. In some embodiments, therapy by administration of one or more antibodies of the invention is combined with administration of one or more therapies such as, but not limited to, chemotherapies, radiation therapies, hormonal therapies, and/or biological therapies/immunotherapies.

The present invention encompasses treatment protocols that provide better prophylactic and therapeutic profiles than current single agent therapies or combination therapies for a B-cell malignancy, or one or more symptoms thereof. The invention provides FcγRIIB antibody based therapies for the prevention, treatment, management, or amelioration of a B-cell malignancy, or one or more symptoms thereof. In particular, the invention provides prophylactic and therapeutic protocols for the prevention, treatment, management, or amelioration of a B-cell malignancy, or one or more symptoms thereof, comprising the administration of a FcγRIIB-specific antibody, an analog, derivative or an antigen-fragment thereof to a subject in need thereof.

The agonistic antibodies of the invention are useful for treating or preventing any B cell malignancies, particularly non-Hodgkin's lymphoma and chronic lymphocytic leukemia. Other B-cell malignancies include small lymphocytic lymphoma, Burkitt's lymphoma, mantle cell lymphomas diffuse small cleaved cell lymphomas, most follicular lymphomas and some diffuse large B cell lymphomas (DLBCL). FcγRIIB, is a target for deregulation by chromosomal translocation in malignant lymphoma, particularly in B-cell non-Hodgkin's lymphoma (See Callanan et al. (2000) "*The IgG Fc Receptor, FcgammaRIIB, Is A Target For Deregulation By Chromosomal Translocation In Malignant Lymphoma*," Proc. Natl. Acad. Sci. U.S.A., 97(1):309-314). Thus, the antibodies of the invention are useful for treating or preventing any chronic lymphocytic leukemia of the B cell lineage. Chronic lymphocytic leukemia of the B cell lineage are reviewed by Freedman (See Freedman (1990) "*Immunobiology Of Chronic Lymphocytic Leukemia*," Hemtaol. Oncol. Clin. North Am. 4:405-429). Although not intending to be bound by any mechanism of action, the agonistic antibodies of the invention inhibit or prevent B cell malignancies inhibiting B cell proliferation and/or activation. The invention also encompasses the use of the agonistic antibodies of the invention in combination with other therapies known (e.g., chemotherapy and radiotherapy) in the art for the prevention and/or treatment of B cell malignancies. The invention also encompasses the use of the agonistic antibodies of the invention in combination with other antibodies known in the art for the treatment and or prevention of B-cell malignancies. For example, the agonistic antibodies of the invention can be used in combination with the anti-C22 or anti-CD19 antibodies disclosed by Goldenberg et al. (U.S. Pat. No. 6,306,393), anti-CD20 antibodies, anti-CD33 antibodies, or anti-CD52 antibodies.

Antibodies of the invention can also be used in combination with for example but not by way of limitation, ONCOSCINT® (111In-satumomab pantedide) (target: CEA), VERLUMA® (99Tc-nofetumomab merpentan) (target: GP40), PROSTASCINT® (capromab pentedide) (target: PSMA), CEA-SCAN® (arcitumomab) (target: CEA), RITUXAN® (rituximab) (target: CD20), HERCEPTIN® (trastuzumab) (target: HER-2), CAMPATH® (alemtuzumab (target: CD52), MYLOTARG® (gemtuzumab ozogamicin) (target: CD33), and ZEVALIN® (ibritumomab tiuxetan) (target: CD20).

B. Autoimmune Disease and Inflammatory Diseases

The agonistic antibodies of the invention may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically effective amount of the antibodies or fragments thereof of the invention. The invention also provides methods for preventing, treating, or managing one or more symptoms associated with an inflammatory disorder in a subject further comprising, administering to said subject a therapeutically effective amount of one or more anti-inflammatory agents. The invention also provides methods for preventing, treating, or managing one or more symptoms associated with an autoimmune disease further comprising, administering to said subject a therapeutically effective amount of one or more immunomodulatory agents.

The antibodies of the invention can also be used in combination with any of the antibodies known in the art for the treatment and/or prevention of autoimmune disease or inflammatory disease. A non-limiting example of the antibodies or Fc fusion proteins that are used for the treatment or prevention of inflammatory disorders is presented in Table 6A, and a non-limiting example of the antibodies or Fc fusion proteins that are used for the treatment or prevention of autoimmune disorder is presented in Table 6B. The antibodies of the invention can for example, enhance the efficacy of treatment of the therapeutic antibodies or Fc fusion proteins presented in Tables 6A and 6B. For example, but not by way of limitation, the antibodies of the invention can enhance the immune response in the subject being treated with any of the antibodies or Fc fusion proteins in Tables 6A or 6B.

Antibodies of the invention can also be used in combination with, for example, but not by way of limitation, ORTHOCLONE OKT3® (muromonab), REOPRO® (abciximab), ZENAPEX® (declizumab), SIMULEC® (basiliximab), RITUXAN® (rituximab), SYNAGIS® (palivizumab), and REMICADE® (infliximab).

Antibodies of the invention can also be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of autoimmune or inflammatory disorders (Weeratna et al. (2001) "*CpG ODN Can Re-Direct The Th Bias Of Established Th2 Immune Responses In Adult And Young Mice*," FEMS Immunol Med Microbiol., 32(1):65-71, which is incorporated herein by reference).

Examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In certain embodiments of the invention, the antibodies of the invention may be used to treat an autoimmune disease that is more prevalent in one sex. For example, the prevalence of Graves' disease in women has been associated with expression of FcγRIIB2 (see Estienne et al. (2002) "*Androgen-Dependent Expression Of FcgammaRIIB2 By Thyrocytes From Patients With Autoimmune Graves' Disease: A Possible Molecular Clue For Sex Dependence Of Autoimmune Disease,*" FASEB J. 16:1087-1092).

Antibodies of the invention can also be used to reduce the inflammation experienced by animals, particularly mammals, with inflammatory disorders. In a specific embodiment, an antibody reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in the not administered said antibody. In another embodiment, a combination of antibodies reduce the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said antibodies.

TABLE 6A

Antibodies for Inflammatory Diseases and Autoimmune Diseases That Can Be Used In Combination With The Antibodies Of The Invention

| Antibody Name | Target Antigen | Product Type | Isotype | Indication |
| --- | --- | --- | --- | --- |
| 5G1.1 | Complement (C5) | Humanised | IgG | Rheumatoid Arthritis |
| 5G1.1 | Complement (C5) | Humanised | IgG | SLE |
| 5G1.1 | Complement (C5) | Humanised | IgG | Nephritis |
| 5G1.1-SC | Complement (C5) | Humanised | ScFv | Cardiopulmano Bypass |
| 5G1.1-SC | Complement (C5) | Humanised | ScFv | Myocardial Infarction |
| 5G1.1-SC | Complement (C5) | Humanised | ScFv | Angioplasty |
| ABX-CBL | CBL | Human | | GvHD |
| ABX-CBL | CD147 | Murine | IgG | Allograft rejection |
| ABX-IL8 | IL-8 | Human | IgG2 | Psoriasis |
| Antegren | VLA-4 | Humanised | IgG | Multiple Sclerosis |
| Anti-CD11a | CD11a | Humanised | IgG1 | Psoriasis |
| Anti-CD18 | CD18 | Humanised | Fab'2 | Myocardial infarction |
| Anti-LFA1 | CD18 | Murine | Fab'2 | Allograft rejection |
| Antova | CD40L | Humanised | IgG | Allograft rejection |
| Antova | CD40L | Humanised | IgG | SLE |
| BTI-322 | CD2 | Rat | IgG | GvHD, Psoriasis |
| CDP571 | TNF-alpha | Humanised | IgG4 | Crohn's |
| CDP571 | TNF-alpha | Humanised | IgG4 | Rheumatoid Arthritis |
| CDP850 | E-selectin | Humanised | | Psoriasis |
| Corsevin M | Fact VII | Chimeric | | Anticoagulant |
| D2E7 | TNF-alpha | Human | | Rheumatoid Arthritis |
| Hu23F2G | CD11/18 | Humanised | | Multiple Sclerosis |
| Hu23F2G | CD11/18 | Humanised | IgG | Stroke |
| IC14 | CD14 | | | Toxic shock |
| ICM3 | ICAM-3 | Humanised | | Psoriasis |
| IDEC-114 | CD80 | Primatised | | Psoriasis |
| IDEC-131 | CD40L | Humanised | | SLE |
| IDEC-131 | CD40L | Humanised | | Multiple Sclerosis |
| IDEC-151 | CD4 | Primatised | IgG1 | Rheumatoid Arthritis |
| IDEC-152 | CD23 | Primatised | | Asthma/Allergy |
| Infliximab | TNF-alpha | Chimeric | IgG1 | Rheumatoid Arthritis |

TABLE 6A-continued

Antibodies for Inflammatory Diseases and Autoimmune Diseases That Can Be Used In Combination With The Antibodies Of The Invention

| Antibody Name | Target Antigen | Product Type | Isotype | Indication |
|---|---|---|---|---|
| Infliximab | TNF-alpha | Chimeric | IgG1 | Crohn's |
| LDP-01 | beta2-integrin | Humanised | IgG | Stroke |
| LDP-01 | beta2-integrin | Humanised | IgG | Allograft rejection |
| LDP-02 | alpha4beta7 | Humanised | | Ulcerative Colitis |
| MAK-195F | TNF alpha | Murine | Fab'2 | Toxic shock |
| MDX-33 | CD64 (FcR) | Human | | Autoimmune haematogical disorders |
| MDX-CD4 | CD4 | Human | IgG | Rheumatoid Arthritis |
| MEDI-507 | CD2 | Humanised | | Psoriasis |
| MEDI-507 | CD2 | Humanised | | GvHD |
| OKT4A | CD4 | Humanised | IgG | Allograft rejection |
| OrthoClone OKT4A | CD4 | Humanised | IgG | Autoimmune disease |
| Orthoclone/ anti-CD3 OKT3 | CD3 | Murine | mIgG2a | Allograft rejection |
| RepPro/ Abciximab | gpIIbIIIa | Chimeric | Fab | Complications of coronary angioplasty |
| rhuMab-E25 | IgE | Humanised | IgG1 | Asthma/Allergy |
| SB-240563 | IL5 | Humanised | | Asthma/Allergy |
| SB-240683 | IL-4 | Humanised | | Asthma/Allergy |
| SCH55700 | IL-5 | Humanised | | Asthma/Allergy |
| Simulect | CD25 | Chimeric | IgG1 | Allograft rejection |
| SMART a-CD3 | CD3 | Humanised | | Autoimmune disease |
| SMART a-CD3 | CD3 | Humanised | | Allograft rejection |
| SMART a-CD3 | CD3 | Humanised | IgG | Psoriasis |
| Zenapax | CD25 | Humanised | IgG1 | Allograft rejection |

TABLE 6B

Antibodies for Autoimmune Disorders

| Antibody | Indication | Target Antigen |
|---|---|---|
| ABX-RB2 | | antibody to CBL antigen on T cells, B cells and NK cells fully human antibody from the Xenomouse |
| IL1-ra | rheumatoid arthritis | recombinant anti-inflammatory protein |
| sTNF-RI | chronic inflammatory disease rheumatoid arthritis | soluble tumor necrosis factor a - receptor type I blocks TNF action |
| 5c8 (Anti CD-40 ligand antibody) | Phase II trials were halted in Oct. 99 examine "adverse events" | CD-40 |
| IDEC 131 | systemic lupus erythyematous (SLE) | anti CD40 humanized |
| IDEC 151 | rheumatoid arthritis | primatized; anti-CD4 |
| IDEC 152 | asthma | primatized; anti-CD23 |
| IDEC 114 | psoriasis | primatized anti-CD80 |
| MEDI-507 | rheumatoid arthritis; multiple sclerosis Crohn's disease psoriasis | anti-CD2 |
| LDP-02 (anti-b7 mAb) | inflammatory bowel disease Chron's disease ulcerative colitis | a4b7 integrin receptor on white blood cells (leukocytes) |
| SMART Anti-Gamma Interferon antibody | autoimmune disorders | Anti-Gamma Interferon |
| Verteportin | rheumatoid arthritis | |
| Thalomid (thalidomide) | leprosy - approved for market Chron's disease rheumatoid arthritis | inhibitor of tumor necrosis factor alpha (TNF alpha) |
| SelCIDs (selective cytokine inhibitory drugs) | | highly specific inhibitors of phosphodiesterase type 4 enzyme (PDE-4) increases levels of cAMP (cyclic adenosine monophosphate) |

TABLE 6B-continued

Antibodies for Autoimmune Disorders

| Antibody | Indication | Target Antigen |
|---|---|---|
| | | activates protein kinase A (PKA) blocks transcription factor NK-kB prevents transcription of TNF-a gene decreases production of TNF-α |
| IMiDs (immunomodulatory drugs) | general autoimmune disorders | structural analogues of thalidomideinhibit TNF-a |
| MDX-33 | blood disorders caused by autoimmune reactions Idiopathic Thrombocytopenia Purpurea (ITP) autoimmune hemolytic anemia | monoclonal antibody against FcRI receptors |
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response regulates cytokines) |
| VX-745 | specific to inflammation involved in chemical signaling of immune response onset and progression of inflammation | inhibitor of P38MAP kinase mitogen activated protein kinase |
| Enbrel (etanercept) | | targets TNF (tumor necrosis factor) |
| IL-8 | | fully human MAB against IL-8 (interleukin 8) (blocks IL-8 blocks inflammatory response) |
| 5G1.1 | rheumatoid arthritis pemphigoid (dangerous skin rash) psoriasis lupus | a C5 complement inhibitor |
| Apogen MP4 | | recombinant antigen selectively destroys disease associated T-cells induces apoptosis T-cells eliminated by programmed cell death no longer attack body's own cells specific apogens target specific T-cells |

C. Allergy

The invention provides methods for treating or preventing an IgE-mediated and or FcεRI-mediated allergic disorder in a subject in need thereof, comprising administering to said subject a therapeutically effective amount of the agonistic antibodies or fragments thereof of the invention. Although not intending to be bound by a particular mechanism of action, antibodies of the invention are useful in inhibiting FcεRI-induced mast cell activation, which contributes to acute and late phase allergic responses (Metcalfe et al. (1997) "*Mast Cells*," Physiol. Rev. 77:1033-1079). Preferably, the agonistic antibodies of the invention have enhanced therapeutic efficacy and/or reduced side effects in comparison with the conventional methods used in the art for the treatment and/or prevention of IgE mediated allergic disorders. Conventional methods for the treatment and/or prevention of IgE mediated allergic disorders include, but are not limited to, anti-inflammatory drugs (e.g., oral and inhaled corticosteroids for asthma), antihistamines (e.g., for allergic rhinitis and atopic dermatitis), cysteinyl leukotrienes (e.g., for the treatment of asthma); anti-IgE antibodies; and specific immunotherapy or desensitization.

Examples of IgE-mediated allergic responses include, but are not limited to, asthma, allergic rhinitis, gastrointestinal allergies, eosinophilia, conjunctivitis, atopic dermatitis, urticaria, anaphylaxis, or golmerular nephritis.

The invention encompasses molecules, e.g., immunoglobulins, engineered to form complexes with FcεRI and human FcγRIIB, i.e., specifically bind FcεRI and human FcγRIIB. Preferably, such molecules have therapeutic efficacy in IgE and FcεRI-mediated disorders. Although not intending to be bound by a particular mechanism of action, the therapeutic efficacy of these engineered molecules is, in part, due to their ability to inhibit mast cell and basophil function.

In a specific embodiment, molecules that specifically bind FcεRI and human FcγRIIB are chimeric fusion proteins comprising a binding site for FcεRI and a binding site for FcγRIIB. Such molecules may be engineered in accordance with standard recombinant DNA methodologies known to one skilled in the art. In a preferred specific embodiment, a chimeric fusion protein for use in the methods of the invention comprises an F(ab') single chain of an anti-FcγRIIB monoclonal antibody of the invention fused to a region used as a bridge to link the huFcε to the C-terminal region of the F(ab') single chain of the anti-FcγRIIB monoclonal antibody. One exemplary chimeric fusion protein for use in the methods of the invention comprises the following: $V_L/C_H$ (FcγRIIB)-hinge-$V_H/C_H$ (FcγRIIB)-LINKER-$C_H$ε2-$C_H$ε3-$C_H$ε4. The linker for the chimeric molecules may be five, ten, preferably fifteen amino acids in length. The length of the linker may vary to provide optimal binding of the molecule to both FcγRIIB and FcεRI. In a specific embodiment, the linker is a 15 amino acid linker, consisting of the sequence: $(Gly_4Ser)_3$. Although not intending to be bound by a particular mechanism of action, the flexible peptide linker facilitates chain pairing and minimizes possible refolding and it will also allow the chimeric molecule to reach the two receptors, i.e., FcγRIIB and FcεRI on the cells and cross-link them. Preferably, the chimeric molecule is cloned into a mammalian expression vector, e.g., pCI-neo, with a compatible promoter, e.g., cytomegalovirus promoter. The fusion protein prepared in accordance with the methods of the invention will contain the binding site for FcεRI (CHε2CHε3) and for FcγRIIB (VL/CL,-hinge-VH/CH). The nucleic acid encoding the fusion protein prepared in accordance with the methods of the invention is preferably transfected into 293 cells and the secreted protein is purified using common methods known in the art.

Binding of the chimeric molecules to both human FcεRI and FcγRIIB may be assessed using common methods known to one skilled in the art for determining binding to an FcγR. Preferably, the chimeric molecules of the invention have therapeutic efficacy in treating IgE mediated disorders, for example, by inhibiting antigen-driven degranulation and inhibition of cell activation. The efficacy of the chimeric molecules of the invention in blocking IgE driven FcεRI-mediated mast cell degranulation may be determined in transgenic mice, which have been engineered to express the human FcεRα and human FcγRIIB, prior to their use in humans.

The invention provides the use of bispecific antibodies for the treatment and/or prevention of IgE-mediated and/or FcεRI-mediated allergic disorders. A bispecific antibody (BsAb) binds to two different epitopes usually on distinct antigens. BsAbs have potential clinical utility and they have been used to target viruses, virally infected cells and bacterial pathogens as well as to deliver thrombolitic agents to blood clots (Cao (1998) "*Bispecific Antibodies As Novel Bioconjugates*," Bioconj. Chem. 9: 635-644; Koelemij et al. (1999) "*Bispecific Antibodies In Cancer Therapy, From The Laboratory To The Clinic*," J. Immunother., 22, 514-524; Segal et al. (1999) "*Bispecific Antibodies In Cancer Therapy*," Curr. Opin. Immunol., 11, 558-562). The technology for the production of BsIgG and other related bispecific molecules is available (see, e.g., Carter et al. (2001) "*Bispecific Human IgG By Design*," J. of Immunol. Methods, 248, 7-15; Segal et al. (2001) "*Introduction: Bispecific Antibodies*," J. of Immunol. Methods, 248, 71-76, which are incorporated herein by reference in their entirety). The instant invention provides bispecific antibodies containing one F(ab') of the anti-FcγRIIB antibody and one F(ab') of an available monoclonal anti-huIgE antibody which aggregates two receptors, FcγRIIB and FcεRI, on the surface of the same cell. Any methodology known in the art and disclosed herein may be employed to generate bispecific antibodies for use in the methods of the invention. In a specific embodiment, the BsAbs will be produced by chemically cross-linking F(ab') fragments of an anti-FcγRIIB antibody and an anti-huIgE antibody as described previously, see, e.g., Glennie et al., 1995, TUMOR IMMUNOBIOLOGY, Oxford University press, Oxford, p. 225; which is incorporated herein by reference in its entirety). The F(ab') fragments may be produced by limited proteolysis with pepsin and reduced with mercaptoethanol amine to provide Fab' fragments with free hinge-region sulfhydryl (SH) groups. The SH group on one of the Fab' (SH) fragments may be alkylated with excess O-phenylenedimaleimide (O-PDM) to provide a free maleimide group (mal). The two preparations Fab'(mal) and Fab'(SH) may be combined at an appropriate ratio, preferably 1:1 to generate heterodimeric constructs. The BsAbs can be purified by size exclusion chromatography and characterized by HPLC using methods known to one skilled in the art.

In particular, the invention encompasses bispecific antibodies comprising a first heavy chain-light chain pair that binds FcγRIIB with greater affinity than said heavy chain-light chain pair binds FcγRIIA, and a second heavy chain-light chain pair that binds IgE receptor, with the provision that said first heavy chain-light chain pair binds FcγRIIB first. The bispecific antibodies of the invention can be engineered using standard techniques known in the art to ensure that the binding to FcγRIIB precedes the binding to the IgE receptor. It will be understood by one skilled in the art that it is possible to engineer the bispecific antibodies, for example, such that said bispecific antibodies bind FcγRIIB with greater affinity than said antibodies bind IgE receptor. Additionally, the bispecific antibodies can be engineered by techniques known in the art, such that the hinge size of the antibody can be increased in length, for example, by adding linkers, to provide the bispecific antibodies with flexibility to bind the IgE receptor and FcγRIIB receptor on the same cell.

The antibodies of the invention can also be used in combination with other therapeutic antibodies or drugs known in the art for the treatment or prevention of IgE-mediated allergic disorders. For example, the antibodies of the invention can be used in combination with any of the following: azelastine (ASTELIN®), beclomethasone dipropionate inhaler (VANCERIL®), beclomethasone dipropionate nasal inhaler/spray (VANCENASE®), Beconase budesonide nasal inhaler/spray (RHINOCORT®), cetirizine (ZYRTEC®), chlorpheniramine, pseudoephedrine, Deconamine (SUDAFED®), cromolyn (ASALCROM®, INTAL®, OPTICROM®), desloratadine (CLARINEX®), fexofenadine and pseudoephedrine (ALEGRA-D®), fexofenadine (ALLEGRA®), flunisolide nasal spray (NASALIDE®), fluticasone propionate nasal inhaler/spray (FLONASE®), fluticasone propionate oral inhaler (FLOVENT®), hydroxyzine (VISTARIL®, ATARAX®), loratadine, pseudoephedrine (CLARITIN-D®), loratadine (CLARITIN®), prednisolone (PREDNISOLONE®, PEDIAPRED® Oral Liquid, MEDROL® prednisone, DELTASONE®, Liquid Predsal-meterol), salmeterol xinafoate (SEREVENT®), triamcinolone acetonide inhaler (AZMACORT®), triamcinolone acetonide nasal inhaler/spray (NASACORT®, or NASA- CORT AQ®). Antibodies of the invention can be used in combination with cytosine-guanine dinucleotides ("CpG")-based products that have been developed (Coley Pharmaceuticals) or are currently being developed as activators of innate and acquired immune responses. For example, the invention encompasses the use of CpG 7909, CpG 8916, CpG 8954 (Coley Pharmaceuticals) in the methods and compositions of the invention for the treatment and/or prevention of IgE-mediated allergic disorders (See also Weeratna et al. (2001) "*CpG ODN Can Re-Direct The Th Bias Of Established Th2 Immune Responses In Adult And Young Mice*," FEMS Immunol Med Microbiol., 32(1):65-71, which is incorporated herein by reference).

The invention encompasses the use of the antibodies of the invention in combination with any therapeutic antibodies known in the art for the treatment of allergy disorders, e.g., XOLAIR™ (Omalizumab; Genentech); rhuMAB-E25 (BioWorld Today, Nov. 10, 1998, p. 1; Genentech); CGP-51901 (humanized anti-IgE antibody), etc.

Additionally, the invention encompasses the use of the antibodies of the invention in combination with other compositions known in the art for the treatment of allergy disorders. In particular, methods and compositions disclosed in Carson et al. (U.S. Pat. No. 6,426,336; US 2002/0035109 A1; US 2002/0010343) is incorporated herein by reference in its entirety.

D. Immunomodulatory Agents and Anti-Inflammatory Agents

The method of the present invention provides methods of treatment for autoimmune diseases and inflammatory diseases comprising administration of the antibodies of the present invention in conjunction with other treatment agents. Examples of immunomodulatory agents include, but are not limited to, methothrexate, ENBREL® (etanerecept), REMICADE™® (infliximab), leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (SAIDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (ALFON™), indomethacin (INDOCIN™), ketoralac (TORADOL™), oxaprozin (DAYPRO™), nabumetone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

E. Anti-Cancer Agents and Therapeutic Antibodies

In a specific embodiment, the methods of the invention encompass the administration of one or more angiogenesis inhibitors such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); EGFr blockers/inhibitors (IRESSA® (gefitinib), TARCEVA® (erlotinib), ERBITUX® (cetuximab), and VECTIBIX™ (panitumumab; ABX-EGF)); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-IC11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-β); Vasculostatin; Vasostatin (calreticulin fragment); ZD6126; ZD 6474; farnesyl transferase inhibitors (FTI); and bisphosphonates.

Anti-cancer agents that can be used in combination with antibodies of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon α-2a; interferon α-2b; interferon α-n1; interferon α-n3; interferon β-I a; interferon γ-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin;

temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include but are not limited to HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ (edrecolomab) which is a murine anti-17-IA cell surface antigen IgG2a antibody (Glaxo Wellcome/Centocor); BEC2 which is a murine anti-idiotype (GD3 epitope) IgG antibody (ImClone System); ERBITUX® (cetuximab) which is a chimeric anti-EGFR IgG antibody (ImClone System); VITAXIN™ which is a humanized anti-αVβ3 integrin antibody (Applied Molecular Evolution/MedImmune); CAMPATH® (alemtuzumab) 1H/LDP-03 which is a humanized anti CD52 IgG1 antibody (Leukosite); Smart M195 which is a humanized anti-CD33 IgG antibody (Protein Design Lab/Kanebo); RITUXAN™ (rituximab) which is a chimeric anti-CD20 IgG1 antibody (IDEC Pharm/Genentech, Roche/Zettyaku); LYMPHOCIDE™® (epratuzumab) which is a humanized anti-CD22 IgG antibody (Immunomedics); ICM3 which is a humanized anti-ICAM3 antibody (ICOS Pharm); IDEC-114 which is a primatied anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (C5) antibody (Alexion Pharm); Humira® which is a human anti-TNF-α antibody (Abbott Laboratories); which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4β7 antibody (LeukoSite/Genentech); OrthoClone OKT4A which is a humanized anti-CD4 IgG antibody (Ortho Biotech); ANTOVA™ (ruplizumab) which is a humanized anti-CD40L IgG antibody (Biogen); ANTEGREN™ (natalizumab) which is a humanized anti-VLA-4 IgG antibody (Elan); and CAT-152 which is a human anti-TGF-$β_2$ antibody (Cambridge Ab Tech).

Other examples of therapeutic antibodies that can be used in combination with the antibodies of the invention are presented in Table 7.

TABLE 7

Monoclonal Antibodies For Cancer Therapy That Can Be Used In Combination With The Antibodies Of The Invention

| Product | Disease | Target |
|---|---|---|
| ABX-EGF | Cancer | EGF receptor |
| OvaRex | ovarian cancer | tumor antigen CA125 |
| BravaRex | metastatic cancers | tumor antigen MUC1 |
| Theragyn (pemtumomabytrrium-90) | ovarian cancer | PEM antigen |
| Therex | breast cancer | PEM antigen |
| blvatuzumab | head & neck cancer | CD44 |
| Panorex | Colorectal cancer | 17-1A |
| ReoPro | PTCA | gp IIIb/IIIa |
| ReoPro | Acute MI | gp IIIb/IIIa |
| ReoPro | Ischemic stroke | gp IIIb/IIIa |
| Bexocar | NHL | CD20 |
| MAb, idiotypic 105AD7 | colorectal cancer vaccine | gp72 |
| Anti-EpCAM | cancer | Ep-CAM |
| MAb, lung cancer | non-small cell lung cancer | NA |
| Herceptin | metastatic breast cancer | HER-2 |
| Herceptin | early stage breast cancer | HER-2 |
| Rituxan | Relapsed/refractory low-grade or follicular NHL | CD20 |
| Rituxan | intermediate & high-grade NHL | CD20 |
| MAb-VEGF | NSCLC, metastatic | VEGF |
| MAb-VEGF | Colorectal cancer, metastatic | VEGF |
| AMD Fab | age-related macular degeneration | CD18 |
| E-26 (2$^{nd}$ gen. IgE) | allergic asthma & rhinitis | IgE |
| Zevalin (Rituxan + yttrium-90) | low grade of follicular, relapsed or refractory, CD20-positive, B-cell NHL and Rituximab-refractory NHL | CD20 |
| Cetuximab + innotecan | refractory colorectal carcinoma | EGF receptor |
| Cetuximab + cisplatin & radiation | newly diagnosed or recurrent head & neck cancer | EGF receptor |
| Cetuximab + gemcitabine | newly diagnosed metastatic pancreatic carcinoma | EGF receptor |
| Cetuximab + cisplatin + 5FU or Taxol | recurrent or metastatic head & neck cancer | EGF receptor |
| Cetuximab + carboplatin + paclitaxel | newly diagnosed non-small cell lung carcinoma | EGF receptor |
| Cetuximab + cisplatin | head & neck cancer (extensive incurable local-regional disease & distant metastases) | EGF receptor |
| Cetuximab + radiation | locally advanced head & neck carcinoma | EGF receptor |
| BEC2 + *Bacillus* Calmette Guerin | small cell lung carcinoma | mimics ganglioside GD3 |
| BEC2 + *Bacillus* Calmette Guerin | melanoma | mimics ganglioside GD3 |
| IMC-1C11 | colorectal cancer with liver metastases | VEGF-receptor |

TABLE 7-continued

Monoclonal Antibodies For Cancer Therapy That Can Be Used
In Combination With The Antibodies Of The Invention

| Product | Disease | Target |
|---|---|---|
| nuC242-DM1 | Colorectal, gastric, and pancreatic cancer | nuC242 |
| LymphoCide | Non-Hodgkins lymphoma | CD22 |
| LymphoCide Y-90 | Non-Hodgkins lymphoma | CD22 |
| CEA-Cide | metastatic solid tumors | CEA |
| CEA-Cide Y-90 | metastatic solid tumors | CEA |
| CEA-Scan (Tc-99m-labeled arcitumomab) | colorectal cancer (radioimaging) | CEA |
| CEA-Scan (Tc-99m-labeled arcitumomab) | Breast cancer (radioimaging) | CEA |
| CEA-Scan (Tc-99m-labeled arcitumomab) | lung cancer (radioimaging) | CEA |
| CEA-Scan (Tc-99m-labeled arcitumomab) | intraoperative tumors (radio imaging) | CEA |
| LeukoScan (Tc-99m-labeled sulesomab) | soft tissue infection (radioimaging) | CEA |
| LymphoScan (Tc-99m-labeled) | lymphomas (radioimaging) | CD22 |
| AFP-Scan (Tc-99m-labeled) | liver 7 gem-cell cancers (radioimaging) | AFP |
| HumaRAD-HN (+yttrium-90) | head & neck cancer | NA |
| HumaSPECT | colorectal imaging | NA |
| MDX-101 (CTLA-4) | Prostate and other cancers | CTLA-4 |
| MDX-210 (her-2 overexpression) | Prostate cancer | HER-2 |
| MDX-210/MAK | Cancer | HER-2 |
| Vitaxin | Cancer | $\alpha v \beta_3$ |
| MAb 425 | Various cancers | EGF receptor |
| IS-IL-2 | Various cancers | Ep-CAM |
| Campath (alemtuzumab) | chronic lymphocytic leukemia | CD52 |
| CD20-streptavidin (+biotin-yttrium 90) | Non-Hodgkins lymphoma | CD20 |
| Avidicin (albumin + NRLU13) | metastatic cancer | NA |
| Oncolym (+iodine-131) | Non-Hodgkins lymphoma | HLA-DR 10 beta |
| Cotara (+iodine-131) | unresectable malignant glioma | DNA-associated proteins |
| C215 (+staphylococcal enterotoxin) | pancreatic cancer | NA |
| MAb, lung/kidney cancer | lung & kidney cancer | NA |
| nacolomab tafenatox (C242 + staphylococcal enterotoxin) | colon & pancreatic cancer | NA |
| Nuvion | T cell malignancies | CD3 |
| SMART M195 | AML | CD33 |
| SMART 1D10 | NHL | HLA-DR antigen |
| CEAVac | colorectal cancer, advanced | CEA |
| TriGem | metastatic melanoma & small cell lung cancer | GD2-ganglioside |
| TriAb | metastatic breast cancer | MUC-1 |
| CEAVac | colorectal cancer, advanced | CEA |
| TriGem | metastatic melanoma & small cell lung cancer | GD2-ganglioside |
| TriAb | metastatic breast cancer | MUC-1 |
| NovoMAb-G2 radiolabeled | Non-Hodgkins lymphoma | NA |
| Monopharm C | colorectal & pancreatic carcinoma | SK-1 antigen |
| GlioMAb-H (+gelonin toxin) | gliorna, melanoma & neuroblastoma | NA |
| Rituxan | Relapsed/refractory low-grade or follicular NHL | CD20 |
| Rituxan | intermediate & high-grade NHL | CD20 |
| ING-1 | adenomcarcinoma | Ep-CAM |

F. Vaccine Therapy

The invention provides a method for enhancing an immune response to a vaccine composition in a subject, said method comprising administering to said subject an antibody or a fragment thereof that specifically binds FcγRIIB with greater affinity than said antibody or a fragment thereof binds FcγRIIA, and a vaccine composition, wherein said antibody or a fragment thereof enhances the immune response to said vaccine composition. In one particular embodiment, said antibody or a fragment thereof enhances the immune response to said vaccine composition by enhancing antigen presentation/and or antigen processing of the antigen to which the vaccine is directed at. Any vaccine composition known in the art is useful in combination with the antibodies or fragments thereof of the invention.

In one embodiment, the invention encompasses the use of the antibodies of the invention in combination with any cancer vaccine known in the art, e.g., CANVAXIN™ (Cancer Vax, Corporation, melanoma and colon cancer); ONCOPH-AGE® (HSPPC-96; Antigenics; metastatic melanoma); HER-2/neu cancer vaccine, etc. The cancer vaccines used in the methods and compositions of the invention can be, for example, antigen-specific vaccines, anti-idiotypic vaccines, dendritic cell vaccines, or DNA vaccines. The invention encompasses the use of the antibodies of the invention with cell-based vaccines as described by Segal et al. (U.S. Pat. No. 6,403,080), which is incorporated herein by reference in its entirety. The cell-based vaccines used in combination with the antibodies of the invention can be either autologous or allogeneic. Briefly, the cancer-based vaccines as described by Segal et al. are based on Opsonokine™ product by Genitrix, LLC. Opsonokines™ are genetically engineered cytokines that, when mixed with tumor cells, automatically attach to the surface of the cells. When the "decorated" cells are administered as a vaccine, the cytokine on the cells activates critical antigen presenting cells in the recipient, while also allowing the antigen presenting cells to ingest the tumor cells. The antigen presenting cells are then able to instruct "killer" T cells to find and destroy similar tumor cells throughout the body. Thus, the Opsonokine™ product converts the tumor cells into a potent anti-tumor immunotherapeutic.

In one embodiment, the invention encompasses the use of the antibodies of the invention in combination with any allergy vaccine known in the art. The antibodies of the invention, can be used, for example, in combination with recombinant hybrid molecules coding for the major timothy grass pollen allergens used for vaccination against grass pollen allergy, as described by Linhart et al. (2002) "Combination Vaccines For The Treatment Of Grass Pollen Allergy Consisting *Of Genetically Engineered Hybrid Molecules With Increased Immunogenicity*," FASEB Journal, 16(10):1301-1303, which is incorporated herein by reference in its entirety. In addition, the antibodies of the invention can be used in combination with DNA-based vaccinations described by Horner et al. (2002) "*Immunostimulatory Dna-Based Therapeutics For Experimental And Clinical Allergy*," Allergy, 57 Suppl, 72:24-29, which is incorporated by reference. Antibodies of the invention can be used in combination with Bacille Clamett-Guerin ("BCG") vaccination as described by Choi et al. (2002) "*Therapeutic Effects Of Bcg Vaccination In Adult Asthmatic Patients: A Randomized, Controlled Trial*," Ann. Allergy Asthma Immunology, 88(6): 584-591); and Barlan et al. (2002) "*The Impact Of In Vivo Calmette-Guerin Bacillus Administration On In Vitro Ige Secretion In Atopic Children*," Journal Asthma, 39(3):239-246, both of which are incorporated herein by reference in entirety, to downregulate IgE secretion. The antibodies of the invention are useful in treating food allergies. In particular, the antibodies of the invention can be used in combination with vaccines or other immunotherapies known in the art (see Hourihane et al. (2002) "*Recent Advances In Peanut Allerg*," Curr. Opin. Allergy Clin. Immunol. 2(3):227-231) for the treatment of peanut allergies.

The methods and compositions of the invention can be used in combination with vaccines, in which immunity for the antigen(s) is desired. Such antigens may be any antigen known in the art. The antibodies of the invention can be used to enhance an immune response, for example, to infectious agents, diseased or abnormal cells such as, but not limited to, bacteria (e.g., gram positive bacteria, gram negative bacteria, aerobic bacteria, *Spirochetes, Mycobacteria, Rickettsias, Chlamydias*, etc.), parasites, fungi (e.g., *Candida albicans, Aspergillus*, etc.), viruses (e.g., DNA viruses, RNA viruses, etc.), or tumors. Viral infections include, but are not limited to, human immunodeficiency virus (HIV); hepatitis A virus, hepatitis B virus, hepatitis C virus, hepatitis D virus, or other hepatitis viruses; cytomagaloviruses, herpes simplex virus-1 (-2, -3, -4, -5, -6), human papilloma viruses; Respiratory syncytial virus (RSV), Parainfluenza virus (PIV), Epstein Barr virus, human metapneumovirus (HMPV), influenza virus, Severe Acute Respiratory Syndrome (SARS) or any other viral infections.

The invention encompasses methods and vaccine compositions comprising combinations of an antibody of the invention, an antigen and a cytokine. Preferably, the cytokine is IL-4, IL-10, or TGF-β.

The invention also encompasses the use of the antibodies of the invention to enhance a humoral and/or cell mediated response against the antigen(s) of the vaccine composition. The invention further encompasses the use of the antibodies of the invention to either prevent or treat a particular disorder, where an enhanced immune response against a particular antigen or antigens is effective to treat or prevent the disease or disorder. Such diseases and disorders include, but are not limited to, viral infections, such as HIV, CMV, hepatitis, herpes virus, measles, etc., bacterial infections, fungal and parasitic infections, cancers, and any other disease or disorder amenable to treatment or prevention by enhancing an immune response against a particular antigen or antigens.

XIV. Breaking Tolerance to an Antigen

Certain cancers may be associated with an ability of the tumors to circumvent an immune response against their antigens, i.e., tolerance to these antigens exists. (See Mapara et al. (2004) "*Tolerance and Cancer: Mechanisms Of Tumor Evasion and Strategies For Breaking Tolerance*," J. Clin. Oncol. 22:1136-1151.) Accordingly, a goal in tumor immunotherapy is to break tolerance to tumor antigens in order to induce an antitumor response. Eliciting an immune response against a foreign antigen that is otherwise recognized by the host as a "self" antigen breaks tolerance to that antigen.

Thus, in certain embodiments, the invention provides a method for breaking tolerance to an antigen in a patient by administering to a patient in need thereof (i.) an antigen-antibody complex comprising the antigen and (ii.) an antibody or fragment thereof that specifically binds the extracellular domain of human FcγRIIB and blocks the Fc binding site of human FcγRIIB, thereby breaking tolerance in said patient to the antigen. The antibody or fragment thereof can be administered before, concurrently with, or after administration of said antigen-antibody complex.

Antigen-presenting cells, such as dendritic cells, coexpress activating and inhibitory Fc gamma receptors. Without being bound by theory, when antibodies that block Fc binding to FcγRIIB are present, the antigen-antibody complexes comprising an antigen are primarily taken up by non-inhibitory receptors on antigen-presenting cells eliciting an immune response to the antigen.

In certain embodiments, the antigen is an antigen that is associated with a cancer or a neoplastic disease. In another aspect, the antigen is specific to a cancer cell or a neoplastic cell. The antigen can also be an antigen of a pathogen, such as, e.g., a virus, a bacterium, or a protozoa. Representative antigens have been disclosed herein.

XV. Compositions and Methods of Administering

The invention provides methods and pharmaceutical compositions comprising antibodies of the invention. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or conjugated molecules of the invention. In a preferred aspect, an antibody or fusion protein or conjugated molecule, is substantially purified (i.e., substantially free from substances that limit its effect or produce undesired side effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human.

Various delivery systems are known and can be used to administer a composition comprising antibodies of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System*," J. Biol. Chem. 262:4429-4432), construction of a nucleic acid as part of a retroviral or other vector, etc.

In some embodiments, the antibodies of the invention are formulated in liposomes for targeted delivery of the antibodies of the invention. Liposomes are vesicles comprised of concentrically ordered phospholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Eppstein et al. (1985) "*Biological Activity Of Liposome-Encapsulated Murine Interferon Gamma Is Mediated By A Cell Membrane Receptor,*" Proc. Natl. Acad. Sci. USA, 82: 3688-3692; Hwang et al. (1980) "*Hepatic Uptake And Degradation Of Unilamellar Sphingomyelin/Cholesterol Liposomes: A Kinetic Study,*" Proc. Natl. Acad. Sci. USA, 77: 4030-4034; U.S. Pat. Nos. 4,485,045 and 4,544,545; all of which are incorporated herein by reference in their entirety.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes that are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposomes see, e.g., Bendas et al. (2001) "*Immunoliposomes: A Promising Approach To Targeting Cancer Therapy,*" BioDrugs, 15(4): 215-224; Allen et al. (1987) "*Large Unilamellar Liposomes With Low Uptake Into The Reticuloendothelial System,*" FEBS Lett. 223: 42-46; Klibanov et al. (1990) "*Amphipathic Polyethyleneglycols Effectively Prolong The Circulation Time Of Liposomes,*" FEBS Lett., 268: 235-237; Blume et al. (1990) "*Liposomes For The Sustained Drug Release In Vivo,*" Biochim. Biophys. Acta., 1029: 91-97; Torchilin. et al. (1996) "*How Do Polymers Prolong Circulation Time Of Liposomes?,*" J. Liposome Res. 6: 99-116; Litzinger et al. (1994) "*Effect Of Liposome Size On The Circulation Time And Intraorgan Distribution Of Amphipathic Poly (Ethylene Glycol)-Containing Liposomes,*" Biochim. Biophys. Acta, 1190: 99-107; Maruyama et al. (1991) "*Effect Of Molecular Weight In Amphipathic Polyethyleneglycol On Prolonging The Circulation Time Of Large Unilamellar Liposomes,*" Chem. Pharm. Bull., 39: 1620-1622; Klibanov et al. (1991) "*Activity Of Amphipathic Poly(Ethylene Glycol) 5000 To Prolong The Circulation Time Of Liposomes Depends On The Liposome Size And Is Unfavorable For Immunoliposome Binding To Target,*" Biochim Biophys Acta, 1062; 142-148; Allen et al. (1994) "*The Use Of Glycolipids And Hydrophilic Polymers In Avoiding Rapid Uptake Of Liposomes By The Mononuclear Phagocyte System,*" Adv. Drug Deliv. Rev., 13: 285-309; all of which are incorporated herein by reference in their entirety. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al. (1982) "*Irreversible Coupling Of Immunoglobulin Fragments To Preformed Vesicles. An Improved Method For Liposome Targeting,*" J. Biol. Chem. 257: 286-288, which is incorporated herein by reference in its entirety.

The antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, STEALTH LIPOSOMES, Boca Rotan: CRC Press, 233-44; Hansen et al. (1995) "*Attachment Of Antibodies To Sterically Stabilized Liposomes: Evaluation, Comparison And Optimization Of Coupling Procedures,*" Biochim. Biophys. Acta, 1239: 133-144; which are incorporated herein by reference in their entirety. In most preferred embodiments, immunoliposomes for use in the methods and compositions of the invention are further sterically stabilized. Preferably, the antibodies of the invention are linked covalently or non-covalently to a hydrophobic anchor, which is stably rooted in the lipid bilayer of the liposome. Examples of hydrophobic anchors include but are not limited to phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., 1997, GENE THERAPY: ADVANCES IN PHARMACOLOGY, Volume 40, Academic Press, San Diego, Calif., p. 399-435, which is incorporated herein by reference in its entirety For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors such as pyridylthiopropionyl-phosphatidylethanolamine. See, e.g., Dietrich et al. (1996) "*Functional Immobilization Of A DNA-Binding Protein At A Membrane Interface Via Histidine Tag And Synthetic Chelator Lipids,*" Biochemistry, 35: 1100-1105; Loughrey et al. (1987) "*A Non-Covalent Method Of Attaching Antibodies To Liposomes,*" Biochim. Biophys. Acta, 901: 157-160; Martin et al. (1982) "*Irreversible Coupling Of Immunoglobulin Fragments To Preformed Vesicles. An Improved Method For Liposome Targeting,*" J. Biol. Chem. 257: 286-288; Martin et al. (1981) "*Immunospecific Targeting Of Liposomes To Cells: A Novel And Efficient Method For Covalent Attachment Of Fab' Fragments Via Disulfide Bonds,*" Biochemistry, 20: 4429-4438; all of which are incorporated herein by reference in their entirety. Although not intending to be bound by a particular mechanism of action, immunoliposomal formulations comprising an antibody of the invention are particularly effective as therapeutic agents, since they deliver the antibody to the cytoplasm of the target cell, i.e., the cell comprising the FcγRIIB receptor to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The invention encompasses immunoliposomes comprising an antibody of the invention or a fragment thereof. In some embodiments, the immunoliposomes further comprise one or more additional therapeutic agents, such as those disclosed herein.

The immunoliposomal compositions of the invention comprise one or more vesicle forming lipids, an antibody of the invention or a fragment or derivative thereof, and optionally a hydrophilic polymer. A vesicle-forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al. (1994) "*Immunoliposomes In Vivo*," Immunomethods, 4: 259-272; Maruyama (2000) "*In Vivo Targeting By Liposomes*," Biol. Pharm. Bull. 23(7): 791-799; Abra et al. (2002) "*The Next Generation Of Liposome Delivery Systems: Recent Experience With Tumor-Targeted, Sterically-Stabilized Immunoliposomes And Active-Loading Gradients*," Journal J. Liposome Research, Res. 12(1&2): 1-3; Park (2002) "*Tumor-Directed Targeting Of Liposomes*," Bioscience Reports, 22(2): 267-281; Bendas et al. (2001) "*Immunoliposomes: A Promising Approach To Targeting Cancer Therapy*," Bio-Drugs, 14(4): 215-224, J. Thomas August, ed., 1997, GENE THERAPY: ADVANCES IN PHARMACOLOGY, Volume 40, Academic Press, San Diego, Calif., p. 399-435, all of which are incorporated herein by reference in their entireties.

Methods of administering an antibody of the invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the antibodies of the invention are packaged in a hermetically sealed container such as an ampoule or sachette indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the antibodies of the invention administered to a patient are 0.01 mg to 1000 mg/day, when used as single agent therapy. In another embodiment the antibodies of the invention are used in combination with other therapeutic compositions and the dosage administered to a patient are lower than when said antibodies are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In another embodiment, the compositions can be delivered in a vesicle, in particular a liposome (See Langer (1990) "*New Methods Of Drug Delivery*," Science 249:1527-1533; Treat et al., in LIPOSOMES in the THERAPY of INFECTIOUS DISEASE and CANCER, Lopez-Berestein and Fidler (eds.), Liss, New York, pp. 353-365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more antibodies of the invention. See, e.g., U.S. Pat. No.

4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel*," Radiotherapy & Oncology 39:179-189, Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety. In one embodiment, a pump may be used in a controlled release system (See Langer, supra; Sefton (1987) "*Implantable Pumps*," CRC Crit. Ref. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis*," Surgery 88:507-516; and Saudek et al. (1989) "*A Preliminary Trial Of The Programmable Implantable Medication System For Insulin Delivery*," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); "*Controlled Drug Bioavailability*," DRUG PRODUCT DESIGN AND PERFORMANCE, Smolen and Ball (eds.), Wiley, New York (1984); Ranger et al. (1983) "Ranger et al. (1983) "*Chemical And Physical Structure Of Polymers as Carriers For Controlled Release Of Bioactive Agents: A Review*," J. Macromol. Sci. Rev. Macromol. Chem. 23:61-126; See also Levy et al. (1985) "*Inhibition Of Calcification Of Bioprosthetic Heart Valves By Local Controlled-Release Diphosphonate*," Science 228:190-192; During et al. (1989) "*Controlled Release Of Dopamine From A Polymeric Brain Implant: In Vivo Characterization*," Ann. Neurol. 25:351-356; Howard et al. (1989) "*Intracerebral Drug Delivery In Rats With Lesion-Induced Memory Deficits*," J. Neurosurg. 7(1):105-112); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533).

Controlled release systems are discussed in the review by Langer (1990) "*New Methods Of Drug Delivery*," Science 249:1527-1533. Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel*," Radiotherapy & Oncology 39:179-189; Song et al. (1995) "*Antibody Mediated Lung Targeting Of Long-Circulating Emulsions*," PDA Journal of Pharmaceutical Science & Technology 50:372-397; Cleek et al. (1997) "*Biodegradable Polymeric Carriers For A bFGF Antibody For Cardiovascular Application*," Pro. Int'l. Symp. Control. Rel. Bioact. Mater. 24:853-854; and Lam et al. (1997) "*Microencapsulation Of Recombinant Humanized Monoclonal Antibody For Local Delivery*," Proc. Int'l. Symp. Control Rel. Bioact. Mater. 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al. (1991) "*Antennapedia Homeobox Peptide Regulates Neural Morphogenesis*," Proc. Natl. Acad. Sci. USA 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage and frequency of administration of antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of antibodies of the invention can include a single treatment or, preferably, can include a series of treatments. In a preferred example, a subject is treated with antibodies of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

XVI. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of antibodies of the invention and a pharmaceutically acceptable carrier.

In one particular embodiment, the pharmaceutical composition comprises of a therapeutically effective amount of an antibody or a fragment thereof that binds FcγRIIB with a greater affinity than said antibody or a fragment thereof binds FcγRIIA, a cytotoxic antibody that specifically binds a cancer antigen, and a pharmaceutically acceptable carrier. In another embodiment, said pharmaceutical composition further comprises one or more anti-cancer agents.

In another particular embodiment, the pharmaceutical composition comprises: (i) a therapeutically effective amount of an antibody or fragment thereof that specifically binds the extracellular domain of human FcγRIIB and blocks the Fc binding site of human FcγRIIB; (ii) a cytotoxic antibody that specifically binds a cancer antigen; and (iii) a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The present invention also provides pharmaceutical compositions and kits comprising a FcγRIIB antagonist for use in the prevention, treatment, management, or amelioration of a B-cell malignancy, or one or more symptoms thereof. In particular, the present invention provides pharmaceutical compositions and kits comprising an FcγRIIB antagonist, an analog, derivative or an anti-FcγRIIB antibody or an antigen-binding fragment thereof.

XVII. Gene Therapy

In a specific embodiment, nucleic acids comprising sequences encoding antibodies or fusion proteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded antibody or fusion protein that mediates a therapeutic or prophylactic effect.

Any of the methods for gene therapy available in the art can be used according to the present invention. Exemplary methods are described below.

For general reviews of the methods of gene therapy, see Goldspiel et al. (1993) "*Human Gene Therapy*," Clinical Pharmacy 12:488-505; Wu et al. (1991) "*Delivery Systems For Gene Therapy*," Biotherapy 3:87-95; Tolstoshev (1993) "*Gene Therapy, Concepts, Current Trials And Future Directions*," Ann. Rev. Pharmacol. Toxicol. 32:573-596; Mulligan (1993) "*The Basic Science Of Gene Therapy*," Science 260: 926-932; and Morgan et al. (1993) "*Human Gene Therapy*," Ann. Rev. Biochem. 62:191-217. Methods commonly known in the art of recombinant DNA technology which can be used are described in Ausubel et al. (eds.), CURRENT PROTOCOLS IN MOLECULAR BIOLOGY, John Wiley & Sons, NY (1993); and Kriegler, GENE TRANSFER AND EXPRESSION, A LABORATORY MANUAL, Stockton Press, NY (1990).

In a preferred aspect, a composition of the invention comprises nucleic acids encoding an antibody, said nucleic acids being part of an expression vector that expresses the antibody in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller et al. (1989) "*Inactivating The Beta 2-Microglobulin Locus In Mouse Embryonic Stem Cells By Homologous Recombination*," Proc. Natl. Acad. Sci. USA 86:8932-8935; and Zijlstra et al. (1989) "*Germ-Line Transmission Of A Disrupted B2 Microglobulin Gene Produced By Homologous Recombination In Embryonic Stem Cells*," Nature 342:435-438).

In another preferred aspect, a composition of the invention comprises nucleic acids encoding a fusion protein, said nucleic acids being a part of an expression vector that expression the fusion protein in a suitable host. In particular, such nucleic acids have promoters, preferably heterologous promoters, operably linked to the coding region of a fusion protein, said promoter being inducible or constitutive, and optionally, tissue-specific. In another particular embodiment, nucleic acid molecules are used in which the coding sequence of the fusion protein and any other desired sequences are flanked by regions that promote homologous recombination at a desired site in the genome, thus providing for intrachromosomal expression of the fusion protein encoding nucleic acids.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or by coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (See, e.g., Wu et al. (1987) "Receptor-Mediated In Vitro Gene Transformation By A Soluble DNA Carrier System," J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (See, e.g., U.S. Patent Application Publication No. 2005/0002903; PCT Publications WO 92/06180; WO 92/22635; WO 92/20316; WO 93/14188; WO 93/20221). Alternatively, the nucleic acid can be introduced intracellularly and incorporated within host cell DNA for expression, by homologous recombination (Koller et al. (1989) "Inactivating The Beta 2-Microglobulin Locus In Mouse Embryonic Stem Cells By Homologous Recombination," Proc. Natl. Acad. Sci. USA 86:8932-8935; and Zijlstra et al. (1989) "Germ-Line Transmission Of A Disrupted B2 Microglobulin Gene Produced By Homologous Recombination In Embryonic Stem Cells," Nature 342:435-438).

In a specific embodiment, viral vectors that contain nucleic acid sequences encoding an antibody or a fusion protein are used. For example, a retroviral vector can be used (See Miller et al. (1993) "Use Of Retroviral Vectors For Gene Transfer And Expression," Meth. Enzymol. 217:581-599). These retroviral vectors contain the components necessary for the correct packaging of the viral genome and integration into the host cell DNA. The nucleic acid sequences encoding the antibody or a fusion protein to be used in gene therapy are cloned into one or more vectors, which facilitate delivery of the nucleotide sequence into a subject. More detail about retroviral vectors can be found in Boesen et al. (1994) "Circumvention Of Chemotherapy-Induced Myelosuppression By Transfer Of The mdr1 Gene," Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy include: Clowes et al. (1994) "Long-Term Biological Response Of Injured Rat Carotid Artery Seeded With Smooth Muscle Cells Expressing Retrovirally Introduced Human Genes," J. Clin. Invest. 93:644-651; Keim et al. (1994) "Retrovirus-Mediated Gene Transduction Into Canine Peripheral Blood Repopulating Cells," Blood 83:1467-1473; Salmons et al. (1993) "Targeting Of Retroviral Vectors For Gene Therapy," Human Gene Therapy 4:129-141; and Grossman et al. (1993) "Retroviruses: Delivery Vehicle To The Liver," Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. For a review of adenovirus-based gene therapy see Kozarsky et al. (1993) "Gene Therapy: Adenovirus Vectors," Current Opinion in Genetics and Development 3:499-503. The use of adenovirus vectors to transfer genes to the respiratory epithelia of rhesus monkeys has been demonstrated by Bout et al. (1994) "Lung Gene Therapy In Vivo Adenovirus-Mediated Gene Transfer To Rhesus Monkey Airway Epithelium," Human Gene Therapy 5:3-10. Other instances of the use of adenoviruses in gene therapy can be found in Rosenfeld et al. (1991) "Adenovirus-Mediated Transfer Of A Recombinant Alpha 1-Antitrypsin Gene To The Lung Epithelium In Vivo," Science 252:431-434; Rosenfeld et al. (1992) "In Vivo Transfer Of The Human Cystic Fibrosis Transmembrane Conductance Regulator Gene To The Airway Epithelium," Cell 68:143-155; Mastrangeli et al. (1993) "Diversity Of Airway Epithelial Cell Targets For In Vivo Recombinant Adenovirus-Mediated Gene Transfer," J. Clin. Invest. 91:225-234; PCT Publication WO94/12649; and Wang et al. (1995) "A Packaging Cell Line For Propagation Of Recombinant Adenovirus Vectors Containing Two Lethal Gene-Region Deletions," Gene Therapy 2:775-783. In a preferred embodiment, adenovirus vectors are used.

Adeno-associated virus (AAV) has also been proposed for use in gene therapy (see, e.g., Walsh et al. (1993) "Gene Therapy For Human Hemoglobinopathies," Proc. Soc. Exp. Biol. Med. 204:289-300 and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to, transfection, electroporation, microinjection, infection with a viral or bacteriophage vector, containing the nucleic acid sequences, cell fusion, chromosome-mediated gene transfer, microcellmediated gene transfer, spheroplast fusion, etc. Numerous techniques are known in the art for the introduction of foreign genes into cells (See, e.g., Loeffler et al. (1993) "*Gene Transfer Into Primary And Established Mammalian Cell Lines With Lipopolyamine-Coated DNA*," Meth. Enzymol. 217:599-618, Cotten et al. (1993) "*Receptor-Mediated Transport Of DNA Into Eukaryotic Cells*," Meth. Enzymol. 217:618-644) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding an antibody or a fusion protein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (See e.g., PCT Publication WO 94/08598; Stemple et al. (1992) "*Isolation Of A Stem Cell For Neurons And Glia From The Mammalian Neural Crest*," Cell 7(1):973-985; Rheinwald (1980) "*Serial Cultivation Of Normal Human Epidermal Keratinocytes*," Meth. Cell Bio. 21A:229-254; and Pittelkow et al. (1986) "*New Techniques For The In Vitro Culture Of Human Skin Keratinocytes And Perspectives On Their Use For Grafting Of Patients With Extensive Burns*," Mayo Clinic Proc. 61:771-777).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

XVIII. Kits

The invention provides a pharmaceutical pack or kit comprising one or more containers filled with antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

XIX. Characterization and Demonstration of Therapeutic Utility

Several aspects of the pharmaceutical compositions or prophylactic or therapeutic agents of the invention are preferably tested in vitro, e.g., in a cell culture system, and then in vivo e.g., in an animal model organism, such as a rodent animal model system, for the desired therapeutic activity prior to use in humans. For example, assays which can be used to determine whether administration of a specific pharmaceutical composition is indicated, include cell culture assays in which a patient tissue sample is grown in culture, and exposed to or otherwise contacted with a pharmaceutical composition, and the effect of such composition upon the tissue sample is observed, e.g., inhibition of or decrease in growth and/or colony formation in soft agar or tubular network formation in three-dimensional basement membrane or extracellular matrix preparation. The tissue sample can be obtained by biopsy from the patient. This test allows the identification of the therapeutically most effective prophylactic or therapeutic molecule(s) for each individual patient. Alternatively, instead of culturing cells from a patient, therapeutic agents and methods may be screened using cells of a tumor or malignant cell line. In various specific embodiments, in vitro assays can be carried out with representative cells of cell types involved in an autoimmune or inflammatory disorder (e.g., T cells), to determine if a pharmaceutical composition of the invention has a desired effect upon such cell types. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc. Additional assays include raft association, CDC, ADCC and apoptosis assays as known in the art and described in the Examples.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary such as the temporal regime of administering the prophylactic and/or therapeutic agents, and whether such agents are administered separately or as an admixture.

Preferred animal models for use in the methods of the invention are for example, transgenic mice expressing FcγR on mouse effector cells, e.g., any mouse model described in U.S. Pat. No. 5,877,396 (which is incorporated herein by reference in its entirety). Transgenic mice for use in the methods of the invention include but are not limited to mice carrying human FcγRIIIA, mice carrying human FcγRIIA, mice carrying human FcγRIIB and human FcγRIIIA, mice carrying human FcγRIIB and human FcγRIIA.

Once the prophylactic and/or therapeutic agents of the invention have been tested in an animal model they can be tested in clinical trials to establish their efficacy. Establishing clinical trials will be done in accordance with common methodologies known to one skilled in the art, and the optimal dosages and routes of administration as well as toxicity profiles of the compositions of the invention can be established using routine experimentation.

The anti-inflammatory activity of the combination therapies of invention can be determined by using various experimental animal models of inflammatory arthritis known in the art and described in Crofford and Wilder, (1993) "*Arthritis and Autoimmunity in Animals*", in ARTHRITIS AND ALLIED CONDITIONS: A TEXTBOOK OF RHEUMATOLOGY, McCarty et al. (eds.), Chapter 30. Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford and Wilder, (1993) "*Arthritis and Autoimmunity in Animals*", in ARTHRITIS AND ALLIED CONDITIONS: A TEXTBOOK OF RHEUMATOLOGY, McCarty et al. (eds.), Chapter 30, incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra et al. (2000) "*Carrageenan-Induced Arthritis In The Rat*," Inflammation, 24(2): 141-155. Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter et al., (1962) "*Carrageenan-Induced Edema In Hind Paw Of The Rat As An Assay For Anti-Inflammatory Drugs*" Proc. Soc. Exp. Biol Med. 111: 544-547. This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al. (1992) "*Experimental Colitis In Animal Models*," Scand. J. Gastroentrol. 27:529-537; Strober (1985) "*Animal Models Of Inflammatory Bowel Disease—An Overview*," Dig. Dis. Sci. 30(12 Suppl):3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for asthma can also be used to assess the efficacy of the combination therapies of invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (Cohn et al. (1997) "*Induction Of Airway Mucus Production By T helper 2 (Th2) Cells: A Critical Role For Interleukin 4 In Cell Recruitment But Not Mucus Production*," J. Exp. Med. 186:1737-1747).

Animal models for autoimmune disorders can also be used to assess the efficacy of the combination therapies of invention. Animal models for autoimmune disorders such as type 1 diabetes, thyroid autoimmunity, systemic lupus eruthematosus, and glomerulonephritis have been developed (Flanders et al. (1999) "*Prevention Of Type I Diabetes From Laboratory To Public Health*," Autoimmunity 29:235-246; Rasmussen et al. (1999) "*Models To Study The Pathogenesis Of Thyroid Autoimmunity*," Biochimie 81:511-515; Foster (1999) "*Relevance Of Systemic Lupus Erythematosus Nephritis Animal Models To Human Disease*," Semin. Nephrol. 19: 12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans.

Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in RELEVANCE OF TUMOR MODELS FOR ANTICANCER DRUG DEVELOPMENT (1999) Fiebig and Burger, eds., CONTRIBUTIONS TO ONCOLOGY (1999) Karger; THE NUDE MOUSE IN ONCOLOGY RESEARCH, (1991) Boven and Winograd, eds.; and ANTICANCER DRUG DEVELOPMENT GUIDE, (1997) Teicher, ed., herein incorporated by reference in their entireties.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

XX. Diagnostic Methods

Labeled antibodies of the invention can be used for diagnostic purposes to detect, diagnose, or monitor diseases, disorders or infections. The invention provides for the detection or diagnosis of a disease, disorder or infection, particularly an autoimmune disease comprising:
  (A) assaying the expression of FcγRIIB in cells or a tissue sample of a subject using one or more antibodies that immunospecifically bind to FcγRIIB; and
  (B) comparing the level of the antigen with a control level, e.g., levels in normal tissue samples, whereby an increase in the assayed level of antigen compared to the control level of the antigen is indicative of the disease, disorder or infection.

Antibodies of the invention can be used to assay FcγRIIB levels in a biological sample using classical immunohistological methods as described herein or as known to those of skill in the art (e.g., Jalkanen et al. (1985) "*Heparan Sulfate Proteoglycans From Mouse Mammary Epithelial Cells: Localization On The Cell Surface With A Monoclonal Antibody*," J. Cell. Biol. 101:976-984; Jalkanen et al. (1987) "*Cell Surface Proteoglycan Of Mouse Mammary Epithelial Cells Is Shed By Cleavage Of Its Matrix-Binding Ectodomain From Its Membrane-Associated Domain*," J. Cell. Biol. 105:3087-3096). Other antibody-based methods useful for detecting protein gene expression include immunoassays, such as the enzyme linked immunosorbent assay (ELISA) and the radio-immunoassay (RIA). Suitable antibody assay labels are known in the art and include enzyme labels, such as, alkaline phosphatase, glucose oxidase; radioisotopes, such as iodine ($^{125}$I, $^{131}$I), carbon ($^{14}$C), sulfur ($^{35}$S), tritium ($^3$H), indium ($^{121}$In), and technetium ($^{99m}$Tc); luminescent labels, such as luminol; and fluorescent labels, such as fluorescein and rhodamine.

One aspect of the invention is the detection and diagnosis of a disease, disorder, or infection in a human. In one embodiment, diagnosis comprises:
  (A) administering (for example, parenterally, subcutaneously, or intraperitoneally) to a subject an effective amount of a labeled antibody that immunospecifically binds to FcγRIIB;
  (B) waiting for a time interval following the administration for permitting the labeled antibody to preferentially concentrate at sites in the subject where FcγRIIB is expressed (and for unbound labeled molecule to be cleared to background level);
  (C) determining background level; and
  (D) detecting the labeled antibody in the subject, such that detection of labeled antibody above the background level indicates that the subject has the disease, disorder, or infection.

In accordance with this embodiment, the antibody is labeled with an imaging moiety which is detectable using an imaging system known to one of skill in the art. Background level can be determined by various methods including, comparing the amount of labeled molecule detected to a standard value previously determined for a particular system.

It is well understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "*Immunopharmacokinetics of Radiolabeled Antibodies and Their Fragments*." (Chapter 13 in TUMOR IMAGING: THE RADIOCHEMICAL DETECTION OF CANCER, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment, the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Having now generally described the invention, the same will be more readily understood through reference to the following examples, which are provided by way of illustration and are not intended to be limiting of the present invention unless specified.

Example 1

Preparation of Monoclonal Antibodies

A mouse monoclonal antibody was produced from clones 3H7 or 2B6 with ATCC accession numbers PTA-4591 and PTA-4592, respectively. A mouse monoclonal antibody that specifically binds FcγRIIB with greater affinity than said monoclonal antibody binds FcγRIIA, was generated. Transgenic FcγRIIA mice (generated in Dr. Ravetch Laboratory, Rockefeller University) were immunized with FcγRIIB purified from supernatant of 293 cells that had been transfected with cDNA encoding the extracellular domain of the human FcγRIIB receptor, residues 1-180. Hybridoma cell lines from spleen cells of these mice were produced and screened for antibodies that specifically bind FcγRIIB with greater affinity than the antibodies bind FcγRIIA.

Antibody Screening and Characterization

Materials and Methods:

Supernatants from hybridoma cultures are screened for immunoreactivity against FcγRIIA or FcγRIIB using ELISA assays. In each case, the plate is coated with 100 ng/well of FcγRIIA or FcγRIIB. The binding of the antibody to the specific receptor is detected with goat anti-mouse HRP conjugated antibody by monitoring the absorbance at 650 nm.

In the blocking ELISA experiment, the ability of the antibody from the hybridoma supernatant to block binding of aggregated IgG to FcγRIIB is monitored. The plate is blocked with the appropriate "blocking agent", washed three times (200 μl/well) with wash buffer (PBS plus 0.1% Tween). The plate is pre-incubated with hybridoma supernatant for 1 hour at 37° C. Subsequent to blocking, a fixed amount of aggregated biotinylated human IgG (1 μg/well) is added to the wells to allow the aggregate to bind to the FcγRIIB receptor. This reaction is carried out for two hours at 37° C. Detection is then monitored, after additional washing, with streptavidin horseradish peroxidase conjugate, which detects the bound aggregated IgG. The absorbance at 650 nm is proportional to the bound aggregated IgG.

In a β-hexoaminidase release assay the ability of an antibody from the hybridoma supernatant to inhibit Fcε-induced release of β-hexoaminidase is monitored. RBL-2H3 cells are transfected with human FcγRIIB; cells are stimulated with various concentration of goat anti-mouse F(ab)$_2$ fragment ranging from 0.03 μg/mL to 30 μg/mL; sensitized with either mouse IgE alone (at 0.01 μg/mL) or with an anti-FcγRIIB antibody. After 1 hour incubation at 37° temperature, the cells are spun down; the supernatant is collected; and the cells are lysed. The β-hexoaminidase activity released in the supernatant is determined in a colorometric assay using p-nitrophenyl N-acetyl-β D-glucoasminide. The release β-hexoaminidase activity is expressed as a percentage of the released activity relative to the total activity.

BIAcore Analysis:

Antibody binding to CD32A-H131, CD32A-R131 or CD32B was analyzed by surface plasmon resonance in a BIAcore 3000 biosensor (Biacore AB, Uppsala, Sweden) by using soluble extracellular domains of the receptors expressed in 293H cells. The capturing antibody, a F(ab')2 fragment of a goat anti-mouse Fc-specific antibody (Jackson Immunoresearch, West Grove, Pa.), was immobilized on the CM-5 sensor chip according to the procedure recommended by the manufacturer. Briefly, the carboxyl groups on the sensor chip surface were activated with an injection of a solution containing 0.2M N-ethyl-N-(3diethylamino-propyl) carbodiimide and 0.05M N-hydroxy-succinimide. The F(ab')2 fragment was then injected over the activated CM-5 surface in 10 mM sodium-acetate, pH 5.0, at flow rate 5 μl/min for 420 sec, followed by 1 M ethanolamine for deactivation. Binding experiments were performed in HBS-P buffer containing 110 mM HEPES, pH 7.4, 150 mM NaCl, and 0.005% P20 surfactant. Each monoclonal antibody was captured on the CM-5 chip by injecting a 300 nM-antibody solution at flow rate 5 μl/min for 240 sec, followed by an injection of the monomeric soluble receptors at concentration of 100 nM and a flow rate 50 μl/min for 120 sec with dissociation time 180 sec. Regeneration of the F(ab')2 GAM surface was performed by pulse injection of 50 mM glycine, pH 1.5 and 50 mM NaOH. Reference curves were obtained by injection of each soluble receptor over the immobilized F(ab')2 GAM surface with no captured antibody. Reference curves were subtracted and responses were normalized to the same level of captured antibody. To obtain kinetic parameters of binding of soluble receptors to captured antibodies, binding curves to corresponding IgG at corresponding concentrations were subtracted. Resulted curves were analyzed by separate ka/kd fit. KD values were calculated as average of four curves at two different concentrations.

FACS Analysis

CHO cells, expressing FcγRIIB are stained with various antibodies and analyzed by FACS. In one series of experiment, the cells are directly labeled to determine if the monoclonal antibodies recognize the receptor.

In the blocking FACS experiment, the ability of the antibody from the hybridoma supernatant to block the binding of aggregated IgG to FcγRIIB is monitored. About 1 million cells (CHO cells expressing FcγRIIB) for each sample are incubated on ice for 30 minutes with 2 μg of the isotype control (mouse IgG1) or with the 2B6 or 3H7 antibody. Cells are washed once with PBS+1% BSA and incubated with 1 μg of aggregated biotinylated human IgG for 30 minutes on ice. Cells are washed and the secondary antibodies are added, goat anti-mouse-FITC to detect the bound antibody and Streptavidin-PE conjugated to detect the bound aggregated biotinylated human IgG and incubated on ice for 30 minutes. Cells are washed and analyzed by FACS.

B Lymphocytes are stained to detect the presence of FcγRIIB and CD20. 200 μl of "buffy coat" for each sample is incubated on ice with 2 μg of isotype control or the monoclonal antibodies, 2B6 or 3H7. Cells are washed once with PBS+1% BSA and incubated with 1l of goat anti mouse-PE antibody for 30 minutes on ice. Cells are washed once and CD20-FITC antibody (2 μg) is added to the samples and incubated on ice for 30 minutes. All samples are washed with PBS+1% BSA once and the cells are analyzed by FACS.

Human PBMCs were stained with 2B6, 3H7, and IV.3 antibodies, followed by a goat anti-mouse-Cyanine (Cy5)

conjugated antibody (two color staining using anti-CD20-FITC conjugated for B lymphocytes, anti-CD14-PE conjugated for monocytes, anti-CD56-PE conjugated for NK cells and anti-CD16-PE conjugated for granulocytes.

ADCC Assay $4-5 \times 10^6$ target cells expressing Her2/neu antigen (IGROV-1 or SKBR-3 cells) are labeled with bis(acetoxymethyl) 2,2':6',2''-terpyridine-t-6''-dicarboxylate (DELFIA BATDA Reagent, Perkin Elmer/Wallac). BATDA reagent is added to the cells and the mixture is incubated at 37° C. preferably under 5% $CO_2$, for at least 30 minutes. The cells are then washed with a physiological buffer, e.g., PBS with 0.125 mM sulfinpyrazole, and media containing 0.125 mM sulfinpyrazole. The labeled target cells are added to effector cells, e.g., PBMC, to produce effector:target ratios of approximately 50:1, 75:1, or 100:1. PBMC is isolated by layering whole blood onto Ficoll-Hypaque (Sigma) and spinning at room temperature for 30 mins at 500 g. The leukocyte layer is harvested as effectors for Europium-based ADCC assays. Frozen or freshly isolated elutriated monocytes (Advanced Biotechnologies, MD) is used as effectors with the tumor target cell lines at varying effector to target ratio of 100:1 to 10:1 and the concentration of the antibodies is titrated from 1-μg/ml. Monocytes obtained as frozen stocks stimulated with cytokines is used as effector cells in ADCC assays. If frozen monocytes perform optimally they will be routinely used otherwise fresh cells will be used. MDM will be prepared by treatment with cytokines GM-CSF or M-CSF that are known to enhance the viability and differentiation of monocytes in culture. MDM will be stimulated with cytokines and the expression of the various FcγRs (I, IIA, IIB, and IIIA) determined by FACS analysis.

The effector and target cells are incubated for at least two hours, and up to 16 hours, at 37° C., under 5% $CO_2$ in the presence of an anti-tumor antibody, specific for an antigen expressed on the target cells, Her2/neu, and in the presence or absence of an anti-FcγRIIB antibody. A chimeric 4D5 antibody that has been engineered to contain the N297A mutation which is used as a negative control since this antibody binds the tumor target cells via its variable region. Loss of glycosylation at this site abolishes binding of the Fc region of the antibody to FcγR. Commercially available human IgG1/k serves as an isotype control for the anti-FcγRIIB antibody. Cell supernatants are harvested and added to an acidic europium solution (e.g., DELFIA Europium Solution, Perkin Elmer/Wallac). The fluorescence of the Europium-TDA chelates formed is quantitated in a time-resolved fluorometer (e.g., Victor 1420, Perkin Elmer/Wallac). Maximal release (MR) and spontaneous release (SR) are determined by incubation of target cells with 1% TX-100 and media alone, respectively. Antibody independent cellular cytotoxicity (AICC) is measured by incubation of target and effector cells in the absence of antibody. Each assay is preferably performed in triplicate. The mean percentage specific lysis is calculated as: Experimental release (ADCC)-AICC)/(MR-SR)×100.

Example 2

Characterization of the Monoclonal Antibody Produced from the 3H7 Clone

The direct binding of different batches of hybridoma cultures to FcγRIIA and FcγRIIB were compared using an ELISA assay (FIG. 1A). Supernatants numbered 1, 4, 7, 9, and 3 were tested for specific binding and their binding was compared to a commercially available antibody, FL18.26. As shown in FIG. 1A, supernatant from clone 7 has the maximal binding to FcγRIIB, which is about four times higher under saturating conditions than the binding of the commercially available antibody to FcγRIIB. However, the supernatant from clone 7 has hardly any affinity for FcγRIIA, as seen in FIG. 1B, whereas the commercially available antibody binds FcγRIIA at least 4 times better.

Direct binding of the antibody produced from the 3H7 clone to FcγRIIA and FcγRIIB. The binding of crude 3H7 supernatant (FIG. 1C) and purified 3H7 supernatant was measured (FIG. 1D). In each case, the supernatant was supplied at a concentration of 70 μg/ml and diluted up to 6-fold. As shown in FIG. 1C, upon saturating conditions, the 3H7 supernatant binds FcγRIIB four times better than it binds FcγRIIA. Upon purification with a protein G column, the absolute binding of the 3H7 supernatant to each immunogen improves.

Blocking of aggregated human IgG binding to FcγRIIB by the antibody produced from the 3H7 clone. If the antibody present in the hybridoma supernatant binds FcγRIIB at the IgG binding site and blocks IgG binding, then the aggregated IgG cannot bind the receptor and hence no absorbance at 650 can be detected. The antibody in effect is a "blocking agent" that blocks the IgG binding site on FcγRIIB. As a control, the ELISA was carried out with no blocking, with a control supernatant, and with supernatant from the 3H7 clone. As shown in FIG. 2, the 3H7 supernatant completely blocks IgG binding, since aggregated IgG cannot bind the receptor as evident from the lack of absorbance at 650 nm. The control supernatant however fails to block IgG binding; aggregated IgG binds the receptor as evident by the reading at 650 nm. The control supernatant behaves similarly to the condition where no blocking was done.

Comparison of the direct binding of the antibody produced from the 3H7 clone to bacterial and mammalian FcγRIIB. As shown in FIG. 3, the supernatant from the 3H7 clone, binds comparably to mammalian and bacterial FcγRIIB. Upon saturating conditions, the 3H7 supernatant binds bacterial and mammalian FcγRIIB about three times better than it binds FcγRIIA. The monoclonal antibody from the 3H7 clone is thus able to specifically bind to mammalian FcγRIIB which has been post-transnationally modified (e.g., glycosylation).

Direct binding of the antibody produced from the 3H7 clone to FcγRIIA, FcγRIIB, and FcγRIIIA. The direct binding of supernatant from the hybridoma cultures from the 3H7 cell line to FcγRIIA, FcγRIIIA and FcγRIIB were compared using an ELISA assay (FIG. 4). The antibody produced from clone 3H7 has no affinity for FcγRIIIA, and binds FcγRIIB with about 4 times greater affinity than it binds FcγRIIA.

Example 3

Characterization of the Monoclonal Antibody Produced from the 2B6 Clone

Comparison of direct binding of the antibody produced from clone 2B6 compared to other three commercially available monoclonal antibodies against FcγRII. The binding of the antibody produced from clone 2B6 to FcγRIIA and FcγRIIB is compared to that of three other commercially available antibodies, AT10, FL18.26, and IV.3, against FcγRII in an ELISA assay. As seen in FIG. 5A, the antibody produced from clone 2B6 binds FcγRIIB up to 4.5 times better than the other commercially available antibodies. Additionally, the antibody produced from clone 2B6 has minimal affinity for FcγRIIA, whereas the other three commercially available antibodies bind FcγRIIA in a saturable manner and twice as much as the antibody from clone 2B6 binds FcγRIIA (FIG. 5B).

Blocking of aggregated human IgG to FcγRIIB by the antibody produced from clone 2B6. The ability of the antibody produced from clone 2B6 to block binding of the aggregated IgG to FcγRIIB was investigated by a blocking ELISA assay and compared to that of the antibody produced by clone 3H7. As shown in FIG. 6A, the control supernatant does not bind FcγRIIB on the IgG binding site and the aggregated IgG can bind the receptor and hence absorbance at 650 nm is maximal. Clone 3H7, however, blocks the IgG binding up to 75%. Clone 2B6 completely blocks the binding of the IgG binding site and does not allow the aggregated IgG to bind the receptor, and even at very high dilutions no absorbance is detected at 650 nm. FIG. 6B represents the data in a bar diagram.

Competition of 2B6 antibody and aggregated IgG in binding FcγRIIB using double-staining FACS assays. A double staining FACS assay was used to characterize the antibody produced from clone 2B6 in CHO cells that had been transfected with full-length mammalian FcγRIIB.

As shown in FIG. 7C, the antibody produced from clone 2B6 effectively blocks the binding of aggregated IgG to the FcγRIIB receptor in CHO cells since no staining is observed for biotinylated aggregated IgG after the cells were pre-incubated with the monoclonal antibody. The cells are only stained in the lower right panel, indicating that most of the cells were bound to the monoclonal antibody from the 2B6 clone. In the control experiments (FIG. 7A), using IgG1 as the isotype control, when the cells are stained with the isotype labeled IgG, no staining is observed since the monomeric IgG does not bind FcγRIIB with any detectable affinity, whereas in FIG. 7B, about 60% of the cells are stained with aggregated IgG, which is capable of binding FcγRIIB.

Specificity and selectivity for CD32B by surface plasmon resonance analysis. Specificity and relative affinities for human CD32B vs. CD32A were studied by surface plasmon resonance analysis. All antibodies were captured on the chip surface by an immobilized F(ab')2 fragment of a goat anti-mouse antibody. Soluble monomeric forms of human CD32A-H131, CD32A-R131 or CD32B were injected to monitor the interaction with the captured antibodies. As shown in FIGS. 8A-C, 2B6 interacted with CD32B (FIG. 8A) in the absence of detectable binding to CD32A (FIGS. 8B and 8C). A well-characterized commercial anti-huCD32 antibody, KB61, was also used in the assay for comparison. KB61 showed binding to both receptors. Therefore, 2B6 reacts exclusively with CD32B in the absence of detectable CD32A recognition.

Monoclonal anti-FcγRIIB antibodies and CD20 co-stain Human B Lymphocytes. A double staining FACS assay was used to characterize the antibody produced from clones 2B6 and 3H7 in human B lymphocytes. Cells were stained with anti-CD20 antibody which was FITC conjugated, to select the B-lymphocyte population, as well as the antibodies produced from clone 3H7 and 2B6, labeled with goat anti-mouse peroxidase. The horizontal axis represents the intensity of the anti-CD20 antibody fluorescence and the vertical axis represents the intensity of the monoclonal antibody fluorescence. As shown in FIGS. 9B and 9C, cells are double stained with the anti-CD20 antibody as well as the antibodies produced from clones 2B6 and 3H7, however, the antibody produced from clone 2B6 shows more intense staining than that produced from clone 3H7. FIG. 9A shows the staining of the isotype control, mouse IgG1.

Staining of CHO cells expressing FcγRIIB. CHO cells, stably expressing FcγRIIB were stained with IgG1 isotype control (FIG. 10A) or with supernatant from the 3H7 hybridoma (FIG. 10B). Goat anti-mouse peroxidase conjugated antibody was used as a secondary antibody. The cells were then analyzed by FACS; cells that are stained with the supernatant from the 3H7 hybridoma show a strong fluorescence signal and a peak shift to the right; indicating the detection of FcγRIIB in the CHO cells by the supernatant produced from the 3H7 hybridoma. Cells stained with the supernatant from the 2B6 hybridoma, also show a significant fluorescence, as compared to cells stained with IgG1, and a peak shift to the right, indicating the detection of FcγRIIB in the CHO cells by the supernatant produced from the 2B6 hybridoma.

CHO cells expressing hyFcγRIIB were incubated with the anti CD32B antibodies, 2B6 or 3H7. Cells were washed and 9 μg/ml of aggregated human IgG were added to the cells on ice. The human aggregated IgG were detected with goat anti human-IgG GITC conjugated. Samples were analyzed by FACS cells labeled with 2B6 or 3H7 showed a significant fluorescence peak in the presence of aggregated human IgG (FIG. 11). 2BG antibody completely blocks binding of aggregated IgG as evidenced by the fluorescent peak shift to the left. Whereas the 3H7 antibody partially blocks binding of aggregated IgG as shown by the intermediate fluorescent peak. The other antibodies, 1D5, 1F2, 2E1, 2H9, and 2D11 do not block binding of aggregated IgG. The amount of each antibody bound to the receptor on the cells was also detected (inset) on a separate set of samples using a goat anti-mouse PE conjugated antibody.

Recognition of CD32B on the cell surface. Experiments were carried out to test the ability of the antibodies to discriminate CD32B from CD32A expressed on cells and to recognize the native CD32B molecule on human cell lines. To assess the antibodies' specificity, 2B6 and the pan-anti-CD32 antibody, FLI.826, were tested in FACS analysis with 293-HEK human cells stably transfected with expression vectors encoding the human CD32A-$R^{131}$ or CD32B proteins, Daudi, Raji and THP-1 (FIGS. 12A-12J).

2B6 reacted with 293-HEK transfected with CD32B as well as Daudi and Raji cells (Burkitt's lymphoma-derived lymphoblastoid lines expressing CD32B), while it did not stain THP1 monocytic cells lines, which are known to express exclusively CD32A ($H^{131}$ form). By contrast, FLI8.26 reacted with all cell lines indicating no preference between CD32A and CD32B.

FACS profiles using 2B6, 3H7, and IV.3 antibodies on human peripheral blood leukocyte. The FACS profile of the anti-FcγRIIB antibodies and IV.3 antibody shows their ability to discriminate between the two FcγRII isoforms, IIB and IIA expressed on the human hematopoietic cells. IV.3, one of the first antibodies (commercially available) used to define FcγRII, shows preferential binding to FcγRIIA.

There are characteristic and functionally significant differences in isoform expression between major human hematopoietic cell types. Human B lymphocytes express exclusively the huFcγRIIB isoform while human monocytes express predominantly the huFcγRIIA isoform. Granulocytes are strongly positive for FcγRIIA and limited evidence suggest that FcγRIIB is marginally expressed in this population (Pricop et al., (2000) *"Differential Modulation Of Stimulatory And Inhibitory Fc Gamma Receptors On Human Monocytes By Th1 And Th2 Cytokines,"* J. Immunol. 166:531-537). To further characterize the reactivity of the anti-FcγRIIB antibodies, huPBL were stained with the anti-FcγRIIB antibodies 2B6 and 3H7 and with IV.3, which preferentially (but not exclusively) recognizes the FcγRIIA isoform of the receptor, leukocytes populations were selected based on FSC vs. SSC gating (FIGS. 13A-13P) and identified with specific markers: CD20 (B cells) (FIGS. 13B, 13D and 13F), CD56 (FIGS. 13I and 13J) or CD16 (NK cells, lymphocyte gate), CD14 (monocytes) (FIGS. 13K, 13M and 13O) and CD16 (granulocytes, granulocyte gate) (FIGS. 13C, 13E, 13G, 13L, 13N and 13P). CD20-positive cells (B cells) were uniformly stained with 2B6, 3H7. IV.3 also stained the majority of CD20-positive cells. No staining was observed for CD16/CD56-positive NK cells, while only a fraction of CD14-(monocytes) and CD16-(granulocytes) positive cells were stained with 2B6, 3H7. In contrast, IV.3 strongly stained the vast majority of CD-14-positive monocytes and the totality of CD16-positive granulocytes (FIGS. 13J and 13O-P). This differential pattern of reactivity between 2B6 and 3H7 on the one side and IV.3 on the other indicates that the new monoclonal antibodies react strongly with FcγRIIB, but not with FCγRIIA, while IV.3 cannot discriminate between FcγRIIA and FcγRIIB isoforms in vivo.

Inhibition Of β-Hexosaminidase Release By 2B6. To examine the potential role of an anti-CD32B antibody in modulating immediate-type hypersensitivity reactions, the effect of inducing a co-aggregation of activating (FcεRI) and inhibitory receptors (FcγRIIB) was investigated. The rat basophilic leukemia cell line, RBL-2H3, was chosen as a model system due its extensive use in the art as an allergy model designed to study the underlying mechanism of IgE-mediated mast cell activation (Ott et al. (2002) "*Downstream of Kinase, p62dok, Is a Mediator of FcRIIB Inhibition of FcRI Signaling*," J. Immunol. 168:4430-9). Transfected RBL cells expressing FcγRIIB were suspended in fresh media containing 0.01 μg/ml of murine anti-DNP IgE and plated in 96 well plates at a concentration of 2×104 cells/well. After overnight incubation at 37° C. in the presence of CO2, cells were washed twice with pre-warmed release buffer (10 mM HEPES, 137 mM NaCl, 2.7 mM KCl, 0.4 mM sodium phosphate monobasic, 5.6 mM glucose, 1.8 mM calcium chloride, 1.3 mM magnesium sulfate and 0.04% BSA, pH 7.4) and treated at 37° C. with serial dilutions of BSA-DNP-FITC complexed with chimeric 4-4-20 antibody or BSA-DNP-FITC complexed with chimeric D265A 4-4-20 antibody in 100 μL buffer/well in the presence of 2B6 antibody, 1F2 antibody or murine IgG1 isotype control. Alternatively cells were challenged with F(ab')2 fragments of a polyclonal goat anti-mouse IgG to aggregate FcεRI (Genzyme). Crosslinking of the FcεRs occurs because the polyclonal antibody recognizes the light chain of the murine IgE antibody bound to FcεRI. This experiment is schematically shown in FIG. 14A.

The reaction was stopped after 30 minutes by placing the cells on ice. 50 μL of supernatant from each well was removed and the cells were osmotically lysed. Cell lysates were incubated with p-Nitrophenyl-N-Acetyl-beta-D-glucosaminide (5 mM) for 90 minutes, the reaction was stopped with glycine (0.1M, pH 10.4) and the absorbance at 405 nm was measured after three minutes. The percentage of β-hexosaminidase released was calculated as total media OD/total supernatant OD/total supernatant+total cell lysate OD.

Results

To test the ability of ch2B6 to limit the inflammatory or allergic responses triggered by the activating receptor, F(ab')2 fragments were used to coaggregate activating receptors or combinations of inhibitory and activating receptors as described above. When cells were sensitized only with IgE, the F(ab')2 fragments of polyclonal goat anti-mouse IgG recognized the light chain of the murine IgE bound to FcεRI, aggregated these activating receptors, and β-hexosaminidase release, a marker for degranulation (Aketani et al. (2001) "*Correlation Between Cytosolic Calcium Concentration And Degranulation In RBL-2H3 Cells In The Presence Of Various Concentrations Of Antigen-Specific IgEs*," Immunol. Lett. 75: 185-189), increased with increasing IgE (FIG. 14B). In contrast, when cells were sensitized with IgE after incubation with 2B6 or 1F2, the F(ab')2 fragment, in effect, co-crosslinked the rat FcεRI with CD32B and resulted in a significant decrease in β-hexosaminidase release when compared to sensitized cells preincubated with an irrelevant murine IgG1 isotype control matched antibody. No degranulation over background levels was detected in cells treated with the anti-CD32B antibodies alone (data not shown). Therefore, the human inhibitory receptor, CD32B, can induce a negative signal in rat basophilic cells, validating these transfectants as a model for the study of anti-human CD32B antibodies.

To test whether anti-CD32B antibodies may also be able to improve such reactions, the co-engagement of the inhibitory receptor with an activating receptor was prevented by a blockade of CD32B. Co-engagement of these receptors is thought to physiologically occur when antigens simultaneously interact with surface-bound IgE through antigenic epitopes and with CD32B through Fc determinants of antigen-specific IgG complexed with the antigen itself (FIG. 15A). To mimic this situation, the RBL-2H3 model was manipulated to obtain co-engagement of FcεRI and CD32B by developing an antigen surrogate that could be complexed with IgE, IgG, or both. HuCD32B+RBL-2H3 cells were sensitized with a murine IgE anti-DNP monoclonal antibody. The challenge antigen, BSA-DNP, was further conjugated to FITC to provide additional epitopes recognized by a chimeric version of 4-4-20, a murine anti-fluorescein antibody whose Fc portion had been substituted with human IgG1 Fc to allow for optimal binding to human CD32B. A chimeric version of 4-4-20 with a human IgG1 Fc bearing a mutation in position 265 (asparagine to alanine) was also generated. This chimeric D265A 4-4-20 antibody lacks the ability to bind FcγRs, including CD32B. BSA-DNP-FITC induced a dose-dependent release of β-hexosaminidase from IgE-sensitized RBL-2H3 cells (FIG. 15C).

The same extent of degranulation was observed when the challenge antigen was BSA-DNP-FITC complexed with chimeric D265A 4-4-20, showing that BSA-DNP-FITC-chimeric D265A 4-4-20, as expected, was unable to recruit CD32B to the activating receptor. In the presence of BSA-DNP-FITC complexed with chimeric 4-4-20, a substantial reduction in β-hexosaminidase release was observed (FIG. 15B). Thus, the polyvalent antigen is capable of aggregating FcεRI with ensuing degranulation, while the surrogate antigen complexed with IgG co-aggregates CD32B resulting in diminished degranulation. To block CD32B while minimizing the chances of simultaneously engaging the FcγR, F(ab)2 fragments of 2B6 where prepared and cells pre-incubated with 2B6 F(ab)2, prior to activation with the immunocomplexed antigen. Under these conditions, the percentage of β-hexosaminidase release was restored to the maximum levels observed in cells treated with the polyvalent antigen alone (FIG. 15C). At higher concentrations of immunocomplexed antigen a diminished degranulation was still observed, presumably due to competition between ch4-4-20 and 2B6 F(ab)2 for the Fc binding site of CD32B. These data show that 2B6 is capable of functionally blocking the Fc binding site of CD32B, preventing the co-ligation of activating and inhibitory receptors by an IgG-complexed antigen. The proposed mode of action may have use in the regulation of immunecomplex-mediated cell activation.

Example 4

Her2/neu Expression in Ovarian and Breast Carcinoma Cell Lines

In order to determine whether IGROV-1, OVCAR-8, and SKBR-3 cells express the Her2/neu antigen, cells were stained with either purified 4D5 or ch4D5 antibody on ice; the unbound antibody was washed out with PBS/BSA buffer containing sodium azide, and the binding of 4D5 or ch4D5 was detected by goat anti-mouse or goat anti-human antibody conjugated to PE (Jackson Laboratories), respectively. An irrelevant IgG1 antibody (Becton Dickinson) served as a control for non-specific binding. As shown in FIGS. 16A-16C, the ovarian tumor cell lines express less Her2/neu antigens than the breast carcinoma cell line and evaluating these cell lines in parallel will determine the stringency of tumor clearance by an anti-FcγRIIB antibody of the invention.

Human monocytes are the effector population involved in ADCC that express both activating and inhibitory receptors. The expression of FcγRs was tested by FACS analysis using several lots of frozen monocytes as these cells will be adoptively transferred as effectors to investigate the role of ch2B6 in tumor clearance. Commercially obtained frozen elutriated monocytes were thawed in basal medium containing 10% human AB serum and in basal medium with human serum and 25-50 ng/ml GM-CSF. Cells were either stained directly or allowed to mature to macrophages for 7-8 days (MDM), lifted off the plastic, and then stained with IV.3-FITC (anti-hu FcγRIIA), 32.2-FITC (anti-FcγRI), CD16-PE (Pharmingen) or 3G8 (anti-FcγRIII)-goat anti-mouse-PE, 3H7 (anti-FcγRIIB), and CD14 marker for monocytes (Pharmingen), along with relevant isotype controls. A representative FACS profile of MDM from two donors, depicting FcγR expression on freshly thawed monocytes and cultured monocytes, is shown in FIGS. 17A-17C.

These results indicate that FcγRIIB is modestly expressed in monocytes (5-30% depending on the donor). However, this expression increases as they mature into macrophages. Preliminary data show that tumor-infiltrating macrophages in human tumor specimens are positively stained for FcγRIIB (data not shown). The pattern of FcγRs and the ability to morphologically differentiate into macrophages was found to be reproducible in several lots of frozen monocytes. These data indicate that this source of cells is adequate for adoptive transfer experiments.

Ch4D5 mediates effective ADCC with ovarian and breast cancer cells lines using PBMC. The ADCC activity of anti-Her2/neu antibody was tested in a europium based assay. The ovarian cell line, IGROV-1, and the breast cancer cell line, SKBR-3, were used as labeled targets in a 4 hour assay with human PBL as effector cells. FIGS. 18A and 18B indicate that ch4D5 is functionally active in mediating lysis of targets expressing Her2/neu. The effect of an antibody of the invention on the ADCC activity of the anti-Her2/neu antibody is subsequently measured.

Example 5

In Vitro ADCC Assay

A chimeric anti-CD32B antibody (ch2B6) and its aglycosylated form (ch2B6Agly) were tested for the ability to mediate in vitro antibody dependent cell-mediated cytotoxicity (ADCC) against CD32B-expressing, B-cell lymphoma lines, Daudi and Raji. A humanized anti-CD32B antibody (h2B6) and its aglycosylated form (hu2B6YA) were also tested in Daudi cells.

The protocol for assessment of antibody dependent cellular cytotoxicity (ADCC) is similar to that previously described in (Ding et al. (1998) "*Two Human T Cell Receptors Bind In A Similar Diagonal Mode To The HLA-A2/Tax Peptide Complex Using Different TCR Amino Acids*," Immunity 8:403-411) and described herein. Briefly, target cells from the CD32B expressing B-cell lymphoma lines, Daudi and Raji, were labeled with the europium chelate bis(acetoxymethyl) 2,2':6', 2"-terpyridine-6,6"-dicarboxylate (DELFIA BATDA Reagent, Perkin Elmer/Wallac) or Indium-111. The labeled target cells were then opsonized (coated) with either chimeric anti-CD32B (ch2B6) or aglycosylated chimeric anti-CD32B (ch2B6Agly) antibodies at the indicated concentrations as shown in FIGS. 20 and 21 or with ch2B6, ch2B6Agly, hu2B6 and hu2b6YA as shown in FIG. 21. Peripheral blood mononuclear cells (PBMC), isolated by Ficoll-Paque (Amersham Pharmacia) gradient centrifugation, were used as effector cells (Effector to Target ratio of 75 to 1). Following a 3.5 hour incubation at 37° C., 5% CO2, cell supernatants were harvested and added to an acidic europium solution (DELFIA Europium Solution, Perkin Elmer/Wallace). The fluorescence of the Europium-TDA chelates formed was quantitated in a time-resolved fluorometer (Victor2 1420, Perkin Elmer/Wallac) or gamma counter (Wizard 1470, Wallace). Maximal release (MR) and spontaneous release (SR) were determined by incubation of target cells with 2% Triton X-100 and media alone, respectively. Antibody independent cellular cytotoxicity (AICC) was measured by incubation of target and effector cells in the absence of antibody. Each assay is performed in triplicate. The mean percentage specific lysis is calculated as: (ADCC-AICC)/(MR-SR)×100.

As shown in FIGS. 20 and 21, chimeric anti-CD32B antibody ch2B6 mediates ADCC in vitro against CD32B-expressing, B-cell lymphoma lines, Daudi and Raji, at concentrations greater than approximately 10 ng/ml. This activity is likely to be Fc-dependent since the aglycoslyated version of this antibody, ch2B6Agly, which is unable to interact with the Fc-receptors has reduced activity in this assay. As shown in FIG. 22, the human aglycosylated form is able to interact with the Fc-receptors.

Example 6

In Vivo ADCC Assay

Six to eight week old female Balb/c nude mice (Jackson Laboratories, Bar Harbor, Me.; Taconic) is utilized for establishing the xenograft ovarian and breast carcinoma models. Mice are maintained at BIOCON, Inc. Rockville, Md. (see attached protocol). Mice are housed in Biosafety Level-2 facilities for the xenograft model using the ascites-derived ovarian cells and pleural effusion-derived breast cancer cells as sources of tumors. Mice are placed in groups of 4 for these experiments and monitored three times weekly. The weight of the mice and survival time are recorded and criteria for growing tumors is abdominal distention and palpable tumors. Mice showing signs of visible discomfort or that reach 5 grams in tumor weight are euthanized with carbon dioxide and autopsied. The antibody-treated animals are placed under observation for an additional two months after the control group.

Establishment of the xenograft tumor model with tumor cell lines. In order to establish the xenograft tumor model, $5 \times 10^6$ viable IGROV-1 or SKBR-3 cells are injected s.c into three age- and weight-matched female nude athymic mice with Matrigel (Becton Dickinson). The estimated weight of the tumor is calculated by the formula: length×(width)$^2$/2 not to exceed 3 grams. For in vivo passaging of cells for expansion, anchorage-dependent tumor is isolated and the cells dissociated by adding 1 μg of collagenase (Sigma) per gram of tumor at 37° C. overnight.

Injection of IGROV-1 cells subcutaneously gives rise to fast growing tumors while the intraperitoneal route induces a peritoneal carcinomatosis which kills the mice in 2 months. Since the IGROV-1 cells form tumors within 5 weeks, at day 1 after tumor cell injection, monocytes as effectors are co-injected i.p. along with therapeutic antibodies ch4D5 and ch2B6 at 4 μg each per gm of mouse body weight (mbw) (Table 8). The initial injection is followed by weekly injections of antibodies for 4-6 weeks thereafter. Human effectors cells are replenished once in two weeks. A group of mice will receive no therapeutic antibody but will be injected with ch4D5 N297A and human IgG1 as isotype control antibodies for the anti-tumor and ch2B6 antibody, respectively.

and autopsied. The antibody-treated animals are followed for two months after this time-point.

Example 7

In Vivo Activity of FcγRIIB Antibodies in Xenograft Murine Model with Human Primary Ovarian and Breast Carcinoma Derived Cells Primary tumors are established from primary ovarian and breast cancers by transferring tumors cells isolated from exudates from patients with carcinomatosis. In order to translate these studies into the clinic, the xenograft model are evaluated with ascites- and pleural effusion-derived tumor cells from two ovarian and two breast carcinoma patients, respectively. Pleural effusion, as a source of breast cancer cells, and implantation of malignant breast tissue have been used to establish xenograft murine models successfully, see, e.g., Sakakibara et al. (1996) "*Growth And Metastasis Of Surgical*

TABLE 8

Exemplary Experimental Set Up In Mice

| 8 mice per group | Tumor cell s.c day 0 | Monocytes i.p at day 1 | ch4D5 (4 μg/gm of mbw day 1 i.p.) | ch4D5 (N297A at 4 μg/gm of mbw day 1 i.p.) | ch2B6 (N297A at 4 μg/gm of mbw day 1 i.p.) | Human (IgG1 4 μg/gm of mbw day 1 i.p.) |
|---|---|---|---|---|---|---|
| A | + | − | − | − | − | − |
| B | + | + | − | − | − | − |
| C | + | + | + | − | − | − |
| D | + | + | + | − | + | − |
| E | + | + | − | − | + | − |
| F | + | + | − | + | − | + |

As shown in Table 8, 6 groups of 8 mice each are required for testing the role of an anti-FcγRIIB antibody in tumor clearance with one target and effector combination, with two different combinations of the antibody concentrations. These groups are (A) tumor cells, (B) tumor cells and monocytes, (C) tumor cells, monocytes, anti-tumor antibody, ch4D5, (D) tumor cells, monocytes, anti-tumor antibody ch4D5, and an anti-FcγRIIB antibody, e.g., ch2B6, (E) tumor cells, monocytes, and an anti-FcγRIIB antibody, e.g., ch2B6, and (F) tumor cells, monocytes, ch4D5 N297A, and human IgG1. Various combination of antibody concentration can be tested in similar schemes.

Studies using the breast cancer cell line, SKBR-3, are carried out in parallel with the IGROV-1 model as SKBR-3 cells over-express Her2/neu. This will increase the stringency of the evaluation of the role of anti-FcγRIIB antibody in tumor clearance. Based on the outcome of the tumor clearance studies with the IGROV-1 cells, modifications are made to experimental design of future experiments with other targets.

The endpoint of the xenograft tumor model is determined based on the size of the tumors (weight of mice), survival time, and histology report for each group in Table 8. Mice are monitored three times a week; criteria for growing tumors are abdominal distention and presence of palpable masses in the peritoneal cavity. Estimates of tumor weight versus days after inoculation is calculated. Based on these three criteria from group D, mice in Table 8 versus the other groups of mice will define the role of anti-FcγRIIB antibodies in enhancement of tumor clearance. Mice that show signs of visible pain or reach 5 grams of tumor weight are euthanized with carbon dioxide

*Specimens Of Human Breast Carcinomas In Scid Mice*," Cancer J. Sci. Am. 2: 291-300, which is incorporated herein by reference in its entirety. These studies will determine the broad range application of the anti-FcγRIIB antibody in tumor clearance of primary cells. Tumor clearance is tested using anti-tumor antibody, ch4D5 and anti-FcγRIIB antibody, e.g., ch2B6, in Balb/c nude mouse model with adoptively transferred human monocytes.

Human ascites and pleural effusion-derived primary tumor cells. Ascites from patients with ovarian cancer and pleural effusions from breast cancer patients are provided by the St. Agnes Cancer Center, Baltimore, Md. The ascites and pleural effusion from patients may contain 40-50% tumor cells and samples with a high expression of Her2neu+ tumor cells will be used to establish the xenograft models.

Ascites and pleural effusion samples are tested for expression of Her2/neu on neoplastic cells prior to establishment of the xenograft tumor model. The percentage of the neoplastic cells versus other cellular subsets that may influence the establishment of the tumor model will be determined. Ascites and pleural effusion from patients with ovarian and breast cancer, respectively are routinely analyzed to determine the level of expression of Her2/neu+ on the neoplastic cells. FACS analysis is used to determine the percentage of Her2/neu+ neoplastic cells in the clinical samples. Samples with high percentage of Her2/neu+ neoplastic cells are selected for initiation of tumors in Balb/c mice.

Histochemistry and Immunochemistry. Histochemistry and immunohistochemistry is performed on ascites and pleural effusion of patients with ovarian carcinoma to analyze structural characteristics of the neoplasia. The markers that are monitored are cytokeratin (to identify ovarian neoplastic and mesothelial cells from inflammatory and mesenchymal cells); calretinin (to separate mesothelial from Her2/neu positive neoplastic cells); and CD45 (to separate inflammatory cells from the rest of the cell population in the samples). Additional markers that will be followed will include CD3 (T cells), CD20 (B cells), CD56 (NK cells), and CD14 (monocytes).

For immunohistochemistry staining, frozen sections and paraffinized tissues are prepared by standard techniques. The frozen as well as the de-paraffinized sections are stained in a similar staining protocol. The endogenous peroxidase of the tissues is quenched by immersing the slides in 3% hydrogen peroxide and washed with PBS for 5 minutes. Sections are blocked and the primary antibody ch4D5 is added in blocking serum for 30 minutes followed by washing the samples with PBS three times. The secondary anti-human antibody conjugated with biotin is added for 30 minutes and the slides are washed in PBS for 5 minutes. Avidin-Biotin peroxidase complex (Vector Labs) is added for 30 minutes followed by washing. The color is developed by incubating the slides in fresh substrate DAB solution and the reaction is stopped by washing in tap water. For H& E staining, the slides are deparaffinized and then hydrated in different alcohol concentrations. The slides are washed in tap water and placed in hematoxylin for 5 minutes. Excess stain is removed with acid-alcohol, followed by ammonia, and water. The slides are placed in Eosin and followed by 90 to 100% alcohol washes for dehydration. Finally, the slides are placed in xylene and mounted with fixative for long-term storage. In all cases, the percentage of tumor cells is determined by Papanicolaou stain.

Histochemical Staining. Ascites from two different patients with ovarian carcinoma were stained by Hematoxylin and Eosin (H & E) and Giemsa to analyze the presence of tumor cells and other cellular types. The result of the histochemical staining is shown in FIG. 19.

Murine Models. Samples from ovarian carcinoma patients are processed by spinning down the ascites at 6370×g for 20 minutes at 4° C., lysing the red blood cells followed by washing the cells with PBS. Based on the percentage of Her2/neu+tumor cells in each sample, two samples, a median and high expressor are selected for s.c inoculation to establish the xenograft model to evaluate the role of anti-FcγRIIB antibody, in clearance of tumors. It has been reported that tumor cells make up 40-50% of the cellular subset of unprocessed ascites, and after purification ~10-50×10$^6$ tumor cells were obtained from 2 liters of ascites (Barker et al. (2001) "*An Immunomagnetic-Based Method For The Purification Of Ovarian Cancer Cells From Patient-Derived Ascites*," Gynecol. Oncol. 82: 57-6382: 57-63). The isolated ascites cells are injected i.p into mice to expand the cells. Approximately 10 mice will be injected i.p and each mouse ascites further passaged into two mice each to obtain ascites from a total of 20 mice, which is used to inject a group of 80 mice. Pleural effusion is handled in a manner similar to ascites and Her2/neu+tumor cells are injected into the upper right and left mammary pads in matrigel. After s.c inoculation of tumor cells, mice are followed for clinical and anatomical changes. As needed, mice may be necropsied to correlate total tumor burden with specific organ localization.

Example 8

Effect of CH2B6 on Tumor Growth

Experimental design. Balb/c Nude female mice (Taconic, Md.) were injected at day 0 with 5×10$^6$ Daudi cells subcutaneously. Mice (5 mice per group) also received i.p. injection of PBS (negative control), 10 μg/g ch4.4.20 (anti-FITC antibody, negative control), 10 μg/g RITUXAN® (rituximab) (positive control) or 10 μg/g ch2B6 once a week starting at day 0. Mice were observed twice a week following injection and tumor size (length and width) was determined using a caliper. Tumor size in mg was estimated using the formula: (length×width$^2$)/2.

RESULTS. As shown in FIG. 23, Daudi cells form subcutaneous tumors in Balb/c nude females starting around day 21 post tumor cell injection. At day 35, subcutaneous tumors were detected in mice receiving PBS (5 mice out of 5) or 10 μg/g ch4.4.20 (5 mice out of 5). Tumors were rarely detected in mice receiving 10 μg/g RITUXAN® (rituximab) (1 mouse out of 5) and were not detected in mice receiving 10 μg/g ch2B6 (0 mice out of 5).

Example 9

Effect of CH2B6 Variants on Tumor Growth in a Murine Xenograft Model

Experimental design. Eight week old Balb/c FoxN1 female mice (Taconic, Germantown, N.Y.) were injected subcutaneously at day 0 with 5×106 Daudi cells as well as intra-peritoneally with 2B6 antibody variants (ch2B6, chN297Q, h2B6, h2B6YA, h2B6YA 31/60, h2B6YA 38/60, h2B6YA 55/60, or h2B6 YA 71 at 2.5 μg, 7.5 μg, or 25 μg), Rituximab (positive control at 2.5 μg, 7.5 μg, 25 μg, or 250 μg) or PBS (negative control). Mice were then treated with antibodies or PBS once a week until day 42 (total of 7 injections) and tumor size was measured twice a week using a caliper. Tumor weight was estimated using the formula: (width$^2$×length)/2.

RESULTS. To evaluate the efficacy of anti-CD32B mAb variants in the prevention of tumor cell growth in vivo, Balb/c FoxN1 mice were simultaneously injected with Daudi cells and anti-CD32B mAb variants (FIGS. 24A-24G). Treatment with the positive control, Rituximab, significantly reduced tumor cell growth in a dose dependent fashion (FIG. 24A). Three different variants of anti-CD32B mAb 2B6 (chimeric 2B6 (ch2B6), humanized 2B6 (h2B6), and a variant in the Fv region (h2B6YA)) were all effective at slowing tumor growth (FIG. 24B). The h2B6YA variant showed a remarkable reduction in tumor growth at a dose of 2.5 μg (0.1 μg/gm). The same dose of Rituximab was not as effective at preventing tumor growth. Four different h2B6YA mAb variants with Fc mutations (h2B6YA 31/60, h2B6YA 38/60, h2B6YA 55/60, and h2B6YA 71) were analyzed to determine if anti-tumor activity in vivo could be improved. Mutants h2B6YA 31/60, h2B6YA 38/60, and h2B6YA 55/60 functioned as well or better than h2B6YA, which contained a wild type Fc (FIGS. 24C, 24D, 24E, and 24F). Mutant h2B6YA 71 showed dose independent activity (FIG. 24G). Tumor cell growth was slowed at doses of 2.5 μg and 25 μg; however, little or no effect on tumor growth was noted at the 7.5 μg dose (FIG. 24G).

These results demonstrate that h2B6YA 31/60 and h2B6YA 55/60 have improved in vivo anti-tumor activity compared to ch2B6 or h2B6YA.

Example 10

Ex Vivo Staining of Daudi for CD20 and CD32B

Experimental design. Daudi tumors were collected from mice treated with h2B6 or h2B6YA at 25 μg. CD20 and CD32B expression was compared with those of Daudi cell expanded in vitro. FACS analysis was performed as described herein.

RESULTS. As shown in FIGS. 25A-25I, cells expanded in vivo maintain CD20 and CD32B expression even after anti-CD32B treatment.

Example 11

Expression of CD32B on B-CLL Cells

The ability of CD32B-specific antibodies to react with CD32B on cells isolated from patients with B-CLL was tested by staining isolated cells in FACS analysis.

Protocol for isolating B-cells from patients. Mononuclear leukocytes from peripheral blood leukocytes from normal donors and B-cell neoplasia patients were isolated by using Ficoll-Paque PLUS (Amesrham Pharmacia Biotech) gradient centrifugation and cryopreserved in aliquots in liquid nitrogen. An aliquot of freshly isolated PBMCs from each patient was washed in PBS containing 10% human serum and analyzed immediately for CD32B expression by standard FACS analysis. Single-cell suspension from lymph node biopsy specimens will be prepared in similar manner, will be immediately analyzed, and will be cryopreserved in liquid nitrogen.

Two cytospin slides were obtained from each samples and one stained immediately with May-Grunwald Giemsa (MGG) for morphological evaluation. Prior to analysis, an aliquot of patient's cells was thawed, the viability evaluated upon thawing and, if necessary (viability upon recovery <80%), subjected to Ficoll-Paque PLUS centrifugation. The amount of tumor cells was estimated by clonality by using anti-kappa or lambda chain antibodies in FACS analysis. Leukocyte phenotyping was performed by using directed conjugated anti-CD3, CD20, CD56, CD14, and CD16 antibodies and proper FSC and SCC gating. B-CLL B-cells were further analyzed for CD5, CD23, CD25, CD27, CD38, CD69, and CD71 (Damle et al. (2002) "*B-Cell Chronic Lymphocytic Leukemia Cells Express A Surface Membrane Phenotype Of Activated, Antigen-Experienced B Lymphocytes*," Blood 99:4087-4093; Chiorazzi et al. (2003) "*B Cell Chronic Lymphocytic Leukemia: Lessons Learned From Studies Of The B Cell Antigen Receptor*," Ann. Rev. Immunol. 21:841-894). Computerized logs were maintained recording the number of vials, number of cells per vial, and cell viability before and after cryopreservation, number of tumor cells or leukocyte phenotype.

Protocol for FACS analysis. Cells were incubated with the anti-CD32B monoclonal antibody, 2B6, followed by a secondary (Cy5 conjugated) goat-anti mouse (Fab)2 fragment antibody. After washes, FITC or PE-conjugated lineage-specific antibodies (anti-CD3, CD19, CD 20 and CD5) were added and the samples were analyzed by using FACSCalibur in a two-color format. CD3-positive cells (T cells) are used as an internal control as they do not express CD32B and do not react with 2B6 antibody. CD20, CD19 and CD5 antibodies identify B cell lineage sub-populations. Preliminary studies were conducted in >10 healthy human subjects to calibrate the amount of individual anti-CD32B antibodies based on the reactivity with the donor's B cells identified by CD20-positivity. For each antibody, the smallest amount of antibody that gave 100% reactivity and the highest MCF value in titration experiments was selected for subsequent use.

RESULTS. As shown in FIG. 26, B cells isolated from B-CLL patients stained intensely with anti-CD32B antibodies. Cells from all five patients are consistently CD32B-positive being reactive with 2B6 antibody, but express B cell-lineage markers only to various degrees. The results indicate that CD32B is expressed on B-cells isolated from patients with B-CLL.

Example 12

Expression of CD32B in Lymph Nodes from Patients with Non-Hodgkin's Lymphoma

To investigate expression of CD32B in lymph nodes from patients with non-Hodgkin's lymphomas, histological analysis and immunohistochemistry was performed on a series of lymphatic tissues from patients with a confirmed diagnosis of B cell neoplasia based on histological and FACS analysis criteria.

Tissue specimens. Frozen lymph nodes were obtained from the Cooperative Human Tissue Network (CHTN), Mid-Atlantic Division (Charlottesville, Va.). The tissue was received in dry ice, and upon arrival sectioned in two portions, one for histopathological analysis of the tumor and the other portion for Immunohistochemistry analysis.

Histopathological analysis and Immunohistochemistry. All eleven cases were fixed in 10% Neutral Buffered Formalin (NBF) and paraffinized in a tissue processor (Miles Scientific). After paraffinization, tissue blocks were sectioned with a Leica Microtome (Leica Microsystems, Bannockburn, Ill.) at 5 microns. The sections were placed in slides, deparaffinized with xylene and proceeded with an Hematoxylin and Eosin (H-E) tissue staining protocol (Luna, Histopathologic methods and Color Atlas Of Special Stains and Tissue Artifacts, (1992) American Histolabs, Inc., Publications Division, Kolb Center, 7605-F Airpark Road, Gaithersburg, Md. 2087). Daudi B cells, a malignant cell line involved in B cell lymphomas, were used as positive controls. Normal tonsil and lymph nodes were used as additional controls to understand the distribution of the cells expressing CD20 and CD32B in normal tissues.

The remaining portions of these samples were placed in cryomolds and embedded in OCT cryocompound (Tissue-Tek). Once the blocks were ready, each was sectioned under a Cryostat (Leica Microsystems) at 6 microns. The slides were placed in 4° C. acetone and fixed for 10 minutes. Hours after fixation the slides were air dried and washed with phosphate buffer saline (PBS). Then endogenous peroxide activity was blocked by 30 minute incubation in a 0.3% hydrogen peroxide solution. The slides were washed in PBS and incubated for 30 minutes with 10% normal goat serum in 2% normal human serum. After this step, the slides were divided in two groups. Two monoclonal antibodies were utilized and incubated on the same tissue in parallel, an anti-CD20 (1F5, ATCC NO. HB-9645, purified at Macrogenics) and the murine monoclonal anti-CD32B antibody, 2B6. Each group was incubated with one monoclonal antibody and their respective Isotype control, IgG1 (BD Biosciences, San Jose, Calif.) for the 2B6/anti-CD32B group and IgG2a (BD Biosciences) for the 1F5/anti-CD20 group. Mouse IgG1 and murine IgG2a were used as Isotype controls for anti-CD32B and anti-CD20, respectively. After one hour of incubation at room temperature, the slides were washed in PBS and incubated with a secondary antibody Goat anti Mouse labeled peroxidase (Jackson ImmunoResearch Laboratories, West Grove, Pa.). After washing with PBS, the sections were incubated in amino-9-ethylcarbazol (AEC) and hydrogen peroxide (Koretz et al. (1987) "*Metachromasia Of 3-amino-9-eth-* ylcarbazole (AEC) And Its Prevention In Immunoperoxidase TEChniques," Histochemistry 86:471-478). Hematoxylin was used as a counterstain.

The expression of anti CD20 and CD32B was scored under a light microscope at low power magnification based on the following criteria: a score of zero (−) meant no detectable reactivity; a score of plus/minus (+/−) meant detectable reaction in 1-10% of the cells; one plus (+) was equivalent to 10-30% positive cells; two pluses (++) for tissue with positive cells ranging from 30-70%; and three pluses (+++) for those tissues where 70% to 100% were positive.

RESULTS. Both positive controls, i.e., a malignant cell line involved in B cell lymphomas (Daudi cells; FIGS. 27A-27B) and normal tissues known to contain lymphatic tissue (tonsil: FIGS. 28A-28C; lymph nodes: FIGS. 29A-29C), responded positively to anti-Cd32B and anti-CD20 antibodies by immunohistochemistry. Normal tonsil tissues and lymph nodes stain differently with anti-CD32B antibodies and anti-CD20 antibodies. Lymphatic follicles showing germinal centers react with anti-CD20, while the cells in the follicles surrounding germinal centers react with anti-CD32B. Thus, morphological differences can be detected by immunohistochemistry with these two antibodies.

A total of ten lymph nodes and one spleen (11 cases) obtained from CHTN were analyzed. See FIGS. 30A-57D. The results are summarized in Table 9.

lymphoma lines and cells from patients with B-cell malignancies. Isolation of cells from patients and reactivity screening is described above.

Raft association. A measure of the ability of the antibody to trigger redistribution of the antigen into specialized membrane microdomains, lipid raft association is conveniently performed by measuring the amount of antibody recovered into the detergent-insoluble cellular fraction after lysis with 0.5% TX-100 at 4° C. (Veri et al. (2001) "*Membrane Raft-Dependent Regulation Of Phospholipase Cgamma-1 Activation In T Lymphocytes*," Mol. Cell Bio. 21:6939-6950; Cragg et al. (2004) "*Antibody Specificity Controls In Vivo Effector Mechanisms Of Anti-Cd20 Reagents*," Blood 103:2738-2743). In a typical experiment, cells will be coated on ice with the antibody of interest and washed. An aliquot will be subjected to additional cross-linking with an appropriate secondary antibody. Pelleted cells will be subjected to TX-100 detergent fractionation. Parallel samples will be solubilized with glucopyranoside, a detergent known to destroy lipid rafts, or directly with SDS-based Laemmli sample buffer to obtain the total amount of cell-associated antibody. The insoluble fractions will be analyzed by SDS-PAGE and western blot. Redistribution to lipid rafts with or without additional cross-linking will be recorded by densitometric comparisons.

CDC. CDC will be assessed by one of several methods known in the art, such as propidium iodide (PI) exclusion in

TABLE 9

SUMMARY OF IMMUNOHISTOCHEMISTRY RESULTS

| Patient Code | Final Pathologic Diagnosis | Tissue | 2B6 | 1F5 |
| --- | --- | --- | --- | --- |
| MG04-CHTN-19 | Diffuse Large B Cell Lymphoma | Lymph Node | ++ | ++ |
| MG04-CHTN-22 | Diffuse Large B Cell Lymphoma | Lymph Node | ++ | +/− |
| MG04-CHTN-26 | Follicular Lymphoma With areas of Diffuse Large B cell Lymphoma | Lymph Node | + | ++ |
| MG04-CHTN-27 | Diffuse Large B cell Lymphoma | Lymph Node | +++ | + |
| MG05-CHTN-03 | Diffuse Small Lymphocytic Lymphoma with Plasmacytoid features | Lymph Node | +++ | +/− |
| MG05-CHTN-05 | Diffuse Large B Cell Lymphoma | Lymph Node | + | ++ |
| MG04-CHTN-30 | Small Lymphocytic Lymphoma | Lymph Node | − | − |
| MG04-CHTN-31 | Diffuse Large B Cell Lymphoma | Lymph Node | ++ | + |
| MG04-CHTN-36 | Diffuse Large B Cell Lymphoma | Spleen | +++ | ++ |
| MG04-CHTN-41 | Mantle Cell Lymphoma/Diffuse Small Cleaved Cell Lymphoma | Lymph Node | ++ | +/− |
| MG04-CHTN-05 | Diffuse Large B Cell Lymphoma | Lymph Node | − | − |

Eight cases were Diffuse Large B Cell Lymphomas, two were Small Lymphocytic Lymphomas, and one was Mantle Cell Lymphoma/Diffuse Small Cleaved Cell Lymphoma. In the small lymphocytic lymphoma category, one had plasmacytoid features. All hematoxylin and eosin (H&E)-stained slides were reviewed for confirmation of the diagnosis.

The expression of CD20 was negative in 18% of the cases and weakly positive in ~30%, and intermediate/strongly positive in the remaining 50% of the cases. CD32B was detected in 80% of the cases and was found to be negative in only two cases.

CD32B expression was detected on 80% of NHL test cases. Expression of CD32B was often detected in more cells than CD20 was detected. CD32B may be a useful target of treatment of NHL.

Example 13

Screening of CD32B-Specific Monoclonal Antibodies

CD32B-specific antibodies will be screened for reactivity, raft association, CDC, and induction of apoptosis in B-cell FACS analysis (Cragg et al. (2004) "*Antibody Specificity Controls In Vivo Effector Mechanisms Of Anti-Cd20 Reagents*," Blood 103:2738-2743) or traditional radiolabel release (e.g., $^{51}$Cr and $^{111}$In release). In brief, cells will be incubated with titrating amounts of the antibodies of interest for 15 min at 37° C. followed by the addition of serum (20% final concentration) as a source of complement and the incubation continued for additional 5 min prior to analysis. Owing to the high variation of human serum, Pel-Freeze rabbit serum will be used as a standard source of complement. Pooled normal human AB serum will also be prepared. Each batch of serum will be tested in red blood cell lysis against rabbit serum for quality assurance.

Apoptosis. Apoptosis induced by soluble or plate immobilized anti-CD32B antibodies will be studied by standard FACS-based methodology by using annexin V membrane translocation and PI staining (Cragg et al. (2004) "*Antibody Specificity Controls In Vivo Effector Mechanisms Of Anti-Cd20 Reagents*," Blood 103:2738-2743) in multi-color analysis to identify the population of interest (e.g. Cy5-CD19). Briefly, cells will be treated for different intervals of time (2 to 18 hours) with titrating amounts of the antibody of interest in free solution or immobilized on 96-well plates. Cells will then be recovered by gentle scraping and/or centrifugation and stained with 1 ug/ml of FITC-annexin V plus 10 ug/ml of PI to distinguish between early apoptosis and secondary necrosis.

Example 14

In Vivo Tumor Clearance Studies in Murine Tumor Xenograft Models of Lymphoma

The ability to prevent tumors in a mouse model of lymphoma is an important criterion to determine the potential for an antibody to proceed into clinical studies.

A number of well characterized Burkitt's lymphoma cell lines are available for use as models of NHL (Epstein et al. (1966) "*Morphological And Virological Investigations On Cultured Burkitt Tumor Lymphoblasts (Strain Raji),*" J. Natl. Cancer Inst. 37:547-559; Klein et al. (1968) "*Surface IgM-Kappa Specificity On A Burkitt Lymphoma Cell In Vivo And In Derived Culture Lines,*" Cancer Res. 28:1300-1310; Klein et al. (1975) "*An EBV-Genome-Negative Cell Line Established From An American Burkitt Lymphoma; Receptor Characteristics. EBV Infectibility And Permanent Conversion Into EBV-Positive Sublines By In Vitro Infection,*" Intervirology 5:319-334; Nilsson et al. (1977) "*Tumorigenicity Of Human Hematopoietic Cell Lines In Athymic Nude Mice,*" Intl. J. Cancer 19:337-344; Ohsugi et al. (1980) "*Tumorigenicity Of Human Malignant Lymphoblasts: Comparative Study With Unmanipulated Nude Mice, Antilymphocyte Serum-Treated Nude Mice, And X-Irradiated Nude Mice,*" J. Natl. Cancer Inst. 65:715-718). A xenograft model of lymphoma formation has been established in nude mice similar to previously reported models (Vallera et al. (2003) "*Preclinical Studies Targeting Normal And Leukemic Hematopoietic Cells With Yttrium-90-Labeled Anti-CD45 Antibody In Vitro And In Vivo In Nude Mice,*" Cancer Biother. Radiopharm. 18:133-145; Vuist et al. (1989) "*Potentiation By Interleukin 2 Of Burkitt's Lymphoma Therapy With Anti-Pan B (Anti-CD19) Monoclonal Antibodies In A Mouse Xenotransplantation Model,*" Cancer Res. 49:3783-3788).

In brief, the Burkitt's lymophoma cell line, Daudi (5-10× $10^6$ cells), will be transplanted subcutaneously into an immunodeficient nu/nu mouse strain. The BALB/c nu/nu mouse strain will be used together with adoptively transferred human PBMC purified from a healthy donor as effector cells. A prevailing effector cell population in human PBMC is represented by NK cells, which exert ADCC via their CD16A (FcγRIIIa). A nu/nu mouse strain in which the murine CD16A gene has been knocked out and which has been genetically engineered to express human CD16A will also be used. This CD16A−/− huCD16Atg, nu/nu mouse allows for the examination of anti-tumor activity in the context of a human Fc receptor without the need for the adoptive transfer of human cells.

Mice will be treated with the selected chimerized antibody injected i.p. on day 1, 4, 7, and 15. A starting dose of 4 ug/g of body weight will be used, but additional doses will be tested to establish the relative potency of the antibodies in this model. RITUXAN® (rituximab) and CAMPATH® (alemtuzumab) will be used for comparison. Furthermore, potential synergism of combination therapy with RITUXAN® (rituximab) or CAMPATH® (alemtuzumab) will also be studied. In these studies, tumor growth and morbidity will be monitored to compare antibody treated and control groups. Mice will be sacrificed immediately if moribund or at the completion of the studies. The tumors will then be excised and gross and microscopic necropsy performed. Cytopathology on paraffin-embedded sections and immunohistochemistry on frozen sections will be performed for a morphological and immunological evaluation of the tumor and cellular infiltrates.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. An isolated antibody, or an antigen-binding fragment thereof, that selectively binds an FcγRIIB receptor, wherein said antibody comprises:
   (A) a heavy chain CDR1 having a sequence of SEQ ID NO:27, a heavy chain CDR2 having a sequence of SEQ ID NO:28, and a heavy chain CDR3 having a sequence of SEQ ID NO:29; and
   (B) a light chain CDR1 having a sequence of SEQ ID NO:36, a light chain CDR2 having a sequence of SEQ ID NO:37, and a light chain CDR3 having a sequence of SEQ ID NO:38.

2. An isolated antibody, or an antigen-binding fragment thereof, that binds FcγRIIB with greater affinity than FcγRIIA, wherein said antibody comprises a heavy chain variable domain comprising the amino acid sequence of SEQ ID NO:35.

3. An isolated antibody, or an antigen-binding fragment thereof, that binds FcγRIIB with greater affinity than FcγRIIA, wherein said antibody comprises a light chain variable domain comprising an amino acid sequence of SEQ ID NO:44.

4. The isolated antibody or antigen-binding fragment of claim 3, wherein said antibody or said fragment additionally comprises a heavy chain variable domain comprising the amino acid sequence of SEQ ID NO:35.

5. The isolated antibody or antigen-binding fragment of claim 1, wherein the antibody is a monoclonal antibody, a chimeric antibody, or a humanized antibody, and said fragment is an antigen-binding fragment thereof.

6. The isolated antibody or antigen-binding fragment of claim 1, wherein said antibody or said fragment antagonizes binding of an antibody Fc region to FcγRIIB.

* * * * *

SEQUENCE LISTING

```
<160> NUMBER OF SEQ ID NOS: 60

<210> SEQ ID NO 1
<211> LENGTH: 5
<212> TYPE: PRT
<213> ORGANISM: artificial
<220> FEATURE:
<223> OTHER INFORMATION: 2B6 Heavy Chain Variable Region CDR1

<400> SEQUENCE: 1

Asn Tyr Trp Ile His
1               5

<210> SEQ ID NO 2
<211> LENGTH: 17
<212> TYPE: PRT
<213> ORGANISM: artificial
<220> FEATURE:
<223> OTHER INFORMATION: 2B6 Heavy Chain Variable Region CDR2

<400> SEQUENCE: 2
```

```
Val Ile Asp Pro Ser Asp Thr Tyr Pro Asn Tyr Asn Lys Lys Phe Lys
1               5                   10                  15

Gly

<210> SEQ ID NO 3
<211> LENGTH: 12
<212> TYPE: PRT
<213> ORGANISM: artificial
<220> FEATURE:
<223> OTHER INFORMATION: 2B6 Heavy Chain Variable Region CDR3

<400> SEQUENCE: 3

Asn Gly Asp Ser Asp Tyr Tyr Ser Gly Met Asp Tyr
1               5                   10

<210> SEQ ID NO 4
<211> LENGTH: 30
<212> TYPE: PRT
<213> ORGANISM: homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 5
<211> LENGTH: 14
<212> TYPE: PRT
<213> ORGANISM: homo sapiens

<400> SEQUENCE: 5

Trp Val Arg Gln Ala Pro Gly Gln Gly Leu Glu Trp Met Gly
1               5                   10

<210> SEQ ID NO 6
<211> LENGTH: 32
<212> TYPE: PRT
<213> ORGANISM: homo sapiens

<400> SEQUENCE: 6

Arg Val Thr Met Thr Thr Asp Thr Ser Thr Ser Thr Ala Tyr Met Glu
1               5                   10                  15

Leu Arg Ser Leu Arg Ser Glu Glu Thr Ala Val Tyr Tyr Cys Ala Arg
            20                  25                  30

<210> SEQ ID NO 7
<211> LENGTH: 11
<212> TYPE: PRT
<213> ORGANISM: homo sapiens

<400> SEQUENCE: 7

Trp Gly Gln Gly Thr Thr Val Thr Val Ser Ser
1               5                   10

<210> SEQ ID NO 8
<211> LENGTH: 11
<212> TYPE: PRT
<213> ORGANISM: artificial
<220> FEATURE:
<223> OTHER INFORMATION: 2B6 light chain variable region CDR1

<400> SEQUENCE: 8

Arg Thr Ser Gln Ser Ile Gly Thr Asn Ile His
```

```
1               5                   10
```

```
<210> SEQ ID NO 9
<211> LENGTH: 7
<212> TYPE: PRT
<213> ORGANISM: artificial
<220> FEATURE:
<223> OTHER INFORMATION: 2B6 light chain variable region CDR2

<400> SEQUENCE: 9

Asn Val Ser Glu Ser Ile Ser
1               5

<210> SEQ ID NO 10
<211> LENGTH: 7
<212> TYPE: PRT
<213> ORGANISM: artificial
<220> FEATURE:
<223> OTHER INFORMATION: 2B6 light chain variable region CDR2

<400> SEQUENCE: 10

Tyr Val Ser Glu Ser Ile Ser
1               5

<210> SEQ ID NO 11
<211> LENGTH: 7
<212> TYPE: PRT
<213> ORGANISM: artificial
<220> FEATURE:
<223> OTHER INFORMATION: 2B6 light chain variable region CDR2

<400> SEQUENCE: 11

Tyr Ala Ser Glu Ser Ile Ser
1               5

<210> SEQ ID NO 12
<211> LENGTH: 9
<212> TYPE: PRT
<213> ORGANISM: artificial
<220> FEATURE:
<223> OTHER INFORMATION: 2B6 light chain variable region CDR3

<400> SEQUENCE: 12

Gln Gln Ser Asn Thr Trp Pro Phe Thr
1               5

<210> SEQ ID NO 13
<211> LENGTH: 23
<212> TYPE: PRT
<213> ORGANISM: homo sapiens

<400> SEQUENCE: 13

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 14
<211> LENGTH: 15
<212> TYPE: PRT
<213> ORGANISM: homo sapiens

<400> SEQUENCE: 14

Trp Tyr Gln Gln Lys Pro Asp Gln Ser Pro Lys Leu Leu Ile Lys
1               5                   10                  15
```

```
<210> SEQ ID NO 15
<211> LENGTH: 32
<212> TYPE: PRT
<213> ORGANISM: homo sapiens

<400> SEQUENCE: 15

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 16
<211> LENGTH: 10
<212> TYPE: PRT
<213> ORGANISM: homo sapiens

<400> SEQUENCE: 16

Phe Gly Gly Gly Thr Lys Val Glu Ile Lys
1               5                   10

<210> SEQ ID NO 17
<211> LENGTH: 321
<212> TYPE: DNA
<213> ORGANISM: artificial
<220> FEATURE:
<223> OTHER INFORMATION: Humanized 2B6 light chain variable
      region-Hu2B6VL-1

<400> SEQUENCE: 17
gaaattgtgc tgactcagtc tccagacttt cagtctgtga ctccaaagga gaaagtcacc    60
atcacctgca ggaccagtca gagcattggc acaaacatac actggtacca gcagaaacca   120
gatcagtctc caaagctcct catcaagaat gtttctgagt ctatctctgg agtcccatcg   180
aggttcagtg gcagtggatc tgggacagat ttcaccctca ccatcaatag cctggaagct   240
gaagatgctg caacgtatta ctgtcaacaa agtaatacct ggccgttcac gttcggcgga   300
gggaccaagg tggagatcaa a                                             321

<210> SEQ ID NO 18
<211> LENGTH: 107
<212> TYPE: PRT
<213> ORGANISM: artificial
<220> FEATURE:
<223> OTHER INFORMATION: Humanized 2B6 light chain variable
      region-Hu2B6VL-1

<400> SEQUENCE: 18

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Asn Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105
```

```
<210> SEQ ID NO 19
<211> LENGTH: 321
<212> TYPE: DNA
<213> ORGANISM: artificial
<220> FEATURE:
<223> OTHER INFORMATION: Humanized 2B6 light chain variable
      region-Hu2B6VL-2

<400> SEQUENCE: 19
gaaattgtgc tgactcagtc tccagacttt cagtctgtga ctccaaagga gaaagtcacc    60
atcacctgca ggaccagtca gagcattggc acaaacatac actggtacca gcagaaacca   120
gatcagtctc caaagctcct catcaagtat gtttctgagt ctatctctgg agtcccatcg   180
aggttcagtg gcagtggatc tgggacagat ttcacccctca ccatcaatag cctggaagct   240
gaagatgctg caacgtatta ctgtcaacaa agtaatacct ggccgttcac gttcggcgga   300
gggaccaagg tggagatcaa a                                              321

<210> SEQ ID NO 20
<211> LENGTH: 107
<212> TYPE: PRT
<213> ORGANISM: artificial
<220> FEATURE:
<223> OTHER INFORMATION: Humanized 2B6 light chain variable
      region-Hu2B6VL-2

<400> SEQUENCE: 20

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
            100                 105

<210> SEQ ID NO 21
<211> LENGTH: 321
<212> TYPE: DNA
<213> ORGANISM: artificial
<220> FEATURE:
<223> OTHER INFORMATION: Humanized 2B6 light chain variable
      region-Hu2B6VL-3

<400> SEQUENCE: 21
gaaattgtgc tgactcagtc tccagacttt cagtctgtga ctccaaagga gaaagtcacc    60
atcacctgca ggaccagtca gagcattggc acaaacatac actggtacca gcagaaacca   120
gatcagtctc caaagctcct catcaagtat gcttctgagt ctatctctgg agtcccatcg   180
aggttcagtg gcagtggatc tgggacagat ttcacccctca ccatcaatag cctggaagct   240
gaagatgctg caacgtatta ctgtcaacaa agtaatacct ggccgttcac gttcggcgga   300
gggaccaagg tggagatcaa a                                              321

<210> SEQ ID NO 22
<211> LENGTH: 106
```

```
<212> TYPE: PRT
<213> ORGANISM: artificial
<220> FEATURE:
<223> OTHER INFORMATION: Humanized 2B6 light chain variable
      region-Hu2B6VL-3

<400> SEQUENCE: 22

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Cys Gln Gln Ser Asn Thr Trp Pro Phe Thr
                85                  90                  95

Phe Gly Gly Gly Thr Lys Val Glu Ile Lys
            100                 105

<210> SEQ ID NO 23
<211> LENGTH: 363
<212> TYPE: DNA
<213> ORGANISM: artificial
<220> FEATURE:
<223> OTHER INFORMATION: Humanized 2B6 heavy chain variable
      region-Hu2B6VH-1

<400> SEQUENCE: 23
caggttcagc tggtgcagtc tggagctgag gtgaagaagc ctggggcctc agtgaaggtc      60
tcctgcaagg cttctggtta cacctttacc aactactgga tacactgggt gcgacaggcc    120
cctggacaag ggcttgagtg gatgggagtg attgatcctt ctgatactta tccaaattac    180
aataaaaagt tcaagggcag agtcaccatg accacagaca catccacgag cacagcctac    240
atggagctga gagcctgag atctgacgac acggccgtgt attactgtgc gagaaacggg    300
gattccgatt attactctgg tatggactac tggggcaag ggaccacggt caccgtctcc    360
tca                                                                 363

<210> SEQ ID NO 24
<211> LENGTH: 121
<212> TYPE: PRT
<213> ORGANISM: artificial
<220> FEATURE:
<223> OTHER INFORMATION: Humanized 2B6 heavy chain variable
      region-Hu2B6VH-1

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Val Ile Asp Pro Ser Asp Thr Tyr Pro Asn Tyr Asn Lys Lys Phe
    50                  55                  60

Lys Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
            85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120

<210> SEQ ID NO 25
<211> LENGTH: 321
<212> TYPE: DNA
<213> ORGANISM: Mus sp.

<400> SEQUENCE: 25
gacatcttgc tgactcagtc tccagccatc ctgtctgtga gtccaggaga gagagtcagt      60
ttttcctgca ggaccagtca gagcattggc acaaacatac actggtatca gcaaagaaca     120
aatggttttc caaggcttct cataaagaat gtttctgagt ctatctctgg gatcccttcc     180
aggtttagtg gcagtggatc aggacagat tttattctta gcatcaacag tgtggagtct      240
gaagatattg cagattatta ttgtcaacaa agtaataccc ggccgttcac gttcggaggg     300
gggaccaagc tggaaataaa a                                               321

<210> SEQ ID NO 26
<211> LENGTH: 121
<212> TYPE: PRT
<213> ORGANISM: Mus sp.

<400> SEQUENCE: 26

Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Lys Ala Thr Leu Thr Val Val Ser Ser Thr Ala Tyr
65                  70                  75                  80

Met Gln Leu Ser Ser Leu Thr Ser Asp Asp Ser Ala Val Tyr Tyr Cys
            85                  90                  95

Ala Arg Asn Gly Asp Ser Asp Tyr Tyr Ser Gly Met Asp Tyr Trp Gly
            100                 105                 110

Gln Gly Thr Ser Val Thr Val Ser Ser
        115                 120

<210> SEQ ID NO 27
<211> LENGTH: 5
<212> TYPE: PRT
<213> ORGANISM: artificial
<220> FEATURE:
<223> OTHER INFORMATION: 3H7 Heavy chain variable region-CDR1

<400> SEQUENCE: 27

Asp Ala Trp Met Asp
1               5

<210> SEQ ID NO 28
<211> LENGTH: 19
<212> TYPE: PRT
<213> ORGANISM: artificial
<220> FEATURE:
```

<223> OTHER INFORMATION: 3H7 Heavy chain variable region CDR2

<400> SEQUENCE: 28

```
Glu Ile Arg Asn Lys Ala Asn Asn Leu Ala Thr Tyr Tyr Ala Glu Ser
1               5                   10                  15
Val Lys Gly
```

<210> SEQ ID NO 29
<211> LENGTH: 6
<212> TYPE: PRT
<213> ORGANISM: artificial
<220> FEATURE:
<223> OTHER INFORMATION: 3H7 Heavy chain variable region CDR3

<400> SEQUENCE: 29

```
Tyr Ser Pro Phe Ala Tyr
1               5
```

<210> SEQ ID NO 30
<211> LENGTH: 30
<212> TYPE: PRT
<213> ORGANISM: artificial
<220> FEATURE:
<223> OTHER INFORMATION: 3H7 Heavy chain variable region FWR1

<400> SEQUENCE: 30

```
Glu Val Lys Phe Glu Glu Ser Gly Gly Gly Leu Val Gln Pro Gly Gly
1               5                   10                  15
Ser Met Lys Leu Ser Cys Ala Ala Ser Gly Phe Thr Phe Ser
            20                  25                  30
```

<210> SEQ ID NO 31
<211> LENGTH: 14
<212> TYPE: PRT
<213> ORGANISM: artificial
<220> FEATURE:
<223> OTHER INFORMATION: 3H7 Heavy chain variable region FWR2

<400> SEQUENCE: 31

```
Trp Val Arg Gln Gly Pro Glu Lys Gly Leu Glu Trp Val Ala
1               5                   10
```

<210> SEQ ID NO 32
<211> LENGTH: 30
<212> TYPE: PRT
<213> ORGANISM: artificial
<220> FEATURE:
<223> OTHER INFORMATION: 3H7 Heavy chain variable region FW3

<400> SEQUENCE: 32

```
Arg Phe Thr Ile Pro Arg Asp Asp Ser Lys Ser Ser Val Tyr Leu His
1               5                   10                  15
Met Asn Ser Leu Arg Ala Glu Asp Thr Gly Ile Tyr Tyr Cys
            20                  25                  30
```

<210> SEQ ID NO 33
<211> LENGTH: 11
<212> TYPE: PRT
<213> ORGANISM: artificial
<220> FEATURE:
<223> OTHER INFORMATION: 3H7 Heavy chain variable region FWR4

<400> SEQUENCE: 33

```
Trp Gly Gln Gly Thr Leu Val Thr Val Ser Ala
1               5                   10
```

```
<210> SEQ ID NO 34
<211> LENGTH: 285
<212> TYPE: DNA
<213> ORGANISM: Mus sp.

<400> SEQUENCE: 34
gaagtgaagt ttgaggagtc tggaggaggc ttggtgcaac ctggaggatc catgaaactc     60
tcttgtgctg cctctggatt cactttagt gacgcctgga tggactgggt ccgccagggt    120
ccagagaagg ggcttgagtg ggttgctgaa attagaaaca aagctaataa tcttgcaaca    180
tactatgctg agtctgtgaa agggaggttc accatcccaa gagatgattc caaaagtagt    240 cccttttgctt actggggcca aggactctg gtcactgtct ctgca                    285

<210> SEQ ID NO 35
<211> LENGTH: 115
<212> TYPE: PRT
<213> ORGANISM: Mus sp.

<400> SEQUENCE: 35

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Gly Pro Glu Lys Gly Leu Glu Trp Val
            35                  40                  45

Ala Glu Ile Arg Asn Lys Ala Asn Asn Leu Ala Thr Tyr Tyr Ala Glu
        50                  55                  60

Ser Val Lys Gly Arg Phe Thr Ile Pro Arg Asp Asp Ser Lys Ser Ser
65                  70                  75                  80

Val Tyr Leu His Met Asn Ser Leu Arg Ala Glu Asp Thr Gly Ile Tyr
                85                  90                  95

Tyr Cys Tyr Ser Pro Phe Ala Tyr Trp Gly Gln Gly Thr Leu Val Thr
            100                 105                 110

Val Ser Ala
        115

<210> SEQ ID NO 36
<211> LENGTH: 11
<212> TYPE: PRT
<213> ORGANISM: artificial
<220> FEATURE:
<223> OTHER INFORMATION: 3H7 light chain variable region CDR1

<400> SEQUENCE: 36

Arg Ala Ser Gln Glu Ile Ser Gly Tyr Leu Ser
1               5                   10

<210> SEQ ID NO 37
<211> LENGTH: 7
<212> TYPE: PRT
<213> ORGANISM: artificial
<220> FEATURE:
<223> OTHER INFORMATION: 3H7 Light chain variable region CDR2

<400> SEQUENCE: 37

Ala Ala Ser Thr Leu Asp Ser
1               5

<210> SEQ ID NO 38
<211> LENGTH: 9
<212> TYPE: PRT
```

```
<213> ORGANISM: artificial
<220> FEATURE:
<223> OTHER INFORMATION: 3H7 light chain variable region CDR3

<400> SEQUENCE: 38

Leu Gln Tyr Val Ser Tyr Pro Tyr Thr
1               5

<210> SEQ ID NO 39
<211> LENGTH: 23
<212> TYPE: PRT
<213> ORGANISM: artificial
<220> FEATURE:
<223> OTHER INFORMATION: 3H7 light chain variable region FWR1

<400> SEQUENCE: 39

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 40
<211> LENGTH: 15
<212> TYPE: PRT
<213> ORGANISM: artificial
<220> FEATURE:
<223> OTHER INFORMATION: 3H7 light chain variable region FWR2

<400> SEQUENCE: 40

Trp Leu Gln Gln Lys Pro Asp Gly Thr Ile Arg Arg Leu Ile Tyr
1               5                   10                  15

<210> SEQ ID NO 41
<211> LENGTH: 32
<212> TYPE: PRT
<213> ORGANISM: artificial
<220> FEATURE:
<223> OTHER INFORMATION: 3H7 light chain variable region FWR3

<400> SEQUENCE: 41

Gly Val Pro Lys Arg Phe Ser Gly Ser Trp Ser Gly Ser Asp Tyr Ser
1               5                   10                  15

Leu Thr Ile Ser Ser Leu Glu Ser Glu Asp Phe Ala Asp Tyr Tyr Cys
            20                  25                  30

<210> SEQ ID NO 42
<211> LENGTH: 10
<212> TYPE: PRT
<213> ORGANISM: artificial
<220> FEATURE:
<223> OTHER INFORMATION: 3H7 light chain variable region FWR4

<400> SEQUENCE: 42

Phe Gly Gly Gly Thr Lys Leu Glu Ile Lys
1               5                   10

<210> SEQ ID NO 43
<211> LENGTH: 321
<212> TYPE: DNA
<213> ORGANISM: Mus sp.

<400> SEQUENCE: 43
gacatccaga tgacccagtc tccatcctcc ttatctgcct ctctgggaga aagagtcagt      60
ctcacttgtc gggcaagtca ggaaattagt ggttacttaa gctggcttca gcagaaacca     120
gatggaacta ttagacgcct gatctacgcc gcatccactt tagattctgg tgtcccaaaa     180
```

-continued

```
aggttcagtg gcagttggtc tgggtcagat tattctctca ccatcagcag ccttgagtct      240
gaagattttg cagactatta ctgtctacaa tatgttagtt atccgtatac gttcggaggg      300
gggaccaagc tggaaataaa a                                                321
```

<210> SEQ ID NO 44
<211> LENGTH: 107
<212> TYPE: PRT
<213> ORGANISM: Mus sp.

<400> SEQUENCE: 44

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Arg Arg Leu Ile
        35                  40                  45

Tyr Ala Ala Ser Thr Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Tyr
                85                  90                  95

Thr Phe Gly Gly Gly Thr Lys Leu Glu Ile Lys
            100                 105
```

<210> SEQ ID NO 45
<211> LENGTH: 22
<212> TYPE: DNA
<213> ORGANISM: artificial
<220> FEATURE:
<223> OTHER INFORMATION: Primer SJ15R

<400> SEQUENCE: 45

```
ggtcactgtc actggctcag gg                                                22
```

<210> SEQ ID NO 46
<211> LENGTH: 28
<212> TYPE: DNA
<213> ORGANISM: artificial
<220> FEATURE:
<223> OTHER INFORMATION: Primer SJ16R

<400> SEQUENCE: 46

```
aggcggatcc aggggccagt ggatagac                                          28
```

<210> SEQ ID NO 47
<211> LENGTH: 26
<212> TYPE: DNA
<213> ORGANISM: artificial
<220> FEATURE:
<223> OTHER INFORMATION: Primer SJ17R

<400> SEQUENCE: 47

```
gcacacgact gaggcacctc cagatg                                            26
```

<210> SEQ ID NO 48
<211> LENGTH: 34
<212> TYPE: DNA
<213> ORGANISM: artificial
<220> FEATURE:
<223> OTHER INFORMATION: Primer SJ18R

```
<400> SEQUENCE: 48
cggcggatcc gatggataca gttggtgcag catc                                  34

<210> SEQ ID NO 49
<211> LENGTH: 9
<212> TYPE: PRT
<213> ORGANISM: artificial
<220> FEATURE:
<223> OTHER INFORMATION: fusion protein partial sequence

<400> SEQUENCE: 49

Lys Lys Phe Ser Arg Ser Asp Pro Asn
1               5

<210> SEQ ID NO 50
<211> LENGTH: 9
<212> TYPE: PRT
<213> ORGANISM: artificial
<220> FEATURE:
<223> OTHER INFORMATION: fusion protein partial sequence

<400> SEQUENCE: 50

Gln Lys Phe Ser Arg Leu Asp Pro Asn
1               5

<210> SEQ ID NO 51
<211> LENGTH: 9
<212> TYPE: PRT
<213> ORGANISM: artificial
<220> FEATURE:
<223> OTHER INFORMATION: fusion protein partial sequence

<400> SEQUENCE: 51

Gln Lys Phe Ser Arg Leu Asp Pro Thr
1               5

<210> SEQ ID NO 52
<211> LENGTH: 9
<212> TYPE: PRT
<213> ORGANISM: artificial
<220> FEATURE:
<223> OTHER INFORMATION: fusion protein partial sequence

<400> SEQUENCE: 52

Lys Lys Phe Ser Arg Leu Asp Pro Thr
1               5

<210> SEQ ID NO 53
<211> LENGTH: 9
<212> TYPE: PRT
<213> ORGANISM: artificial
<220> FEATURE:
<223> OTHER INFORMATION: fusion protein partial sequence

<400> SEQUENCE: 53

Gln Lys Phe Ser His Leu Asp Pro Thr
1               5

<210> SEQ ID NO 54
<211> LENGTH: 9
<212> TYPE: PRT
<213> ORGANISM: artificial
<220> FEATURE:
<223> OTHER INFORMATION: fusion protein partial sequence

<400> SEQUENCE: 54

Lys Lys Phe Ser His Leu Asp Pro Thr
```

<210> SEQ ID NO 55
<211> LENGTH: 5
<212> TYPE: PRT
<213> ORGANISM: artificial
<220> FEATURE:
<223> OTHER INFORMATION: fusion protein partial sequence

<400> SEQUENCE: 55

Ala Pro Ser Ser Ser
1               5

<210> SEQ ID NO 56
<211> LENGTH: 8
<212> TYPE: PRT
<213> ORGANISM: artificial
<220> FEATURE:
<223> OTHER INFORMATION: fusion protein partial sequence

<400> SEQUENCE: 56

Val Pro Ser Met Gly Ser Ser Ser
1               5

<210> SEQ ID NO 57
<211> LENGTH: 363
<212> TYPE: DNA
<213> ORGANISM: Mus sp.

<400> SEQUENCE: 57
caggtccaat tgcagcagcc tgtgactgag ctggtgaggc cgggggcttc agtgatgttg     60
tcctgcaagg cttctgacta ccccttcacc aactactgga tacactgggt aaagcagagg    120
cctggacaag gcctggagtg gatcggagtg attgatcctt ctgatactta tccaaattac    180
aataaaaagt tcaagggcaa ggccacattg actgtagtcg tatcctccag cacagcctac    240
atgcagctca gcagcctgac atctgacgat tctgcggtct attactgtgc aagaaacggt    300
gattccgatt attactctgg tatggactac tggggtcaag gaacctcagt caccgtctcc    360
tca                                                                  363

<210> SEQ ID NO 58
<211> LENGTH: 121
<212> TYPE: PRT
<213> ORGANISM: Mus sp.

<400> SEQUENCE: 58

Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Lys Ala Thr Leu Thr Val Val Val Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Ser Val Thr Val Ser Ser

```
                115                 120

<210> SEQ ID NO 59
<211> LENGTH: 7
<212> TYPE: PRT
<213> ORGANISM: Homo sapiens

<400> SEQUENCE: 59

Ser Asp Pro Asn Phe Ser Ile
1               5

<210> SEQ ID NO 60
<211> LENGTH: 290
<212> TYPE: PRT
<213> ORGANISM: Homo sapiens

<400> SEQUENCE: 60

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Pro Pro Lys
        35                  40                  45

Ala Val Leu Lys Leu Glu Pro Gln Trp Ile Asn Val Leu Gln Glu Asp
    50                  55                  60

Ser Val Thr Leu Thr Cys Arg Gly Thr His Ser Pro Glu Ser Asp Ser
65                  70                  75                  80

Ile Gln Trp Phe His Asn Gly Asn Leu Ile Pro Thr His Thr Gln Pro
                85                  90                  95

Ser Tyr Arg Phe Lys Ala Asn Asn Asn Asp Ser Gly Glu Tyr Thr Cys
            100                 105                 110

Gln Thr Gly Gln Thr Ser Leu Ser Asp Pro Val His Leu Thr Val Leu
        115                 120                 125

Ser Glu Trp Leu Val Leu Gln Thr Pro His Leu Glu Phe Gln Glu Gly
    130                 135                 140

Glu Thr Ile Val Leu Arg Cys His Ser Trp Lys Asp Lys Pro Leu Val
145                 150                 155                 160

Lys Val Thr Phe Phe Gln Asn Gly Lys Ser Lys Lys Phe Ser Arg Ser
                165                 170                 175

Asp Pro Asn Phe Ser Ile Pro Gln Ala Asn His Ser His Ser Gly Asp
            180                 185                 190

Tyr His Cys Thr Gly Asn Ile Gly Tyr Thr Leu Tyr Ser Ser Lys Pro
        195                 200                 205

Val Thr Ile Thr Val Gln Ala Pro Ser Ser Ser Pro Met Gly Ile Ile
    210                 215                 220

Val Ala Val Val Thr Gly Ile Ala Val Ala Ala Ile Val Ala Ala Val
225                 230                 235                 240

Val Ala Leu Ile Tyr Cys Arg Lys Lys Arg Ile Ser Ala Asn Pro Thr
                245                 250                 255

Asn Pro Asp Glu Ala Asp Lys Val Gly Ala Glu Asn Thr Ile Thr Tyr
            260                 265                 270

Ser Leu Leu Met His Pro Asp Ala Leu Glu Glu Pro Asp Asp Gln Asn
        275                 280                 285

Arg Ile
290
```